(12) United States Patent
Willams et al.

(10) Patent No.: US 8,765,812 B2
(45) Date of Patent: *Jul. 1, 2014

(54) THERAPEUTIC COMPOUNDS

(75) Inventors: Spencer John Willams, Kensington (AU); David Stapleton, Wantirna (AU); Steven Zammit, Templestowne (AU); Darren James Kelly, Wonga Park (AU); Richard Ernest Gilbert, Toronto (CA); Henry Krum, Melbourne (AU)

(73) Assignee: Fibrotech Therapeutics Pty Ltd, Wonga Park (AU)

( * ) Notice: Subject to any disclaimer, the term of this patent is extended or adjusted under 35 U.S.C. 154(b) by 77 days.

This patent is subject to a terminal disclaimer.

(21) Appl. No.: 12/309,010

(22) PCT Filed: Jul. 5, 2007

(86) PCT No.: PCT/AU2007/000934

§ 371 (c)(1),
(2), (4) Date: Feb. 4, 2010

(87) PCT Pub. No.: WO2008/003141

PCT Pub. Date: Jan. 10, 2008

(65) Prior Publication Data

US 2010/0130497 A1 May 27, 2010

(30) Foreign Application Priority Data

Jul. 5, 2006 (AU) ............................... 2006903625

(51) Int. Cl.
*A61K 31/5375* (2006.01)
*A61K 31/4409* (2006.01)
*A61K 31/42* (2006.01)
*A61K 31/4192* (2006.01)
*A61K 31/196* (2006.01)
*C07D 295/088* (2006.01)
*C07D 213/30* (2006.01)
*C07D 249/04* (2006.01)
*C07D 261/08* (2006.01)
*C07C 235/38* (2006.01)

(52) U.S. Cl.
CPC ........... *A61K 31/196* (2013.01); *A61K 31/5375* (2013.01); *A61K 31/4409* (2013.01); *A61K 31/42* (2013.01); *A61K 31/4192* (2013.01); *C07D 295/088* (2013.01); *C07D 213/30* (2013.01); *C07D 249/04* (2013.01); *C07D 261/08* (2013.01); *C07C 235/38* (2013.01)
USPC ........ 514/563; 514/359; 514/239.2; 514/357; 514/378; 544/165; 546/337; 548/247; 548/255; 564/170

(58) Field of Classification Search
CPC ........... A61K 31/5375; A61K 31/4409; A61K 31/42; A61K 31/4192; A61K 31/196; C07D 295/088; C07D 213/30; C07D 249/04; C07D 261/08; C07C 235/38
USPC ...... 514/359, 239.2, 357, 378, 563; 544/165; 546/337; 548/247, 255; 564/170
See application file for complete search history.

(56) References Cited

U.S. PATENT DOCUMENTS

| | | |
|---|---|---|
| 3,940,422 A | 2/1976 | Harita et al. |
| 4,026,896 A | 5/1977 | Harita et al. |
| 4,587,356 A | 5/1986 | Lizuka et al. |
| 5,248,825 A | 9/1993 | Dinerstein et al. |
| 5,356,620 A | 10/1994 | Yamamoto et al. |
| 5,663,414 A | 9/1997 | Oinuma et al. |
| 5,723,493 A | 3/1998 | Nagao et al. |
| 6,127,392 A | 10/2000 | Lennox et al. |
| 6,326,510 B1 | 12/2001 | Bernardon |
| 6,646,009 B2 | 11/2003 | Reddy et al. |
| 7,094,801 B2 | 8/2006 | Sikorski et al. |
| 7,250,444 B2 | 7/2007 | Kennedy et al. |
| 7,351,719 B2 | 4/2008 | Stenkamp et al. |
| 7,592,373 B2 | 9/2009 | Lehmann-Lintz et al. |
| 8,106,051 B2 | 1/2012 | Yamamori et al. |
| 2002/0099089 A1 | 7/2002 | Hauel et al. |
| 2005/0222423 A1 | 10/2005 | Saito et al. |
| 2006/0014807 A1 | 1/2006 | Lin |
| 2006/0089413 A1 | 4/2006 | Schmaus et al. |
| 2007/0060646 A1 | 3/2007 | Gericke et al. |
| 2007/0191378 A1 | 8/2007 | Campbell et al. |
| 2007/0281969 A1 | 12/2007 | Colletti et al. |
| 2007/0286892 A1 | 12/2007 | Herzberg et al. |
| 2007/0299101 A1 | 12/2007 | Colletti et al. |
| 2008/0008660 A1 | 1/2008 | Rabenhorst et al. |

(Continued)

FOREIGN PATENT DOCUMENTS

| | | |
|---|---|---|
| DE | 2402398 | 8/1974 |
| EP | 0816329 A1 | 1/1998 |

(Continued)

OTHER PUBLICATIONS

Merriam-Webster Online Dictionary entry for "analogue", (http://www.merriam-webster.com/dictionary/derivative), last accessed May 12, 2010.*
Merriam-Webster Online Dictionary entry for "derivative", (http://www.merriam-webster.com/dictionary/derivative), last accessed Nov. 12, 2010.*
Fura, A. DDT, 2006, 11, pp. 133-142.*
Anari et al. DDT, 2005, 10, pp. 711-717.*
Nedderman, A. N. R. Biopharm. Drug Dispos. 2009, 30, pp. 152-162.*

(Continued)

*Primary Examiner* — Joseph Kosack
*Assistant Examiner* — Matthew Coughlin
(74) *Attorney, Agent, or Firm* — Wolf, Greenfield & Sacks, P.C.

(57) ABSTRACT

Substituted cinnamoyl anthranilate compounds exhibiting anti-fibrotic activity; or derivatives thereof, analogues thereof, pharmaceutically acceptable salts thereof, and metabolites thereof; with the proviso that the compound is not Tranilast.

10 Claims, 34 Drawing Sheets

(56) References Cited

U.S. PATENT DOCUMENTS

| | | | |
|---|---|---|---|
| 2008/0032983 | A1 | 2/2008 | Gericke et al. |
| 2009/0197957 | A1 | 8/2009 | Selley et al. |
| 2009/0226537 | A1 | 9/2009 | Schmaus et al. |
| 2011/0112187 | A1 | 5/2011 | Schneider et al. |
| 2011/0195977 | A1 | 8/2011 | Fancelli et al. |

FOREIGN PATENT DOCUMENTS

| | | | |
|---|---|---|---|
| EP | 0894496 A1 | 2/1999 | |
| EP | 2185150 B1 | 3/2012 | |
| JP | 50-135047 A | 10/1975 | |
| JP | 50-140413 A | 11/1975 | |
| JP | 51-001440 A | 8/1976 | |
| JP | 55-076852 A | 6/1980 | |
| JP | 57-038759 A | 3/1982 | |
| JP | 57038759 A | * 3/1982 | |
| JP | 60-019754 A | 1/1985 | |
| JP | 60-152454 A | 8/1985 | |
| JP | 10259129 A | 9/1998 | |
| JP | 10-306024 | 11/1998 | |
| JP | 10-330254 | 12/1998 | |
| JP | 2003-119132 A | 4/2003 | |
| JP | 2007-509037 A | 4/2007 | |
| JP | 2008-504241 A | 2/2008 | |
| WO | WO 97/37650 A1 | 3/1997 | |
| WO | WO 03/049702 A2 | 6/2003 | |
| WO | WO 2004/047833 | 6/2004 | |
| WO | WO 2006-053390 A1 | 5/2006 | |
| WO | WO 2006/087393 A2 | 8/2006 | |
| WO | WO 2006/102645 A1 | 9/2006 | |
| WO | WO 2006/134120 | 12/2006 | |
| WO | WO 2007/015744 A1 | 2/2007 | |
| WO | WO 2008/003141 A1 | 1/2008 | |
| WO | WO 2008/051047 A1 | 5/2008 | |
| WO | WO 2008/057862 A2 | 5/2008 | |
| WO | WO 2009/068557 A1 | 6/2009 | |
| WO | WO 2009/079692 A1 | 7/2009 | |
| WO | WO 2009/082347 A1 | 7/2009 | |

OTHER PUBLICATIONS

Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Luo et al. Cell, 2009, 136, pp. 823-837.*
Collins, F. W. J. Agric. Food. Chem. 1989, 37, 60-66.*
CAS Registry entry for Registry No. 463307-21-3, which entered STN on Oct. 21, 2002.*
English translation of JP 57038759 A, translated May 2011.*
Cheng, M. S., et al., "Synthesis of propenamides with anti-malarial activities and 3D-QSAR study", Acta Pharmaceutica Sinica, (2003), vol. 38, No. 7, pp. 505-510.
International Preliminary Report on Patentability from corresponding International Application No. PCT/AU2008/001868, date of completion Mar. 25, 2010.
International Search Report for International Application No. PCT/AU2008/001868, mailed Feb. 26, 2009.
Isaji, M., et al., "Selective Inhibition of Collagen Accumulation by N-(3,4-Dimethoxycinnamoyl)Anthranilic Acid (N-5') In Granulation Tissue," Biochemical Pharmacology, (1987), vol. 36, No. 4, pp. 469-474.
Patani et al., "Bioisosterism: a rational approach in drug design", Chem. Rev., (1996), vol. 96, pp. 3147-3176.
STN File Registry, CAS Registry No. 475190-68-2, entered Dec. 5, 2002.
STN File Registry, CAS Registry No. 572907-40-5, entered Aug. 25, 2003.
STN File Registry, CAS Registry No. 850701-35-8, entered May 19, 2005.
STN File Registry, CAS Registry No. 875398-18-8, entered Feb. 27, 2006.
STN File Registry, CAS Registry No. 891611-78-2, entered Jul. 10, 2006.
STN File Registry, CAS Registry No. 900671-62-7, entered Aug. 11, 2006.
STN File Registry, CAS Registry No. 903317-85-1, entered Aug. 22, 2006.
STN File Registry, CAS Registry No. 926525-60-2, entered Mar. 15, 2007.
STN File Registry, CAS Registry No. 926872-74-4, entered Mar. 18, 2007.
STN File Registry, CAS Registry No. 930720-96-0, entered Apr. 18, 2007.
STN File Registry, CAS Registry No. 931079-11-7, entered Apr. 20, 2007.
STN File Registry, CAS Registry No. 938782-52-6, entered Jun. 25, 2007.
Supplementary European Search Report for European Application No. 08865709.3, mailed Jan. 19, 2011.
Written Opinion of the International Searching Authority for International Application No. PCT/AU2008/001868, mailed Feb. 26, 2009.
International Preliminary Report on Patentability from PCT/AU2007/000934, mailed Jan. 6, 2009.
International Search Report and Written Opinion from PCT/AU2007/000934, mailed Aug. 16, 2007.
Supplemental Search Report from EP07763756, mailed Jan. 13, 2011.
Search Report and Written Opinion from Singaporean Application No. 200900016-7, mailed Oct. 14, 2010.
Bain, D. I., et al., "Synthesis of 2-Substituted -4H-3,1-benzoxazin-4-ones", J. Chem. Soc. (C), 1968, pp. 1593-1597.
Hajra, S, et al., "Lewis acid catalyzed intramolecular halo-arylation of tethered alkenes using N-halosuccinimide (NXS) as the halogen source; a general method for the synthesis of chromanones, chromans, quinolones, tetrahydroquinolines and tetralins", Tetrahedron Letters, vol. 46, No. 49, 2005, pp. 8599-8603.
Ishihara, A., et al., "Induction of hydroxyanthranilate hydrocinnamoyl transferase activity by oligo-n-acethylchitooligosaccharides in oats", Phytochemistry, 1998, vol. 47, No. 6, pp. 969-674.
Messiah, N. N., et al., "Synthesis of Some Benzoxazin-4-ones, Qinazolin-4-ones & Related Products", Indian Journal of Chemistry, vol. 13, 1975, pp. 326-328.
Ogita, H., et al., "Synthesis and structure-activity relationship of diarylamide derivatives as selective inhibitors of the proliferation of human coronary artery smooth muscle cells", Bioorg. Med. Chem. Lett., 2001, 4:549-551.
Okazaki, Y., et al., "Metabolism of avenanthramide phytoalexins in oats", the Plant Journal, 2004, vol. 39, pp. 560-557.
Rani, P., et al., "Isoxazolinyl derivatives of anthranilic acid as anti inflammatory agents", Indian Journal of Chemistry, Section B: Organic and Medicinal Chemistry, Council of Scientific and Industrial Research, IN, vol. 42, 2003, pp. 1729-1733.
First Office Action dated Jul. 6, 2012 in Japanese Application No. 2009-516828 and English-language translation.
Supplementary Search Report from Singapore Patent Application 200900016-7, mailed Mar. 26, 2012.
First Office Action dated Oct. 1, 2013 in Japanese Application No. 2010-538278.
Examination Report dated Sep. 4, 2013 in Korean Application No. 10-2009-7000882.
Examination Report dated Aug. 15, 2013 in Mexican Application No. MX/a/2009/000001.
Mifsud et al., Intervention with Tranilast Attenuates Renal Pathology and Albuminuria in Advanced Experimental Diabetic Nephropathy, Nephron Physiology, 2003, vol. 95, pp. 83-91.

(56) References Cited

OTHER PUBLICATIONS

Hiroi et al., Anti-tumor Effect of N-[3,4-dimethoxycinnamoyl]-anthranilic Acid (tranilast) on Experimental Pancreatic Cancer, J. Nippon. Med. Sch., 2002, vol. 69, No. 3, pp. 224-234.

[No Name Listed] "Expert Scientific Group on Phase One Clinical Trials Final Report", (Nov. 30, 2006), pp. C1, C35-C38.

Anari, M. R., et al., "Bridging cheminformatic metabolite predictions and tandem mass spectrometry", DDT (2005), vol. 10, pp. 711-717.

Cancer Drug Design and Discovery Neidle, Stephen, ed. (Elsevier/Academic Press, 2008), p. 427.

Collins, F. W., "Oat Phenolics: Avenanthramides, Novel Substituted N-Cinnamoylanthranilate Alkaloids from Oat Groats and Hulls", Agric. Food Chem., (1989), vol. 37, pp. 60-66.

Fura, A., "Role of pharmacologically active metabolites in drug discovery and development", DDT, (2006), vol. 11, pp. 133-142.

Gura, T., "Systems for Identifying New Drugs Are Often Faulty", Science, (Nov. 7, 1997) vol. 278, No. 5340, pp. 1041-1042.

Kamb, A., "What's wrong with our cancer models?", Nature Reviews Drug Discovery, (Feb. 2005), vol. 4, pp. 161-165.

Leaf, C., "Why are we losing the war on cancer (and how to win it)", Health Administrator, (2005), vol. XVII, No. 1, pp. 172-183.

Luo, J., et al., "Principles of Cancer Therapy: Oncogene and Non-oncogene Addiction", Cell, (2009), vol. 136, pp. 823-837.

Nedderman, A. N. R., "Metabolites in Safety Testing: Metabolite Identification Strategies in Discovery and Development", Biopharm. Drug Dispos., (2009), vol. 30, pp. 152-162.

\* cited by examiner

A

B

THERAPEUTIC COMPOUNDS

RELATED APPLICATIONS

This application is a national stage filing under 35 U.S.C. §371 of International Application No. PCT/AU2007/000934, filed Jul. 5, 2007, which claims the benefit of Australian Patent Application No. 2006903625, filed Jul. 5, 2006.

FIELD OF THE INVENTION

The present invention relates to compounds for the treatment of medical disorders. The present invention further relates to the use of the compounds for the treatment of medical disorders, in particular conditions associated with tissue fibrosis.

BACKGROUND OF THE INVENTION

Tranilast (n-[3,4-dimethoxycinnamoyl] anthranilic acid) is an anti-fibrotic agent used in Japan for the treatment of fibrotic skin disorders such as keloids [8] and scleroderma [9]. Although the precise mechanisms and mode of action are incompletely understood, its ability to inhibit ERK phosphorylation [20], a major intermediate in the TGF-β signalling pathway, may underlie its antifibrotic effects, with known actions of tranilast including the inhibition of TGF-β-induced extracellular matrix production in a range of cell types [10, 11, 14, 16]. Tranilast has also been shown to attenuate TGF-β-induced collagen synthesis in cardiac fibroblasts using an experimental model of diabetic cardiac disease [15].

Fibrosis is a common response to a range of tissue insults that may lead to organ dysfunction. Diseases that are characterised by such pathological fibrosis include hepatic cirrhosis, pulmonary interstitial fibrosis, glomerulonephritis, heart failure (ischaemic and non-ischaemic), diabetic nephropathy, scleroderma, excessive scar tissue post surgery or device insertion, progressive kidney disease, glomerulonephritis, hypertension, heart failure due to ischaemic heart disease, valvular heart disease or hypertensive heart disease and hypertrophic scars. In addition, the elaboration of pathological matrix also has a role in fibroproliferative tumor progression and metastasis.

Diabetic subjects have a two- to fivefold increase risk of developing heart failure [1]. In addition to ischaemic heart disease, heart failure in diabetes is also associated with a cardiomyopathy, independent of coronary artery disease [2]. This so-called "diabetic cardiomyopathy" is characterised histologically by myocardial fibrosis with reduced myocardial elasticity, impaired contractility and overt cardiac dysfunction [3-6]. Accordingly, strategies that reduce the pathological accumulation of extracellular matrix have been advocated as potential therapies for the treatment and prevention of heart failure in both diabetic and nondiabetic states [7].

Current treatment of chronic heart failure focuses on the modulation of the neurohormonal activation that typically develops in response to the evolving functional abnormalities. However, despite such therapy, frequently used in combination, cardiac dysfunction continues to progress in the majority of patients. Given the importance of pathological fibrosis in adverse cardiac remodelling, a potential role of antifibrotic agents has been suggested [1,6]. Studies conducted over more than a decade have consistently indicated a major role for the prosclerotic growth factor, transforming growth factor-β (TGF-β) in organ fibrosis and dysfunction [1,7], such that blockade of its expression and action represent an important therapeutic target.

Tranilast has also been shown to reduce inflammation in allergic diseases, such as allergic rhinitis and bronchial asthma, etc. [42].

In addition, tranilast has been shown to have anti-proliferative activity [43, 44].

However, it has recently been shown [19] that genetic factors in certain patients, specifically a Gilbert's syndrome UGT1A1 variant, confers susceptibility to tranilast-induced hyperbilirubinemia. Such hyperbilirubinemia may be associated with tranilast itself or the formation, in vivo, of the following tranilast metabolite

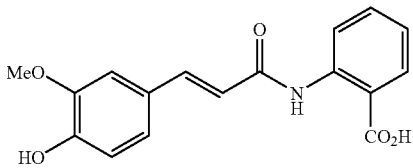 [SMILES: COc1cc(/C=C/C(=O)Nc2ccccc2C(=O)O)ccc1O]

It would be useful to provide further compounds with potential anti-fibrotic, anti-inflammatory, and anti-proliferative or anti-neoplastic activity for the treatment or prevention of diseases associated with fibrosis diseases characterised by inflammation and neoplastic disease (both benign and malignant), and as alternatives/adjuncts to tranilast.

It is an object of the present invention to overcome or at least alleviate one or more of the difficulties and/or deficiencies related to the prior art.

SUMMARY OF THE INVENTION

In a first aspect, the present invention provides a compound of the Formula 1,

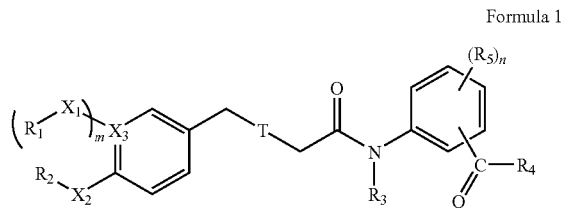

Formula 1 the groups $R_1$, $R_2$, $R_3$, $R_4$, $R_5$, $X_1$, $X_2$ and $X_3$ and the integers m and n being selected such that the compound exhibits anti-fibrotic activity and wherein T is a single or double bond, or derivatives thereof, analogues thereof, pharmaceutically acceptable salts thereof or metabolites thereof;
with the proviso that the compound is not Tranilast.

Preferably, $R_1$ and $R_2$, which may be the same or different, are selected from the group consisting of H, $NHR_6$, $NR_6R_7$, $OR_8$, halogen, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, fused $C_5$ to $C_{20}$ aryl or alkaryl, and a hydrocarbon chain containing a heterocyclic or fused ring; any of which may be optionally substituted;

$R_3$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring; any of which may be optionally substituted;

$R_4$ is selected from the group consisting of H, OH, $OR_6$, $NR_6$ or $NR_6R_7$;

$R_5$ is selected from the group consisting of H, $NHR_6$, $NR_6R_7$, $OR_8$, halogen, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, fused $C_5$ to $C_{20}$ aryl or alkaryl, and a hydrocarbon chain containing a heterocyclic or fused ring; any of which may be optionally substituted;

$X_1$ and $X_2$, which may be the same or different, are selected from the group consisting of a bond, C, O, N and S;

$X_3$ is C or N;

T is a single or double bond;

m is the integer 0 or 1;

n is an integer between 0 and 4;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

or derivatives thereof, analogues thereof, pharmaceutically acceptable salts thereof, and metabolites thereof;

wherein when $X_3$ is N, n is 0.

In a preferred aspect, the present invention provides a compound of the Formula 2

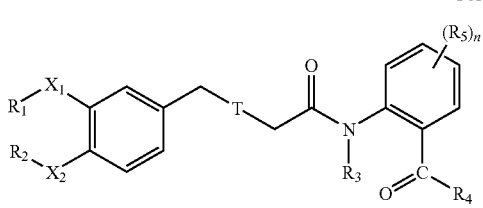

Formula 2 wherein $R_1$ and $R_2$, which may be the same or different, are selected from the group consisting of a $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne and a chain containing a heterocyclic or fused ring; any of which may be optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkene, $C_3$ to $C_{10}$ alkyne and a chain consisting of a heterocyclic or fused ring; any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_3$ is selected from the group consisting of H, $C_1$ to $C_{10}$ alkyl, $C_3$ to $C_{10}$ cycloalkyl, $C_3$ to cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or derivatives thereof, analogues thereof, pharmaceutically acceptable salts thereof and metabolites thereof;

with the proviso that when $X_1$ and $X_2$ are both 0 or a bond, and one of $R_1$ or $R_2$ is a $C_1$ to $C_4$ alkyl, the other of $R_1$ or $R_2$ is $C_4$ to $C_{10}$ alkyl, $C_3$ to $C_{10}$ cycloalkyl, $C_3$ to $C_{10}$ cycloalkylmethyl, $C_3$ to $C_{10}$ alkyne, or a chain containing a heterocyclic or fused ring; and with the proviso that the compound is not Tranilast.

It has surprisingly been found that compounds of the above Formula 1 or Formula 2 may exhibit anti-fibrotic activity, and in certain cases, significant enhanced antifibrotic activity.

Preferred compounds are those in which $X_1$ and $X_2$ are O.

More preferably, those compounds are those wherein:

$X_1$ and $X_2$ are O;

$R_1$ or $R_2$ is methyl;

$R_3$ is H;

$R_4$ is OH or $NHR_6$;

$R_5$ is preferably H or a halogen, e.g. Br, I, Cl or F, more preferably Br;

$R_1$ or $R_2$ is an alkyne, a chain containing a triazole, a cyclopentyl group, a cyclohexyl group, a cyclopentylmethyl group or a cyclohexylmethyl group; and R is H.

In a particularly preferred form, the compounds may be selected from those in which $R_1$ or $R_2$ is methyl.

Preferably one of $R_1$ and $R_2$ is methyl and the other of $R_1$ and $R_2$ is a $C_3$ to $C_{10}$ cycloalkyl, $C_3$ to $C_{10}$ cycloalkylmethyl, $C_3$ to $C_{10}$ alkyne or a chain containing a triazole. Preferably the triazole is a 1,4-disubstituted 1,2,3-triazole.

Where $R_1$ or $R_2$ is an alkyne, preferably the alkyne is a $C_5$ to $C_8$ terminal or non-terminal alkyne, most preferably propargyl.

DETAILED DESCRIPTION OF THE INVENTION

The term "alkyl" as used herein includes linear and branched alkyl radicals, for example, methyl, ethyl, propyl, isopropyl, butyl, isobutyl, sec-butyl, tert-butyl, etc.

The term "aryl" as used herein refers to substituted or unsubstituted aromatic rings that are fused, unfused or linked and may include one or more heteroatoms.

The term "fused ring" as used herein refers to two or more rings joined together through one or more atoms. The term includes substituted or unsubstituted fused rings.

Preferred compounds of the present invention are of the Formula 3

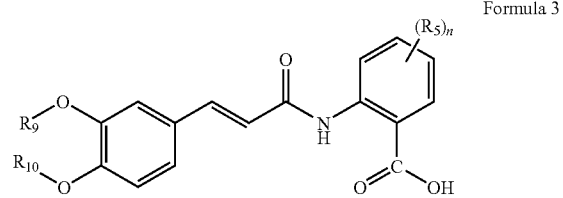

Formula 3 wherein $R_9$ or $R_{10}$, which may be the same or different, are selected from the group consisting of H, $C_1$ to $C_{10}$ alkyl, $C_3$ to $C_8$ terminal or non-terminal alkyne or a cyclopentyl, cyclohexyl, cyclohexylmethyl or cyclopentylmethyl group;

or derivatives thereof, analogues thereof, pharmaceutically acceptable salts thereof and metabolites thereof;

with the proviso that when one of $R_1$ or $R_2$ is a $C_1$ to $C_4$ alkyl, the other of $R_1$ or $R_2$ is a $C_4$ to $C_{10}$ alkyl, $C_3$ to $C_{10}$ cycloalkyl, $C_3$ to $C_{10}$ cycloalkylmethyl, $C_3$ to $C_{10}$ alkyne or a chain containing a heterocyclic or fused ring, or any of which are optionally substituted; and with the proviso that the compound is not Tranilast.

In a preferred embodiment, the present invention provides a compound of the Formula 3, wherein one of $R_9$ or $R_{10}$ includes a $C_3$ to $C_8$ alkyne and the other of $R_9$ or $R_{10}$ is methyl. The alkyne may be a terminal or non-terminal alkyne.

In a further embodiment, the compound has the Formula 4 or Formula 5

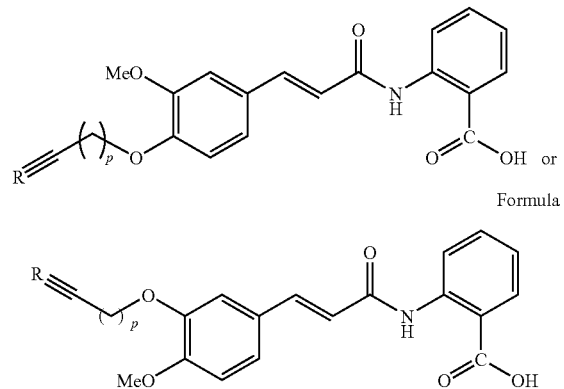

Formula 4

Formula 5 wherein p is an integer between 1 and 10, preferably between 1 and 6; and R is selected from the group consisting of H and $C_1$ to $C_{10}$ alkyl;

or derivatives thereof, analogues thereof, pharmaceutically acceptable salts thereof and metabolites thereof.

In a further embodiment, the compound has the Formula 6 or Formula 7

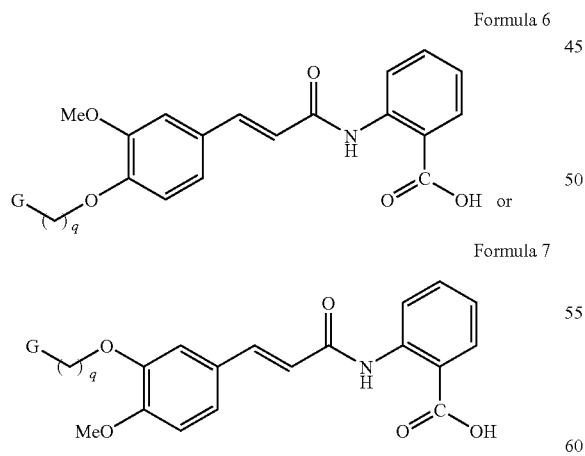

Formula 6

Formula 7 wherein G is a cyclopentyl ring, a cyclohexyl ring or a 1,4-disubstituted 1,2,3-triazole; and q is an integer between 0 and 10, preferably between 0 and 6 or derivatives thereof, analogues thereof, pharmaceutically acceptable salts thereof, and metabolites thereof.

The compounds of the present invention may be selected from one or more of the group consisting of

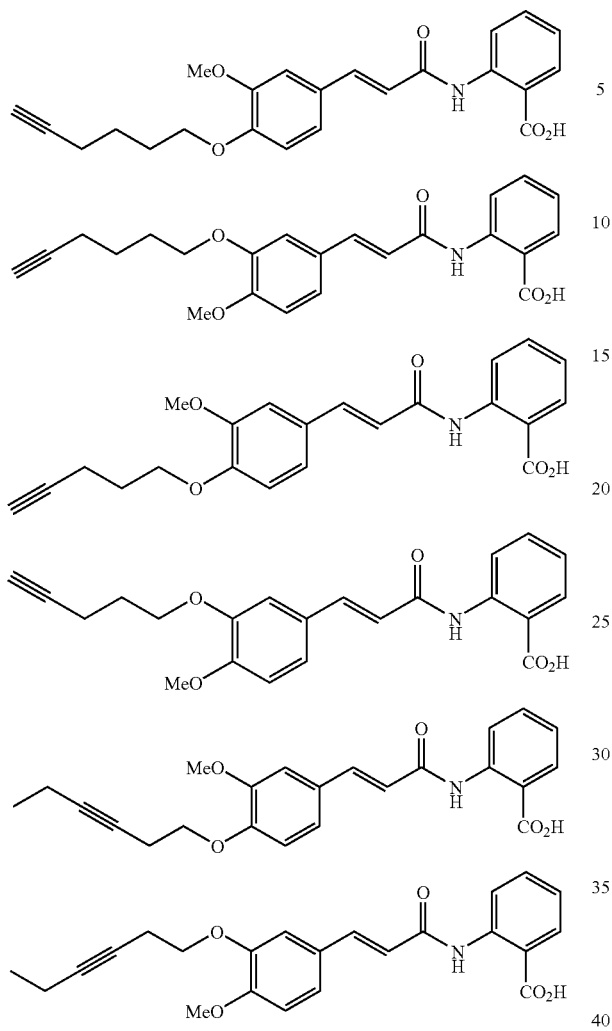
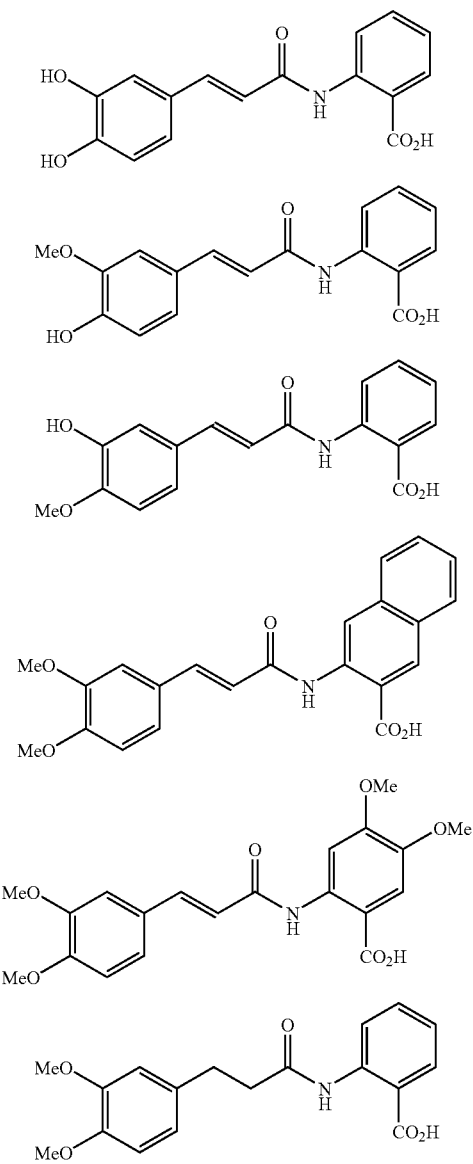
or derivatives thereof, analogues thereof, pharmaceutically acceptable salts thereof and metabolites thereof.
Preferred compounds include
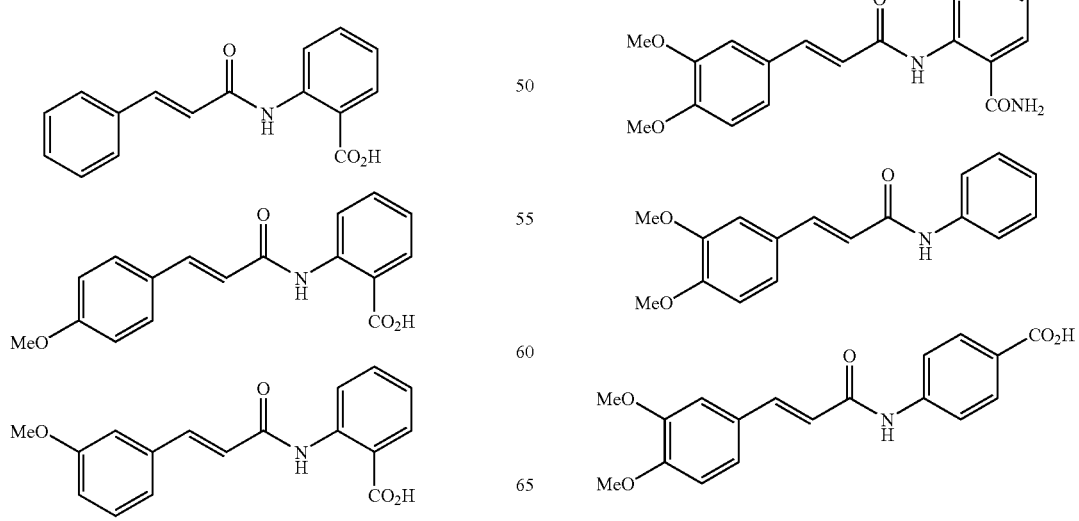

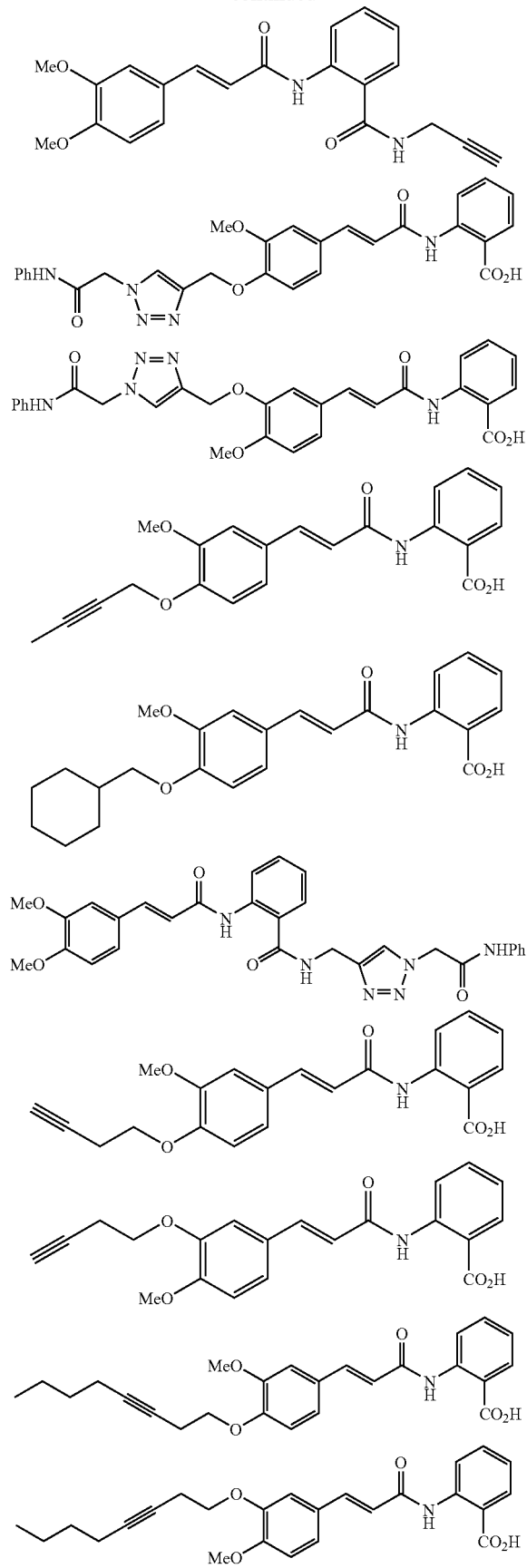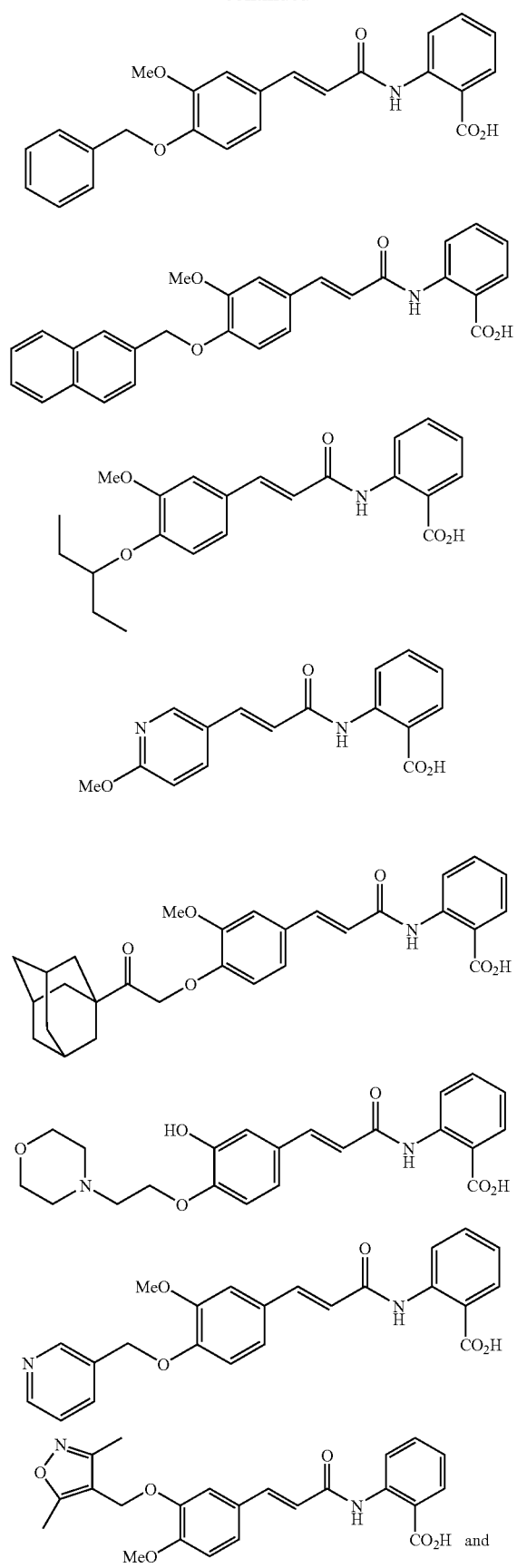

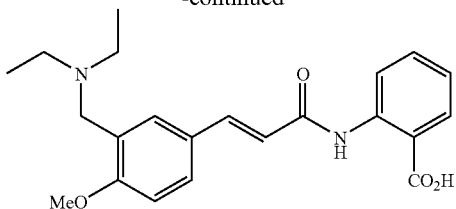

or derivatives thereof, analogues thereof, pharmaceutically acceptable salts thereof and metabolites thereof.

In a particularly preferred embodiment, the compound has the Formula

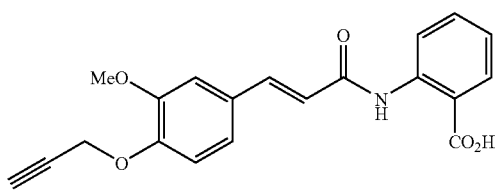 [SMILES: C#CCOc1ccc(/C=C/C(=O)Nc2ccccc2C(=O)O)cc1OC]

In a further aspect, the present invention provides a pharmaceutical composition for the treatment of a disease or condition associated with fibrosis including a compound of the Formula 1

Formula 1

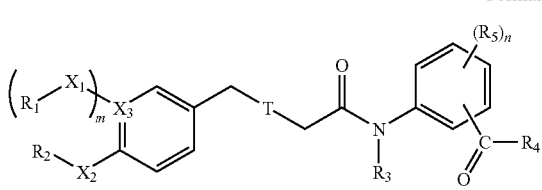

the groups $R_1$, $R_2$, $R_3$, $R_4$, $R_5$, $X_1$, $X_2$ and $X_3$ and the integers m and n being selected such that the compound exhibits anti-fibrotic activity and wherein T is a single or double bond;

or derivatives thereof, analogues thereof, pharmaceutically acceptable salts thereof or metabolites thereof;

together with a pharmaceutically acceptable diluent, carrier or excipient;

with the proviso that the compound is not Tranilast.

In a still further aspect, the present invention provides a pharmaceutical composition for the treatment of a disease or condition characterised by inflammation and/or benign or malignant neoplastic disease, including a compound of the Formula 1, as set out above.

In a preferred embodiment, the present invention provides a pharmaceutical composition for the treatment of a disease or condition associated with fibrosis including a compound of the Formula 2

Formula 2

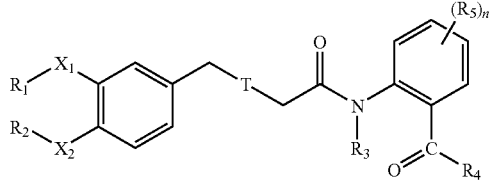

wherein $R_1$ and $R_2$, which may be the same or different, are selected from the group consisting of $C_1$ to $C_{10}$ alkyl, $C_3$ or $C_{10}$ cycloalkyl, $C_3$ to $C_{10}$ cycloalkylmethyl, $C_3$ to $C_{10}$ alkene, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkene, $C_3$ to $C_{10}$ alkyne, and a chain consisting of a heterocyclic or fused ring, any of which may be optionally substituted;

$R_6$ and $R_7$, which may be the same of different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or derivatives thereof, analogues thereof, pharmaceutically acceptable salts thereof and metabolites thereof;

with the proviso that when $X_1$ and $X_2$ are both O or a bond and one of $R_1$ or $R_2$ is a $C_1$ to $C_4$ alkyl, the other of $R_1$ or $R_2$ is a $C_4$ to $C_{10}$ alkyl, $C_3$ to $C_{10}$ cycloalkyl, $C_3$ to $C_{10}$ cycloalkylmethyl, $C_3$ to $C_{10}$ alkyne, or a chain containing a heterocyclic or fused ring; and with the proviso that the compound is not Tranilast;

together with a pharmaceutically acceptable diluent, carrier or excipient.

In a further preferred embodiment, the present invention provides a pharmaceutical composition for the treatment of a disease or condition characterised by inflammation and/or benign or malignant neoplastic disease, including a compound of the Formula 3, as set out above.

The pharmaceutically acceptable diluent, carrier or excipient may be selected from any suitable carrier or excipient known in the art.

The pharmaceutical composition may be formulated in any suitable form, including, but not limited to, formulations for oral, injectable, rectal, parenteral, subcutaneous, intravenous, intramuscular or other delivery. The pharmaceutical composition may be formulated in any suitable form, including, but not limited to tablet, capsule, caplet, injectable, ampoule, vial, ready-to-use solution, lyophilised material, suppository, bolus or implant form.

The formulation of such compositions is well known to persons skilled in the art. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences,* 18th Edition, Mack Publishing Company, Pennsylvania, USA.

Except insofar as any conventional media or agent is incompatible with the terminal groups of the dendrimer polymer described herein, use thereof in the pharmaceutical compositions of the present invention is contemplated. Supplementary active ingredients may also be incorporated into the compositions.

It is especially advantageous to formulate compositions in unit dosage form for ease of administration and uniformity of dosage. "Unit dosage form" as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect of the present invention there is provided use of an effective amount of a compound as described above in the prophylactic or therapeutic treatment of, or in the manufacture of a medicament for treatment of, a human or non-human animal patient.

In a still further aspect of the present invention there is provided a method for the treatment of a disease indicator or physiological deficiency in a mammalian, including human, patient, which method includes administering to a patient requiring such treatment a prophylactically or therapeutically effective amount of a pharmaceutical composition, as described above.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include, but are not limited to, oral, rectal, topical, nasal, inhalation, transdermal or parenteral (e.g. subcutaneous, intramuscular and intravenous), intraocular and intravitreal (ie, into the eye's vitreous) routes. Formulations for oral administration include, but are not limited to, discrete units such as capsules, tablets, lozenges and the like. Other routes include, but are not limited to, intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include, but are not limited to, the step of bringing the active compound into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active ingredient, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables The compound of the present invention may also be formulated for delivery in a system designed to administer the compound intranasally or by inhalation, for example as a finely dispersed aerosol spray containing the active component.

Other delivery systems may include sustained release delivery systems. Preferred sustained release delivery systems are those which may provide for release of the compound of the present invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system may be used, some of which are adapted for implantation.

The compound of the present invention is administered in prophylactically or therapeutically effective amounts. A prophylactically or therapeutically effective amount means that amount necessary to at least partly attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and may be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily doses of the compound may be from about 0.01 mg/kg per day to 1000 mg/kg per day. Small doses (0.01-1 mg/kg per day) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

In a further preferred embodiment, pharmaceutically acceptable carriers or excipients may be selected from one or more of sterile aqueous salt solutions, suspensions and emulsions, including saline and buffered media, Ringer's dextrose, dextrose and sodium chloride, and lactated Ringer's solution. Intravenous vehicles include fluid and nutrient replenishers, electrolyte replenishers, such as those based on Ringer's dextrose, and the like. For administration by non-intravenous routes, the carrier can be in the form of clotted plasma, preferably the patient's clotted plasma. Alternatively the carrier can be a plasma-free, physiologically compatible, biodegradable solid or semi-solid, such as a gel, suspension or water soluble jelly. Acacia, methylcellulose and other cellulose derivatives, sodium alginate and tragacanth suspensions or gels are suitable for use as carriers in the practice of this invention, for example, sodium carboxymethylcellulose 2.5%, tragacanth 1.25% and guar gum 0.5%.

In a further aspect the present invention provides a method of treating a disease or condition associated with fibrosis, including administering to an animal, including a human in need of such treatment, a pharmaceutical composition including the compound of the Formula 1

Formula 1

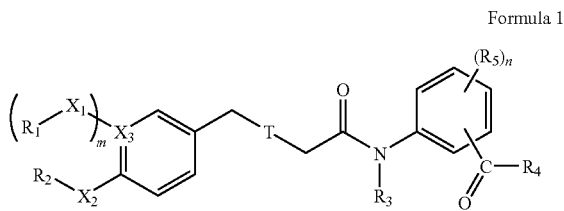

the groups $R_1$, $R_2$, $R_3$, $R_4$, $R_5$, $X_1$, $X_2$ and $X_3$, and the integers m and n being selected such that the compound exhibits anti-fibrotic activity and wherein T is a single or double bond;

or derivatives thereof, analogues thereof, pharmaceutically acceptable salts thereof or metabolites thereof;

with the proviso that the compound is not Tranilast.

In a still further aspect, the present invention provides a method of treating a disease or condition characterised by inflammation and/or a benign or malignant neoplastic disease including administering to an animal, including a human in need of such treatment, a pharmaceutical composition including the compound of the Formula 1

Formula 1

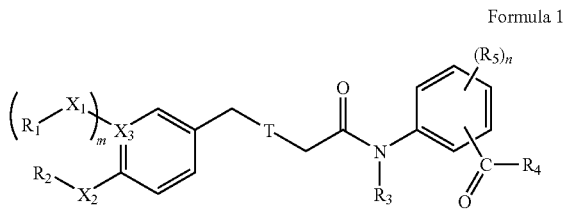

the groups $R_1$, $R_2$, $R_3$, $R_4$, $R_5$, $X_1$, $X_2$ and $X_3$, and the integers m and n being selected such that the compound exhibits anti-fibrotic activity and wherein T is a single or double bond;

or derivatives thereof, analogues thereof, pharmaceutically acceptable salts thereof or metabolites thereof;

with the proviso that the compound is not Tranilast; together with a pharmaceutically acceptable carrier, diluent or excipient.

In a preferred embodiment, the present invention provides a method of treating a disease or condition associated with fibrosis, including administering to an animal, including a human in need of such treatment, a pharmaceutical composition including a compound of the Formula 2

Formula 2

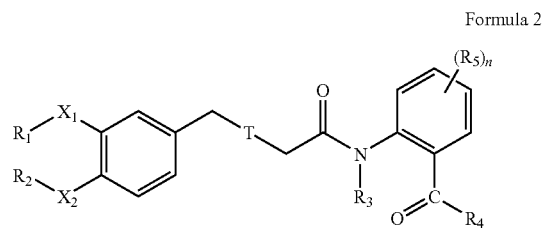

wherein $R_1$ and $R_2$, which may be the same or different, are selected from the group consisting of $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne and a chain containing a heterocyclic or fused ring, any of which are optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkene, $C_3$ to $C_{10}$ alkyne, and a chain consisting of a heterocyclic or fused ring, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or derivatives thereof, analogues thereof, pharmaceutically acceptable salts thereof and metabolites thereof;

with the proviso that when $X_1$ and $X_2$ are both O or a bond and one of $R_1$ or $R_2$ is a $C_1$ to $C_4$ alkyl, the other of $R_1$ or $R_2$ is a $C_4$ to $C_{10}$ alkyl, $C_3$ to $C_{10}$ cycloalkyl, $C_3$ to $C_{10}$ cycloalkylmethyl, $C_3$ to $C_{10}$ alkyne, or a chain containing a heterocyclic or fused ring; and with the proviso that the compound is not Tranilast, together with a pharmaceutically acceptable carrier, diluent or excipient.

The disease or condition associated with fibrosis may be selected from fibrotic skin disorders, such as keloids, hypertrophic scars and scleroderma; lung disease, such as pulmonary fibrosis; heart disease, such as heart failure due to ischaemic heart disease, valvular heart disease and hypertensive heart disease, diabetic cardiomyopathy and hypertension; and kidney disease, such as progressive kidney disease, due to, glomerulonephritis and diabetic nephropathy and cirrhosis of the liver. In a preferred embodiment, the disease or condition is diabetic heart disease or diabetic kidney disease. In a further preferred embodiment, the disease or condition is diabetic cardiomyopathy.

The term "kidney disease", as used herein, refers to a disorder of at least one kidney in a subject that compromises the function of the kidney. The kidney disease may result from a primary pathology of the kidney (e.g., injury to the glomerulus or tubule), or another organ (e.g., pancreas) which adversely affects the ability of the kidney to perform biological functions. A kidney disease in the human can be the direct or indirect effect of disease. Examples of a kidney disease as a result or consequence of an indirect effect on the kidneys is kidney disease as a consequence of diabetes or systemic lupus. A kidney disease may be the result or a consequence of any change, damage, or trauma to the glomerulus, tubules or interstitial tissue in either the renal cortex or renal medulla of the kidney.

The term "kidney disease" as used herein refers to a progressive kidney disease that over time (e.g., days, weeks, months, years) leads to a loss of renal function.

The kidney disease may include, but is not limited to, a progressive glomerular kidney disease including without limitation diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis) or secondary glomerulonephritis (e.g., diabetic nephropathy, ischemic nephropathy).

The term "renal function" as used herein refers to a physiological property of the kidney, such as the ability to retain protein thereby preventing proteinuria. Renal function can be assessed using methods known in the art such as determining one or more of glomerular filtration rate (e.g., creatinine clearance), excretion of protein in urine, blood urea nitrogen, and serum or plasma creatinine.

A progressive kidney disease treated by the compositions and methods described herein includes any kidney disease that can, ultimately, lead to end-stage renal disease. A progressive kidney disease that can be treated by the compositions and methods of the invention can be, for example, associated with endogenous iron deposit in the kidney (e.g., glomerulus, tubules).

Diabetic cardiomyopathy refers to any one or more cardiac pathology and/or dysfunction in a subject, which is a complication of either Type I or Type II diabetes in the subject. The diabetes may be symptomatic or asymptomatic. Cardiac pathology which is characteristic of diabetic cardiomyopathy includes myocellular hypertrophy, myocardial fibrosis, and in some cases left ventricular hypertrophy. The pathologies which are contemplated arise independently from complications arising from coronary artery disease, although both diabetic complications and coronary artery complications may be present in the same subject. Diastolic dysfunction, such as an impairment in early diastolic filling, a prolongation of isovolumetric relaxation and increased atrial filling is also characteristic of diabetic cardiomyopathy, and may be identified using Doppler methods such as Doppler 2-dimensional echocardiography (for example Redford M M et al., "Burden of systolic and diastolic dysfunction in the community". JAMA (2003) 289:194-203) or radionuclide imaging for early or mild dysfunction and by standard echocardiograph testing for more severe dysfunction.

Cardiac fibrosis refers to the formation of fibrous tissue, including cellular and extracellular components, in the lining and muscle of the heart. If present in sufficient quantities, the fibrous tissue will result in a decrease in the contractility and/or relaxation of one or more regions of the heart, resulting in functional deficit in cardiac output.

In a still further aspect, the present invention provides a method of treating a disease or condition characterised by inflammation and/or a benign or malignant neoplastic disease including administering to an animal, including a human in need of such treatment, a pharmaceutical composition including a compound of the Formula 2

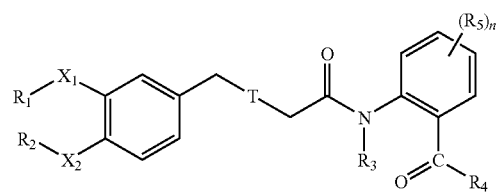

Formula 2 wherein $R_1$ and $R_2$, which may be the same or different, are selected from the group consisting of $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkene, $C_3$ to $C_{10}$ alkyne, and a chain consisting of a heterocyclic or fused ring, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or derivatives thereof, analogues thereof, pharmaceutically acceptable salts thereof and metabolites thereof;

with the proviso that when $X_1$ and $X_2$ are both O or a bond and one of $R_1$ or $R_2$ is a $C_1$ to $C_4$ alkyl, the other of $R_1$ or $R_2$ is a $C_4$ to $C_{10}$ alkyl, $C_3$ to $C_{10}$ cycloalkyl, $C_3$ to $C_{10}$ cycloalkylmethyl, $C_3$ to $C_{10}$ alkyne, or a chain containing a heterocyclic or fused ring; and with the proviso that the compound is not Tranilast, together with a pharmaceutically acceptable carrier or excipient.

The disease or condition characterised by inflammation may be selected from allergic rhinitis, bronchial asthma, rheumatoid arthritis, multiple sclerosis, type I and type II diabetes, systemic lupus, erythematosis, transplant rejection and inflammatory bowel disease.

The benign or malignant neoplastic disease may be any such disease known to the skilled person.

The term "benign or malignant neoplastic disease" as used herein refers to any growth or tumour caused by abnormal and uncontrolled cell division.

In a further aspect, the present invention provides a process for preparing a compound of the Formula 2

Formula 2

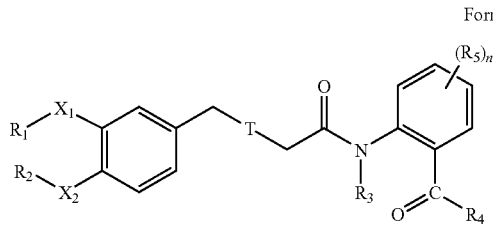

wherein $R_1$ and $R_2$, which may be the same or different, are selected from the group consisting of a $C_1$ to $C_{10}$ alkyl, $C_3$ to $C_{10}$ cycloalkyl, a $C_3$ to $C_{10}$ cycloalkylmethyl, $C_3$ to $C_{10}$ alkene, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkyne, and a chain consisting of a heterocyclic or fused ring, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring; any of which may be optionally substituted; and $R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkyne, aryl, $C_5$ to $C_{20}$ alkaryl, and a hydrocarbon chain containing a heterocyclic or fused ring; and n is an integer between 0 and 4;

or derivatives thereof, analogues thereof, pharmaceutically acceptable salts thereof and metabolites thereof;

which process includes the steps of providing a substituted cinnamoyl anthranilate as a piperidinium salt via a piperidine-catalyzed Knoevenagel condensation of a carboxyacetamidobenzoic acid and a benzaldehyde derivative and conversion of the piperidinium salt to the corresponding free acid, according to Scheme 1;

Scheme 1

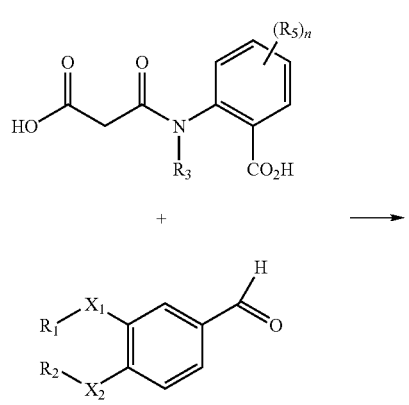

In a still further aspect the present invention provides a process for preparing a compound of the Formula 2

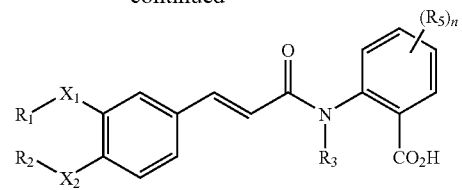

Formula 2

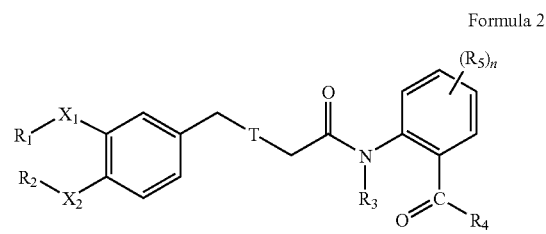

wherein $R_1$ and $R_2$, which may be the same or different, are selected from the group consisting of a $C_1$ to $C_{10}$ alkyl, $C_3$ to $C_{10}$ cycloalkyl, a $C_3$ to $C_{10}$ cycloalkylmethyl, $C_3$ to $C_{10}$ alkene, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkyne, and a chain consisting of a heterocyclic or fused ring, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring; any of which may be optionally substituted; and $R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkyne, aryl, $C_5$ to $C_{20}$ alkaryl, and a hydrocarbon chain containing a heterocyclic or fused ring; and n is an integer between 0 and 4;

or derivatives thereof, analogues thereof, pharmaceutically acceptable salts thereof and metabolites thereof;

which process includes the steps of converting a substituted cinnamic acid to the corresponding acid chloride or acid bromide and condensing with an aminobenzamide, or aniline according to Scheme 2:

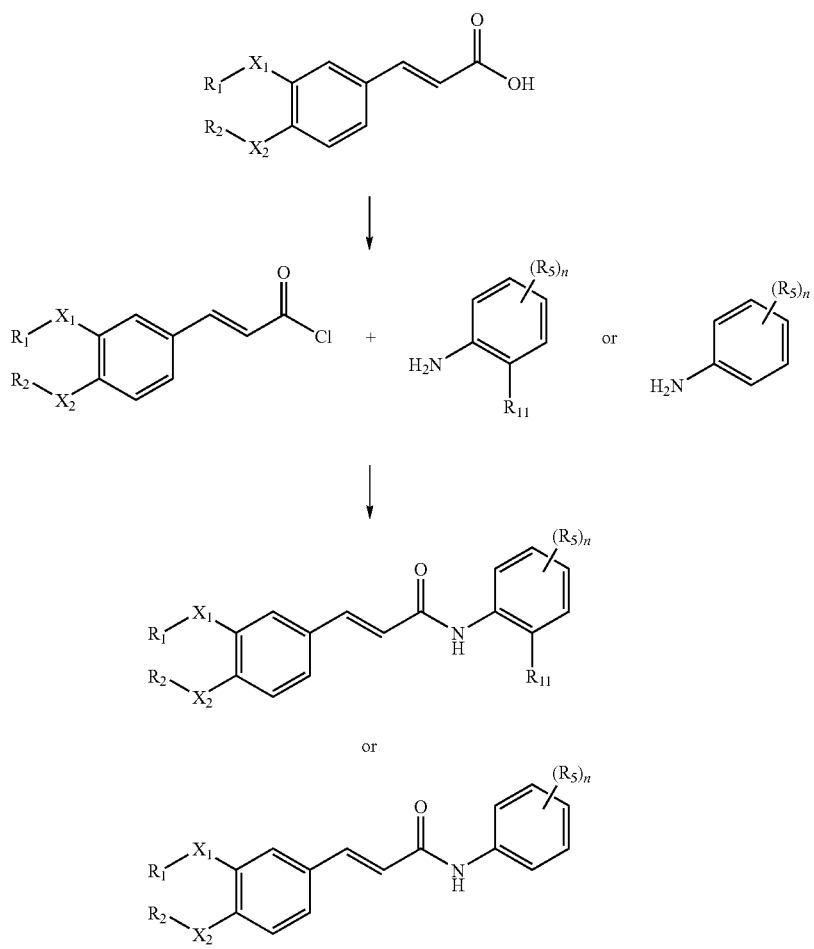

wherein $R_{11}$ is selected from the group consisting of H, a carboxylic acid, an ester or an amide.

In a further aspect, the present invention provides a process for the preparation of a compound of the Formula 8 or Formula 9

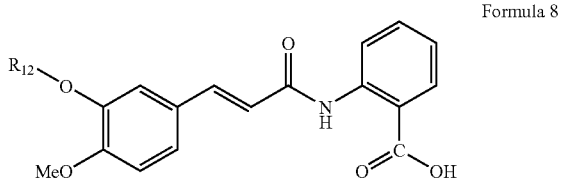

Formula 8

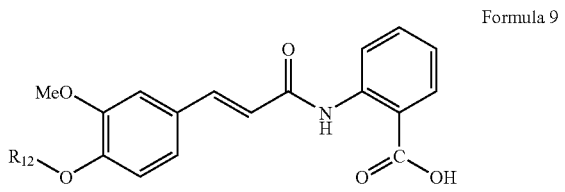

Formula 9 where $R_{12}$ is a $C_3$ to $C_{10}$ terminal or non-terminal alkyne which process includes the steps of:

(i) alkynylating vanillin or isovanillin with an alkynyl halide or alkynyl sulfonate in the presence of a base; and (ii) reacting the product of (i) with 2-[(carboxyacetyl)amino] benzoic acid.

One embodiment of this process is described schematically below; and includes the steps of:

(i) alkynylating vanillin or isovanillin with a propargyl halide or propargyl sulfonate in the presence of a base; and (ii) reacting the product of (I) with 2-[(carboxyacetyl)amino] benzoic acid.

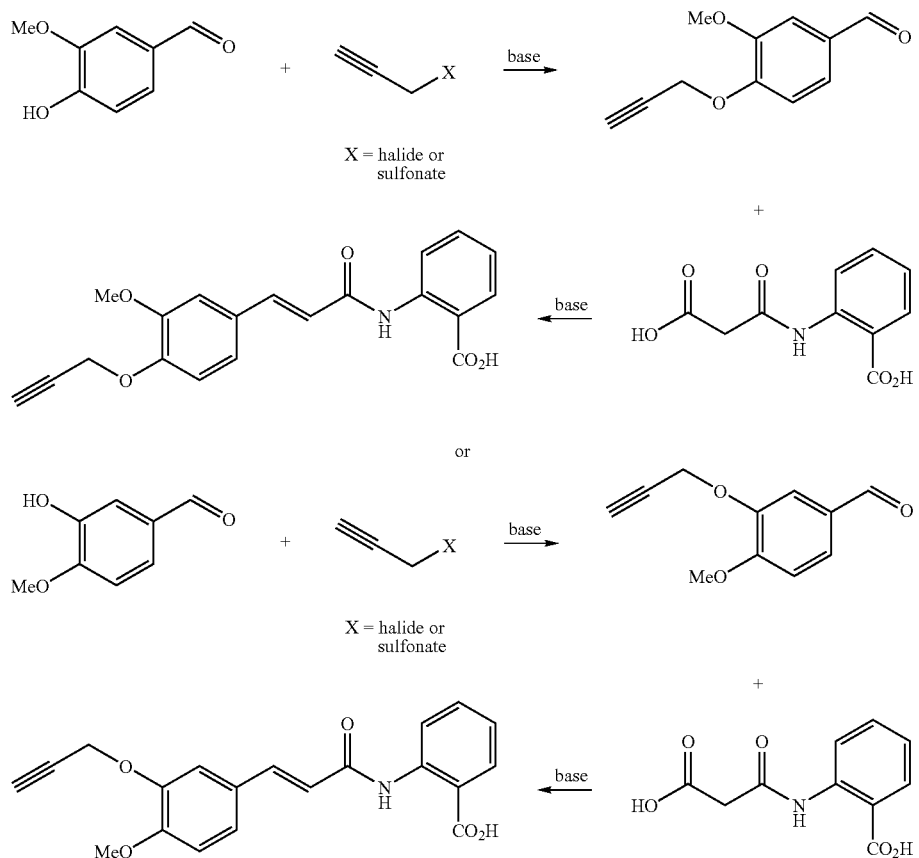

In a still further aspect, the present invention provides a process for the preparation of a compound of the Formula 6 or Formula 7

Formula 6

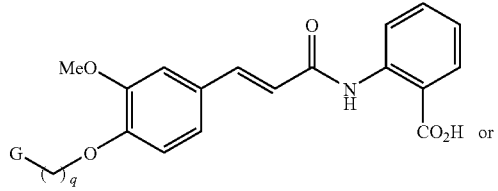

or

Formula 7

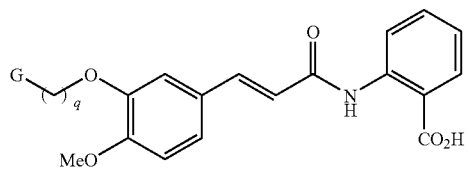

wherein G is a 1,4-disubstituted 1,2,3-triazole ring; and q is an integer between 0 and 10, preferably between 1 and 6; which process includes the steps of
reacting an azide and a compound of the Formula 4 or Formula 5

Formula 4

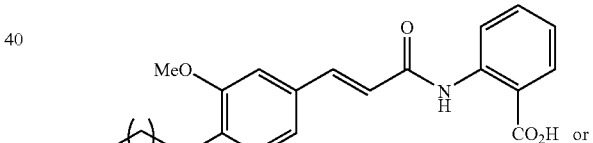 or

Formula 5

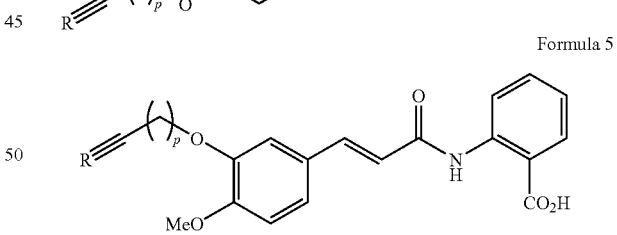

wherein R is H, and p is an integer between 1 and 10, in the presence of a copper catalyst.

The copper catalyst may be of any suitable type known to the skilled person, including but not limited to copper(II) sulfate (or other copper(II) salts), in the presence of a reducing agent (such as sodium ascorbate, triscarboxyethyl phosphine), copper(I) bromide, copper(I) iodide (or other copper (I) salts), copper(II)/copper(0) couples, copper powder, nanosized copper particles, carbon supported copper particles, and the like, any of which may be used in the presence of ligands such as tris(benzyltriazolylmethyl)amine, cuproine or other metal binding ligands.

EXAMPLES

Example 1

General Description of Synthetic Chemistry

Figure 1:
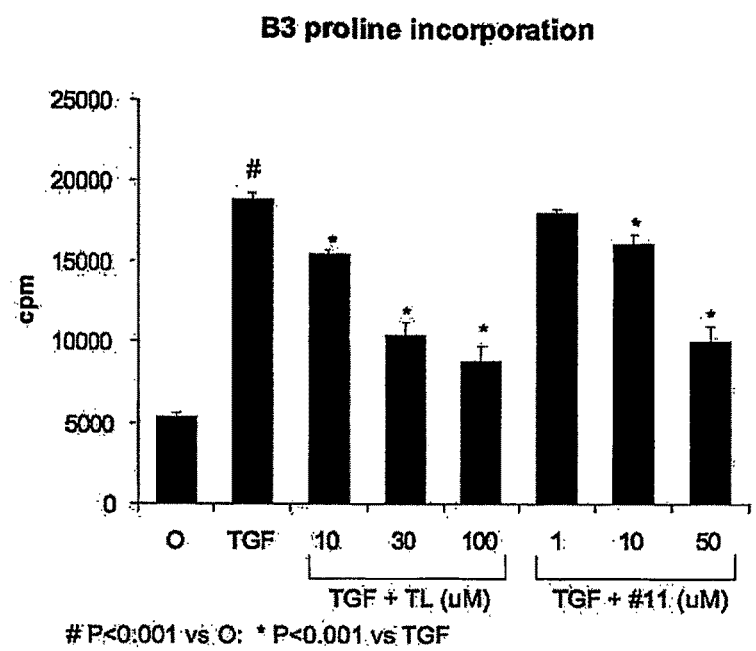
FIGS. 1 & 2: In vitro effects of FT011 and tranilast on transforming growth factor-β induced $^3$H-proline incorporation in cultured rat mesangial cells (concentration of compounds in μM). Values are expressed as mean±sem. #p<0.05 versus cells grown in control medium,
*p<0.05 versus TGF-β treated cells.

Two general approaches were used for the synthesis of various substituted cinnamoyl anthranilates. In the first approach via a piperidine-catalyzed Knoevenagel condensation of a carboxyacetamidobenzoic acid and a benzaldehyde derivative thereof to provide a substituted cinnamoyl anthranilate as a piperidinium salt followed by acidification and recrystallization to produce a cinnamoyl anthranilate as the free acid providing an N-cinnamoyl-4-aminobenzoic acid via the following synthesis.

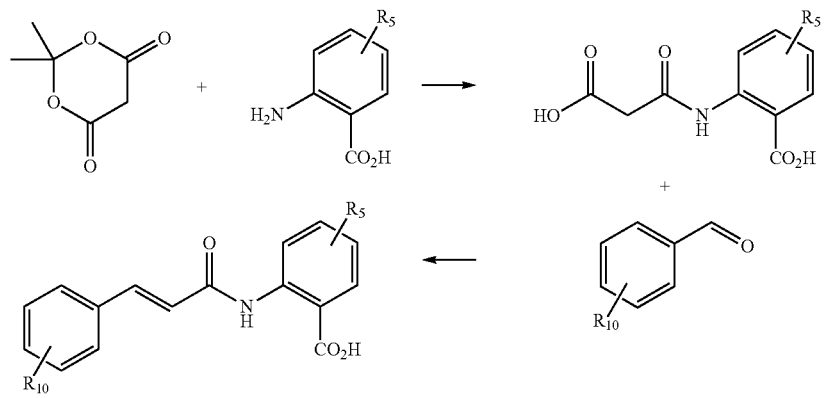

In the second approach, converting a substituted cinnamic acid to the corresponding acid chloride and condensing with a 2-aminobenzamide, or aniline.

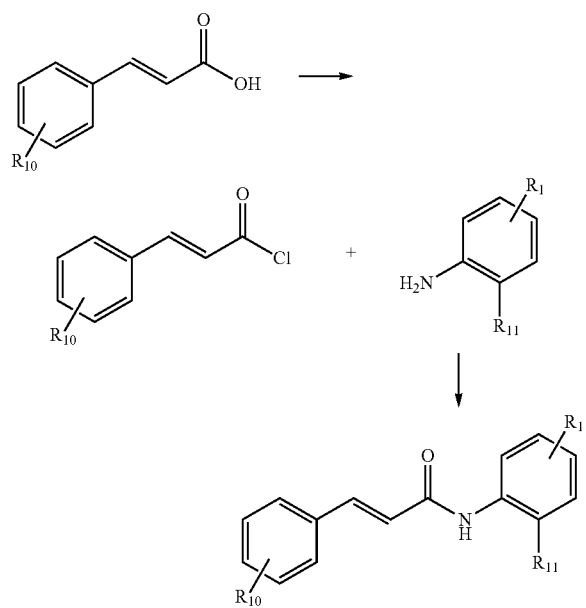

The benzaldehyde precursors required for the above reactions were either obtained from commercial sources, or were synthesized by alkylation of precursor phenolic benzaldehydes with assorted alkyl halides or alkyl tosylates (derived in turn from the corresponding alcohols). Alkylations were typically performed using potassium carbonate as base in acetone. Carboxyacetamidobenzoic acids were obtained by the condensation of various anthranilic acid derivatives with Meldrum's acid. 2-Aminobenzamides were synthesized by the reaction of primary amines with isatoic anhydride. Saturation of the internal alkene of tranilast was performed by reduction with hydrogen in the presence of palladium on carbon catalyst. Cinnamic acids were prepared by Knoevenagel condensation of benzaldehydes with malonic acid. Formation of triazole substituted derivatives was performed using copper(I) catalyzed condensation of azides and terminal alkynes and provides only the 1,4-regioisomer.

Experimental

High resolution mass spectra (HRMS) were obtained using on a Finnigan hybrid linear quadrupole ion trap-Fourier transform (LTQ-FT) mass spectrometer (Thermo Electron, San Jose, Calif.) equipped with an electrospray ionization source. Proton nuclear magnetic resonance ($^1$H NMR) and proton decoupled carbon nuclear magnetic resonance ($^{13}$C NMR) spectra were obtained on Unity 400, Innova 400 and Innova 500 instruments (Melbourne, Australia) operating at 400 MHz and 500 MHz for $^1$H and at 100 MHz and 125 MHz for $^{13}$C. All signals were referenced to solvent peaks (CDCl$_3$: 7.26 ppm for $^1$H and 77.0 ppm for $^{13}$C; DMSO-d$_6$: 2.49 ppm for $^1$H and 39.5 ppm for $^{13}$C). Infrared (IR) spectra were obtained using a PerkinElmer Spectrum One FT-IR spectrometer with zinc selenide/diamond Universal ATR Sampling Accessory. Melting points were obtained using a Reichert-Jung hot stage apparatus and are corrected. Analytical thin layer chromatography (TLC) was conducted on 2 mm thick silica gel GF$_{254}$ (Merck). Compounds were visualised with solutions of 20% w/w phosphomolybdic acid in ethanol, 20% w/w potassium permanganate in water, or under UV (365 nm). Flash chromatography was performed according to the method of Still et al., [20] with Merck Silica Gel 60. Petrol refers to the fraction boiling at 40-60° C. All other reagents were used as received.

Procedure 1

Anthranilic acid (1.1 eq.) was added to a solution of Meldrum's acid (1.0 eq.) in toluene. The reaction flask was fitted with a Dean-Stark apparatus and the suspension was heated to reflux for 3 h. The suspension was cooled, and the precipitate collected by filtration, washed with toluene and dried.

Procedure 2

Piperidine (1.1 eq.) was added to a suspension of an aldehyde (1.1 eq.) and diacid (1.0 eq.) in toluene. The reaction flask was fitted with a Dean-Stark apparatus and heated to reflux for 4 h, cooled to rt and stirred for 1 h. The resulting suspension was filtered, and the filter cake was washed with toluene to afford the piperidinium salt. The piperidinium salt was dissolved in MeOH (5 mL/g) and water (2 mL per/g) at 40° C. The solution was acidified and the resulting precipitate was collected by filtration.

Procedure 3

Propargyl bromide (1.1-1.5 eq.) was added to a suspension of the phenol (1.0 eq.) and potassium carbonate (2.0 eq.) in acetone. The suspension was heated to reflux for 16 h and then the suspension was filtered, using acetone to rinse the filter cake. The filtrate was concentrated under reduced pressure, and water was added to the residue and the aqueous phase was extracted with EtOAc. The organic extract was washed with water, brine, dried and concentrated.

Procedure 4

4-Methylbenzenesulfonyl chloride (1.5 eq.) was added to a cooled solution of alcohol (1.0 eq.) and pyridine (2.0 eq.) in $CH_2Cl_2$ at 0° C. The solution was stirred at 0° C. for 1 h, warmed to rt and stirred for 4 h. Water was added and the aqueous phase was extracted with ether. The organic extract was washed with 1 M HCl, saturated aqueous $NaHCO_3$, water, brine and dried. The solvent was removed under reduced pressure and the crude product was purified by flash chromatography, to afford the methylbenzenesulfonate. The methylbenzenesulfonate (1.5 eq.) was added to a suspension of phenol (1.0 eq.), potassium carbonate (3.0 eq.) and sodium iodide (0.1 eq.) in acetonitrile. The suspension was heated to reflux for 16 h, filtered, and the filter cake rinsed with acetonitrile. The filtrate was concentrated under reduced pressure. Water was added to the residue and the aqueous phase was extracted with EtOAc, washed with water, brine, dried and concentrated.

2-[(Carboxyacetyl)amino]benzoic acid

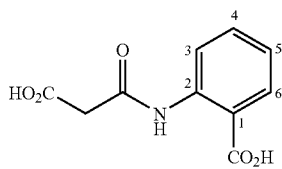

Anthranilic acid (181 g, 1.32 mol) and Meldrum's acid (200 g, 1.39 mol) in toluene (1.50 L) were treated according to Procedure 1. 2-[(Carboxyacetyl)amino]benzoic acid (263 g, 89%) was obtained as a colourless solid; mp 171-173° C., lit. [21] 178-180° C.; $\delta_H$ (500 MHz, DMSO-$d_6$) 3.45 (br s, 2H, $CH_2$), 7.16 (t, $J_{3,4}=J_{4,5}=8.0$ Hz, 1H, H4), 7.59 (td, $J_{4,5}=J_{5,6}=8.0, J_{3,5}=1.5$ Hz, 1H, H5), 7.97 (dd, $J_{3,4}=8.0, J_{3,5}=1.5$ Hz, 1H, H3), 8.44 (d, $J_{5,6}=8.0$ Hz, 1H, H6), 11.27 (s, 1H, NH), 12.83 (br s, 1H, $CO_2H$), 13.57 (br s, 1H, $CO_2H$); $\delta_C$ (125 MHz, DMSO-$d_6$) 45.0, 117.0, 120.3, 123.1, 131.2, 134.1, 140.4, 164.9, 169.1, 169.3.

(E)-2-[[3-(3,4-Dimethoxyphenyl)-1-oxo-2-propenyl]amino]benzoic acid (tranilast) (1)

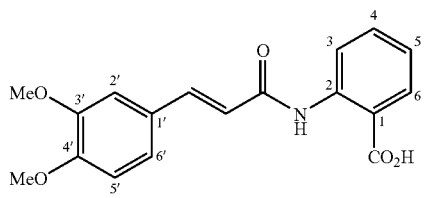

Piperidine (0.96 mL, 9.7 mmol) was added to a suspension of 3,4-dimethoxybenzaldehyde (1.6 g, 9.7 mmol) and 2-[(carboxyacetyl)amino]benzoic acid (1.9 g, 8.6 mmol) in toluene (5.0 mL) and treated according to Procedure 2, acidifying with 1 M HCl. (E)-2-[[3-(3,4-Dimethoxyphenyl)-1-oxo-2-propenyl]amino]benzoic acid (tranilast) (2.1 g, 74%) was obtained as a yellow crystalline solid; mp 208-209° C., lit. [22] 206° C.; $\delta_H$ (500 MHz, DMSO-$d_6$) 3.79 (s, 3H, $OCH_3$), 3.82 (s, 3H, $OCH_3$), 6.79 (d, J=15.5 Hz, 1H, CH=CHCO), 6.99 (d, $J_{5',6'}=8.5$ Hz, 1H, H5'), 7.16 (t, $J_{3,4}=J_{4,5}=7.9$ Hz, 1H, H4), 7.25 (d, $J_{5',6'}=8.5$ Hz, 1H, H6'), 7.38 (s, 1H, H2'), 7.56 (d, J=15.5 Hz, 1H, CH=CHCO), 7.61 (t, $J_{4,5}=J_{5,6}=7.9$ Hz, 1H, H5), 8.00 (d, $J_{3,4}=7.9$ Hz, 1H, H3), 8.62 (d, $J_{5,6}=7.9$ Hz, 1H, H6), 11.30 (s, 1H, NH), 13.61 (br s, 1H, $CO_2H$).

(E)-2[(1-oxo-3-phenyl-2-propenyl)amino]benzoic acid (2)

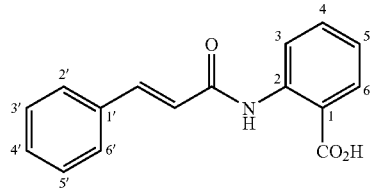 [SMILES: O=C(/C=C/c1ccccc1)Nc1ccccc1C(=O)O]

Piperidine (0.42 mL, 4.2 mmol) was added to a suspension of benzaldehyde (0.43 mL, 4.2 mmol) and 2-[(carboxyacetyl)amino]benzoic acid (0.83 g, 3.7 mmol) in toluene (5.0 mL) and treated according to Procedure 2, acidifying with 1 M HCl. (E)-2-[(1-oxo-3-phenyl-2-propenyl)amino]benzoic acid (0.95 g, 96%) was obtained as a pale yellow crystalline solid; mp 188-189° C., lit. [23] 196-197° C.; $\delta_H$ (500 MHz, DMSO-$d_6$) 6.88 (d, J=16.0 Hz, 1H, CH=CHCO), 7.18 (t, $J_{3,4}=J_{4,5}=8.0$, 1H, H4), 7.41-7.45 (m, 3H, H3', H4', H5'), 7.62 (td, $J_{4,5}=J_{5,6}=8.0, J_{3,5}=1.5$ Hz, 1H, H5), 7.62 (d, J=16.0 Hz, 1H, CH=CHCO), 7.72-7.74 (m, 2H, H2', H6'), 8.00 (dd, $J_{3,4}=8.0, J_{3,5}=1.5$ Hz, 1H, H3), 8.59 (d, $J_{5,6}=8.0$ Hz, 1H, H6), 11.32 (s, 1H, NH).

(E)-2-[[3-(4-Methoxyphenyl)-1-oxo-2-propenyl]amino]benzoic acid (3)

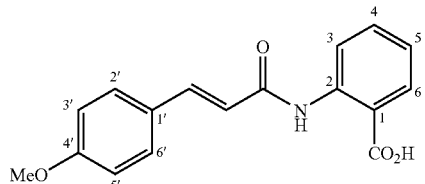

Piperidine (0.42 mL, 4.2 mmol) was added to a suspension of 4-methoxybenzaldehyde (0.51 mL, 4.2 mmol) and 2-[(carboxyacetyl)amino]benzoic acid (0.83 g, 3.7 mmol) in toluene (5.0 mL) and treated according to Procedure 2, acidifying with 1 M HCl. (E)-2-[[3-(4-Methoxyphenyl)-1-oxo-2-propenyl]amino]benzoic acid (0.95 g, 86%) was obtained as a pale yellow crystalline solid; mp 194-195° C., lit. [24] 195-198° C.; $\delta_H$ (500 MHz, DMSO-$d_6$) 3.80 (s, 3H, $OCH_3$), 6.72 (d, J=15.5 Hz, 1H, CH=CHCO), 6.98 (d, $J_{2',3'}=J_{5',6'}=9.0$ Hz, 2H, H3', H5'), 7.16 (t, $J_{3,4}=J_{4,5}=8.0$ Hz, 1H, H4), 7.57 (d, J=15.5 Hz, 1H, CH=CHCO), 7.60 (t, $J_{4,5}=J_{5,6}=8.0$ Hz, 1H, H5), 7.68 (d, $J_{2',3'}=J_{5',6'}=9.0$ Hz, 2H, H2', H6'), 7.99 (d, $J_{3,4}=8.0$ Hz, 1H, H3), 8.60 (d, $J_{5,6}=8.0$ Hz, 1H, H6), 11.28 (s, 1H, NH).

(E)-2-[[3-(3-Methoxyphenyl)-1-oxo-2-propenyl]amino]benzoic acid (4)

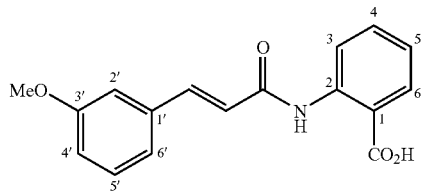 [SMILES: COc1cccc(/C=C/C(=O)Nc2ccccc2C(=O)O)c1]

Piperidine (0.35 mL, 3.54 mmol) was added to a suspension of 3-methoxybenzaldehyde (0.43 mL, 3.5 mmol) and 2-[(carboxyacetyl)amino]benzoic acid (0.70 g, 3.1 mmol) in toluene (5.0 mL) and treated according to Procedure 2, acidifying with 1 M HCl. (E)-2-[[3-(3-Methoxyphenyl)-1-oxo-2-propenyl]amino]benzoic acid (0.71 g, 76%) as a yellow crystalline solid; mp 183-184° C., lit. [24] 183-185° C.; $\delta_H$ (500 MHz, DMSO-$d_6$) 3.80 (s, 3H, OCH$_3$), 6.91 (d, J=15.5 Hz, 1H, CH=CHCO), 6.98 (dd, $J_{4',5'}=8.0$, $J_{2',4'}=2.0$ Hz, 1H, H4'), 7.18 (t, $J_{3,4}=J_{4,5}=8.0$ Hz, 1H, H4), 7.23-7.36 (m, 3H, H2', H5', H6'), 7.59 (d, J=15.5 Hz, 1H, CH=CHCO), 7.62 (td, $J_{4,5}=J_{5,6}=8.0$, $J_{3,5}=1.5$ Hz, 1H, H5), 7.99 (dd, $J_{3,4}=8.0$, $J_{3,5}=1.5$ Hz, 1H, H3), 8.58 (d, $J_{5,6}=8.0$ Hz, 1H, H6), 11.31 (s, 1H, NH).

(E)-2-[[3-(3,4-Dihydroxyphenyl)-1-oxo-2-propenyl]amino]benzoic acid (5)

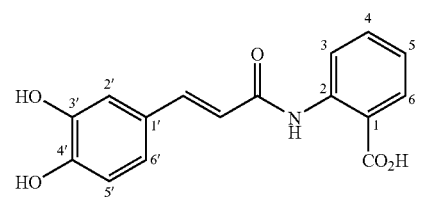 [SMILES: O=C(/C=C/c1ccc(O)c(O)c1)Nc1ccccc1C(=O)O]

Piperidine (0.39 mL, 4.0 mmol) was added to a suspension of 3,4-dihydroxybenzaldehyde (0.55 g, 4.0 mmol) and 2-[(carboxyacetyl)amino]benzoic acid (0.74 g, 3.3 mmol) in toluene (5.0 mL) and treated according to Procedure 2, acidifying with 1 M HCl. (E)-2-[[3-(3,4-Dihydroxyphenyl)-1-oxo-2-propenyl]amino]benzoic acid (0.82 g, 83%) was obtained as a brown crystalline solid; mp 204-206° C.; lit. [24] 204-206° C.; $\delta_H$ (500 MHz, DMSO-$d_6$) 6.50 (d, J=15.5 Hz, 1H, CH=CHCO), 6.77 (d, $J_{5',6'}=8.0$ Hz, 1H, H5'), 7.00 (dd, $J_{5',6'}=8.0$, =2.0 Hz, 1H, H6'), 7.08 (d, $J_{2',6'}=2.0$ Hz, 1H, H2'), 7.14 (t, $J_{3,4}=J_{4,5}=8.0$ Hz, 1H, H4), 7.44 (d, J=15.5 Hz, 1H, CH=CHCO), 7.61 (td, $J_{4,5}=J_{5,6}=8.0$, $J_{3,5}=1.5$ Hz, 1H, H5), 8.00 (dd, $J_{3,4}=8.0$, $J_{3,5}=1.5$ Hz, 1H, H3), 8.58 (d, $J_{5,6}=8.0$ Hz, 1H, H6), 9.11 (s, 1H, OH), 9.52 (s, 1H, OH), 11.25 (s, 1H, NH).

(E)-2-[[3-(4-Hydroxy-3-methoxyphenyl)-1-oxo-2-propenyl]amino]benzoic acid (6)

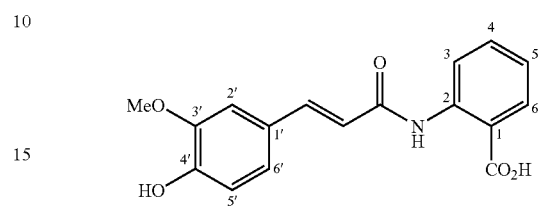

Piperidine (0.50 mL, 5.1 mmol) was added to a suspension of 4-hydroxy-3-methoxybenzaldehyde (0.77 g, 5.1 mmol) and 2-[(carboxyacetyl)amino]benzoic acid (1.0 g, 4.5 mmol) in toluene (5.0 mL) and treated according to Procedure 2, acidifying with 1 M HCl. (E)-2-[[3-(4-Hydroxy-3-methoxyphenyl)-1-oxo-2-propenyl]amino]benzoic acid (1.1 g, 78%) was obtained as a yellow crystalline solid; mp 207.5-208.5° C., lit. [25] 230-233° C.; $\delta_H$ (500 MHz, DMSO-$d_6$) 3.83 (s, 3H, OCH$_3$), 6.71 (d, J=15.5 Hz, 1H, CH=CHCO), 6.80 (d, $J_{5',6'}=8.5$ Hz, 1H, H5'), 7.13 (dd, $J_{5',6'}=8.5$, $J_{2',6'}=1.5$ Hz, 1H, H6'), 7.15 (t, $J_{3,4}=J_{4,5}=8.0$ Hz, 1H, H4), 7.34 (d, $J_{2',6'}=1.5$ Hz, 1H, H2'), 7.52 (d, J=15.5 Hz, 1H, CH=CHCO), 7.60 (td, $J_{4,5}=J_{5,6}=8.0$, $J_{3,5}=2.0$ Hz, 1H, H5), 8.00 (dd, $J_{3,4}=8.0$, $J_{3,5}=2.0$ Hz, 1H, H3), 8.62 (d, $J_{5,6}=8.0$ Hz, 1H, H6), 9.57 (s, 1H, OH), 11.27 (s, 1H, NH), 13.61 (br s, 1H, CO$_2$H).

(E)-2-[[3-(3-Hydroxy-4-methoxyphenyl)-1-oxo-2-propenyl]amino]benzoic acid (7)

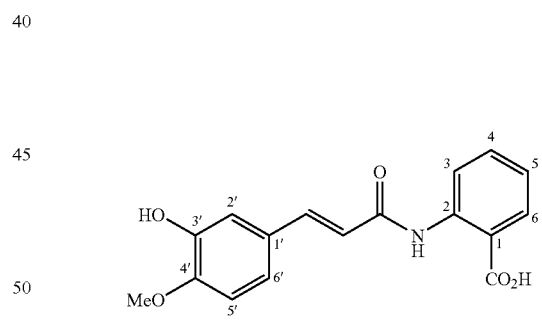

Piperidine (0.25 mL, 2.5 mmol) was added to a suspension of 3-hydroxy-4-methoxybenzaldehyde (0.39 g, 2.5 mmol) and 2-[(carboxyacetyl)amino]benzoic acid (0.50 g, 2.2 mmol) in toluene (5.0 mL) and treated according to Procedure 2, acidifying with 1 M HCl. (E)-2-[[3-(3-Hydroxy-4-methoxyphenyl)-1-oxo-2-propenyl]amino]benzoic acid (0.53 g, 76%) was obtained as a yellow crystalline solid; mp 215-216° C., lit [25] 219-222° C.; $\delta_H$ (500 MHz, DMSO-$d_6$) 3.81 (s, 3H, OCH$_3$), 6.59 (d, J=15.5 Hz, 1H, CH=CHCO), 6.80 (d, $J_{5',6'}=8.5$ Hz, 1H, H5'), 7.10-7.13 (m, 2H, H2', H6'), 7.15 (t, $J_{3,4}=J_{4,5}=8.0$ Hz, 1H, H4), 7.47 (d, J=15.5 Hz, 1H, CH=CHCO), 7.60 (td, $J_{4,5}=J_{5,6}=8.0$, $J_{3,5}=1.5$ Hz, 1H, H5), 7.99 (dd, $J_{3,4}$=8.0, $J_{3,5}$=1.5 Hz, 1H, H3), 8.58 (d, $J_{5,6}$=8.0 Hz, 1H, H6), 11.25 (s, 1H, NH), 13.56 (br s, 1H, $CO_2H$).

3-(2-Carboxyacetamido)-2-naphthoic acid

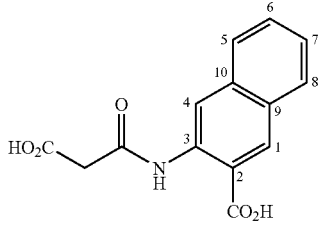 [SMILES: O=C(O)CC(=O)Nc1cc2ccccc2cc1C(=O)O]

3-Aminonaphthoic acid (0.60 g, 2.6 mmol) was added to a solution of Meldrum's acid (0.46 g, 3.2 mmol) in toluene (5.0 mL) and treated according to Procedure 1. 3-(2-Carboxyacetamido)-2-naphthoic acid (0.71 g, 81%) was obtained as a brown solid; mp 225-227° C.; $\delta_H$ (400 MHz, DMSO-$d_6$) 3.50 (br s, 2H, $CH_2$), 7.49 (t, $J_{6,7}$=$J_{7,8}$=8.0 Hz, 1H, H7), 7.61 (t, $J_{5,6}$=$J_{6,7}$=8.0 Hz, 1H, H6), 7.88 (d, $J_{7,8}$=8.0 Hz, 1H, H8), 8.02 (d, $J_{5,6}$=8.0 Hz, H5), 8.67 (s, 1H, H4), 8.88 (s, 1H, H1), 11.31 (s, 1H, NH); $\delta_C$ (100 MHz, DMSO-$d_6$) 44.9, 117.1, 117.9, 125.7, 127.2, 128.3, 129.0, 129.2, 133.0, 135.4, 135.6, 164.7, 169.0, 169.2; $v_{max}$ 1134, 1195, 1245, 1369, 1552, 1661, 1697, 3099 cm$^{-1}$.

(E)-3-[[3-(3,4-Dimethoxyphenyl)-1-oxo-2-propenyl]amino]-2-naphthoic acid (8)

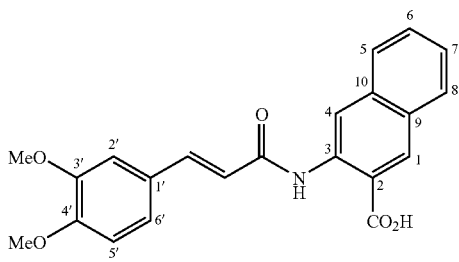 [SMILES: COc1ccc(/C=C/C(=O)Nc2cc3ccccc3cc2C(=O)O)cc1OC]

Piperidine (0.23 mL, 2.3 mmol) was added to a suspension of 3,4-dimethoxybenzaldehyde (0.38 g, 2.3 mmol) and 3-(2-carboxyacetamido)-2-naphthoic acid (0.56 g, 2.0 mmol) in toluene (5.0 mL) and treated according to Procedure 2, acidifying with 1 M HCl. (E)-3-[[3-(3,4-Dimethoxyphenyl)-1-oxo-2-propenyl]amino]-2-naphthoic acid (0.51 g, 66%) was obtained as a yellow crystalline solid; mp 212-213° C.; $\delta_H$ (400 MHz, DMSO-$d_6$) 3.80 (s, 3H, $OCH_3$), 3.84 (s, 3H, $OCH_3$), 6.82 (d, J=15.6 Hz, 1H, CH=CHCO), 6.99 (d, =8.2 Hz, 1H, H5'), 7.25 (dd, 4,6=8.2, $J_{2',6'}$=2.0 Hz, 1H, H6'), 7.38 (d, $J_{2',6'}$=2.0 Hz, 1H, H2'), 7.49 (t, $J_{6,7}$=$J_{7,8}$=8.0 Hz, 1H, H7), 7.58 (d, J=15.6 Hz, 1H, CH=CHCO), 7.62 (t, $J_{5,6}$=$J_{6,7}$=8.0 Hz, 1H, H6), 7.89 (d, $J_{7,8}$=8.0 Hz, 1H, H8), 8.03 (d, $J_{5,6}$=8.0 Hz, H5), 8.71 (s, 1H, H1), 9.05 (s, 1H, H4), 11.30 (s, 1H, NH); $\delta_C$ (100 MHz, DMSO-$d_6$) 55.6, 55.7, 110.4, 111.6, 117.1, 117.6, 120.1, 122.6, 125.6, 127.1, 127.3, 128.2, 129.1, 129.3, 133.1, 135.5, 136.3, 141.4, 149.0, 150.6, 164.2, 169.5;

HRMS (ESI) Calculated for $C_{22}H_{19}NO_6$ $[M+H]^+$ 378.1336. found 378.1345; $v_{max}$ 797, 1022, 1134, 1233, 1512, 1665, 1693, 3048 cm$^{-1}$.

2-[(Carboxyacetyl)amino]-4,5-dimethoxybenzoic acid

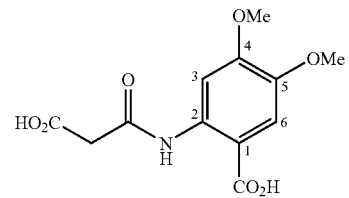

4,5-Dimethoxyanthranilic acid (0.50 g, 2.5 mmol) was added to a solution of Meldrum's acid (0.42 g, 2.9 mmol) in toluene (5.0 mL) and treated according to Procedure 1. 2-[(Carboxyacetyl)amino]-4,5-dimethoxybenzoic acid (0.70 g, 97%) was obtained as a brown solid; $\delta_H$ (400 MHz, DMSO-$d_6$) 3.43 (br s, 2H, $CH_2$), 3.75 (s, 3H, $OCH_3$), 3.79 (s, 3H, $OCH_3$), 7.42 (s, 1H, H3), 8.24 (s, 1H, H6), 11.40 (s, 1H, NH).

(E)-2-[[3-(3,4-Dimethoxyphenyl)-1-oxo-2-propenyl]amino]-4,5-dimethoxybenzoic acid (9)

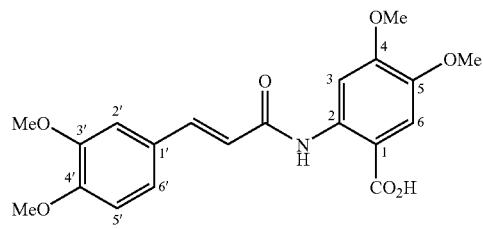 [SMILES: COc1ccc(/C=C/C(=O)Nc2cc(OC)c(OC)cc2C(=O)O)cc1OC]

Piperidine (0.28 mL, 2.8 mmol) was added to a suspension of 3,4-dimethoxybenzaldehyde (0.46 g, 2.8 mmol) and 2-[(carboxyacetyl)amino]benzoic acid (0.46 g, 2.5 mmol) in toluene (5.0 mL) and treated according to Procedure 2, acidifying with 1 M HCl. (E)-2-[[3-(3,4-Dimethoxyphenyl)-1-oxo-2-propenyl]amino]-4,5-dimethoxybenzoic acid (0.69 g, 72%) was obtained as a pale yellow crystalline solid; mp 236-239° C., lit. [26] 190-191° C.; $\delta_H$ (400 MHz, DMSO-$d_6$) 3.76 (s, 3H, $OCH_3$), 3.79 (s, 3H, $OCH_3$), 3.83 (s, 3H, 2×$OCH_3$), 6.76 (d, J=15.2 Hz, 1H, CH=CHCO), 6.98 (d, $J_{5',6'}$=8.4 Hz, 1H, H5'), 7.21 (d, $J_{5',6'}$=8.4 Hz, 1H, H6'), 7.36 (s, 1H, H2'), 7.44 (s, 1H, H3), 7.53 (d, J=15.2 Hz, 1H, CH=CHCO), 8.45 (s, 1H, H6), 11.37 (s, 1H, NH).

2-[[3-(3,4-Dimethoxyphenyl)-1-oxopropyl]amino]benzoic acid (10)

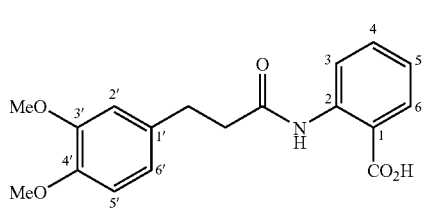 [SMILES: COc1ccc(CCC(=O)Nc2ccccc2C(=O)O)cc1OC]

Palladium on carbon (5%, 50 mg) was added to a solution of (E)-2-[[3-(3,4-dimethoxyphenyl)-1-oxo-2-propenyl]amino]benzoic acid (tranilast) (0.50 g, 1.5 mmol) in THF (9.0 mL), EtOH (1.0 mL) and AcOH (1 drop). The suspension was stirred under an atmosphere of hydrogen for 16 h and filtered. The filtrate was concentrated under reduced pressure and the crude product was recrystallised from EtOAc/petrol to give 2-[[3-(3,4-dimethoxyphenyl)-1-oxopropyl]amino]benzoic acid (0.39 g, 77%) as a colourless crystalline solid; mp 137° C., lit. [24] 136-137.5° C.; $\delta_H$ (500 MHz, DMSO-$d_6$) 2.68 (t, J=7.5 Hz, 2H, $CH_2$CO), 2.87 (t, J=7.5 Hz, 2H, $CH_2$Ar), 3.68 (s, 3H, $OCH_3$), 3.70 (5, 3H, $OCH_3$), 6.74 (d, $J_{5',6'}$=8.2 Hz, 1H, H6'), 6.82 (d, $J_{5',6'}$=8.2 Hz, 1H, H5'), 6.86 (s, 1H, H2'), 7.12 (t, $J_{3,4}$=$J_{4,5}$=8.0 Hz, 1H, H4), 7.57 (t, $J_{4,5}$=$J_{5,6}$=8.0 Hz, 1H, H5), 7.95 (d, $J_{3,4}$=8.0 Hz, 1H, H3), 8.47 (d, $J_{5,6}$=8.0 Hz, 1H, H6), 11.11 (s, 1H, NH), 13.57 (br s, 1H, $CO_2H$).

3-Methoxy-4-propargyloxybenzaldehyde

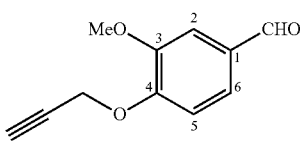

Propargyl bromide (219 mL, 80% w/v, 1.48 mol) was added to a suspension of vanillin (150 g, 0.986 mol) and potassium carbonate (408 g, 2.96 mol) in acetone (1.50 L) and treated according to Procedure 3. 3-Methoxy-4-propargyloxybenzaldehyde (162 g, 86%) was obtained as yellow crystalline solid; mp 95° C.; $\delta_H$ (400 MHz, $CDCl_3$) 2.56 (t, J=2.5 Hz, 1H, C≡CH), 3.95 (s, 3H, $OCH_3$), 4.86 (d, J=2.5 Hz, 2H, $OCH_2$), 7.14 (d, $J_{5,6}$=6.8 Hz, 1H, H5), 7.44 (d, $J_{2,6}$=1.4 Hz, 1H, H2), 7.47 (dd, $J_{5,6}$=6.8, $J_{2,6}$=1.4 Hz, 1H, H6), 9.87 (s, 1H, CHO); $\delta_C$ (100 MHz, $CDCl_3$) 56.0, 56.6, 77.2, 77.4, 109.4, 112.5, 126.3, 130.9, 150.0, 152.1, 190.9; HRMS (ESI) Calculated for $C_{11}H_{10}O_3$ $[M+H]^+$ 191.0703. found 191.0706; $v_{max}$ 1006, 1130, 1259, 1586, 1677, 2119, 2845, 2932, 3266 $cm^{-1}$.

(E)-2-[[3-(3-Methoxy-4-propargyloxy)phenyl)-1-oxo-2-propenyl]amino]benzoic acid (11)

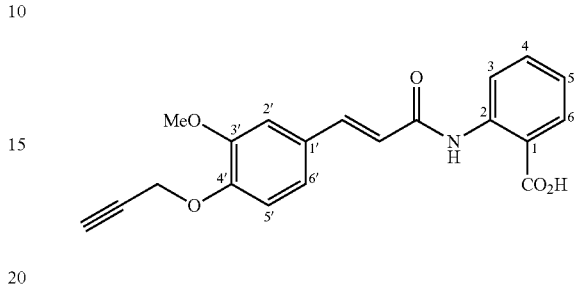

Piperidine (85.0 mL, 85.6 mmol) was added to a suspension of 3-methoxy-4-propargyloxybenzaldehyde (163 g, 85.6 mmol) and 2-[(carboxyacetyl)amino]benzoic acid (182 g, 81.5 mmol) in toluene (1.0 L) and treated according to Procedure 2, acidifying with 50% AcOH. The crude product was recrystallised from EtOH (35 mL/g), filtered and washed with cold EtOH to afford (E)-2-[[3-(3-methoxy-4-propargyloxyphenyl)-1-oxo-2-propenyl]amino]benzoic acid (222 g, 77%) as a yellow crystalline solid; mp 191-193° C.; $\delta_H$ (400 MHz, DMSO-$d_6$) 3.59 (t, J=2.4 Hz, 1H, HC≡C), 3.84 (s, 3H, $OCH_3$), 4.84 (d, J=2.4 Hz, 2H, $OCH_2$), 6.81 (d, J=15.6 Hz, 1H, CH=CHCO), 7.05 (d, $J_{5',6'}$=8.4 Hz, 1H, H5'), 7.16 (t, $J_{3,4}$=$J_{4,5}$=8.0 Hz, 1H, H4), 7.25 (d, $J_{5',6'}$=8.4 Hz, 1H, H6'), 7.41 (s, 1H, H2'), 7.56 (d, J=15.6 Hz, 1H, CH=CHCO), 7.61 (t, $J_{4,5}$=$J_{5,6}$=8.0 Hz, 1H, H5), 8.00 (d, $J_{3,4}$=8.0 Hz, 1H, H3), 8.62 (d, $J_{5,6}$=8.0 Hz, 1H, H6), 11.31 (s, 1H, NH), 13.57 (br S, 1H, $CO_2H$); $\delta_C$ (100 MHz, DMSO-$d_6$) 55.6, 55.9, 78.6, 79.1, 110.8, 113.5, 116.6, 120.4, 120.4, 122.2, 122.7, 128.2, 131.2, 134.0, 141.0, 141.5, 148.3, 149.3, 164.1, 169.5; HRMS (ESI) calculated for $C_2OH_{17}NO_5$ $[M+H]^+$ 352.1179. found 352.1187; $v_{max}$ 755, 1010, 1140, 1253, 1502, 1582, 1657, 3278, 3522 $cm^{-1}$.

(E)-3-(3,4-Dimethoxyphenyl)-2-propenoic acid

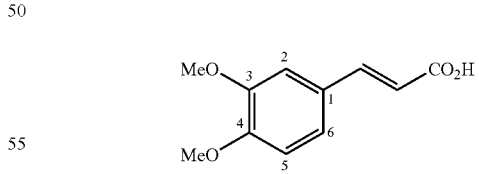

A solution of 3,4-dimethoxybenzaldehyde (5.0 g, 30 mmol) and malonic acid (4.7 g, 45 mmol) in a mixture of piperidine (0.5 mL) and pyridine (15 mL) was heated to 120° C. and stirred overnight. The mixture was cooled to rt and acidified with conc. HCl. The resulting precipitate was filtered and washed with water to give (E)-3-(3,4-dimethoxyphenyl)-2-propenoic acid (5.1 g, 81%) as a pale brown solid; $\delta_H$ (400 MHz, DMSO-$d_6$) 3.78 (s, 3H, $OCH_3$), 3.79 (s, 3H, $OCH_3$), 6.42 (d, J=16.0 Hz, 1H, CH=CH$CO_2H$), 6.96 (d, $J_{5,6}$=8.0 Hz, 1H, H5), 7.19 (d, $J_{5,6}$=8.0 Hz, 1H, H6), 7.30 (s, 1H, H2), 7.51 (d, J=16.0 Hz, 1H, CH=CHCO$_2$H).

(E)-2-[[3-(3,4-Dimethoxyphenyl)-1-oxo-2-propenyl]amino]benzamide (12)

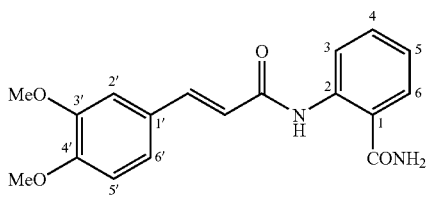 [SMILES: COc1ccc(/C=C/C(=O)Nc2ccccc2C(N)=O)cc1OC]

A suspension of (E)-3-(3,4-dimethoxyphenyl)-2-propenoic acid (0.51 g, 2.5 mmol) in toluene (5.0 mL) was treated with thionyl chloride (0.53 mL, 7.3 mmol) and catalytic DMF (1 drop). The solution was heated to 50° C. and stirred for 1 h and the solvent was removed under reduced pressure to give the acid chloride as a yellow solid. A solution of the acid chloride (2.5 mmol) in pyridine (2.0 mL) and THF (2.0 mL) was added to a solution of 2-aminobenzamide (0.40 g, 2.9 mmol) in pyridine (1.0 mL). The suspension was stirred at it for 16 h, cooled to 0° C. and acidified with 1 M HCl. The crude product was filtered, dried and recrystallised from acetonitrile to give (E)-2-[[3-(3,4-dimethoxyphenyl)-1-oxo-2-propenyl]amino]benzamide (0.32 g, 40%) as a pale red crystalline solid; mp 184-186° C., lit. [27]193-194° C.; $\delta_H$ (400 MHz, DMSO-d$_6$) 3.79 (s, 3H, OCH$_3$), 3.82 (s, 3H, OCH$_3$), 6.72 (d, J=15.4 Hz, 1H, CH=CHCO), 6.98 (d, $J_{5',6'}$=8.0 Hz, 1H, H5'), 7.13 (t, $J_{3,4}$=$J_{4,5}$=8.0 Hz, 1H, H4), 7.22 (dd, $J_{5',6'}$=8.0 Hz, $J_{2',6'}$=1.6 Hz, 1H, H6'), 7.36 (d, $J_{2',6'}$=1.6 Hz, 1H, H2'), 7.50 (t, $J_{4,5}$=$J_{5,6}$=8.0 Hz, 1H, H5), 7.52 (d, J=15.4 Hz, 1H, CH=CHCO), 7.73 (s, 1H, NH$_2$), 7.80 (d, $J_{3,4}$=8.0 Hz, 1H, H3), 8.30 (s, 1H, NH$_2$), 8.57 (d, $J_{5,6}$=8.0 Hz, 1H, H6), 11.79 (s, 1H, NH).

(E)-[3-(3,4-Dimethoxyphenyl)-1-oxo-2-propenyl]aminobenzene (13)

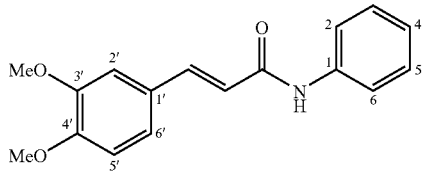

A suspension of (E)-3-(3,4-dimethoxyphenyl)-2-propenoic acid (0.51 g, 2.5 mmol) in CHCl$_3$ (5.0 mL) was treated with thionyl chloride (0.53 mL, 7.3 mmol) and catalytic DMF (1 drop). The solution was heated to reflux and stirred for 16 h and the solvent was removed under reduced pressure to give the acid chloride as a yellow solid. A solution of the acid chloride (2.5 mmol) in CH$_2$Cl$_2$ (2.0 mL) was added to a solution of aniline (0.25 mL, 2.7 mmol) and NEt$_3$ (0.75 mL, 5.4 mmol) in CH$_2$Cl$_2$ (2.0 mL). The mixture was stirred at rt for 16 h and diluted with water. The aqueous phase was extracted with EtOAc and the combined organic extracts were washed with water, brine and dried. The crude product was recrystallised from acetonitrile to give (E)-[3-(3,4-dimethoxyphenyl)-1-oxo-2-propenyl]aminobenzene (0.23 g, 33%) as a colourless crystalline solid; mp 131-133° C., lit. [28] 111° C.; $\delta_H$ (400 MHz, DMSO-d$_6$) 3.79 (s, 3H, OCH$_3$), 3.81 (s, 3H, OCH$_3$), 6.69 (d, J=15.5 Hz, 1H, CH=CHCO), 7.01 (d, $J_{5',6'}$=8.0 Hz, 1H, H5'), 7.04 (t, $J_{3,4}$=$J_{4,5}$=8.0 Hz, 1H, H4), 7.17 (d, $J_{5',6'}$=8.0 Hz, 1H, H6'), 7.21 (s, 1H, H2'), 7.31 (t, $J_{2,3}$=$J_{3,4}$=8.0 Hz, 2H, H3, H5), 7.51 (d, J=16.0 Hz, 1H, CH=CHCO), 7.68 (d, $J_{2,3}$=$J_{5,6}$=8.0 Hz, 2H, H2, H6), 10.09 (s, 1H, NH).

4-[(Carboxyacetyl)amino]benzoic acid

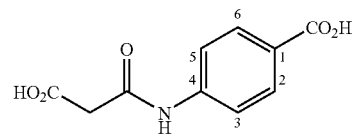

4-Aminobenzoic acid (0.50 g, 3.6 mmol) was added to a solution of Meldrum's acid (0.63 g, 4.4 mmol) in toluene (5.0 mL) and treated according to Procedure 1. 4-[(Carboxyacetyl)amino]benzoic acid (0.74 g, 91%) was obtained as a colourless solid; $\delta_H$ (400 MHz, DMSO-d$_6$) 3.38 (br s, 2H, CH$_2$), 7.68 (t, $J_{2,3}$=$J_{5,6}$=8.0 Hz, 1H, H2, H6), 7.89 (d, $J_{2,3}$=$J_{5,6}$=8.0, 1H, H3, H5), 10.44 (s, 1H, NH), 12.70 (br s, 1H, CO$_2$H).

(E)-4-[[3-(3,4-Dimethoxyphenyl)-1-oxo-2-propenyl]amino]benzoic acid (14)

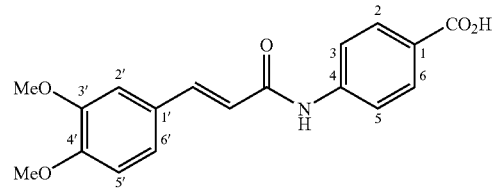 [SMILES: COc1ccc(/C=C/C(=O)Nc2ccc(C(=O)O)cc2)cc1OC]

Piperidine (0.39 mL, 4.0 mmol) was added to a suspension of 3,4-dimethoxybenzaldehyde (0.66 g, 4.0 mmol) and 4-[(carboxyacetyl)amino]benzoic acid (0.74 g, 3.3 mmol) in toluene (5.0 mL) and treated according to Procedure 2, acidifying with 1 M HCl. The crude product was recrystallised from EtOH providing (E)-4-[[3-(3,4-dimethoxyphenyl)-1-oxo-2-propenyl]amino]benzoic acid (0.58 g, 53%) as a yellow crystalline solid; mp 258-259° C., lit. [24] 267-269° C.; $\delta_H$ (400 MHz, DMSO-d$_6$) 3.80 (s, 3H, OCH$_3$), 3.82 (s, 3H, OCH$_3$), 6.72 (d, J=15.6 Hz, 1H, CH=CHCO), 7.01 (d, $J_{5',6'}$=8.2 Hz, 1H, H5'), 7.20 (d, $J_{5',6'}$=8.2 Hz, 1H, H6'), 7.22 (s, 1H, H2'), 7.56 (d, J=15.6 Hz, 1H, CH=CHCO), 7.80 (d, $J_{2,3}=J_{5,6}=8.4$ Hz, 2H, H3, H5), 7.90 (d, $J_{2,3}=J_{5,6}=8.4$ Hz, 1H, H2, H6), 10.43 (s, 1H, NH), 12.68 (br s, 1H, CO$_2$H).

2-Amino-N-propargylbenzamide

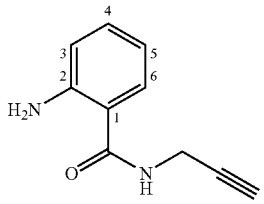

A solution of propargylamine (1.00 mL, 14.6 mmol) in DMF (4.0 mL) was added dropwise to a solution of isatoic anhydride (1.57 g, 9.72 mmol) in DMF (8.0 mL) at 45° C. The solution was stirred at 45° C. for 16 h and diluted with water and CH$_2$Cl$_2$. The aqueous phase was extracted with CH$_2$Cl$_2$ washed with water, brine, dried and concentrated. The crude product was recrystallised from EtOAc/petrol to give 2-amino-N-propargylbenzamide (0.85 g, 51%) as a colourless solid; mp 100-101° C., lit. [29] 98-100° C.; $\delta_H$ (400 MHz, DMSO-d$_6$) 3.08 (t, J=2.4 Hz, 1H, C≡CH), 3.97 (dd, J=5.6, 2.4 Hz, 2H, CH$_2$), 6.45 (s, 2H, NH$_2$), 6.49 (t, $J_{4,5}=J_{5,6}=7.8$ Hz, 1H, H5), 6.68 (d, $J_{3,4}=7.8$ Hz, 1H, H3), 7.13 (t, $J_{3,4}=J_{4,5}=7.8$ Hz, 1H, H4), 7.46 (d, $J_{5,6}=7.8$ Hz, 1H, H6), 6.61 (t, J=5.6 Hz, 1H, NH).

(E)-2-[[3-(3,4-Dimethoxyphenyl)-1-oxo-2-propenyl]amino]-N-propargylbenzamide (15)

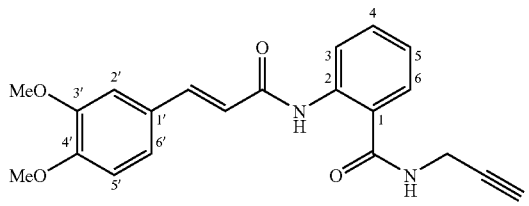 [SMILES: C#CCNC(=O)c1ccccc1NC(=O)/C=C/c1ccc(OC)c(OC)c1]

A suspension of (E)-3-(3,4-dimethoxyphenyl)-2-propenoic acid (0.85 g, 4.1 mmol) in toluene (8.5 mL) was treated with thionyl chloride (0.89 mL, 12 mmol) and catalytic DMF (1 drop). The solution was heated to reflux and stirred for 16 h and the solvent was removed under reduced pressure to give the acid chloride as a yellow solid. A solution of the acid chloride (4.1 mmol) in pyridine (6.0 mL) was added to a solution of 2-amino-N-2-propynyl-benzamide (0.74 g, 4.3 mmol) in pyridine (2.0 mL). The mixture was stirred at rt for 16 h, cooled to 0° C. and acidified with 1M NCl. The product was filtered, dried and recrystallised from acetonitrile providing (E)-[[3-(3,4-dimethoxyphenyl)-1-oxo-2-propenyl]amino]-N-propargylbenzene (1.05 g, 71%) as a colourless crystalline solid; mp 174-176° C.; $\delta_H$ (400 MHz, DMSO-d$_6$) 3.17 (t, J=2.4 Hz, 1H, C≡CH), 3.79 (s, 3H, OCH$_3$), 3.83 (s, 3H, OCH$_3$), 4.08 (dd, J=5.6, 2.4 Hz, 2H, CH$_2$), 6.76 (d, J=15.6 Hz, 1H, CH=CHCO), 6.98 (d, $J_{5',6'}=8.0$ Hz, 1H, H5'), 7.16 (t, $J_{3,4}=J_{4,5}=8.0$ Hz, 1H, H4), 7.23 (dd, $J_{5',6'}=8.0$, $J_{2',6'}=1.6$ Hz, 1H, H6'), 7.38 (d, $J_{2',6'}=1.6$ Hz, 1H, H2'), 7.52 (dt, $J_{4,5}=J_{5,6}=8.0$, $J_{3,5}=1.2$ Hz, 1H, H5), 7.75 (dd, $J_{3,4}=8.0$, $J_{3,5}=1.2$ Hz, 1H, H3), 8.55 (d, $J_{5,6}=8.0$ Hz, 1H, H6), 9.23 (t, J=5.6 Hz, 1H, NH), (s, 1H, NH); $\delta_C$ (100 MHz, DMSO-d$_6$) 28.6, 55.5, 55.6, 73.2, 80.8, 110.2, 111.5, 119.8, 120.1, 120.9, 122.7, 122.8, 127.3, 128.2, 132.2, 139.4, 141.6, 149.0, 150.6, 164.0, 168.1; HRMS (ESI) calculated for C$_{21}$H$_{20}$N$_2$O$_4$ [M+Na]$^+$ 387.1315. found 387.1316; $\nu_{max}$ 1017, 1265, 1447, 1512, 1584, 1600, 1659, 3043, 3329 cm$^{-1}$.

5-Bromo-2-[(carboxyacetyl)amino]benzoic acid

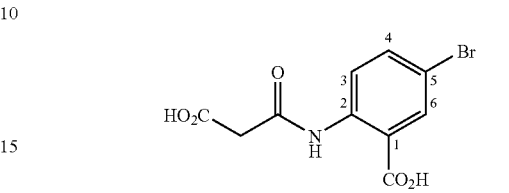

5-Bromoanthranilic acid (0.30 g, 1.4 mmol) was added to a solution of Meldrum's acid (0.24 g, 1.7 mmol) in toluene (5.0 mL) and treated according to Procedure 1. 5-Bromo-2-[(carboxyacetyl)amino]benzoic acid (0.34 mg, 81%) was obtained as a pale brown solid; $\delta_H$ (500 MHz, DMSO-d$_6$) 3.48 (s, 2H, CH$_2$), 7.78 (d, $J_{3,4}=8.4$ Hz, 1H, H4), 8.04 (s, 1H, H6), 8.40 (d, $J_{3,4}=8.4$ Hz, 1H, H3), 11.20 (s, 1H, NH), 12.80 (br s, 1H, CO$_2$H); $\delta_C$ (125 MHz, DMSO-d$_6$) 44.7, 114.5, 119.4, 122.5, 133.1, 136.4, 139.4, 164.7, 167.8, 168.9.

(E)-2-[[3-(3,4-Dimethoxyphenyl)-1-oxo-2-propenyl]amino]-5-bromobenzoic acid (16)

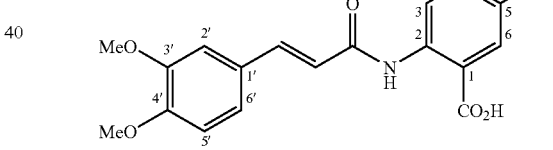

Piperidine (0.13 mL, 1.4 mmol) was added to a suspension of 3,4-dimethoxybenzaldehyde (0.22 g, 1.4 mmol) and 5-bromo-2-[(carboxyacetyl)amino]benzoic acid (0.34 g, 1.1 mmol) in toluene (4.0 mL) and treated according to Procedure 2, acidifying with 1 M HCl. (E)-2-[[3-(3,4-Dimethoxyphenyl)-1-oxo-2-propenyl]amino]-5-bromobenzoic acid (0.30 g, 66%) was obtained as a yellow crystalline solid; mp 210-213° C.; $\delta_H$ (400 MHz, DMSO-d$_6$) 3.79 (s, 3H, OCH$_3$), 3.82 (s, 3H, OCH$_3$), 6.78 (d, J=15.6 Hz, 1H, CH=CHCO), 6.98 (d, $J_{5',6'}=8.4$ Hz, 1H, H5'), 7.24 (d, $J_{5',6'}=8.4$ Hz, 1H, H6'), 7.36 (s, 1H, H2'), 7.56 (d, J=15.6 Hz, 1H, CH=CHCO), 7.78 (dd, $J_{3,4}=8.4$, $J_{4,6}=2.0$ Hz, 1H, H4), 8.06 (d, $J_{4,6}=2.0$ Hz, 1H, H6), 8.62 (d, $J_{3,4}=8.4$ Hz, 1H, H3), 11.30 (s, 1H, NH), 13.61 (br s, 1H, CO$_2$H); $\delta_C$ (100 MHz, DMSO-d$_6$) 28.6, 55.5, 55.6, 110.4, 111.6, 114.0, 119.5, 122.5, 122.7, 127.1, 133.1, 136.4, 140.2, 142.0, 149.0, 150.7, 164.2, 168.1; HRMS (ESI) calculated for $C_{13}H_{16}BrNO_5$ [M+Na]$^+$ 428.0104. found 428.0105; $v_{max}$ 1026, 1247, 1510, 1595, 1698, 2515, 2829, 3226, 3619 cm$^{-1}$.

4-Methoxy-3-propargyloxybenzaldehyde

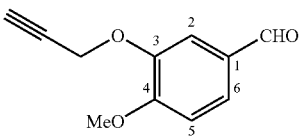

Propargyl bromide (2.90 mL, 80% w/v, 19.7 mmol) was added to a suspension of vanillin (2.00 g, 13.1 mmol) and potassium carbonate (5.46 g, 39.4 mmol) in acetone (20 mL) and treated according to Procedure 3. 4-Methoxy-3-propargyloxybenzaldehyde (2.01 g, 80%) was obtained as a colourless crystalline solid; mp 66-67° C.; $\delta_H$ (400 MHz, CDCl$_3$) 2.54 (t, J=2.4 Hz, 1H, C≡CH), 3.95 (s, 3H, OCH$_3$), 4.81 (d, J=2.4 Hz, 1H, OCH$_2$), 7.00 (d, J$_{5,6}$=8.4 Hz, 1H, H5), 7.50-7.53 (m, 2H, H2, H6), 9.85 (s, 1H, CHO); $\delta_C$ (100 MHz, CDCl$_3$) 56.1, 56.6, 76.4, 77.6, 110.9, 111.9, 127.3, 129.9, 147.3, 154.9, 190.6; HRMS (ESI) Calculated for $C_{11}H_{10}O_3$ [M+H]$^+$ 191.0703. found 191.0704; $v_{max}$ 1014, 1130, 1261, 1584, 1678, 2119, 2841, 2932, 3262 cm$^{-1}$.

(E)-2-[[3-(4-Methoxy-3-propargyloxyphenyl)-1-oxo-2-propenyl]amino]benzoic acid (17)

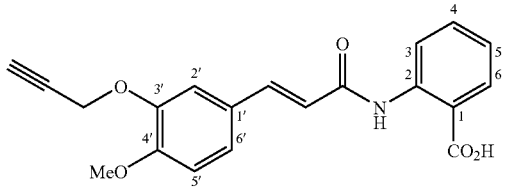 [SMILES: C#CCOc1cc(/C=C/C(=O)Nc2ccccc2C(=O)O)ccc1OC]

Piperidine (0.70 mL, 7.1 mmol) was added to a suspension of 4-methoxy-3-propargyloxybenzaldehyde (1.34 g, 7.06 mmol) and 2-[(carboxyacetyl)amino]benzoic acid (1.50 g, 6.72 mmol) in toluene (5.0 mL) and treated according to Procedure 2, acidifying with 20% AcOH. The crude product was recrystallised from EtOH, filtered and washed with cooled EtOH to afford (E)-2-[[3-(3-methoxy-4-(prop-2-ynyloxy)phenyl)-1-oxo-2-propenyl]amino]benzoic acid (1.50 g, 64%) as a yellow crystalline solid; mp 183-185° C.; $\delta_H$ (400 MHz, DMSO-d$_6$) 3.58 (t, J=2.0 Hz, 1H, HC≡C), 3.81 (s, 3H, OCH$_3$), 4.87 (d, J=2.0 Hz, 2H, OCH$_2$), 6.75 (d, J=15.6 Hz, 1H, CH=CHCO), 7.03 (d, J$_{5',6'}$=8.4 Hz, 1H, H5'), 7.16 (t, J$_{3,4}$=J$_{4,5}$=8.0 Hz, 1H, H4), 7.29 (d, J$_{5',6'}$=8.4 Hz, 1H, H6'), 7.44 (s, 1H, H2'), 7.54 (d, J=15.6 Hz, 1H, CH=CHCO), 7.60 (t, J$_{4,5}$=J$_{5,6}$=8.0 Hz, 1H, H5), 8.00 (d, J$_{3,4}$=8.0 Hz, 1H, H3), 8.61 (d, J$_{5,6}$=8.0 Hz, 1H, H6), 11.34 (s, 1H, NH), 13.60 (br s, 1H, CO$_2$H); $\delta_C$ (100 MHz, DMSO-d$_6$) 55.6, 56.1, 78.4, 79.2, 112.0, 112.6, 116.6, 120.0, 120.3, 122.7, 123.5, 127.0, 131.1, 134.0, 141.1, 141.5, 146.6, 151.0, 164.1, 169.5; HRMS (ESI) calculated for $C_{20}H_{17}NO_6$ [M+Na]$^+$ 374.0999. found 374.1002; $v_{max}$ 750, 1029, 1135, 1217, 1506, 1582, 1667, 3270, 3520 cm$^{-1}$.

3-Methoxy-4-(pent-2-ynyloxy)benzaldehyde

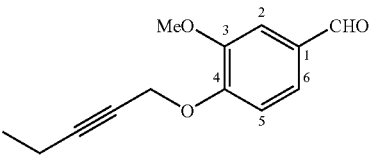 [SMILES: CCC#CCOc1ccc(C=O)cc1OC]

1-Bromopent-2-yne (0.67 mL, 6.6 mmol) was added to a suspension of vanillin (0.50 g, 3.3 mmol) and potassium carbonate (1.37 g, 9.85 mmol) in acetone (5.0 mL) and treated according to Procedure 3. 3-Methoxy-4-(pent-2-ynyloxy)benzaldehyde (0.60 g, 84%) was obtained as a yellow crystalline solid; mp 47-50° C.; $\delta_H$ (400 MHz, CDCl$_3$) 1.11 (t, J=7.6 Hz, 2H, CH$_2$CH$_3$), 2.20 (tq, J=7.6, 2.4 Hz, 3H, CH$_2$CH$_3$), 3.93 (s, 3H, OCH$_3$), 4.83 (t, J=2.4 Hz, 2H, OCH$_2$), 7.13 (d, J$_{5,6}$=8.0 Hz, 1H, H5), 7.42 (s, 1H, H2), 7.45 (d, J$_{5,6}$=8.0 Hz, H6), 9.86 (s, 1H, CHO); $\delta_C$ (100 MHz, CDCl$_3$) 12.5, 13.4, 56.0, 57.3, 73.1, 90.7, 109.2, 112.3, 126.4, 130.5, 149.9, 152.5, 190.9; $v_{max}$ 997, 1136, 1263, 1508, 1586, 1682, 2230, 2298, 2845, 2932 cm$^{-1}$.

(E)-2-[[3-(3-Methoxy-4-(pent-2-ynyloxy)phenyl)-1-oxo-2-propenyl]amino]benzoic acid (18)

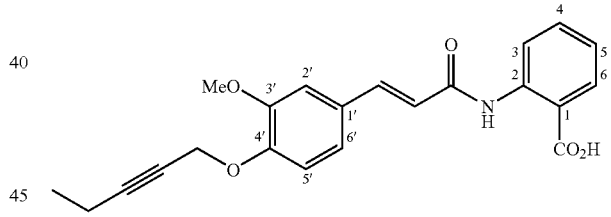

Piperidine (0.22 mL, 2.2 mmol) was added to a suspension of 3-methoxy-4-(pent-2-ynyl)oxybenzaldehyde (0.50 g, 2.3 mmol) and 2-[(carboxyacetyl)amino]benzoic acid (0.49 g, 2.2 mmol) in toluene (5.0 mL) and treated according to Procedure 2, acidifying with 20% AcOH. (E)-2-[[3-(3-Methoxy-4-(pent-2-ynyloxy)phenyl)-1-oxo-2-propenyl]amino]benzoic acid (0.50 g, 60%) was obtained as a colourless crystalline solid; mp 185.5-186.5° C.; $\delta_H$ (400 MHz, DMSO-d$_6$) 1.05 (t, J=7.4 Hz, 2H, CH$_2$CH$_3$), 2.20 (q, J=7.4 Hz, 3H, CH$_2$CH$_3$), 3.84 (s, 3H, OCH$_3$), 4.78 (s, 2H, OCH$_2$), 6.80 (d, J=15.6 Hz, 1H, CH=CHCO), 7.03 (d, J$_{5',6'}$=8.4 Hz, 1H, H5'), 7.16 (t, J$_{3,4}$=J$_{4,5}$ 8.0 Hz, 1H, H4), 7.24 (d, J$_{5',6'}$=8.4 Hz, 1H, H6'), 7.39 (s, 1H, H2'), 7.56 (d, J=15.6 Hz, 1H, CH=CHCO), 7.61 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.31 (s, 1H, NH), 13.53 (br s, 1H, CO$_2$H); $\delta_C$ (100 MHz, DMSO-d$_6$) 11.7, 13.5, 56.6, 56.4, 74.7, 89.3, 110.7, 113.3, 116.6, 120.2, 120.3, 122.2, 122.7, 127.9, 131.1, 134.0, 141.0, 141.5, 148.5, 149.2, 164.1, 169.5; HRMS (ESI) calculated for $C_{22}H_{21}NO_6$ [M+Na]$^+$ 402.1312. found 402.1317; $v_{max}$ 747, 1001, 1253, 1508, 1583, 1661, 2980, 3246, 3523 cm$^{-1}$.

4-Methoxy-3-(pent-2-ynyloxy)benzaldehyde

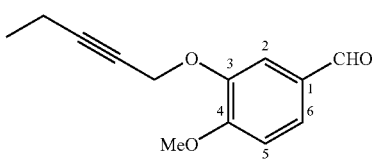 [SMILES: CCC#CCOc1cc(C=O)ccc1OC]

1-Bromopent-2-yne (0.67 mL, 6.6 mmol) was added to a suspension of vanillin (0.50 g, 3.3 mmol) and potassium carbonate (1.37 g, 9.85 mmol) in acetone (5.0 mL) and treated according to Procedure 3. 4-Methoxy-3-(pent-2-ynyloxy)benzaldehyde (0.69 g, 96%) was obtained as a yellow crystalline solid; mp 38-39° C.; $\delta_H$ (400 MHz, CDCl$_3$) 1.10 (t, J=7.6 Hz, 2H, CH$_2$CH$_3$), 2.20 (tq, J=7.6, 2.0 Hz, 3H, CH$_2$CH$_3$), 3.95 (s, 3H, OCH$_3$), 4.79 (t, J=2.0 Hz, 2H, OCH$_2$), 6.99 (d, $J_{5,6}$=8.0 Hz, 1H, H5), 7.49 (dd, $J_{5,6}$=8.0, $J_{2,6}$=2.0 Hz, 1H, H6), 7.54 (d, $J_{2,6}$=2.0 Hz, 1H, H2), 9.85 (s, 1H, CHO); $\delta_C$ (100 MHz, CDCl$_3$) 12.5, 13.5, 56.1, 57.3, 73.4, 90.5, 110.7, 111.8, 126.9, 129.9, 147.6, 154.8, 190.8; $v_{max}$ 1007, 1130, 1261, 1508, 1583, 1683, 2230, 2290, 2841, 2976 cm$^{-1}$.

(E)-2-[[3-(4-Methoxy-3-(pent-2-ynyloxy)phenyl)-1-oxo-2-propenyl]amino]benzoic acid (19)

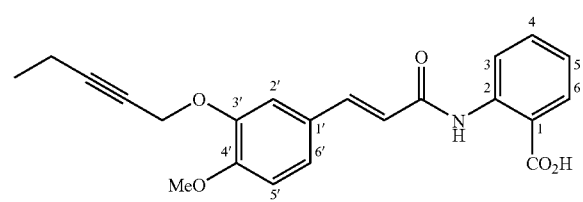 [SMILES: CCC#CCOc1cc(/C=C/C(=O)Nc2ccccc2C(=O)O)ccc1OC]

Piperidine (0.24 mL, 2.5 mmol) was added to a suspension of 4-methoxy-3-(pent-2-ynyl)oxybenzaldehyde (0.54 g, 2.5 mmol) and 2-[(carboxyacetyl)amino]benzoic acid (0.53 g, 2.4 mmol) in toluene (5.0 mL) and treated according to Procedure 2, acidifying with 20% AcOH. (E)-2-[[3-(4-Methoxy-3-(pent-2-ynyloxy)phenyl)-1-oxo-2-propenyl]amino]benzoic acid (0.50 g, 60%) was obtained as a yellow crystalline solid; mp 124-125° C.; $\delta_H$ (400 MHz, DMSO-d$_6$) 1.06 (t, J=7.4 Hz, 2H, CH$_2$CH$_3$), 2.23 (q, J=7.4 Hz, 3H, CH$_2$CH$_3$), 3.80 (s, 3H, OCH$_3$), 4.81 (s, 2H, OCH$_2$), 6.73 (d, J=15.6 Hz, 1H, CH=CHCO), 7.01 (d, $J_{5',6'}$=8.4 Hz, 1H, H5'), 7.16 (t, $J_{3,4}$=$J_{4,5}$=8.0 Hz, 1H, H4), 7.28 (dd, $J_{5',6'}$=8.4, $J_{2',6'}$=1.6 Hz, 1H, H6'), 7.42 (d, $J_{2',6'}$=1.6 Hz, 1H, H2'), 7.57 (d, J=15.6 Hz, 1H, CH=CHCO), 7.61 (t, $J_{4,5}$=$J_{5,6}$=8.0 Hz, 1H, H5), 8.00 (d, $J_{3,4}$=8.0 Hz, 1H, H3), 8.62 (d, $J_{5,6}$=8.0 Hz, 1H, H6), 11.31 (s, 1H, NH), 13.59 (br s, 1H, CO$_2$H); $\delta_C$ (100 MHz, DMSO-d$_6$) 11.7, 13.6, 55.6, 56.6, 74.9, 89.3, 111.9, 112.5, 116.5, 119.9, 120.3, 122.7, 123.3, 127.0, 131.1, 134.0, 141.1, 141.6, 146.8, 151.0, 164.1, 169.5; HRMS (ESI) calculated for C$_{22}$H$_{21}$NO$_6$ [M+Na]$^+$ 402.1312. found 402.1317; $v_{max}$ 753, 1015, 1257, 1506, 1584, 1659, 2920, 3246, 3520 cm$^{-1}$.

(E)-2-[[3-(3-Methoxy-4-((1-(2-oxo-2-(phenylamino)ethyl)-1H-1,2,3-triazol-4-yl)methoxy)phenyl)-1-oxo-2-propenyl]amino]benzoic acid (20)

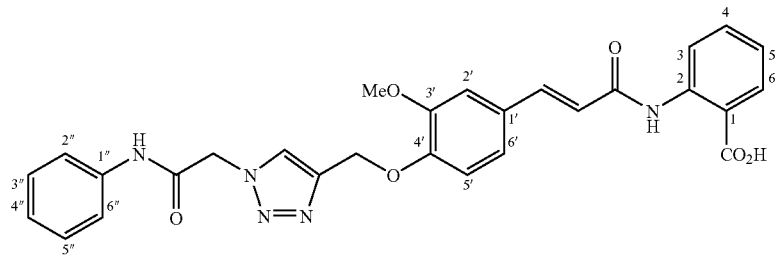 [SMILES: COc1cc(/C=C/C(=O)Nc2ccccc2C(=O)O)ccc1OCc1cn(CC(=O)Nc2ccccc2)nn1]

Sodium ascorbate (28 mg, 140 μmol), tris-(benzyltriazolylmethyl)amine (15 mg, 28 μmol) and copper sulfate (4.5 mg, 28 μmol) were added to a solution of (E)-2-[[3-(3-methoxy-4-propargyloxyphenyl)-1-oxo-2-propenyl]amino]benzoic acid (0.50 g, 1.4 mmol) and 2-azido-N-phenylacetamide (0.25 g, 1.4 mmol) in DMSO (20 mL) and water (5.0 mL). The solution was stirred at rt for 16 h and diluted with water. The suspension was filtered and the filter cake was washed with water and dried. The crude product was recrystallised from acetonitrile to afford (E)-2-[[3-(3-methoxy-4-((1-(2-oxo-2-(phenylamino)ethyl)-1H-1,2,3-triazol-4-yl)methoxy)phenyl)-1-oxo-2-propenyl]amino]benzoic acid (0.60 g, 80%) as a colourless solid; mp 220-222° C.; $\delta_H$ (400 MHz, DMSO-d$_6$) 3.82 (s, 3H, OCH$_3$), 5.21 (s, 2H, CH$_2$), 5.36 (s, 2H, CH$_2$), 6.80 (d, J=15.6 Hz, 1H, CH=CHCO), 7.08 (t, J=8.0 Hz, 1H, H4"), 7.16 (t, $J_{3,4}$=$J_{4,5}$=8.0 Hz, 1H, H4), 7.21-7.28 (m, 2H, H6', H5'), 7.39 (s, 1H, H2'), 7.31 (t, $J_{2",3"}$=$J_{3",4"}$=$J_{4",5"}$=$J_{5",6"}$=8.0 Hz, 2H, H3", H5"), 7.56-7.63 (m, 4H, CH=CHCO, H5, H2", H6"), 8.00 (d, $J_{3,4}$=8.0 Hz, 1H, H3), 8.27 (s, 1H, C=CHN), 8.62 (d, $J_{5,6}$=8.0 Hz, 1H, H6), 10.48 (s, 1H, NH), 11.30 (s, 1H, NH), 13.60 (br s, 1H, CO$_2$H); $\delta_C$ (100 MHz, DMSO-d$_6$) 52.2, 55.6, 61.4, 110.5, 112.9, 116.6, 119.2, 120.1, 120.4, 122.6, 122.8, 123.8, 126.6, 127.6, 129.0, 131.2, 134.1, 138.5, 141.1, 141.7, 142.2, 149.1, 149.4, 164.2, 169.5; HRMS (ESI) calculated for C$_{28}$H$_{25}$N$_5$O$_6$ [M+Na]$^+$ 550.1697. found 550.1691; $v_{max}$ 1239, 1585, 1665, 2605, 3000, 3250 cm$^{-1}$.

(E)-2-[[3-(4-Methoxy-3-((1-(2-oxo-2-(phenylamino)ethyl)-1H-1,2,3-triazol-4-yl)methoxy)phenyl)-1-oxo-2-propenyl]amino]benzoic acid (21)

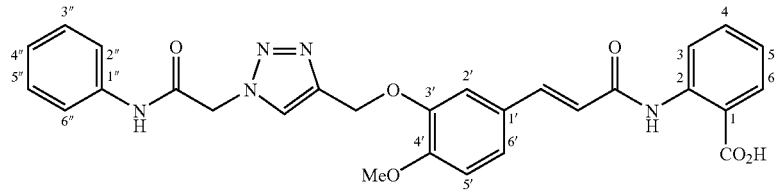 [SMILES: COc1ccc(/C=C/C(=O)Nc2ccccc2C(=O)O)cc1OCc1cn(CC(=O)Nc2ccccc2)nn1]

Sodium ascorbate (22 mg, 110 μmol), tris-(benzyltriazolylmethyl)amine (12 mg, 23 μmol) and copper sulfate (3.6 mg, 22 μmol) were added to a solution of (E)-2-[[3-(4-methoxy-3-propargyloxyphenyl)-1-oxo-2-propenyl]amino]benzoic acid (0.40 g, 1.1 mmol) and 2-azido-N-phenylacetamide (0.20 g, 1.1 mmol) in DMSO (16 mL) and water (4.0 mL). The solution was stirred at rt for 16 h and diluted with water. The suspension was filtered and the filter cake was washed with water and dried. The crude product was recrystallised from AcOH to afford (E)-2-[[3-(3-methoxy-4-((1-(2-oxo-2-(phenylamino)ethyl)-1H-1,2,3-triazol-4-yl)methoxy)phenyl)-1-oxo-2-propenyl]amino]benzoic acid (0.60 g, 80%) as a yellow solid; mp 253-255° C.; $\delta_H$ (400 MHz, DMSO-$d_6$) 3.79 (s, 3H, OCH$_3$), 5.25 (s, 2H, CH$_2$), 5.37 (s, 2H, CH$_2$), 6.82 (d, J=15.6 Hz, 1H, CH=CHCO), 7.01 (t, $J_{5',6'}$=8.0 Hz, 1H, H5'), 7.05 (t, $J_{3'',4''}=J_{4'',5''}$=8.0 Hz, 1H, H4''), 7.16 (t, $J_{3,4}=J_{4,5}$=8.0 Hz, 1H, H4), 7.27-7.34 (m, 3H, H2', H6', H3'', H5''), 7.57-7.62 (m, 4H, CH=CHCO, H5, H2'', H6''), 8.00 (d, $J_{3,4}$=8.0 Hz, 1H, H3), 8.29 (s, 1H, C=CHN), 8.64 (d, $J_{5,6}$=8.0 Hz, 1H, H6), 10.48 (s, 1H, NH), 11.32 (s, 1H, NH), 13.50 (br s, 1H, CO$_2$H); $\delta_C$ (100 MHz, DMSO-$d_6$) 52.2, 55.5, 61.6, 111.8, 112.0, 116.5, 119.2, 120.0, 120.3, 122.7, 123.1, 123.8, 126.5, 127.2, 128.9, 131.2, 134.0, 138.4, 141.1, 141.7, 142.4, 147.7, 150.8, 164.2, 169.5; HRMS (ESI) calculated for C$_{28}$H$_{25}$N$_5$O$_6$ [M+Na]$^+$ 550.1697. found 550.1702; $v_{max}$ 1259, 1580, 1667, 2599, 3952, 3345 cm$^{-1}$.

4-(But-2-ynyloxy)-3-methoxybenzaldehyde

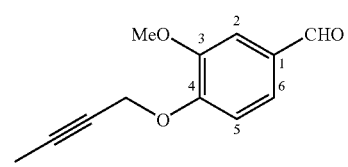

1-Bromobut-2-yne (0.36 mL, 4.0 mmol) was added to a suspension of vanillin (0.55 g, 3.6 mmol) and potassium carbonate (1.79 g, 10.9 mmol) in acetone (10 mL) and treated according to Procedure 3. 4-(But-2-ynyloxy)-3-methoxybenzaldehyde (0.70 g, 95%) was obtained as a pale yellow crystalline solid; mp 90-92° C.; $\delta_H$ (400 MHz, CDCl$_3$) 1.84 (t, J=2.2 Hz, 3H, CH$_3$), 3.93 (s, 3H, OCH$_3$), 4.81 (q, J=2.2 Hz, 2H, OCH$_2$), 7.12 (d, $J_{5,6}$=8.4 Hz, 1H, H5), 7.42 (d, $J_{2,6}$=2.0 Hz, 1H, H2), 7.45 (dd, $J_{5,6}$=8.4, $J_{2,6}$=2.0 Hz, 1H, H6), 9.86 (s, 1H, CHO); $\delta_C$ (100 MHz, CDCl$_3$) 4.0, 56.2, 57.5, 73.2, 85.2, 109.4, 112.4, 126.7, 130.7, 150.1, 152.7, 191.2; $v_{max}$ 991, 1259, 1504, 1586, 1679, 2226, 2302, 2833, 2921 cm$^{-1}$.

(E)-2-{[3-(4-(But-2-ynyloxy)-3-methoxyphenyl)-1-oxo-2-propenyl]amino}benzoic acid (22)

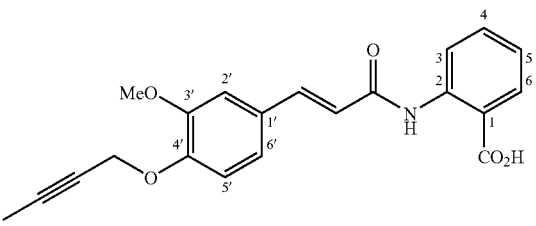 [SMILES: CC#CCOc1ccc(/C=C/C(=O)Nc2ccccc2C(=O)O)cc1OC]

Piperidine (0.34 mL, 3.4 mmol) was added to a suspension of 4-(but-2-ynyloxy)-3-methoxybenzaldehyde (0.70 g, 3.4 mmol) and 2-[(carboxyacetyl)amino]benzoic acid (0.70 g, 3.4 mmol) in toluene (10 mL) and treated according to Procedure 2, acidifying with 20% AcOH. (E)-2-{[3-(4-(But-2-ynyloxy)-3-methoxyphenyl)-1-oxo-2-propenyl]amino}benzoic acid (0.70 g, 61%) was obtained as a yellow crystalline solid; mp 194-195° C.; $\delta_H$ (400 MHz, DMSO-$d_6$) 1.82 (s, 3H, CH$_3$), 3.83 (s, 3H, OCH$_3$), 4.77 (s, 2H, OCH$_2$), 6.79 (d, J=15.6 Hz, 1H, CH=CHCO), 7.02 (d, $J_{5',6'}$=8.4 Hz, 1H, H5'), 7.14 (t, $J_{3,4}=J_{4,5}$=8.0 Hz, 1H, H4), 7.23 (d, $J_{5',6'}$=8.4 Hz, 1H, H6'), 7.38 (s, 1H, H2'), 7.55 (d, J=15.6 Hz, 1H, CH=CHCO), 7.60 (t, $J_{4,5}=J_{5,6}$=8.0 Hz, 1H, H5), 8.00 (d, $J_{3,4}$=8.0 Hz, 1H, H3), 8.61 (d, $J_{5,6}$=8.0 Hz, 1H, H6), 11.33 (s, 1H, NH), 13.59 (br s, 1H, CO$_2$H); $\delta_C$ (100 MHz, DMSO-$d_6$) 3.2, 55.7, 56.4, 74.6, 83.9, 110.7, 113.3, 116.8, 120.3, 120.4, 122.3, 122.8, 127.9, 131.2, 134.0, 141.1, 141.6, 148.6, 149.3, 164.2, 169.5; HRMS (ESI) calculated for C$_{21}$H$_{19}$NO$_6$ [M+Na]$^+$ 388.1155. found 388.1158; $v_{max}$ 753, 1253, 1506, 1584, 1659, 2917, 3239, 3516 cm$^{-1}$.

3-(But-2-ynyloxy)-4-methoxybenzaldehyde

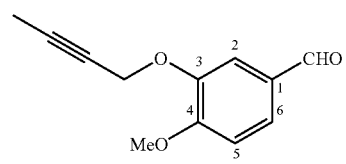

1-Bromobut-2-yne (0.37 mL, 4.0 mmol) was added to a suspension of vanillin (0.56 g, 3.7 mmol) and potassium carbonate (1.82 g, 11.0 mmol) in acetone (10 mL) and treated according to Procedure 3. 3-(But-2-ynyloxy)-4-methoxybenzaldehyde (0.72 g, 96%) was obtained as a pale yellow crystalline solid; mp 81-83° C.; $\delta_H$ (400 MHz, CDCl$_3$) 1.84 (t, J=2.0 Hz, 3H, CH$_3$), 3.95 (s, 3H, OCH$_3$), 4.77 (q, J=2.0 Hz, 2H, OCH$_2$), 6.99 (d, $J_{5,6}$=8.0 Hz, 1H, H5), 7.49 (dd, $J_{5,6}$=8.4, $J_{2,6}$=2.0 Hz, 1H, H6), 7.51 (d, $J_{2,6}$=2.0 Hz, 1H, H2), 9.86 (s, 1H, CHO); $\delta_C$ (100 MHz, CDCl$_3$) 3.7, 56.1, 57.1, 73.2, 84.7, 110.6, 111.4, 126.9, 129.9, 147.6, 154.8, 190.8; $v_{max}$ 1003, 1259, 1506, 1583, 1681, 2226, 2297, 2841, 2916 cm$^{-1}$.

(E)-2-{[3-(3-(But-2-ynyloxy)-4-methoxyphenyl)-1-oxo-2-propenyl]amino}benzoic acid (23)

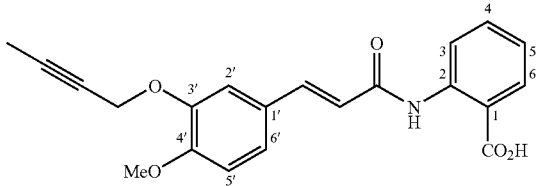 [SMILES: CC#CCOc1cc(/C=C/C(=O)Nc2ccccc2C(=O)O)ccc1OC]

Piperidine (0.35 mL, 3.5 mmol) was added to a suspension of 4-methoxy-3-(but-2-ynyl)oxybenzaldehyde (0.72 g, 3.5 mmol) and 2-[(carboxyacetyl)amino]benzoic acid (0.72 g, 3.2 mmol) in toluene (10 mL) and treated according to Procedure 2, acidifying with 20% AcOH. (E)-2-{[3-(3-(But-2-ynyloxy)-4-methoxyphenyl)-1-oxo-2-propenyl]amino}benzoic acid (0.81 g, 69%) was obtained as a yellow crystalline solid; mp 170-171° C.; $\delta_H$ (400 MHz, DMSO-d$_6$) 1.82 (t, J=2.0 Hz, 3H, CH$_3$), 3.80 (s, 3H, OCH$_3$), 4.80 (d, J=2.0 Hz, 2H, OCH$_2$), 6.74 (d, J=15.6 Hz, 1H, CH=CHCO), 7.00 (d, 8.4 Hz, 1H, H5'), 7.16 (t, $J_{3,4}$=$J_{4,5}$=8.0 Hz, 1H, H4), 7.27 (d, $J_{5',6'}$=8.4 Hz, 1H, H6'), 7.40 (s, 1H, H2'), 7.54 (d, J=15.6 Hz, 1H, CH=CHCO), 7.61 (t, $J_{4,5}$=$J_{5,6}$=8.0 Hz, 1H, H5), 8.00 (d, $J_{3,4}$=8.0 Hz, 1H, H3), 8.61 (d, $J_{5,6}$=8.0 Hz, 1H, H6), 11.31 (s, 1H, NH), 13.57 (br s, 1H, CO$_2$H); $\delta_C$ (100 MHz DMSO-d$_6$) 3.2, 55.6, 56.5, 74.7, 83.7, 111.9, 112.3, 116.6, 120.0, 120.3, 122.7, 123.2, 127.1, 131.2, 134.1, 141.1, 141.6, 146.9, 151.0, 164.1, 169.5; HRMS (ESI) calculated for C$_{21}$H$_{19}$NO$_5$ [M+Na]$^+$ 388.1155. found 388.12158; $v_{max}$ 749, 1261, 1512, 1584, 1659, 2917, 3239, 3520 cm$^{-1}$.

4-Cyclopentyloxy-3-methoxybenzaldehyde

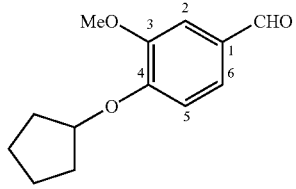 [SMILES: COc1cc(C=O)ccc1OC1CCCC1]

Bromocyclopentane (7.0 mL, 66 mmol) was added to a suspension of vanillin (5.0 g, 33 mmol) and potassium carbonate (13.6 g, 99 mmol) in EtOH (75 mL) and treated according to Procedure 3. 4-Cyclopentyloxy-3-methoxybenzaldehyde (7.1 g, 98%) was obtained as a yellow oil; $\delta_H$ (400 MHz, CDCl$_3$) 1.62 (m, 2H, CH$_2$), 1.78-2.04 (m, 6H, CH$_2$), 3.89 (s, 3H, OCH$_3$), 4.86 (tt, J=6.0, 3.2 Hz, 1H, OCH), 6.94 (d, $J_{5,6}$=8.0 Hz, 1H, H5), 7.38 (d, $J_{2,6}$=2.0 Hz, 1H, H2), 7.41 (dd, $J_{5,6}$=8.0, $J_{2,6}$=2.0 Hz, 1H, H6), 9.82 (s, 1H, CHO); $\delta_C$ (100 MHz, CDCl$_3$) 24.1, 32.8, 56.0, 80.6, 109.4, 112.8, 126.6, 129.5, 150.2, 153.4, 190.9; $v_{max}$ 977, 1260, 1504, 1580, 1680, 2869, 2956 cm$^{-1}$.

(E)-2-{[3-(4-Cyclopentyloxy-3-methoxyphenyl)-1-oxo-2-propenyl]amino}benzoic acid (26)

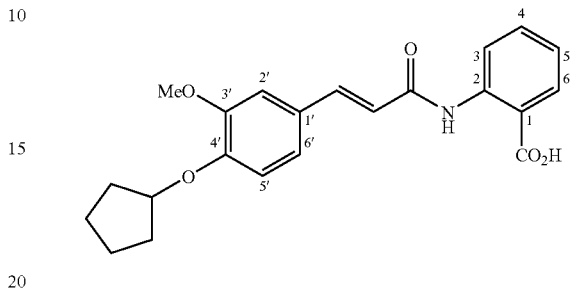

Piperidine (0.45 mL, 4.5 mmol) was added to a suspension of 4-cyclopentyloxy-3-methoxybenzaldehyde (1.0 g, 4.5 mmol) and 2-[(carboxyacetyl)amino]benzoic acid (0.92 g, 4.1 mmol) in toluene (5.0 mL) and treated according to Procedure 2, acidifying with 1 M HCl. The crude product was recrystallised from EtOH/water providing (E)-2-{[3-(4-cyclopentyloxy-3-methoxyphenyl)-1-oxo-2-propenyl]amino}benzoic acid (1.06 g, 67%) as a pale yellow crystalline solid; mp 96-98° C.; $\delta_H$ (400 MHz, DMSO-d$_6$) 1.46 (m, 2H, CH$_2$), 1.67-1.71 (m, 4H, CH$_2$), 1.90 (m, 2H, CH$_2$), 3.81 (s, 3H, OCH$_3$), 4.82 (t, J=5.6 Hz, 1H, OCH), 6.76 (d, J=15.6 Hz, 1H, CH=CHCO), 6.94 (d, $J_{5',6'}$=8.4 Hz, 1H, H5'), 7.15 (t, $J_{3,4}$=$J_{4,5}$=8.0 Hz, 1H, H4), 7.19 (dd, $J_{5',6'}$=8.4, $J_{5',6'}$=1.6 Hz, 1H, H6'), 7.35 (d, $J_{2',6'}$=1.6 Hz, 1H, H2'), 7.54 (d, J=15.6 Hz, 1H, CH=CHCO), 7.60 (t, $J_{4,5}$=$J_{5,6}$=8.0 Hz, 1H, H5), 8.00 (d, $J_{3,4}$=8.0 HZ, 1H, H3), 8.62 (d, $J_{5,6}$=8.0 Hz, 1H, H6), 11.28 (s, 1H, NH), 13.59 (br s, 1H, CO$_2$H); $\delta_C$ (100 MHz, DMSO-d$_6$) 23.7, 32.3, 55.7, 79.5, 110.9, 114.0, 116.5, 119.7, 120.3, 122.5, 122.6, 127.0, 131.1, 134.0, 141.1, 141.7, 149.0, 149.6, 164.2, 169.5; HRMS (ESI) calculated for C$_{22}$H$_{23}$NO$_5$ [M+Na]$^+$ 404.1468. found 404.1468; $v_{max}$ 747, 1261, 1506, 1584, 1659, 2964, 3524 cm$^{-1}$.

4-Cyclohexyloxy-3-methoxybenzaldehyde

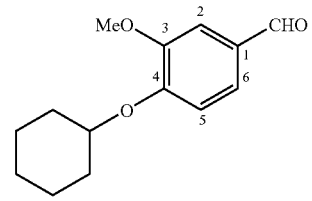 [SMILES: COc1cc(C=O)ccc1OC1CCCCC1]

Bromocyclohexane (8.0 mL, 66 mmol) was added to a suspension of vanillin (5.0 g, 33 mmol), potassium carbonate (13.6 g, 99 mmol) and sodium iodide (0.49 g, 3.3 mmol) in EtOH (75 mL) and treated according to Procedure 3 for 64 h. The crude product was purified by flash chromatography with 10-15% EtOAc/petrol as eluent to give 4-cyclohexyloxy-3-methoxybenzaldehyde (2.8 g, 37%) as a pale yellow oil; $\delta_H$ (400 MHz, CDCl$_3$) 1.27-1.43 (m, 4H, CH$_2$), 1.56 (m, 2H, CH$_2$), 1.85 (m, 2H, CH$_2$), 2.06 (m, 2H, CH$_2$), 3.91 (s, 3H, OCH$_3$), 4.37 (tt, J=9.4, 3.6 Hz, 1H, OCH), 6.98 (d, $J_{5,6}$=8.0 Hz, 1H, H5), 7.40 (d, $J_{2,6}$=2.0 Hz, 1H, H2), 7.42 (dd, $J_{5,6}$=8.0, $J_{2,6}$=2.0 Hz, 1H, H6), 9.83 (s, 1H, CHO); $\delta_C$ (100 MHz, CDCl$_3$) 23.9, 25.4, 31.6, 56.0, 76.9, 109.8, 113.2, 126.5, 129.7, 150.5, 153.0, 190.8; $v_{max}$ 1133, 1263, 1504, 1581, 1680, 2857, 2933 cm$^{-1}$.

(E)-2-{[3-(4-Cyclohexyloxy-3-methoxyphenyl)-1-oxo-2-propenyl]amino}benzoic acid (27)

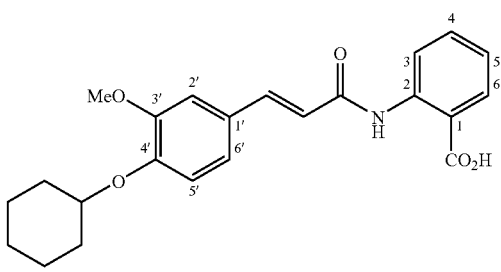 [SMILES: COc1cc(/C=C/C(=O)Nc2ccccc2C(=O)O)ccc1OC1CCCCC1]

Piperidine (0.45 mL, 4.5 mmol) was added to a suspension of 4-cyclohexyloxy-3-methoxybenzaldehyde (1.06 g, 4.54 mmol) and 2-[(carboxyacetyl)amino]benzoic acid (0.92 g, 4.1 mmol) in toluene (5.0 mL) and treated according to Procedure 2, acidifying with 1 M HCl. The crude product was recystallised from EtOH/water providing (E)-2-{[3-(4-cyclohexyloxy-3-methoxyphenyl)-1-oxo-2-propenyl] amino}benzoic acid (0.98 g, 60%) as a colourless crystalline solid; mp 90-92° C.; $\delta_H$ (400 MHz, DMSO-d$_6$) 1.25-1.52 (m, 6H, CH$_2$), 1.70 (m, 2H, CH$_2$), 1.89 (m, 2H, CH$_2$), 3.82 (s, 3H, OCH$_3$), 4.33 (m, 1H, OCH), 6.76 (d, J=15.6 Hz, 1H, CH=CHCO), 6.99 (d, $J_{5',6'}$=8.4 Hz, 1H, H5'), 7.15 (t, = $J_{3,4}$=$J_{4,6}$=8.0 Hz, 1H, H4), 7.19 (d, $J_{5,6}$=8.4 Hz, 1H, H6'), 7.35 (s, 1H, H2'), 7.55 (d, J=15.6 Hz, 1H, CH=CHCO), 7.60 (t, $J_{4,5}$=$J_{5,6}$=8.0 Hz, 1H, H5), 8.00 (d, $J_{3,4}$=8.0 Hz, 1H, H3), 8.62 (d, $J_{5,6}$=8.0 Hz, 1H, H6), 11.29 (s, 1H, NH), 13.56 (br s, 1H, CO$_2$H); $\delta_C$ (100 MHz, DMSO-d$_6$) 23.2, 25.1, 31.4, 55.7, 79.4, 111.2, 114.8, 116.6, 119.8, 120.3, 122.4, 122.6, 127.3, 131.1, 134.0, 141.1, 141.6, 148.6, 150.0, 164.2, 169.5; HRMS (ESI) calculated for C$_{23}$H$_{25}$NO$_5$ [M+Na]$^+$ 418.1625. found 418.1625; $v_{max}$ 745, 1259, 1504, 1588, 1659, 2929, 3520 cm$^{-1}$.

4-Cyclohexylmethoxy-3-methoxybenzaldehyde

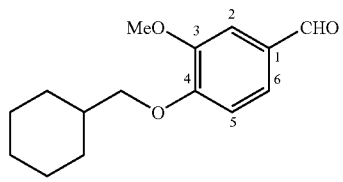 [SMILES: COc1cc(C=O)ccc1OCC1CCCCC1]

Bromomethylcyclohexane (0.78 mL, 4.2 mmol) was added to a suspension of vanillin (0.43 g, 2.8 mmol) and potassium carbonate (1.17 g, 8.47 mmol) in EtOH (7.0 mL) and treated according to Procedure 3 for 64 h. 4-Cyclohexylmethoxy-3-methoxybenzaldehyde (0.65 g, 93%) was obtained as a yellow oil; $\delta_H$ (400 MHz, CDCl$_3$) 1.05 (m, 2H, CH$_2$), 1.15-1.36 (m, 4H, CH$_2$), 1.73 (m, 2H, CH$_2$), 1.87-1.98 (m, 2H, CH$_2$, CH), 3.88 (d, J=6.0 Hz, 2H, OCH$_2$), 3.92 (s, 3H, OCH$_3$), 6.95 (d, $J_{5,6}$=8.0 Hz, 1H, H5), 7.40 (d, $J_{2,6}$=2.0 Hz, 1H, H2), 7.42 (dd, $J_{5,6}$=8.0, $J_{2,6}$=2.0 Hz, 1H, H6), 9.84 (s, 1H, CHO); $\delta_C$ (100 MHz, CDCl$_3$) 25.6, 26.4, 29.8, 37.3, 56.1, 74.5, 109.3, 111.4, 126.8, 129.8, 149.9, 154.4, 190.9; $v_{max}$ 1133, 1265, 1508, 1586, 1683, 2853, 2925 cm$^{-1}$.

(E)-2-{[3-(4-Cyclohexylmethoxy-3-methoxyphenyl)-1-oxo-2-propenyl]amino}benzoic acid (28)

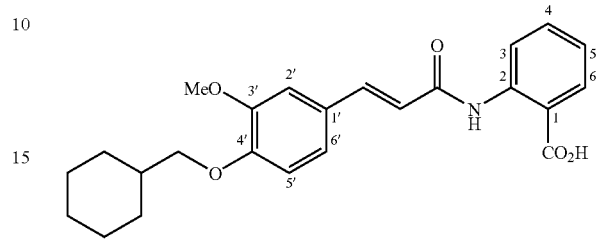

Piperidine (0.24 mL, 2.4 mmol) was added to a suspension of 4-cyclohexylmethoxy-3-methoxybenzaldehyde (0.59 g, 2.4 mmol) and 2-[(carboxyacetyl)amino]benzoic acid (0.48 g, 2.1 mmol) in toluene (5.0 mL) and treated according to Procedure 2, acidifying with 1 M HCl. The crude product was recystallised from EtOH/water providing (E)-2-{[3-(4-cyclohexylmethoxy-3-methoxyphenyl)-1-oxo-2-propenyl] amino}benzoic acid (0.45 g, 51%) as a colourless crystalline solid; mp 207-210° C.; $\delta_H$ (400 MHz, DMSO-d$_6$) 1.03 (m, 2H, CH$_2$), 1.20 (m, 4H, CH$_2$), 1.63-1.82 (m, 5H, CH$_2$, CH), 3.79 (d, J=6.4 Hz, 1H, OCH$_2$), 3.83 (s, 3H, OCH$_3$), 6.76 (d, J=15.6 Hz, 1H, CH=CHCO), 6.96 (d, $J_{5',6'}$=8.4 Hz, 1H, H5'), 7.18 (t, $J_{3,4}$=$J_{4,5}$=8.0 Hz, 1H, H4), 7.21 (d, $J_{5',6'}$=8.4 Hz, $J_{2',6'}$=1.8 Hz, 1H, H6'), 7.36 (s, $J_{2',6'}$=1.8 Hz, 1H, H2'), 7.55 (d, J=15.6 Hz, 1H, CH=CHCO), 7.62 (t, $J_{4,5}$=$J_{5,6}$=8.0 Hz, 1H, H5), 8.00 (d, $J_{3,4}$=8.0 Hz, 1H, H3), 8.62 (d, $J_{5,6}$=8.0 Hz, 1H, H6), 11.27 (s, 1H, NH), 13.58 (br s, 1H, CO$_2$H); $\delta_C$ (100 MHz, DMSO-d$_6$) 25.2, 26.0, 29.2, 37.0, 55.8, 73.3, 110.7, 112.6, 116.6, 119.7, 120.3, 122.6, 127.1, 131.1, 134.0, 141.0, 141.6, 149.1, 150.2, 164.2, 169.4; HRMS (ESI) calculated for C$_{23}$H$_{25}$NO$_5$ [M+Na]$^+$ 432.1781. found 432.1781; $v_{max}$ 759, 1142, 1504, 1581, 1667, 2925, 3123 cm$^{-1}$.

3-Cyclopentyloxy-4-methoxybenzaldehyde

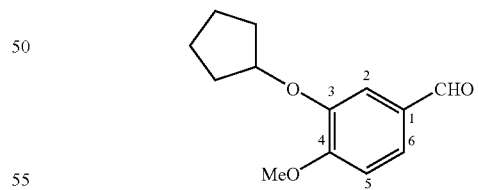

Bromocyclopentane (1.4 mL, 13 mmol) was added to a suspension of isovanillin (1.0 g, 6.6 mmol) and potassium carbonate (2.7 g, 10 mmol) in EtOH (15 mL) and treated according to Procedure 3. 3-Cyclopentyloxy-4-methoxybenzaldehyde (1.4 g, 97%) was obtained as a yellow oil; $\delta_H$ (400 MHz, CDCl$_3$) 1.63 (m, 2H, CH$_2$), 1.79-1.93 (m, 4H, CH$_2$), 1.99 (m, 2H, CH$_2$), 3.93 (s, 3H, OCH$_3$), 4.85 (tt, J=6.4, 3.2 Hz, 1H, OCH), 6.96 (d, $J_{5,6}$=8.0 Hz, 1H, H5), 7.39 (d, $J_{2,6}$=2.0 Hz, 1H, H2), 7.42 (dd, $J_{5,6}$=8.0, $J_{2,6}$=2.0 Hz, 1H, H6), 9.84 (s, 1H, CHO); $\delta_C$ (100 MHz, CDCl$_3$) 24.1, 32.7, 56.1, 80.5, 110.7, 112.1, 126.3, 130.0, 148.2, 155.4, 191.0; $v_{max}$ 1001, 1132, 1261, 1431, 1508, 1584, 1683, 2956 cm$^{-1}$.

(E)-2-{[3-(3-Cyclopentyloxy-4-methoxyphenyl)-1-oxo-2-propenyl]amino}benzoic acid (29)

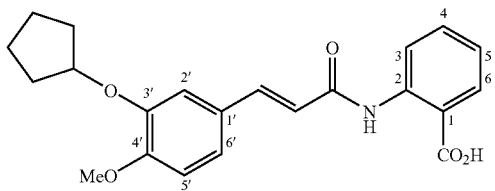 [SMILES: COc1ccc(/C=C/C(=O)Nc2ccccc2C(=O)O)cc1OC1CCCC1]

Piperidine (0.63 mL, 5.8 mmol) was added to a suspension of 3-cyclopentyloxy-4-methoxybenzaldehyde (1.4 g, 6.4 mmol) and 2-[(carboxyacetyl)amino]benzoic acid (1.3 g, 5.8 mmol) in toluene (5.0 mL) and treated according to Procedure 2, acidifying with 1 M HCl. The crude product was recrystallised from EtOH/water providing (E)-2-{[3-(3-cyclopentyloxy-4-methoxyphenyl)-1-oxo-2-propenyl]amino}benzoic acid (1.4 g, 67%) as a yellow crystalline solid; mp 211-217° C.; $\delta_H$ (400 MHz, DMSO-d$_6$) 1.57 (m, 2H, CH$_2$), 1.70-1.72 (m, 4H, CH$_2$), 1.91 (m, 2H, CH$_2$), 3.78 (s, 3H, OCH$_3$), 4.90 (t, J=5.6 Hz, 1H, OCH), 6.75 (d, J=15.6 Hz, 1H, CH=CHCO), 6.98 (d, $J_{5',6'}$=8.4 Hz, 1H, H5'), 7.16 (t, $J_{3,4}=J_{4,5}$=8.0 Hz, 1H, H4), 7.24 (d, $J_{5',6'}$=8.4 Hz, 1H, Fe), 7.31 (s, 1H, H2'), 7.55 (d, J=15.6 Hz, 1H, CH=CHCO), 7.60 (t, $J_{4,5}=J_{5,6}$=8.0 Hz, 1H, H5), 8.00 (d, $J_{3,4}$=8.0 Hz, 1H, H3), 8.60 (d, $J_{5,6}$=8.0 Hz, 1H, H6), 11.25 (s, 1H, NH), 13.57 (br s, 1H, CO$_2$H); $\delta_C$ (100 MHz, DMSO-d$_6$) 23.6, 32.2, 55.6, 79.5, 112.0, 113.6, 116.7, 119.9, 120.4, 122.2, 122.7, 127.2, 131.1, 134.0, 141.0, 141.6, 147.1, 151.5, 164.2, 169.4; HRMS (ESI) calculated for C$_{22}$H$_{23}$NO$_5$ [M+Na]$^+$ 404.1468. found 404.1468; $v_{max}$ 751, 1254, 1504, 1583, 1661, 2948, 3516 cm$^{-1}$.

(E)-2-(3-(3,4-Dimethoxyphenyl)acrylamido)-N-((1-(2-oxo-2-(phenylamino)ethyl)-1H-1,2,3-triazol-4-yl)methyl)benzamide (32)

Sodium ascorbate (5.4 mg, 27 μmol), tris-(benzyltriazolylmethyl)amine (2.9 mg, 5.5 μmol) and copper sulfate (0.88 mg, 5.5 μmol) were added to a solution of (E)-2-[[3-(3,4-dimethoxyphenyl)-1-oxo-2-propenyl]amino]-N-(prop-2-ynyl)benzamide (100 mg, 0.27 mmol) and 2-azido-N-phenylacetamide (48 mg, 0.27 mmol) in DMSO (4.0 mL) and water (1.0 mL). The solution was stirred at rt for 16 h and diluted with water. The suspension was filtered and the filter cake was washed with water and dried. The product was recrystallised from acetonitrile and (E)-2-(3-(3,4-dimethoxyphenyl)acrylamido)-N-((1-(2-oxo-2-(phenylamino)ethyl)-1H-1,2,3-triazol-4-yl)methyl)benzamide (127 mg, 86%) was obtained as a colourless solid; mp 189-191° C.; $\delta_H$ (400 MHz, DMSO-d$_6$) 3.77 (s, 3H, OCH$_3$), 3.81 (s, 3H, OCH$_3$), 4.59 (d, J=6.8 Hz, 2H, CH$_2$NH), 5.30 (s, 2H, CH$_2$N), 6.79 (d, J=15.6 Hz, 1H, CH=CHCO), 6.96 (d, $J_{5',6'}$=8.4 Hz, 1H, H5'), 7.06 (t, $J_{3'',4''}=J_{4'',5''}$=8.0 Hz, 1H, H4''), 7.15 (t, $J_{3,4}=J_{4,5}$=8.4 Hz, 1H, H4), 7.23 (dd, $J_{5',6'}$=8.4, $J_{2',6'}$=1.6 Hz, 1H, H6'), 7.28 (t, $J_{2'',3''}=J_{3'',4''}=J_{4'',5''}=J_{5'',6''}$=8.0 Hz, 2H, H3'', H5''), 7.37 (d, $J_{2',6'}$=1.6 Hz, 1H, H2'), 7.50-7.56 (m, 4H, CH=CHCO, H5, H2'', H6''), 7.78 (d, $J_{3,4}$=8.0 Hz, 1H, H3), 8.08 (s, 1H, C=CH), 8.57 (d, $J_{5,6}$=8.0 Hz, 1H, H6), 9.37 (t, J=5.6 Hz, 1H, CH$_2$NH), 10.43 (s, 1H, NHPh), 11.40 (s, 1H, NH); $\delta_C$ (100 MHz, DMSO-d$_6$) 34.9, 40.4, 52.2, 55.5, 55.6, 110.4, 111.5, 119.2, 119.9, 120.7, 120.8, 122.6, 122.7, 123.7, 124.6, 127.3, 128.1, 128.9, 131.9, 138.4, 139.2, 141.5, 144.5, 148.9, 150.6, 164.0, 164.2, 168.3; HRMS (ESI) calculated for C$_{29}$H$_{28}$N$_6$O$_5$ [M+Na]$^+$ 563.2013. found 516.2015; $v_{max}$ 755, 1023, 1259, 1516, 1671, 3262 cm$^{-1}$.

4-(Hex-5-ynyloxy)-3-methoxybenzaldehyde

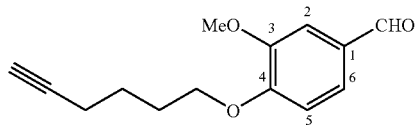

4-Methylbenzenesulfonyl chloride (2.9 g, 15 mmol), 5-hexyn-1-ol (1.1 mL, 10 mmol) and pyridine (1.6 mL, 20 mmol) in CH$_2$Cl$_2$ (10 mL) were treated according to Procedure 4 giving hex-5-ynyl 4-methylbenzenesulfonate (2.1 g, 83%) as a colourless oil. Vanillin (0.84 g, 5.6 mmol) was alkylated with hex-5-ynyl 4-methylbenzenesulfonate (2.1 g, 8.3 mmol) according to Procedure 4 and the crude product was recrystallised from EtOAc/petrol to provide 4-(hex-5-ynyloxy)-3-methoxybenzaldehyde (0.80 g, 62%) as a colourless crystalline solid; mp 67-68° C.; $\delta_H$ (400 MHz, CDCl$_3$) 1.74 (p, J=7.0 Hz, 2H, CH$_2$), 1.97 (t, J=2.8 Hz, 1H, C≡CH), 2.02 (p, J=7.0 Hz, 2H, CH$_2$), 2.30 (td, J=7.0, 2.8 Hz, 2H, CH$_2$C≡CH), 3.92 (s, 3H, OCH$_3$), 4.14 (t, J=7.0 Hz, 2H, OCH$_2$), 6.97 (d, $J_{5,6}$=8.0 Hz, 1H, H5), 7.41 (s, 1H, H2), 7.43 (d, $J_{5,6}$=8.0 Hz, 1H, H6), 9.85 (s, 1H, CHO); $\delta_C$ (100 MHz,

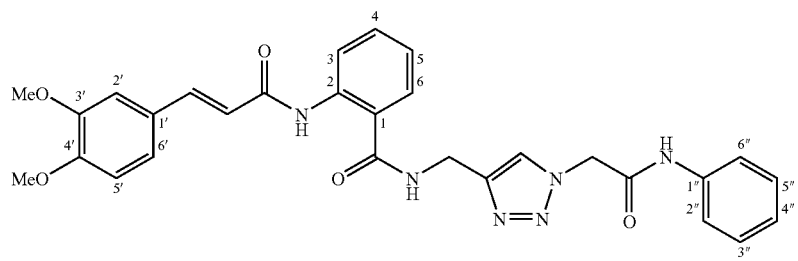 [SMILES: COc1ccc(/C=C/C(=O)Nc2ccccc2C(=O)NCc2cn(CC(=O)Nc3ccccc3)nn2)cc1OC]

CDCl$_3$) 18.1, 24.9, 27.9, 56.0, 68.5, 68.8, 83.9, 109.3, 111.4, 126.7, 130.0, 149.9, 154.0, 190.9; v$_{max}$ 1029, 1269, 1584, 1681, 2956, 3246 cm$^{-1}$.

(E)-2-[[3-(4-(Hex-5-ynyloxy)-3-methoxyphenyl)-1-oxo-2-propenyl]amino]benzoic acid (33)

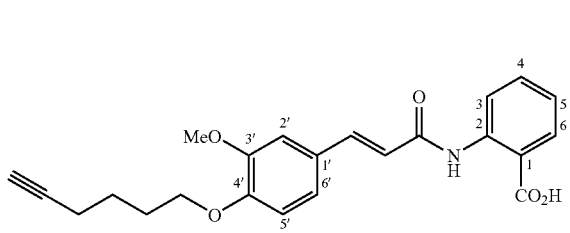 [SMILES: C#CCCCCOc1ccc(/C=C/C(=O)Nc2ccccc2C(=O)O)cc1OC]

Piperidine (0.30 mL, 3.0 mmol) was added to a suspension of 4-(hex-5-ynyloxy)-3-methoxybenzaldehyde (0.70 g, 3.0 mmol) and 2-[(carboxyacetyl)amino]benzoic acid (0.61 g, 2.7 mmol) in toluene (5.0 mL) and treated according to Procedure 2, acidifying with 1 M HCl. The crude product was recrystallised from EtOH/water providing (E)-2-[[3-(4-(Hex-5-ynyloxy)-3-methoxyphenyl)-1-oxo-2-propenyl]amino] benzoic acid (0.78 g, 73%) as a yellow crystalline solid; mp 148-150° C.; $\delta_H$ (400 MHz, DMSO-d$_6$) 1.59 (p, J=7.6 Hz, 2H, CH$_2$), 1.81 (p, J=7.6 Hz, 2H, CH$_2$), 2.24 (dt, J=7.6, 2.4 Hz, 2H, CH$_2$CCH), 2.78 (t, J=2.4 Hz, 1H, CCH), 3.83 (s, 3H, OCH$_3$), 4.01 (t, J=7.6 Hz, 2H, OCH$_2$), 6.77 (d, J=15.6 Hz, 1H, CH=CHCO), 6.98 (d, J$_{5',6'}$=8.0 Hz, 1H, H5'), 7.16 (t, J$_{3,4}$=J$_{4,5}$=8.0 Hz, 1H, H4), 7.22 (d, J$_{5',6'}$=8.0 Hz, 1H, H6'), 7.37 (s, 1H, H2'), 7.55 (d, J=15.6 Hz, 1H, CH=CHCO), 7.61 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.27 (s, 1H, NH), 13.56 (br s, 1H, CO$_2$H); $\delta_C$ (100 MHz, DMSO-d$_6$) 17.4, 24.6, 27.8, 55.7, 67.6, 71.4, 84.3, 110.7, 112.6, 116.6, 119.8, 120.3, 122.6, 122.7, 127.2, 131.1, 134.0, 141.1, 141.6, 149.1, 150.0, 164.2, 169.4; HRMS (ESI) calculated for C$_{23}$H$_{23}$NO$_5$ [M+H]$^+$ 394.1649. found 394.1649; v$_{max}$ 755, 1237, 1508, 1609, 1669, 2944, 3424, 3567 cm$^{-1}$.

3-(Hex-5-ynyloxy)-4-methoxybenzaldehyde

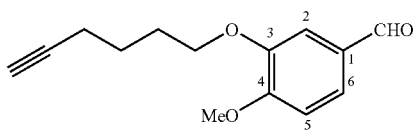 [SMILES: C#CCCCCOc1cc(C=O)ccc1OC]

Isovanillin (0.78 g, 5.2 mmol) was alkylated using hex-5-ynyl 4-methylbenzenesulfonate (1.95 g, 7.73 mmol according to Procedure 4. The crude product was recrystallised from EtOAc/petrol to provide 3-(hex-5-ynyloxy)-4-methoxybenzaldehyde (0.68 g, 57%) as a colourless crystalline solid; mp 66-67° C.; $\delta_H$ (400 MHz, CDCl$_3$) 1.74 (p, J=7.2 Hz, 2H, CH$_2$), 1.96-2.0 (m, 3H, CH$_2$, C≡CH), 2.30 (td, J=7.2, 2.8 Hz, 2H, CH$_2$C≡CH), 3.95 (s, 3H, OCH$_3$), 4.11 (t, J=7.2 Hz, 2H, OCH$_2$), 6.97 (d, J$_{5,6}$=8.0 Hz, 1H, H5), 7.40 (d, J$_{2,6}$=1.6 Hz, 1H, H2), 7.44 (dd, J$_{5,6}$=8.0 Hz, J$_{2,6}$=1.6 Hz, 1H, H6), 9.84 (s, 1H, CHO); $\delta_C$ (100 MHz, CDCl$_3$) 18.1, 25.0, 28.0, 56.2, 68.4, 68.7, 83.9, 110.3, 110.6, 126.7, 130.1, 149.0, 154.9, 190.9; v$_{max}$ 1018, 1263, 1582, 1679, 2933, 3238 cm$^{-1}$.

(E)-2-[[3-(3-(Hex-5-ynyloxy)-4-methoxyphenyl)-1-oxo-2-propenyl]amino]benzoic acid (34)

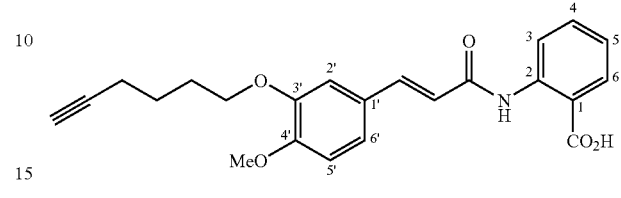

Piperidine (0.26 mL, 2.6 mmol) was added to a suspension of 3-(hex-5-ynyloxy)-4-methoxybenzaldehyde (0.60 g, 2.6 mmol) and 2-[(carboxyacetyl)amino]benzoic acid (0.52 g, 2.4 mmol) in toluene (5.0 mL) and treated according to Procedure 2, acidifying with 1M HCl. The crude product was recrystallised from EtOH/water providing (E)-2-[[3-(3-(hex-5-ynyloxy)-4-methoxyphenyl)-1-oxo-2-propenyl]amino] benzoic acid (0.64 g, 70%) as a pale yellow crystalline solid; mp 135-137° C.; $\delta_H$ (400 MHz, DMSO-d$_6$) 1.62 (p, J=7.2 Hz, 2H, CH$_2$), 1.82 (p, J=7.2 Hz, 2H, CH$_2$), 2.25 (dt, J=7.2, 2.4 Hz, 2H, CH$_2$CCH), 2.78 (t, J=2.4 Hz, 1H, CCH), 3.80 (s, 3H, OCH$_3$), 4.05 (t, J=7.2 Hz, 2H, OCH$_2$), 6.77 (d, J=15.6 Hz, 1H, CH=CHCO), 6.99 (d, J$_{5',6'}$=8.0 Hz, 1H, H5'), 7.16 (t, J$_{3,4}$=J$_{4,5}$=8.0 Hz, 1H, H4), 7.23 (d, J$_{5',6'}$=8.0 Hz, 1H, H6'), 7.37 (s, 1H, H2'), 7.55 (d, J=15.6 Hz, 1H, CH=CHCO), 7.61 (t, J$_{4,5}$=J$_{5,6}$=8.0 Hz, 1H, H5), 8.00 (d, J$_{3,4}$=8.0 Hz, 1H, H3), 8.61 (d, J$_{5,6}$=8.0 Hz, 1H, H6), 11.27 (s, 1H, NH), 13.58 (br s, 1H, CO$_2$H); $\delta_C$ (100 MHz, DMSO-d$_6$) 18.1, 25.3, 28.5, 56.3, 68.4, 72.1, 85.0, 112.3, 112.5, 117.3, 120.5, 121.0, 123.3, 127.9, 131.8, 134.7, 141.7, 142.3, 149.0, 151.5, 164.8, 170.1; HRMS (ESI) calculated for C$_{23}$H$_{23}$NO$_5$ [M+H]$^+$ 394.1649. found 394.1650; v$_{max}$ 753, 1257, 1512, 1586, 1675, 2941, 3242, 3536 cm$^{-1}$.

3-Methoxy-4-(pent-4-ynyloxy)benzaldehyde

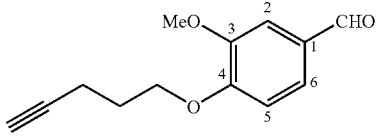 [SMILES: C#CCCCOc1ccc(C=O)cc1OC]

4-Methylbenzenesulfonyl chloride (5.7 g, 30 mmol), 4-pentyn-1-ol (1.8 mL, 20 mmol) and pyridine (3.2 mL, 40 mmol) in CH$_2$Cl$_2$ (20 mL) were treated according to Procedure 4 giving pent-4-ynyl 4-methylbenzenesulfonate (4.60 g, 97%) as a colourless oil. Vanillin (0.98 g, 6.4 mmol) was alkylated with pent-4-ynyl 4-methylbenzenesulfonate (2.3 g, 8.3 mmol) according to Procedure 4 and the crude product was recrystallised from EtOAc/petrol to provide 3-methoxy-4-(pent-4-ynyloxy)benzaldehyde (1.25 g, 89%) as a colourless crystalline solid; mp 91-92° C.; $\delta_H$ (400 MHz, CDCl$_3$) 1.98 (t, J=2.8 Hz, 1H, C≡CH), 2.09 (p, J=7.0 Hz, 2H, CH$_2$), 2.43 (td, J=7.0, 2.8 Hz, 2H, CH$_2$C≡CH), 3.91 (s, 3H, OCH$_3$), 4.21 (t, J=7.0 Hz, 2H, OCH$_2$), 6.99 (d, J$_{5,6}$=8.0 Hz, 1H, H5), 7.40 (s, 1H, H2), 7.43 (d, J$_{5,6}$=8.0 Hz, 1H, H6), 9.84 (s, 1H, CHO); $\delta_C$ (100 MHz, CDCl$_3$) 15.1, 27.8, 56.0, 67.3, 69.1, 83.1, 109.3, 111.5, 126.7, 130.1, 149.9, 153.9, 190.8; $v_{max}$ 1028, 1265, 1583, 1674, 2956, 3214 cm$^{-1}$.

(E)-2-[[3-(3-Methoxy-4-(pent-4-ynyloxy)phenyl)-1-oxo-2-propenyl]amino]benzoic acid (35)

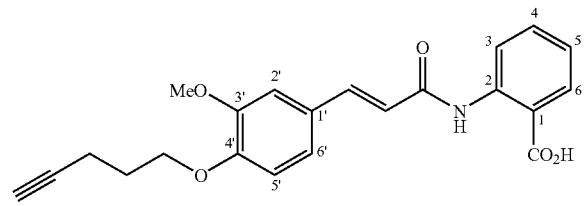 [SMILES: C#CCCCOc1ccc(/C=C/C(=O)Nc2ccccc2C(=O)O)cc1OC]

Piperidine (0.45 mL, 4.6 mmol) was added to a suspension of 3-methoxy-4-(pent-1-ynyloxy)benzaldehyde (1.0 g, 4.6 mmol) and 2-[(carboxyacetyl)amino]benzoic acid (0.93 g, 4.2 mmol) in toluene (10 mL) and treated according to Procedure 2, acidifying with 1 M HCl. The crude product was recrystallised from EtOH/water providing (E)-2-[[3-(3-methoxy-4-(pent-4-ynyloxy)phenyl)-1-oxo-2-propenyl]amino]benzoic acid (1.2 g, 75%) as a pale yellow crystalline solid; mp 166.5-167.5° C.; $\delta_H$ (400 MHz, DMSO-d$_6$) 1.89 (p, J=7.6 Hz, 2H, CH$_2$), 2.32 (dt, J=7.6, 2.4 Hz, 2H, CH$_2$CCH), 2.81 (t, J=2.4 Hz, 1H, CCH), 3.84 (s, 3H, OCH$_3$), 4.06 (t, J=7.6 Hz, 2H, OCH$_2$), 6.78 (d, J=15.6 Hz, 1H, CH=CHCO), 6.99 (d, J$_{5',6'}$=8.0 Hz, 1H, H5'), 7.17 (t, J$_{3,4}$=J$_{4,5}$=8.0 Hz, 1H, H4), 7.22 (dd, J$_{5',6'}$=8.0, J$_{2',6'}$=2.0 Hz, 1H, H6'), 7.37 (d, J$_{2',6'}$=2.0 Hz, 1H, H2'), 7.55 (d, J=15.6 Hz, 1H, CH=CHCO), 7.60 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.27 (s, 1H, NH), 13.56 (br s, 1H, CO$_2$H); $\delta_C$ (100 MHz, DMSO-d$_6$) 14.5, 27.7, 55.7, 66.7, 71.7, 83.6, 110.7, 112.7, 116.6, 120.0, 120.3, 122.6, 122.7, 127.4, 131.1, 134.0, 141.1, 141.6, 149.2, 149.8, 164.1, 169.4; HRMS (ESI) calculated for C$_{22}$H$_{21}$NO$_5$ [M+H]$^+$ 380.1492. found 380.1493; $v_{max}$ 755, 1257, 1506, 1584, 1657, 2929, 3266, 3519 cm$^{-1}$.

4-Methoxy-3-(pent-4-ynyloxy)benzaldehyde

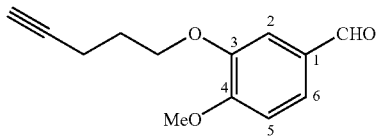 [SMILES: C#CCCCOc1cc(C=O)ccc1OC]

Isovanillin (0.98 g, 6.4 mmol) was alkylated with pent-4-ynyl 4-methylbenzenesulfonate (2.3 g, 8.3 mmol) according to Procedure 4. The crude product was recrystallised from EtOAc/petrol to provide 4-methoxy-3-(pent-4-ynyloxy)benzaldehyde (1.16 g, 83%) as a colourless crystalline solid; mp 73-74° C.; $\delta_H$ (400 MHz, CDCl$_3$) 1.98 (t, J=2.4 Hz, 1H, CCH), 2.06 (p, J=7.0 Hz, 2H, CH$_2$), 2.43 (td, J=7.0, 2.4 Hz, 2H, CH$_2$C≡CH), 3.94 (s, 3H, OCH$_3$), 4.18 (t, J=7.0 Hz, 2H, OCH$_2$), 6.97 (d, J$_{5',6'}$=8.0 Hz, 1H, H5), 7.43 (s, 1H, H2), 7.45 (d, J$_{5,6}$=8.0 Hz, 1H, H6), 9.84 (s, 1H, CHO); $\delta_C$ (100 MHz, CDCl$_3$) 15.1, 27.9, 56.1, 67.3, 69.1, 83.2, 110.6, 110.7, 126.7, 130.0, 148.9, 154.9, 190.9; $v_{max}$ 1025, 1263, 1584, 1665, 2849, 2936, 3254 cm$^{-1}$.

(E)-2-[[3-(4-Methoxy-3-(pent-4-ynyloxy)phenyl)-1-oxo-2-propenyl]amino]benzoic acid (36)

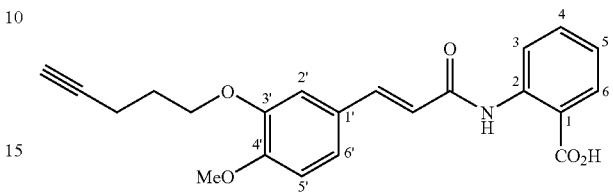

Piperidine (0.45 mL, 4.6 mmol) was added to a suspension of 4-methoxy-3-(pent-1-ynyloxy)benzaldehyde (1.0 g, 4.6 mmol) and 2-[(carboxyacetyl)amino]benzoic acid (0.93 g, 4.2 mmol) in toluene (10 mL) and treated according to Procedure 2, acidifying with 1 M HCl. The crude product was recrystallised from EtOH/water providing (E)-2-[[3-(4-methoxy-3-(pent-4-ynyloxy)phenyl)-1-oxo-2-propenyl]amino]benzoic acid (1.2 g, 77%) as a yellow crystalline solid; mp 154-156° C.; $\delta_H$ (400 MHz, DMSO-d$_6$) 1.91 (p, 7.6 Hz, 2H, CH$_2$), 2.34 (dt, J=7.6, 2.4 Hz, 2H, CH$_2$CCH), 2.82 (t, J=2.4 Hz, 1H, CCH), 3.80 (s, 3H, OCH$_3$), 4.10 (t, J=7.6 Hz, 2H, OCH$_2$), 6.78 (d, J=15.6 Hz, 1H, CH=CHCO), 6.99 (d, J$_{5',6'}$=8.0 Hz, 1H, H5'), 7.15 (t, J$_{3,4}$=J$_{4,5}$=8.0 Hz, 1H, H4), 7.25 (d, J$_{5',6'}$=8.0 Hz, 1H, H6'), 7.38 (s, 1H, H2'), 7.55 (d, J=15.6 Hz, 1H, CH=CHCO), 7.60 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.26 (s, 1H, NH), 13.56 (br s, 1H, CO$_2$H); $\delta_C$ (100 MHz, DMSO-d$_6$) 14.5, 27.8, 55.6, 66.8, 71.6, 83.8, 111.7, 111.8, 116.6, 119.9, 120.3, 122.6, 122.8, 127.2, 131.1, 134.0, 141.1, 141.6, 148.1, 150.9, 164.1, 169.4; HRMS (ESI) calculated for C$_{22}$H$_{21}$NO$_5$ [M+H]$^+$ 380.1492. found 380.1490; $v_{max}$ 754, 1257, 1510, 1584, 1659, 2944, 3250, 3512 cm$^{-1}$.

4-(But-3-ynyloxy)-3-methoxybenzaldehyde

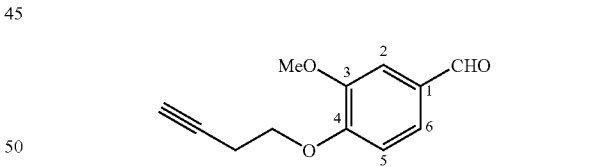

4-Methylbenzenesulfonyl chloride (5.7 g, 30 mmol), 3-butyn-1-ol (1.5 mL, 20 mmol) and pyridine (3.2 mL, 40 mmol) in CH$_2$Cl$_2$ (20 mL) were treated according to Procedure 4 giving but-3-ynyl 4-methylbenzenesulfonate (4.15 g, 93%) as a colourless oil. Vanillin (0.86 g, 5.7 mmol) was alkylated with but-3-ynyl 4-methylbenzenesulfonate (1.9 g, 8.5 mmol) according to Procedure 4 and the crude product was recystallised from EtOAc/petrol to provide 4-(but-3-ynyloxy)-3-methoxybenzaldehyde (0.39 g, 34%) as a colourless crystalline solid; mp 101-102° C.; $\delta_H$ (400 MHz, CDCl$_3$) 2.07 (t, J=2.8 Hz, 1H, C≡CH), 2.79 (td, J=7.2, 2.8 Hz, 2H, CH$_2$C≡CH), 3.93 (s, 3H, OCH$_3$), 4.25 (t, J=7.2 Hz, 2H, OCH$_2$), 7.00 (d, J$_{5,6}$=8.0 Hz, 1H, H5), 7.42 (d, J$_{2,6}$=2.0 Hz, 1H, H2), 7.45 (dd, J$_{5,6}$=8.0, J$_{2,6}$=2.0 Hz, 1H, H6), 9.86 (s, 1H, CHO); $\delta_C$ (100 MHz, CDCl$_3$) 13.3, 56.1, 67.0, 70.5, 79.6, 109.6, 112.0, 126.6, 130.5, 149.9, 153.3, 190.9; $v_{max}$ 1021, 1269, 1586, 1677, 2940, 3246 cm$^{-1}$.

(E)-2-[[3-(4-(But-3-ynyloxy)-3-methoxyphenyl)-1-oxo-2-propenyl]amino]benzoic acid (37)

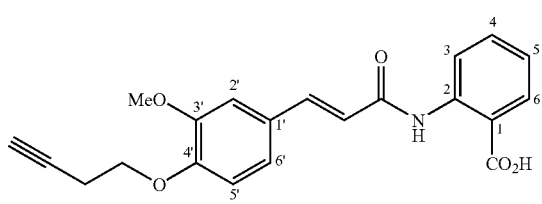 [SMILES: C#CCCOc1ccc(/C=C/C(=O)Nc2ccccc2C(=O)O)cc1OC]

Piperidine (0.19 mL, 1.9 mmol) was added to a suspension of 3-methoxy-4-(but-1-ynyloxy)benzaldehyde (0.39 g, 1.7 mmol) and 2-[(carboxyacetyl)amino]benzoic acid (0.39 g, 1.9 mmol) in toluene (5 mL) and treated according to Procedure 2, acidifying with 1M HCl. The crude product was recrystallised from EtOH/water providing (E)-2-[[3-(4-(but-3-ynyloxy)-3-methoxyphenyl)-1-oxo-2-propenyl]amino] benzoic acid (0.48 g, 75%) as a yellow crystalline solid; mp 178-180° C.; $\delta_H$ (400 MHz, DMSO-d$_6$) 2.61 (dt, J=6.8, 2.4 Hz, 2H, CH$_2$CCH), 2.86 (t, J=2.4 Hz, 1H, CCH), 3.81 (s, 3H, OCH$_3$), 4.06 (t, J=6.8 Hz, 2H, OCH$_2$), 6.77 (d, J=15.6 Hz, 1H, CH=CHCO), 6.98 (d, J$_{5',6'}$=8.0 Hz, 1H, H5'), 7.13 (t, J$_{3,4}$=J$_{4,5}$=8.0 Hz, 1H, H4), 7.20 (d, J$_{5,6}$'=8.0 Hz, 1H, H6'), 7.36 (s, 1H, H2'), 7.53 (d, J=15.6 Hz, 1H, CH=CHCO), 7.58 (t, J$_{4,5}$=J$_{5,6}$=8.0 Hz, 1H, H5), 7.97 (d, J$_{3,4}$=8.0 Hz, 1H, H3), 8.59 (d, J$_{5,6}$=8.0 Hz, 1H, H6), 11.25 (s, 1H, NH), 13.56 (br s, 1H, CO$_2$H); $\delta_C$ (100 MHz, DMSO-d$_6$) 19.6, 56.4, 67.2, 73.2, 82.0, 111.5, 113.6, 117.3, 120.8, 121.0, 123.2, 123.3, 128.4, 131.8, 134.7, 141.7, 142.2, 149.8, 150.1, 164.8, 170.1; HRMS (ESI) calculated for C$_{21}$H$_{19}$NO$_5$ [M+H]$^+$ 366.1336. found 366.1337; $v_{max}$ 755, 1263, 1512, 1603, 1689, 3257, 3401 cm$^{-1}$.

3-(But-3-ynyloxy)-4-methoxybenzaldehyde

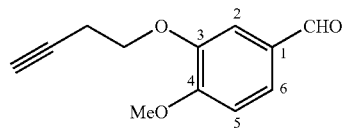

Isovanillin (0.95 g, 6.2 mmol) was alkylated with but-3-ynyl 4-methylbenzenesulfonate (2.1 g, 9.4 mmol) according to Procedure 4. The crude product was recrystallised from EtOAc/petrol to provide 3-(but-3-ynyloxy)-4-methoxybenzaldehyde (0.44 g, 35%) as a colourless crystalline solid; mp 63-65° C.; $\delta_H$ (400 MHz, CDCl$_3$) 2.06 (t, J=2.8 Hz, 1H, C≡CH), 2.76 (td, J=7.2, 2.8 Hz, 2H, CH$_2$C≡CH), 3.96 (s, 3H, OCH$_3$), 4.22 (t, J=7.2 Hz, 2H, OCH$_2$), 6.99 (d, J$_{5,6}$=8.0 Hz, 1H, H5), 7.43 (d, J$_{2,6}$=1.4 Hz, 1H, H2), 7.45 (dd, J$_{5,6}$=8.0, J$_{2,6}$=1.4 Hz, 1H, H6), 9.85 (s, 1H, CHO); $\delta_C$ (100 MHz, CDCl$_3$) 19.4, 56.2, 67.0, 70.3, 79.8, 110.9, 111.2, 127.1, 130.1, 148.4, 154.9, 190.7; $v_{max}$ 1015, 1124, 1231, 1586, 1675, 2821, 3305 cm$^{-1}$.

(E)-2-[[3-(3-(But-3-ynyloxy)-4-methoxyphenyl)-1-oxo-2-propenyl]amino]benzoic acid (38)

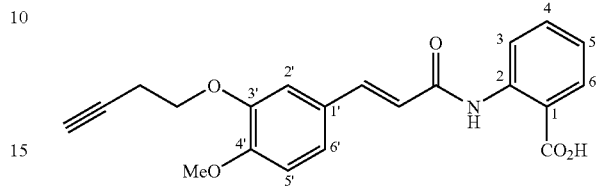

Piperidine (0.17 mL, 1.7 mmol) was added to a suspension of 4-methoxy-3-(but-1-ynyloxy)benzaldehyde (0.35 g, 1.7 mmol) and 2-[(carboxyacetyl)amino]benzoic acid (0.35 g, 1.6 mmol) in toluene (5 mL) and treated according to Procedure 2, acidifying with 1 M HCl. The crude product was recrystallised from EtOH/water providing (E)-2-[[3-(3-(but-3-ynyloxy)-4-methoxyphenyl)-1-oxo-2-propenyl]amino] benzoic acid (0.40 g, 70%) as a colourless crystalline solid; mp 197-198° C.; $\delta_H$ (400 MHz, DMSO-d$_6$) 2.65 (dt, J=6.8, 2.4 Hz, 2H, CH$_2$CCH), 2.90 (t, J=2.4 Hz, 1H, CCH), 3.80 (s, 3H, OCH$_3$), 4.13 (t, J=6.8 Hz, 2H, OCH$_2$), 6.80 (d, J=15.6 Hz, 1H, CH=CHCO), 7.00 (d, J$_{5',6'}$=8.0 Hz, 1H, H5'), 7.16 (t, J$_{3,4}$=J$_{4,5}$=8.0 Hz, 1H, H4), 7.26 (d, J$_{5',6'}$=8.0 Hz, 1H, H6'), 7.40 (s, 1H, H2'), 7.55 (d, J=15.6 Hz, 1H, CH=CHCO), 7.61 (t, J$_{4,5}$=J$_{5,6}$=8.0 Hz, 1H, H5), 7.99 (d, J$_{3,4}$=8.0 Hz, 1H, H3), 8.61 (d, J$_{5,6}$=8.0 Hz, 1H, H6), 11.27 (s, 1H, NH), 13.58 (br s, 1H, CO$_2$H); $\delta_C$ (100 MHz, DMSO-d$_6$) 19.0, 55.6, 66.6, 72.5, 81.4, 111.9, 111.9, 116.6, 120.0, 120.3, 122.7, 123.0, 127.3, 131.1, 134.0, 141.0, 141.5, 147.8, 150.7, 164.2, 169.4; HRMS (ESI) calculated for C$_{21}$H$_{19}$NO$_6$ [M+H]$^+$ 366.1335. found 366.1337; $v_{max}$ 753, 1263, 1512, 1581, 1671, 2833, 3250 cm$^{-1}$.

4-(Hex-3-ynyloxy)-3-methoxybenzaldehyde

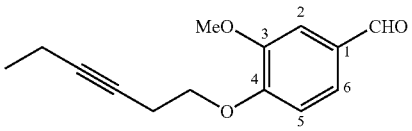

4-Methylbenzenesulfonyl chloride (5.7 g, 30 mmol), 3-hexyn-1-ol (1.5 mL, 20 mmol) and pyridine (3.2 mL, 40 mmol) in CH$_2$Cl$_2$ (20 mL) were treated according to Procedure 4 giving hex-3-ynyl 4-methylbenzenesulfonate (3.8 g, 75%) as a colourless oil. Vanillin (0.76 g, 5.0 mmol) was alkylated with hex-3-ynyl 4-methylbenzenesulfonate (1.9 g, 7.5 mmol) according to Procedure 4 and the crude product was recrystallised from EtOAc/petrol to provide 4-(hex-3-ynyloxy)-3-methoxybenzaldehyde (0.45 g, 39%) as a colourless crystalline solid; mp 80-81° C.; $\delta_H$ (400 MHz, CDCl$_3$) 1.12 (t, J=7.6 Hz, 3H, CH$_3$), 2.17 (tq, J=7.6, 2.4 Hz, 2H, CH$_3$CH$_2$), 2.73 (tt, J=7.6, 2.4 Hz, 2H, OCH$_2$CH$_2$C), 3.92 (s, 3H, OCH$_3$), 4.19 (t, J=7.6 Hz, 2H, OCH$_2$), 7.00 (d, J$_{5,6}$=8.0 Hz, 1H, H5), 7.41 (d, J$_{2,6}$=1.6 Hz, 1H, H2), 7.44 (dd, J$_{5,6}$=8.0, J$_{2,6}$=1.6 Hz, 1H, H6), 9.85 (s, 1H, CHO); $\delta_C$ (100 MHz, CDCl$_3$) 12.4, 14.0, 19.5, 56.0, 67.6, 74.3, 84.0, 109.5, 111.8, 126.6, 130.3, 149.9, 153.5, 190.8; $v_{max}$ 1023, 1134, 1263, 1586, 1680, 2877, 2972 cm$^{-1}$.

(E)-2-[[3-(4-(Hex-3-ynyloxy)-3-methoxyphenyl)-1-oxo-2-propenyl]amino]benzoic acid (39)

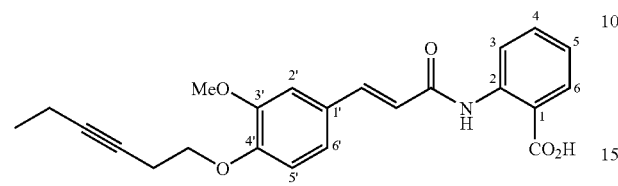

Piperidine (0.17 mL, 1.7 mmol) was added to a suspension of 3-methoxy-4-(hex-3-ynyloxy)benzaldehyde (0.40 g, 1.7 mmol) and 2-[(carboxyacetyl)amino]benzoic acid (0.35 g, 1.6 mmol) in toluene (5 mL) and treated according to Procedure 2, acidifying with 1 M HCl. The crude product was recrystallised from EtOH providing (E)-2-[[3-(4-(hex-3-ynyloxy)-3-methoxyphenyl)-1-oxo-2-propenyl]amino]benzoic acid (0.40 g, 65%) as a colourless crystalline solid; mp 165-166° C.; $\delta_H$ (400 MHz, DMSO-d$_6$) 1.04 (t, J=7.6 Hz, 3H, CH$_3$), 2.14 (q, J=7.6 Hz, 2H, CH$_3$CH$_2$), 2.61 (t, J=7.6 Hz, 1H, OCH$_2$CH$_2$C), 3.83 (s, 3H, OCH$_3$), 4.05 (t, J=7.6 Hz, 2H, OCH$_2$), 6.79 (d, J=15.6 Hz, 1H, CH=CHCO), 6.99 (d, J$_{5',6'}$=8.0 Hz, 1H, H5'), 7.16 (t, J$_{3,4}$=J$_{4,5}$=8.0 Hz, 1H, H4), 7.22 (d, J$_{5',6'}$=8.0 Hz, 1H, H6'), 7.38 (s, 1H, H2'), 7.55 (d, J=15.6 Hz, 1H, CH=CHCO), 7.61 (t, J$_{4,5}$=J$_{5,6}$=8.0 Hz, 1H, H5), 7.99 (d, J$_{3,4}$=8.0 Hz, 1H, H3), 8.61 (d, J$_{5,6}$=8.0 Hz, 1H, H6), 11.27 (s, 1H, NH), 13.57 (br s, 1H, CO$_2$H); $\delta_C$ (100 MHz, DMSO-d$_6$) 11.7, 14.0, 19.2, 55.7, 76.9, 76.1, 83.0, 110.9, 113.0, 116.6, 120.1, 120.3, 122.5, 122.6, 127.6, 131.1, 134.0, 141.0, 141.5, 149.1, 149.5, 164.1, 169.4; HRMS (ESI) calculated for C$_{23}$H$_{23}$NO$_5$ [M+H]$^+$ 394.1649. found 394.1647; $v_{max}$ 755, 1235, 1510, 1601, 1669, 3234, 3563 cm$^{-1}$.

3-(Hex-3-ynyloxy)-4-methoxybenzaldehyde

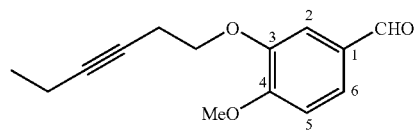 [SMILES: CCC#CCCOc1cc(C=O)ccc1OC]

Isovanillin (0.76 g, 5.0 mmol) was alkylated with hex-3-ynyl 4-methylbenzenesulfonate (1.9 g, 7.53 mmol) according to Procedure 4. The crude product was recrystallised from EtOAc/petrol to provide 3-(hex-3-ynyloxy)-4-methoxybenzaldehyde (0.58 g, 50%) as a colourless crystalline solid; mp 86.5-87.5° C.; $\delta_H$ (400 MHz, CDCl$_3$) 1.13 (t, J=7.6 Hz, 3H, CH$_3$), 2.17 (tq, J=7.6, 2.4 Hz, 2H, CH$_3$CH$_2$), 2.72 (tt, J=7.6, 2.4 Hz, 2H, OCH$_2$CH$_2$C), 3.95 (s, 3H, OCH$_3$), 4.17 (t, J=7.6 Hz, 2H, OCH$_2$), 6.98 (d, J$_{5,6}$=8.0 Hz, 1H, H5), 7.44 (d, J$_{2,6}$=1.6 Hz, 1H, H2), 7.47 (dd, J$_{5,6}$=8.0, J$_{2,6}$=1.6 Hz, 1H, H6), 9.85 (s, 1H, CHO); $\delta_C$ (100 MHz, CDCl$_3$) 12.4, 14.1, 19.6, 56.2, 67.6, 74.5, 83.9, 110.8, 111.0, 126.9, 130.1, 148.6, 154.8, 190.8; $v_{max}$ 1019, 1134, 1265, 1586, 1683, 2841, 2977 cm$^{-1}$.

(E)-2-[[3-(3-(Hex-3-ynyloxy)-4-methoxyphenyl)-1-oxo-2-propenyl]amino]benzoic acid (40)

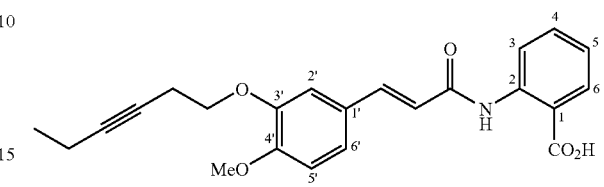

Piperidine (0.21 mL, 2.2 mmol) was added to a suspension of 4-methoxy-3-(hex-3-ynyloxy)benzaldehyde (0.50 g, 2.2 mmol) and 2-[(carboxyacetyl)amino]benzoic acid (0.44 g, 2.0 mmol) in toluene (5 mL) and treated according to Procedure 2, acidifying with 1 M HCl. The crude product was recrystallised from EtOH providing (E)-2-[[3-(3-(hex-3-ynyloxy)-4-methoxyphenyl)-1-oxo-2-propenyl]amino]benzoic acid (0.58 g, 75%) as a yellow crystalline solid; mp 163-165° C.; $\delta_H$ (400 MHz, DMSO-d$_6$) 1.05 (t, J=7.6 Hz, 3H, CH$_3$), 2.15 (q, J=7.6 Hz, 2H, CH$_3$CH$_2$), 2.62 (t, J=7.6 Hz, 1H, OCH$_2$CH$_2$C), 3.80 (s, 3H, OCH$_3$), 4.09 (t, J=7.6 Hz, 2H, OCH$_2$), 6.80 (d, J=15.6 Hz, 1H, CH=CHCO), 6.99 (d, J$_{5',6'}$=8.0 Hz, 1H, H5'), 7.16 (t, J$_{3,4}$=J$_{4,5}$=8.0 Hz, 1H, H4), 7.25 (d, J$_{5',6'}$=8.0 Hz, 1H, H6'), 7.40 (s, 1H, H2'), 7.55 (d, J=15.6 Hz, 1H, CH=CHCO), 7.60 (t, J$_{4,5}$=J$_{5,6}$=8.0 Hz, 1H, H5), 8.00 (d, J$_{3,4}$=8.0 Hz, 1H, H3), 8.61 (d, J$_{5,6}$=8.0 Hz, 1H, H6), 11.26 (s, 1H, NH), 13.58 (br s, 1H, CO$_2$H); $\delta_C$ (100 MHz, DMSO-d$_6$) 11.8, 14.0, 19.3, 55.6, 67.0, 76.2, 83.0, 111.9, 112.0, 116.6, 120.0, 120.3, 122.6, 123.0, 127.3, 131.1, 134.0, 141.0, 141.6, 147.9, 150.8, 164.2, 169.4; HRMS (ESI) calculated for C$_{23}$H$_{23}$NO$_5$ [M+H]$^+$ 394.1649. found 394.1648; $v_{max}$ 755, 1253, 1510, 1604, 1657, 3238, 3524 cm$^{-1}$.

3-Methoxy-4-(oct-3-ynyloxy)benzaldehyde

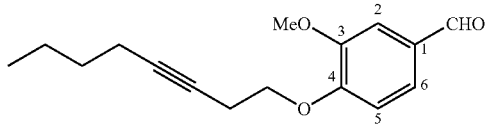 [SMILES: CCCCC#CCCOc1ccc(C=O)cc1OC]

4-Methylbenzenesulfonyl chloride (5.70 g, 30 mmol), 3-octyn-1-ol (1.52 mL, 20 mmol) and pyridine (3.24 mL, 40 mmol) in CH$_2$Cl$_2$ (20 mL) were treated according to Procedure 4 giving oct-3-ynyl 4-methylbenzenesulfonate (5.21 g, 93%) as a colourless oil. Vanillin (0.90 g, 5.94 mmol) was alkylated with oct-3-ynyl 4-methylbenzenesulfonate (2.50 g, 8.92 mmol) according to Procedure 4 and the crude product was recrystallised from purified by flash chromatography with 10% EtOAc/petrol as eluent to give 3-methoxy-4-(oct-3-ynyloxy)benzaldehyde (0.25 g, 16%) as a colourless crystalline solid; mp 64.5-65.5° C.; $\delta_H$ (400 MHz, CDCl$_3$) 0.86 (t, J=7.2 Hz, 3H, CH$_3$), 1.32-1.44 (m, 4H, CH$_3$CH$_2$CH$_2$), 2.12 (t, J=7.2 Hz, 2H, CH$_2$CH$_2$CH$_2$), 2.69 (t, J=7.2 Hz, 2H, CH$_2$CH$_2$O), 3.88 (s, 3H, OCH$_3$), 4.15 (t, J=7.2 Hz, 2H, OCH$_2$), 6.96 (d, J$_{5,6}$=8.0 Hz, 1H, H5), 7.37 (s, 1H, H2), 7.39 (d, J$_{5,6}$=8.0 Hz, 1H, H6), 9.80 (s, 1H, CHO); $\delta_C$ (100 MHz, CDCl$_3$) 13.5, 18.3, 19.5, 21.8, 30.8, 55.9, 67.5, 74.8, 82.5, 109.4, 111.7, 126.4, 130.2, 149.7, 153.4, 190.7; $v_{max}$ 1020, 1132, 1262, 1508, 1584, 1684, 2931 cm$^{-1}$.

(E)-2-[[3-(3-Methoxy-4-(oct-3-ynyloxy)phenyl)-1-oxo-2-propenyl]amino]benzoic acid (41)

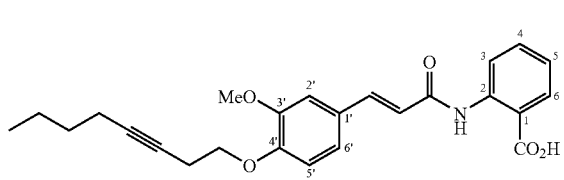 [SMILES: CCCCC#CCCOc1ccc(/C=C/C(=O)Nc2ccccc2C(=O)O)cc1OC]

Piperidine (95 µL, 0.96 mmol) was added to a suspension of 3-methoxy-4-(oct-3-ynyloxy)benzaldehyde (0.25 g, 0.96 mmol) and 2-[(carboxyacetyl)amino]benzoic acid (0.20 g, 0.90 mmol) in toluene (5 mL) and treated according to Procedure 2, acidifying with 20% AcOH. The crude product was recrystallised from EtOH/water providing (E)-2-[[3-(3-methoxy-4-(oct-3-ynyloxy)phenyl)-1-oxo-2-propenyl]amino]benzoic acid (0.30 g, 79%) as a colourless crystalline solid; mp 169-170° C.; $\delta_H$ (400 MHz, DMSO-d$_6$) 0.85 (t, J=7.2 Hz, 3H, CH$_3$), 1.31-1.42 (m, 4H, CH$_3$CH$_2$CH$_2$), 2.13 (t, J=7.2 Hz, 2H, CH$_2$), 2.60 (t, J=7.2 Hz, 2H, CH$_2$CH$_2$O), 3.83 (s, 3H, OCH$_3$), 4.05 (t, J=7.2 Hz, 2H, OCH$_2$), 6.76 (d, J=15.6 Hz, 1H, CH=CHCO), 7.00 (d, J$_{5',6'}$=8.0 Hz, 1H, H5'), 7.15 (t, J$_{3,4}$=J$_{4,5}$=8.0 Hz, 1H, H4), 7.22 (dd, J$_{5',6'}$=8.0, J$_{2',6'}$=1.6 Hz, 1H, H6'), 7.37 (d, J$_{5',6'}$=1.6 Hz, 1H, H2'), 7.55 (d, J=15.6 Hz, 1H, CH=CHCO), 7.60 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.30 (s, 1H, NH), 13.55 (br s, 1H, CO$_2$H); $\delta_C$ (100 MHz, DMSO-d$_6$) 13.4, 17.7, 19.2, 21.3, 30.4, 55.7, 67.0, 76.7, 81.6, 110.9, 113.0, 116.7, 120.1, 120.3, 122.5, 122.6, 127.6, 131.1, 133.9, 141.0, 141.5, 149.1, 149.5, 164.1, 169.4; HRMS (ESI) calculated for C$_{25}$H$_{27}$NO$_5$ [M+H]$^+$ 421.1962. found 421.1962; $v_{max}$ 757, 1143, 1220, 1514, 1601, 1652, 1690, 2939 cm$^{-1}$.

4-Methoxy-3-(oct-3-ynyloxy)benzaldehyde

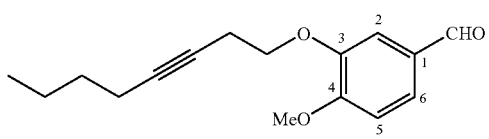 [SMILES: CCCCC#CCCOc1cc(C=O)ccc1OC]

Isovanillin (0.90 g, 5.9 mmol) was alkylated with oct-3-ynyl 4-methylbenzenesulfonate (2.5 g, 8.9 mmol) according to Procedure 2. The crude product was recrystallised from purified by flash chromatography with 10% EtOAc/petrol as eluent to give 4-methoxy-3-(oct-3-ynyloxy)benzaldehyde (0.52 g, 34%) as a colourless crystalline solid; mp 42-43° C.; $\delta_H$ (400 MHz, CDCl$_3$) 0.90 (t, J=7.2 Hz, 3H, CH$_3$), 1.37-1.49 (m, 4H, CH$_3$CH$_2$CH$_2$), 2.16 (tt, J=7.2, 2.4 Hz, 2H, CH$_2$), 2.72 (tt, J=7.2, 2.4 Hz, 2H, CH$_2$CH$_2$O), 3.95 (s, 3H, OCH$_3$), 4.17 (t, J=7.2 Hz, 2H, OCH$_2$), 6.98 (d, J$_{5,6}$=8.0 Hz, 1H, H5), 7.44 (d, J$_{2,6}$=2.0 Hz, 1H, H2), 7.47 (dd, J$_{5,6}$=8.0, J$_{2,6}$=2.0 Hz, 1H, H6), 9.85 (s, 1H, CHO); $\delta_C$ (100 MHz, CDCl$_3$) 13.6, 18.4, 19.7, 21.9, 30.9, 56.2, 67.6, 75.1, 82.5, 110.8, 111.0, 126.9, 130.1, 148.6, 154.9, 190.8; $v_{max}$ 1019, 1132, 1262, 1508, 1585, 1684, 2932 cm$^{-1}$.

(E)-2-[[3-(4-Methoxy-3-(oct-3-ynyloxy)phenyl)-1-oxo-2-propenyl]amino]benzoic acid (42)

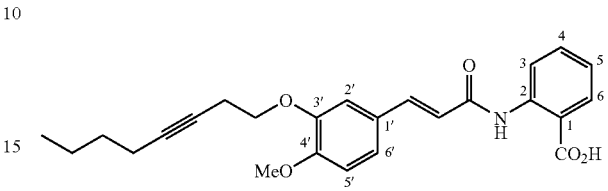

Piperidine (190 µL, 1.9 mmol) was added to a suspension of 4-methoxy-3-(oct-3-ynyloxy)benzaldehyde (0.50 g, 1.9 mmol) and 2-[(carboxyacetyl)amino]benzoic acid (0.39 g, 1.7 mmol) in toluene (5 mL) and treated according to Procedure 2, acidifying with 20% AcOH. The crude product was recrystallised from EtOH/water providing (E)-2-[[3-(4-methoxy-3-(oct-3-ynyloxy)phenyl)-1-oxo-2-propenyl]amino]benzoic acid (0.60 g, 82%) as a colourless crystalline solid; mp 157-158° C.; $\delta_H$ (400 MHz, DMSO-d$_6$) 0.85 (t, J=7.2 Hz, 3H, CH$_3$), 1.32-1.42 (m, 4H, CH$_3$CH$_2$CH$_2$), 2.14 (t, J=7.2 Hz, 2H, CH$_2$), 2.62 (t, J=7.2 Hz, 2H, CH$_2$CH$_2$O), 3.80 (s, 3H, OCH$_3$), 4.10 (t, J=7.2 Hz, 2H, OCH$_2$), 6.80 (d, J=15.6 Hz, 1H, CH=CHCO), 7.00 (d, J$_{5',6'}$=8.0 Hz, 1H, H5'), 7.16 (t, J$_{3,4}$=J$_{4,5}$=8.0 Hz, 1H, H4), 7.25 (d, J$_{5,6}$'=8.0 Hz, 1H, H6'), 7.40 (s, 1H, H2'), 7.55 (d, J=15.6 Hz, 1H, CH=CHCO), 7.61 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.27 (s, 1H, NH), 13.58 (br s, 1H, CO$_2$H); $\delta_C$ (100 MHz, DMSO-d$_6$) 13.4, 17.8, 19.3, 21.3, 30.5, 55.6, 67.1, 76.9, 81.5, 111.9, 112.1, 116.6, 120.0, 120.3, 122.6, 122.9, 127.3, 131.1, 134.0, 141.0, 141.5, 147.9, 150.8, 164.2, 169.4; HRMS (ESI) calculated for C$_{25}$H$_{27}$NO$_5$ [M+H]$^+$ 421.1962. found 421.1962; $v_{max}$ 757, 1131, 1259, 1515, 1582, 1671, 2954, 3335 cm$^{-1}$.

4-Benzyloxy-3-methoxybenzaldehyde

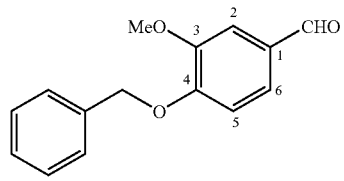 [SMILES: COc1cc(C=O)ccc1OCc1ccccc1]

Benzyl bromide (1.2 mL, 9.9 mmol) was added to a suspension of vanillin (1.0 g, 6.6 mmol) and potassium carbonate (2.7 g, 20 mmol) in acetone (10 mL) and treated according to Procedure 3. The crude product was recrystallised from EtOH to give 4-benzyloxy-3-methoxybenzaldehyde (1.0 g, 64%) as a colourless crystalline solid; mp 61-62° C.; $\delta_H$ (400 MHz, CDCl$_3$) 3.95 (s, 3H, OCH$_3$), 5.25 (s, 2H, OCH$_2$), 6.99 (d, J$_{5,6}$=8.0 Hz, 1H, H5), 7.32-7.45 (m, 7H, H2, H6, Ph), 9.84 (s, 1H, CHO); $\delta_C$ (100 MHz, CDCl$_3$) 56.1, 70.8 109.3, 112.4, 126.6 127.2, 128.2, 128.7, 130.3, 136.0, 150.1, 153.6, 190.9; $v_{max}$ 988, 1133, 1259, 1505, 1583, 1672 cm$^{-1}$.

(E)-2-[[3-(4-Benzyloxy-3-methoxyphenyl)-1-oxo-2-propenyl]amino]benzoic acid (43)

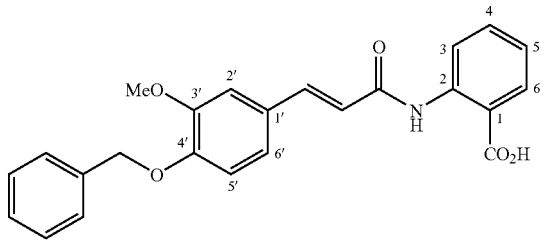 [SMILES: COc1cc(/C=C/C(=O)Nc2ccccc2C(=O)O)ccc1OCc1ccccc1]

Piperidine (0.20 mL, 2.1 mmol) was added to a suspension of 4-benzyloxy-3-methoxybenzaldehyde (0.50 g, 2.1 mmol) and 2-[(carboxyacetyl)amino]benzoic acid (0.42 g, 1.9 mmol) in toluene (5 mL) and treated according to Procedure 2, acidifying with 20% AcOH. The crude product was recrystallised from EtOH providing (E)-2-[[3-(4-benzyloxy-3-methoxyphenyl)-1-oxo-2-propenyl]amino]benzoic (0.48 g, 63%) as a yellow crystalline solid; mp 197-199° C.; $\delta_H$ (400 MHz, DMSO-d$_6$) 3.84 (s, 3H, OCH$_3$), 5.13 (s, 2H, OCH$_2$), 6.79 (d, J=15.6 Hz, 1H, CH=CHCO), 7.07 (d, $J_{5',6'}$=8.0 Hz, 1H, H5'), 7.16 (t, $J_{3,4}=J_{4,5}$=8.0 Hz, 1H, H4), 7.22 (d, $J_{5',6'}$=8.0 Hz, 1H, H6'), 7.31-7.46 (m, 6H, H2', Ph), 7.55 (d, J=15.6 Hz, 1H, CH=CHCO), 7.61 (t, $J_{4,5}=J_{5,6}$=8.0 Hz, 1H, H5), 8.00 (d, $J_{3,4}$=8.0 Hz, 1H, H3), 8.62 (d, $J_{5,6}$=8.0 Hz, 1H, H6), 11.28 (s, 1H, NH), 13.60 (br s, 1H, CO$_2$H); do (100 MHz, DMSO-d$_6$) 55.7, 69.8, 110.7, 113.1, 116.6, 120.0, 120.3, 122.5, 122.7, 127.5, 127.8, 127.9, 128.4, 131.1, 134.0, 136.8, 141.1, 141.6, 149.3, 149.6, 164.2, 169.5; HRMS (ESI) calculated for C$_{24}$H$_{21}$NO$_5$ [M–H]$^-$ 402.1336. found 402.1342; $v_{max}$ 697, 1133, 1233, 1516, 1599, 1673, 1697, 3035 cm$^{-1}$.

3-Methoxy-4-(naphth-2-ylmethoxy)benzaldehyde

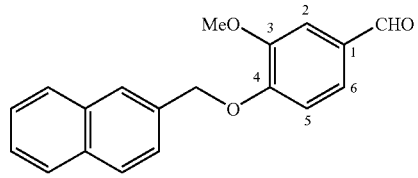 [SMILES: COc1cc(C=O)ccc1OCc1ccc2ccccc2c1]

2-(Bromomethyl)naphthalene (1.3 g, 5.9 mmol) was added to a suspension of vanillin (0.60 g, 3.9 mmol) and potassium carbonate (1.6 g, 12 mmol) in acetone (10 mL) and treated according to Procedure 3. The crude product was recrystallised from EtOAc/petrol providing 3-methoxy-4-(naphth-2-ylmethoxy)benzaldehyde (0.87 g, 75%) as a colourless crystalline solid; mp 107-108° C.; $\delta_H$ (400 MHz, CDCl$_3$) 3.97 (s, 3H, OCH$_3$), 5.41 (s, 2H, OCH$_2$), 7.38 (m, 1H, Naphth-H), 7.44 (d, $J_{2,6}$=1.6 Hz, 1H, H2), 7.48-7.50 (m, 3H, H6, Naphth-H), 7.55 (m, 1H, Naphth-H), 7.83-7.89 (m, 4H, Naphth-H), 9.84 (s, 1H, CHO); $\delta_C$ (100 MHz, CDCl$_3$) 56.3, 71.3 109.7, 112.8, 125.1 126.4, 126.5, 126.6, 126.8, 128.0, 128.2, 128.9, 130.6, 133.4, 133.5, 133.7, 150.4, 153.8, 191.1; $v_{max}$ 991, 1131, 1263, 1505, 1580, 1672, 2884 cm$^{-1}$.

(E)-2-[[3-(3-Methoxy-4-(naphth-2-ylmethoxy)phenyl)-1-oxo-2-propenyl]amino]benzoic acid (44)

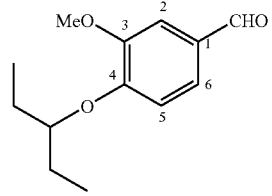

Piperidine (0.27 mL, 2.7 mmol) was added to a suspension of 3-methoxy-4-(naphth-2-ylmethoxy)benzaldehyde (0.80 g, 2.7 mmol) and 2-[(carboxyacetyl)amino]benzoic acid (0.55 g, 2.5 mmol) in toluene (5 mL) and treated according to Procedure 2, acidifying with 20% AcOH. The crude product was recrystallised from EtOH providing (E)-2-[[3-(3-methoxy-4-(naphth-2-ylmethoxy)phenyl)-1-oxo-2-propenyl] amino]benzoic (0.74 g, 66%) as a yellow crystalline solid; mp 197-200° C.; $\delta_H$ (400 MHz, DMSO-d$_6$) 3.86 (s, 3H, OCH$_3$), 5.30 (s, 2H, OCH$_2$), 6.76 (d, J=15.6 Hz, 1H, CH=CHCO), 7.00 (d, $J_{5',6'}$=8.0 Hz, 1H, H5'), 7.15 (1, $J_{3,4}=J_{4,5}$=8.0 Hz, 1H, H4), 7.22 (dd, $J_{5',6'}$=8.0, $J_{2',6'}$=1.6 Hz, 1H, H6'), 7.37 (d, $J_{2',6'}$=1.6 Hz, 1H, H2'), 7.50-7.63 (m, 5H, CH=CHCO, H5, Naphth-H), 7.91-8.01 (m, 5H, H3, Naphth-H), 8.63 (d, $J_{5,6}$=8.0 Hz, 1H, H6), 11.31 (s, 1H, NH), 13.59 (br s, 1H, CO$_2$H); $\delta_C$ (100 MHz, DMSO-d$_6$) 55.7, 70.1, 110.8, 113.4, 116.6, 120.1, 120.3, 122.5, 122.7, 125.9, 126.2, 126.4, 126.6, 127.6, 127.7, 127.8, 128.1, 131.2, 132.6, 132.7, 134.0, 134.5, 141.1, 141.6, 149.3, 149.6, 164.2, 169.5; HRMS (ESI) calculated for C$_{28}$H$_{23}$NO$_5$ [M–H]$^-$ 452.1493. found 452.1495; $v_{max}$ 1135, 1260, 1511, 1584, 1668, 3055 cm$^{-1}$.

3-Methoxy-4-(pent-3-yloxy)benzaldehyde

3-Bromopentane (1.2 mL, 9.9 mmol) was added to a suspension of vanillin (1.0 g, 6.6 mmol), potassium carbonate (2.7 g, 20 mmol) in EtOH (10 mL) and treated according to Procedure 3. The crude product was purified by flash chromatography with 10% EtOAc/petrol as eluent to give 3-methoxy-4-(pent-3-yloxy)benzaldehyde (0.69 g, 47%) as a pale yellow oil; $\delta_H$ (400 MHz, CDCl$_3$) 0.96 (t, J=7.2 Hz, 6H, CH$_3$), 1.73 (m, 4H, CH$_2$), 3.88 (s, 3H, OCH$_3$), 4.23 (m, 1H, OCH), 6.94 (d, $J_{5,6}$=8.0 Hz, 1H, H5), 7.40 (s, 1H, H2), 7.41 (d, $J_{5,6}$=8.0 Hz, 1H, H6), 9.81 (s, 1H, CHO); $\delta_C$ (100 MHz, CDCl$_3$) 9.6, 26.1, 56.0, 81.9, 109.8, 113.1, 126.5, 129.7, 150.5, 154.0, 190.7; ν$_{max}$ 1133, 1263, 1504, 1582, 1682, 2967 cm$^{-1}$.

(E)-2-[[3-(3-Methoxy-4-(pent-3-yloxy)phenyl)-1-oxo-2-propenyl]amino]benzoic acid (45)

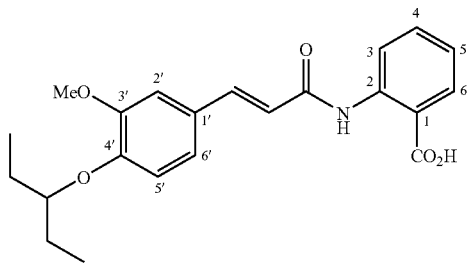 [SMILES: CCC(CC)Oc1ccc(/C=C/C(=O)Nc2ccccc2C(=O)O)cc1OC]

Piperidine (220 μL, 2.2 mmol) was added to a suspension of 3-methoxy-4-(pent-3-yloxy)benzaldehyde (0.50 g, 2.2 mmol) and 2-[(carboxyacetyl)amino]benzoic acid (0.46 g, 2.1 mmol) in toluene (5 mL) and treated according to Procedure 2, acidifying with 20% AcOH. The crude product was recrystallised from EtOH/water providing (E)-2-[[3-(3-methoxy-4-(pent-3-yloxy)phenyl]amino]benzoic acid (0.52 g, 66%) as a yellow crystalline solid; mp 82-85° C.; δ$_H$ (400 MHz, DMSO-d$_6$) 0.88 (t, J=7.2 Hz, 6H, CH$_3$), 1.60 (p, J=7.2 Hz, 4H, CH$_2$), 3.82 (s, 3H, OCH$_3$), 4.25 (t, J=7.2 Hz, 1H, OCH), 6.76 (d, J=15.6 Hz, 1H, CH=CHCO), 6.98 (d, J$_{5',6'}$=8.0 Hz, 1H, H5'), 7.15 (t, J$_{3,4}$=J$_{4,5}$=8.0 Hz, 1H, H4), 7.20 (dd, J$_{5',6'}$=8.0, J$_{2',6'}$=1.6 Hz, 1H, H6'), 7.36 (d, J$_{2',6'}$=1.6 Hz, 1H, H2'), 7.55 (d, J=15.6 Hz, 1H, CH=CHCO), 7.60 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.28 (s, 1H, NH), 13.58 (br s, 1H, CO$_2$H); δ$_C$ (100 MHz, DMSO-d$_6$) 9.3, 25.5, 55.7, 80.1, 111.2, 114.5, 116.6, 119.8, 120.3, 122.5, 122.6, 127.1, 131.1, 134.0, 141.1, 141.6, 149.6, 149.9, 164.2, 169.5; HRMS (ESI) calculated for C$_{22}$H$_{25}$NO$_5$ [M−H]$^−$ 382.1555. found 382.1649; ν$_{max}$ 749, 1139, 1259, 1505, 1584, 1650, 2934 cm$^{-1}$.

(E)-2-[[3-(6-Methoxypyridin-3-yl)-1-oxo-2-propenyl]amino]benzoic acid (46)

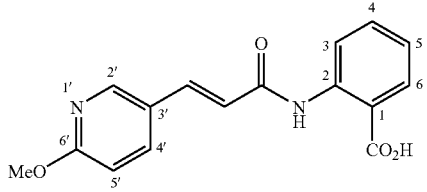 [SMILES: COc1ccc(/C=C/C(=O)Nc2ccccc2C(=O)O)cn1]

Piperidine (220 μL, 2.2 mmol) was added to a suspension of 6-methoxy-3-pyridine carboxaldehyde (0.30 g, 2.2 mmol) and 2-[(carboxyacetyl)amino]benzoic acid (0.44 g, 2.1 mmol) in toluene (5 mL) and treated according to Procedure 2, acidifying with 20% AcOH. The crude product was recrystallised from EtOH providing (E)-2-[[3-(6-methoxypyridin-3-yl)-1-oxo-2-propenyl]amino]benzoic acid (0.33 g, 56%) as a colourless crystalline solid; mp 209-211° C.; δ$_H$ (400 MHz, DMSO-d$_6$) 3.85 (s, 3H, OCH$_3$), 6.82 (d, J=15.6 Hz, 1H, CH=CHCO), 6.85 (d, J$_{5',6'}$=8.0 Hz, 1H, H5'), 7.13 (t, J$_{3,4}$=J$_{4,5}$=8.0 Hz, 1H, H4), 7.57 (d, J=15.6 Hz, 1H, CH=CHCO), 7.58 (t, J$_{4,5}$=J$_{5,6}$=8.0 Hz, 1H, H5), 7.98 (d, J$_{3,4}$=8.0 Hz, 1H, H3), 8.14 (dd, J$_{5',6'}$=8.0, J$_{2',6'}$=1.6 Hz, 1H, H6'), 8.43 (d, J$_{2',6'}$=1.6 Hz, 1H, H2'), 8.57 (d, J$_{5,6}$=8.0 Hz, 1H, H6), 11.29 (s, 1H, NH), 13.58 (br s, 1H, CO$_2$H); δ$_C$ (100 MHz, DMSO-d$_6$) 53.5, 111.0, 116.7, 120.3, 121.4, 122.8, 124.2, 131.1, 134.0, 137.3, 138.0, 140.9, 148.4, 163.7, 164.4, 169.4; HRMS (ESI) calculated for C$_{16}$H$_{14}$N$_2$O$_4$ [M−H]$^−$ 297.0870. found 297.0877; ν$_{max}$ 749, 1249, 1591, 1683, 3246 cm$^{-1}$.

3-Methoxy-4-(adaman-2-yl-2-oxoethoxy)benzaldehyde

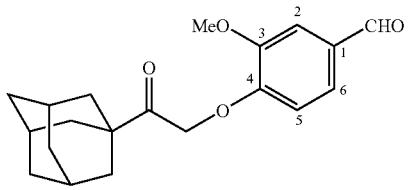 [SMILES: COc1cc(C=O)ccc1OCC(=O)C12CC3CC(CC(C3)C1)C2]

1-Adamantyl bromomethyl ketone (300 mg, 1.19 mmol) was added to a suspension of vanillin (120 mg, 0.791 mmol), potassium carbonate (329 mg, 2.38 mmol) in acetone (5 mL) and treated according to Procedure 3. The crude product was recrystallised from EtOAc/petrol to give 3-methoxy-4-(adaman-2-yl-2-oxoethoxy)benzaldehyde (0.210 g, 81%) as a pale yellow oil; δ$_H$ (400 MHz, CDCl$_3$) 1.73-1.81 (m, 6H, CH$_2$), 1.93 (d, J=2.0 Hz, 6H, CH$_2$), 2.09 (s, 3H, CH), 3.95 (s, 3H, OCH$_3$), 5.05 (s, 2H, OCH$_2$), 6.70 (d, J$_{5,6}$=7.4 Hz, 1H, H5), 7.38 (dd, J$_{5,6}$=7.4, J$_{2,6}$=1.6 Hz, 1H, H6), 7.43 (d, J$_{2,6}$=1.6 Hz, 1H, H2), 9.85 (s, 1H, CHO); δ$_C$ (100 MHz, CDCl$_3$) 27.9, 36.6, 38.3, 45.8, 56.3, 69.4, 109.9, 112.0, 126.4, 130.9, 150.1, 153.1, 190.1, 207.9; ν$_{max}$ 1001, 1133, 1259, 1507, 1587, 1680, 2850, 2904 cm$^{-1}$.

(E)-2-[[3-(3-Methoxy-4-(adaman-2-yl-2-oxoethoxy)phenyl)-1-oxo-2-propenyl]amino]benzoic acid (47)

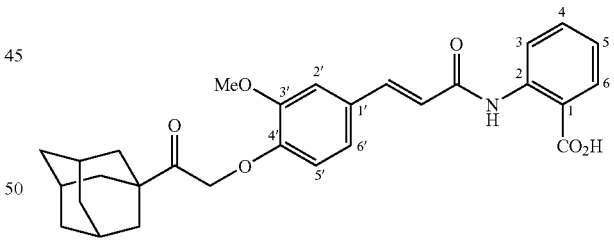

Piperidine (63 μL, 0.64 mmol) was added to a suspension of 3-methoxy-4-(adaman-2-yl-2-oxoethoxy)benzaldehyde (0.21 g, 0.64 mmol) and 2-[(carboxyacetyl)amino]benzoic acid (0.13 g, 0.58 mmol) in toluene (5 mL) and treated according to Procedure 2, acidifying with 20% AcOH. The crude product was recrystallised from EtOH providing (E)-2-[[3-(3-methoxy-4-(adaman-2-yl-2-oxoethoxy)phenyl)-1-oxo-2-propenyl]amino]benzoic acid (0.17 g, 59%) as a colourless crystalline solid; mp 112-114° C.; δ$_H$ (400 MHz, DMSO-d$_6$) 1.66-1.72 (m, 6H, CH$_2$), 1.85-1.86 (m, 6H, CH$_2$), 2.00 (s, 3H, CH), 3.84 (s, 3H, OCH$_3$), 5.12 (s, 2H, OCH$_2$), 6.74 (d, J$_{5',6'}$=8.0 Hz, 1H, H5'), 7.14-7.18 (m, 2H, H4, H6'), 7.37 (d, J$_{2',6'}$=1.6 Hz, 1H, H2'), 7.54 (d, J=15.6 Hz, 1H, CH=CHCO), 7.60 (t, J$_{4,5}$=J$_{5,6}$=8.0

Hz, 1H, H5), 8.00 (d, J$_{3,4}$=8.0 Hz, 1H, H3), 8.62 (d, J$_{5,6}$=8.0 Hz, 1H, H6), 11.28 (s, 1H, NH), 13.53 (br s, 1H, CO$_2$H); δ$_C$ (100 MHz, DMSO-d$_6$) 28.0, 36.6, 37.8, 45.4, 56.5, 69.5, 111.7, 113.4, 117.3, 120.7, 121.0, 123.0, 123.4, 128.2, 131.8, 134.7, 141.8, 142.3, 149.7, 150.0, 164.9, 170.2, 209.4; HRMS (ESI) calculated for C$_{23}$H$_{31}$NO$_6$ [M+Na]$^+$ 512.2044 found 512.2045; v$_{max}$ 749, 1143, 1249, 1508, 1588, 1687, 1712, 2848, 2908, 3380 cm$^{-1}$.

(E)-2-[[3-(3-Methoxy-4-(2-morpholinoethoxy)phenyl)-1-oxo-2-propenyl]amino]benzoic acid (48)

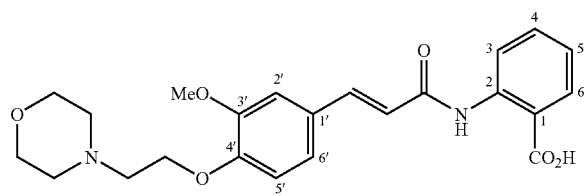 [SMILES: COc1cc(/C=C/C(=O)Nc2ccccc2C(=O)O)ccc1OCCN1CCOCC1]

Piperidine (75 μL, 0.75 mmol) was added to a suspension of 3-methoxy-4-(adaman-2-yl-2-oxoethoxy)benzaldehyde (0.20 g, 0.75 mmol) and 2-[(carboxyacetyl)amino]benzoic acid (0.15 g, 0.69 mmol) in toluene (5 mL) and treated according to Procedure 2, neutralizing with 20% AcOH. The aqueous phase was extracted with CH$_2$Cl$_2$, washed with water, brine, dried and concentrated. The crude product was recrystallised from MeOH providing (E)-2-[[3-(3-methoxy-4-(2-morpholinoethoxy)phenyl)-1-oxo-2-propenyl]amino]benzoic acid (65 mg, 22%) as a pale brown solid; mp 195-201° C.; δ$_H$ (400 MHz, DMSO-d$_6$) 2.62 (m, 4H, CH$_2$N), 2.83 (t, J=4.4 Hz, 4H, CH$_2$), 3.61 (t, J=3.3 Hz, 4H, OCH$_2$), 3.81 (s, 3H, OCH$_3$), 4.15 (t, J=4.4 Hz, 2H, OCH$_2$), 6.74 (d, J=15.6 Hz, 1H, CH=CHCO), 7.00 (d, J$_{5',6'}$=8.0 Hz, 1H, H5'), 7.12 (t, J$_{3,4}$=J$_{4,5}$=8.0 Hz, 1H, H4), 7.20 (d, J$_{5',6'}$=8.0 Hz, 1H, H6'), 7.35 (s, 1H, H2'), 7.53 (d, J=15.6 Hz, 1H, CH=CHCO), 7.55 (t, J$_{4,5}$=J$_{5,6}$=8.0 Hz, 1H, H5), 8.00 (d, J$_{3,4}$=8.0 Hz, 1H, H3), 8.62 (d, J$_{5,6}$=8.0 Hz, 1H, H6), 11.81 (s, 1H, NH); δ$_C$ (100 MHz, DMSO-d$_6$) 53.4, 55.7, 56.6, 65.7, 110.7, 113.0, 118.0, 120.0, 120.3, 122.4, 122.5, 127.6, 131.2, 133.3, 141.1, 141.3, 149.2, 149.6, 164.1, 168.7; HRMS (ESI) calculated for C$_{23}$H$_{26}$N$_2$O$_6$ [M+H]$^+$ 427.1864 found 427.1864; v$_{max}$ 764, 1139, 1249, 1502, 1583, 1621, 1676, 2964 cm$^{-1}$.

(E)-2-[[3-(3-Methoxy-4-(pyridin-3-ylmethoxy)phenyl)-1-oxo-2-propenyl]amino]benzoic acid (49)

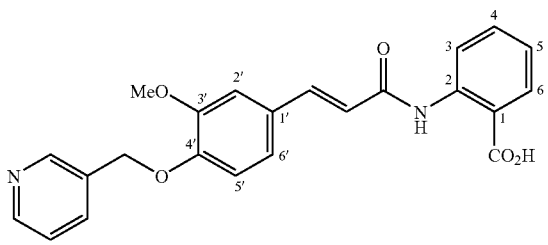 [SMILES: COc1cc(/C=C/C(=O)Nc2ccccc2C(=O)O)ccc1OCc1cccnc1]

3-Bromomethylpyridine (0.30 mg, 1.2 mmol) was added to a suspension of vanillin (0.12 g, 0.79 mmol), potassium carbonate (0.33 g, 2.4 mmol) in acetone (5.0 mL) and treated according to Procedure 3. 3-Methoxy-4-(pyridin-3-ylmethoxy)benzaldehyde (88 mg, 46%) was obtained as a brown oil. Piperidine (36 μL, 0.36 mmol) was added to a suspension of 3-methoxy-4-(pyridin-3-ylmethoxy)benzaldehyde (0.88 mg, 0.36 mmol) and 2-[(carboxyacetyl)amino]benzoic acid (73 mg, 0.33 mmol) in toluene (5 mL) and treated according to Procedure 2, acidifying with 20% AcOH. (E)-2-[[3-(3-Methoxy-4-(pyridin-3-ylmethoxy)phenyl)-1-oxo-2-propenyl]amino]benzoic acid (58 mg, 44%) was obtained as a pure brown crystalline solid; mp 245-251° C.; δ$_H$ (400 MHz, DMSO-d$_6$) 3.84 (s, 3H, OCH$_3$), 5.18 (s, 2H, OCH$_2$), 6.80 (d, J=15.6 Hz, 1H, CH=CHCO), 7.12 (d, J$_{5',6'}$=8.0 Hz, 1H, H5'), 7.16 (t, J$_{3,4}$=J$_{4,5}$=8.0 Hz, 1H, H4), 7.24 (d, J$_{5',6'}$=8.0 Hz, 1H, H6'), 7.40-7.45 (m, 2H, H2', Ar—H), 7.56 (d, J=15.6 Hz, 1H, CH=CHCO), 7.60 (t, J$_{4,5}$=J$_{5,6}$=8.0 Hz, 1H, H5), 7.87 (d, J=8.0 Hz, 1H, Ar—H), 8.00 (d, J$_{3,4}$=8.0 Hz, 1H, H3), 8.55-8.67 (m, 3H, H6, Ar—H), 11.32 (s, 1H, NH); δ$_C$ (100 MHz, DMSO-d$_6$) 55.7, 67.6, 110.8, 113.4, 116.7, 120.2, 120.3, 122.4, 122.7, 123.6, 127.9, 131.1, 132.4, 133.9, 135.9, 141.0, 141.5, 149.1, 149.2, 149.3, 164.2, 169.5; HRMS (ESI) calculated for C$_{23}$H$_{20}$N$_2$O$_5$ [M+H]$^+$ 404.1445 found 404.1445; v$_{max}$ 758, 1257, 1509, 1586, 1671, 2931 cm$^{-1}$.

(E)-2-[[3-(3,5-Dimethylisoxazol-4-yl)methoxy)-4-methoxyphenyl)-1-oxo-2-propenyl]amino]benzoic acid (50)

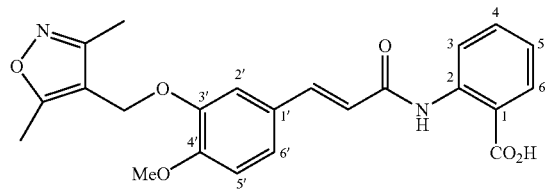 [SMILES: COc1ccc(/C=C/C(=O)Nc2ccccc2C(=O)O)cc1OCc1c(C)noc1C]

Piperidine (97 μL, 0.99 mmol) was added to a suspension of 3-((3,5-dimethylisoxazol-4-yl)methoxy)-4-methoxybenzaldehyde (0.26 g, 0.99 mmol) and 2-[(carboxyacetyl)amino]benzoic acid (0.20 g, 0.90 mmol) in toluene (5 mL) and treated according to Procedure 2, acidifying with 20% AcOH. The crude product was recrystallised from EtOH/water providing (E)-2-[[3-((3-(3,5-dimethylisoxazol-4-yl)methoxy)-4-methoxyphenyl)-1-oxo-2-propenyl]amino]benzoic acid (0.21 g, 54%) as an orange/brown crystalline solid; mp 227-229° C.; δ$_H$ (400 MHz, DMSO-d$_6$) 2.21 (s, 3H, CH$_3$), 2.38 (s, 3H, CH$_3$), 3.82 (s, 3H, OCH$_3$), 4.94 (s, 2H, OCH$_2$), 6.81 (d, J=15.6 Hz, 1H, CH=CHCO), 7.10 (d, J$_{5',6'}$=8.0 Hz, 1H, H5'), 7.16 (t, J$_{3,4}$=J$_{4,5}$=8.0 Hz, 1H, H4), 7.26 (d, J$_{5',6'}$=8.0 Hz, 1H, H6'), 7.39 (s, 1H, H2'), 7.57 (d, J=15.6 Hz, 1H, CH=CHCO), 7.61 (t, J$_{4,5}$=J$_{5,6}$=8.0 Hz, 1H, H5), 8.00 (d, J$_{3,4}$=8.0 Hz, 1H, H3), 8.63 (d, J$_{5,6}$=8.0 Hz, 1H, H6), 11.31 (s, 1H, NH), 13.62 (br s, 1H, CO$_2$H); δ$_C$ (100 MHz, DMSO-d$_6$) 10.3, 11.2, 56.4, 60.5, 111.0, 111.6, 114.9, 117.3, 121.0, 123.0, 123.3, 128.8, 131.8, 134.6, 141.7, 142.2, 149.8, 150.3, 160.3, 164.8, 168.2, 170.1; HRMS (ESI) calculated for $C_{23}H_{22}N_2O_6$ [M+Na]$^+$ 445.1370. found 445.1369; $v_{max}$ 1141, 1256, 1511, 1584, 1665, 2940, 3326 cm$^{-1}$.

(E)-2-[[3-(3-((Diethylamino)methyl)-4-methoxyphenyl)-1-oxo-2-propenyl]amino]benzoic acid (51)

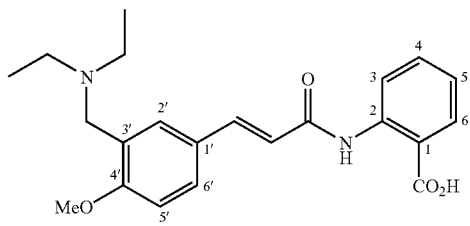 [SMILES: CCN(CC)Cc1cc(/C=C/C(=O)Nc2ccccc2C(=O)O)ccc1OC]

Piperidine (97 µL, 0.99 mmol) was added to a suspension of 3-((diethylamino)methyl)-4-methoxybenzaldehyde (0.22 g, 0.99 mmol) and 2-[(carboxyacetyl)amino]benzoic acid (0.20 g, 0.90 mmol) in toluene (5 mL) and treated according to Procedure 2, neutralizing with 20% AcOH. The resulting precipitate was filtered and washed with water providing (E)-2-[[3-(3-((diethylamino)methyl)-4-methoxyphenyl)-1-oxo-2-propenyl]amino]benzoic acid (0.17 g, 50%) as a colourless crystalline solid; mp 202-205° C.; $\delta_H$ (400 MHz, DMSO-d$_6$) 1.14 (t, J=7.2 Hz, 4H, CH$_2$CH$_3$), 2.87 (q, J=7.2 Hz, 6H, CH$_2$CH$_3$), 3.79 (s, 3H, OCH$_3$), 3.98 (s, 2H, NCH$_2$), 6.51 (d, J=15.6 Hz, 1H, CH=CHCO), 6.98 (t, $J_{3,4}=J_{4,5}$=8.0 Hz, 1H, H4), 7.03 (d, $J_{5',6'}$=8.0 Hz, 1H, H5'), 7.34 (t, $J_{4,5}=J_{5,6}$=8.0 Hz, 1H, H5), 7.46 (d, J=15.6 Hz, 1H, CH=CHCO), 7.57 (dd, $J_{5',6'}$=8.0, $J_{2',6'}$=1.6 Hz, 1H, H6'), 7.76 (d, $J_{2',6'}$=1.6 Hz, 1H, H2'), 7.98 (d, $J_{3,4}$=8.0 Hz, 1H, H3), 8.54 (d, $J_{5,6}$=8.0 Hz, 1H, H6), 13.34 (br s, 1H, CO$_2$H); $\delta_C$ (100 MHz, DMSO-d$_6$) 9.38, 46.4, 49.8, 55.6, 111.4, 118.9, 121.2, 121.5, 122.1, 126.9, 130.2, 130.8, 130.9, 139.2, 140.7, 158.8, 163.3, 169.7; HRMS (ESI) calculated for $C_{22}H_{26}N_2O_4$ [M+H]$^+$ 383.1965. found 383.1964; $v_{max}$ 823, 1264, 1366, 1500, 1579, 1609, 1674, 2943, 3478 cm$^{-1}$.

| | Comparative structures | |
|---|---|---|
| FT no. | Structure | Formula and molecular weight |
| 001 | ![structure] | $C_{18}H_{17}NO_5$ 327.33 |
| 002 | ![structure] | $C_{16}H_{13}NO_3$ 267.28 |
| 003 | ![structure] | $C_{17}H_{15}NO_4$ 297.31 |
| 004 | ![structure] | $C_{17}H_{15}NO_4$ 297.31 |
| 005 | ![structure] | $C_{16}H_{13}NO_5$ 299.28 |

Comparative structures

| FT no. | Structure | Formula and molecular weight |
|---|---|---|
| 006 | MeO, HO-phenyl-CH=CH-C(=O)-NH-phenyl-CO$_2$H | C$_{17}$H$_{15}$NO$_5$ 313.30 |
| 007 | HO, MeO-phenyl-CH=CH-C(=O)-NH-phenyl-CO$_2$H | C$_{17}$H$_{15}$NO$_5$ 313.30 |
| 008 | MeO, MeO-phenyl-CH=CH-C(=O)-NH-naphthyl-CO$_2$H | C$_{22}$H$_{19}$NO$_5$ 377.39 |
| 009 | MeO, MeO-phenyl-CH=CH-C(=O)-NH-phenyl(OMe, OMe)-CO$_2$H | C$_{20}$H$_{21}$NO$_7$ 387.38 |
| 010 | MeO, MeO-phenyl-CH$_2$-CH$_2$-C(=O)-NH-phenyl-CO$_2$H | C$_{18}$H$_{19}$NO$_5$ 329.35 |

Structures of the present invention

| FT no. | Structure | Formula and molecular weight |
|---|---|---|
| 011 | MeO, HC≡C-CH$_2$-O-phenyl-CH=CH-C(=O)-NH-phenyl-CO$_2$H | C$_{20}$H$_{17}$NO$_5$ 351.35 |
| 012 | MeO, MeO-phenyl-CH=CH-C(=O)-NH-phenyl-CONH$_2$ | C$_{18}$H$_{18}$N$_2$O$_4$ 326.35 |

-continued
| FT no. | Structure | Formula and molecular weight |
|---|---|---|
| 013 | 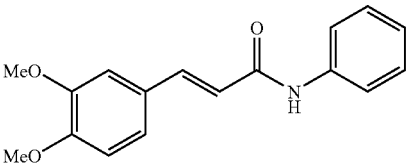 [SMILES: COc1ccc(/C=C/C(=O)Nc2ccccc2)cc1OC] | $C_{17}H_{17}NO_3$ 283.32 |
| 014 | 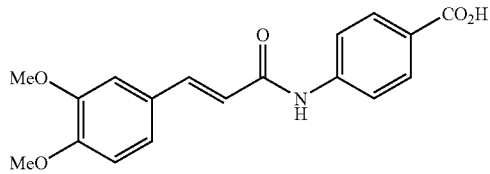 [SMILES: COc1ccc(/C=C/C(=O)Nc2ccc(C(=O)O)cc2)cc1OC] | $C_{18}H_{17}NO_5$ 327.33 |
| 015 | 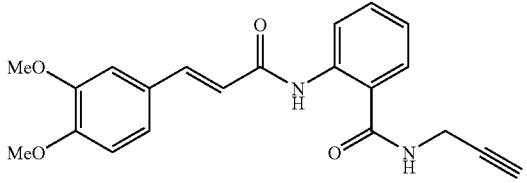 [SMILES: C#CCNC(=O)c1ccccc1NC(=O)/C=C/c1ccc(OC)c(OC)c1] | $C_{21}H_{20}N_2O_4$ 364.39 |
| 016 | 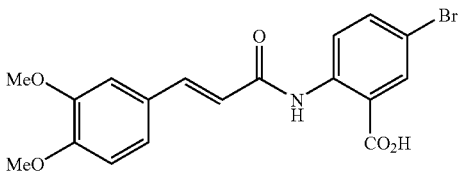 [SMILES: COc1ccc(/C=C/C(=O)Nc2ccc(Br)cc2C(=O)O)cc1OC] | $C_{18}H_{16}BrNO_5$ 406.23 |
| 017 | 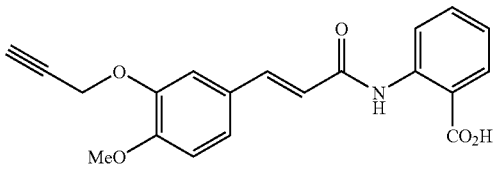 [SMILES: C#CCOc1cc(/C=C/C(=O)Nc2ccccc2C(=O)O)ccc1OC] | $C_{20}H_{17}NO_5$ 353.35 |
| 018 | 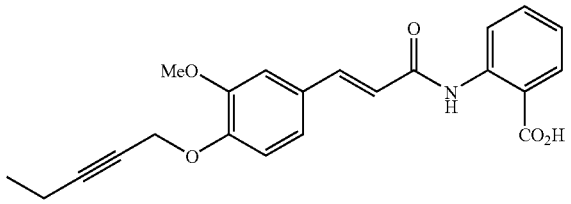 [SMILES: CCC#CCOc1ccc(/C=C/C(=O)Nc2ccccc2C(=O)O)cc1OC] | $C_{22}H_{21}NO_5$ 379.41 |
| 019 | 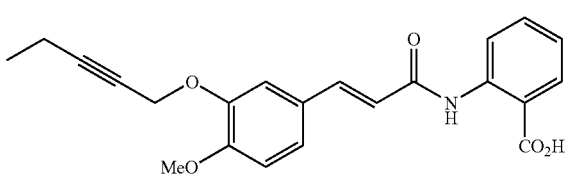 [SMILES: CCC#CCOc1cc(/C=C/C(=O)Nc2ccccc2C(=O)O)ccc1OC] | $C_{22}H_{21}NO_5$ 379.41 |

-continued

Structures of the present invention

| FT no. | Structure | Formula and molecular weight |
|---|---|---|
| 020 | 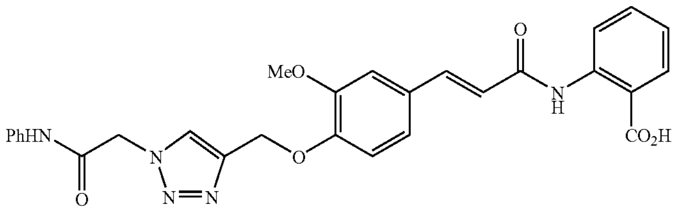 | $C_{28}H_{25}N_5O_6$ 527.53 |
| 021 | 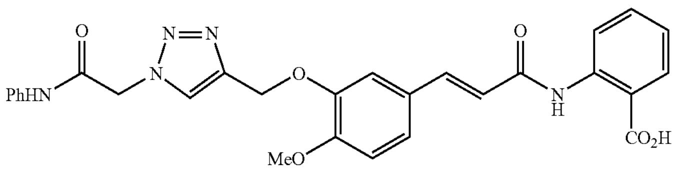 | $C_{28}H_{25}N_6O_6$ 527.53 |
| 022 | 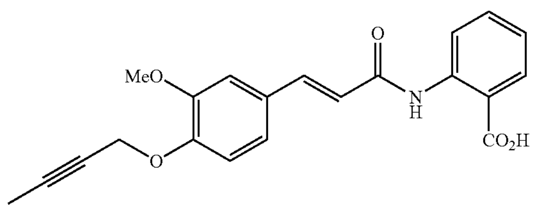 [SMILES: CC#CCOc1ccc(/C=C/C(=O)Nc2ccccc2C(=O)O)cc1OC] | $C_{21}H_{19}NO_5$ 365.38 |
| 023 | 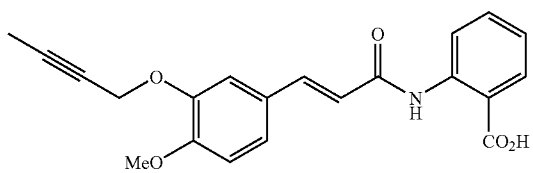 [SMILES: CC#CCOc1cc(/C=C/C(=O)Nc2ccccc2C(=O)O)ccc1OC] | $C_{21}H_{19}NO_5$ 365.38 |
| 026 | 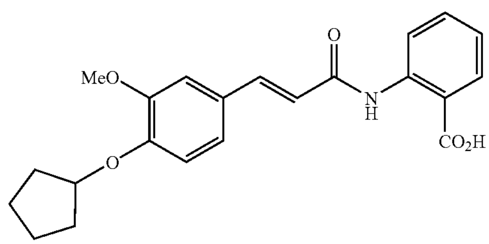 [SMILES: COc1cc(/C=C/C(=O)Nc2ccccc2C(=O)O)ccc1OC1CCCC1] | $C_{22}H_{23}NO_5$ 381.42 |
| 027 | 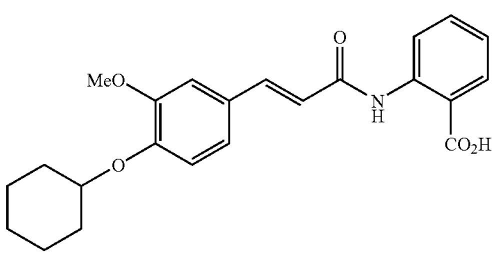 [SMILES: COc1cc(/C=C/C(=O)Nc2ccccc2C(=O)O)ccc1OC1CCCCC1] | $C_{23}H_{25}NO_5$ 395.45 |
| 028 | 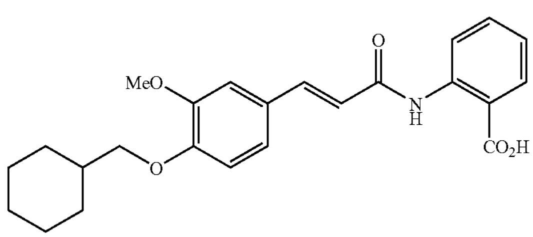 [SMILES: COc1cc(/C=C/C(=O)Nc2ccccc2C(=O)O)ccc1OCC1CCCCC1] | $C_{24}H_{27}NO_5$ 409.47 |

Structures of the present invention

| FT no. | Structure | Formula and molecular weight |
|---|---|---|
| 029 | (cyclopentyloxy-methoxyphenyl cinnamamide with 2-carboxyphenyl) | $C_{22}H_{23}NO_5$ 381.42 |
| 032 | (3,4-dimethoxycinnamamide-phenyl-carboxamide-methyl-triazole-acetamide-NHPh) | $C_{29}H_{28}N_6O_5$ 540.57 |
| 033 | (methoxy, hex-5-ynyloxy phenyl cinnamamide with 2-carboxyphenyl) | $C_{23}H_{23}NO_5$ 393.43 |
| 034 | (hex-5-ynyloxy, methoxy phenyl cinnamamide with 2-carboxyphenyl) | $C_{23}H_{23}NO_5$ 393.43 |
| 035 | (methoxy, pent-4-ynyloxy phenyl cinnamamide with 2-carboxyphenyl) | $C_{22}H_{21}NO_5$ 379.41 |
| 036 | (pent-4-ynyloxy, methoxy phenyl cinnamamide with 2-carboxyphenyl) | $C_{22}H_{21}NO_5$ 379.41 |
| 037 | (methoxy, but-3-ynyloxy phenyl cinnamamide with 2-carboxyphenyl) | $C_{21}H_{19}NO_5$ 365.38 |
| 038 | (but-3-ynyloxy, methoxy phenyl cinnamamide with 2-carboxyphenyl) | $C_{21}H_{19}NO_5$ 365.38 |

-continued
| FT no. | Structure | Formula and molecular weight |
|---|---|---|
| 039 | 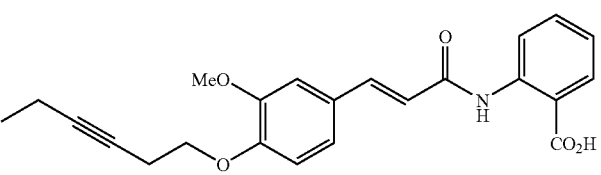 [SMILES: CCC#CCCOc1ccc(/C=C/C(=O)Nc2ccccc2C(=O)O)cc1OC] | $C_{23}H_{23}NO_5$ 393.43 |
| 040 | 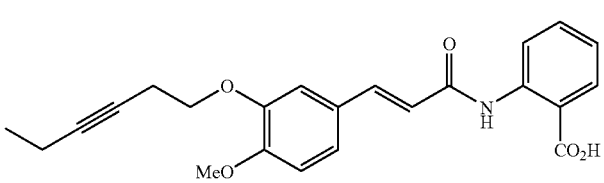 [SMILES: CCC#CCCOc1cc(/C=C/C(=O)Nc2ccccc2C(=O)O)ccc1OC] | $C_{23}H_{23}NO_5$ 393.43 |
| 041 | 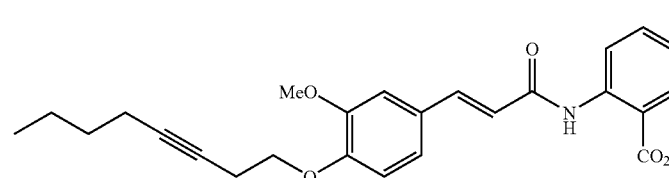 | $C_{25}H_{27}NO_5$ 421.49 |
| 042 | 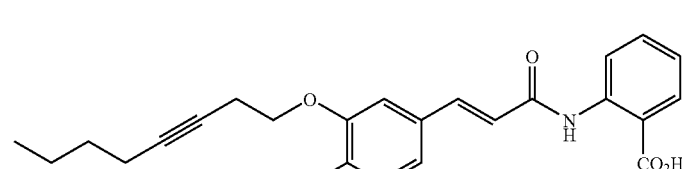 | $C_{25}H_{27}NO_5$ 421.49 |
| 043 | 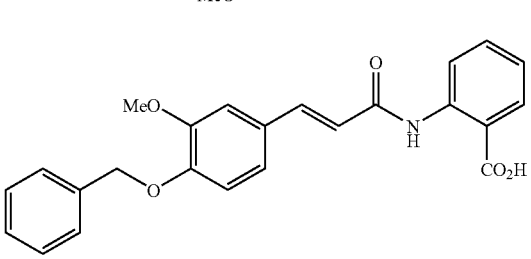 | $C_{24}H_{21}NO_5$ 403.43 |
| 044 | 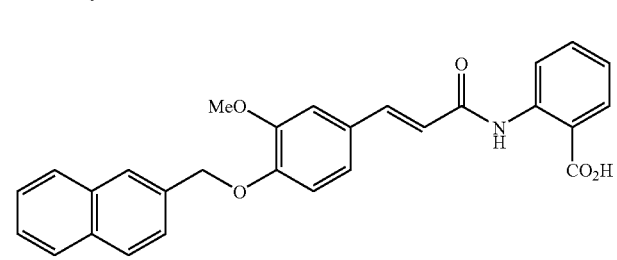 | $C_{28}H_{23}NO_5$ 453.49 |
| 045 | 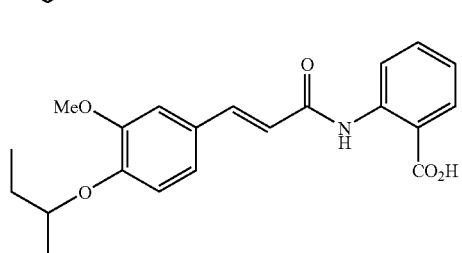 | $C_{22}H_{25}NO_5$ 383.44 |

-continued
| | Structures of the present invention | |
|---|---|---|
| FT no. | Structure | Formula and molecular weight |
| 046 | | $C_{16}H_{14}N_2O_4$ 298.29 |
| 047 | | $C_{29}H_{31}NO_6$ 489.56 |
| 048 | | $C_{23}H_{26}N_2O_6$ 426.46 |
| 049 | | $C_{23}H_{20}N_2O_5$ 404.42 |
| 050 | | $C_{23}H_{22}N_2O_6$ 422.43 |
| 051 | | $C_{22}H_{26}N_2O_4$ 382.45 |
Proposed Compounds
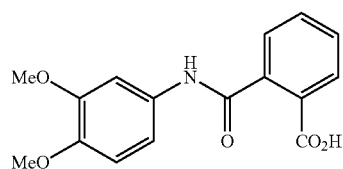
60
-continued
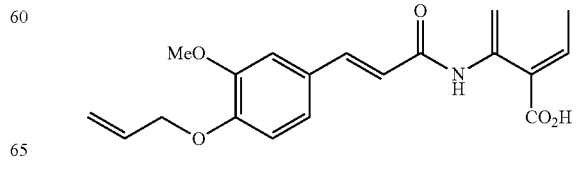
65

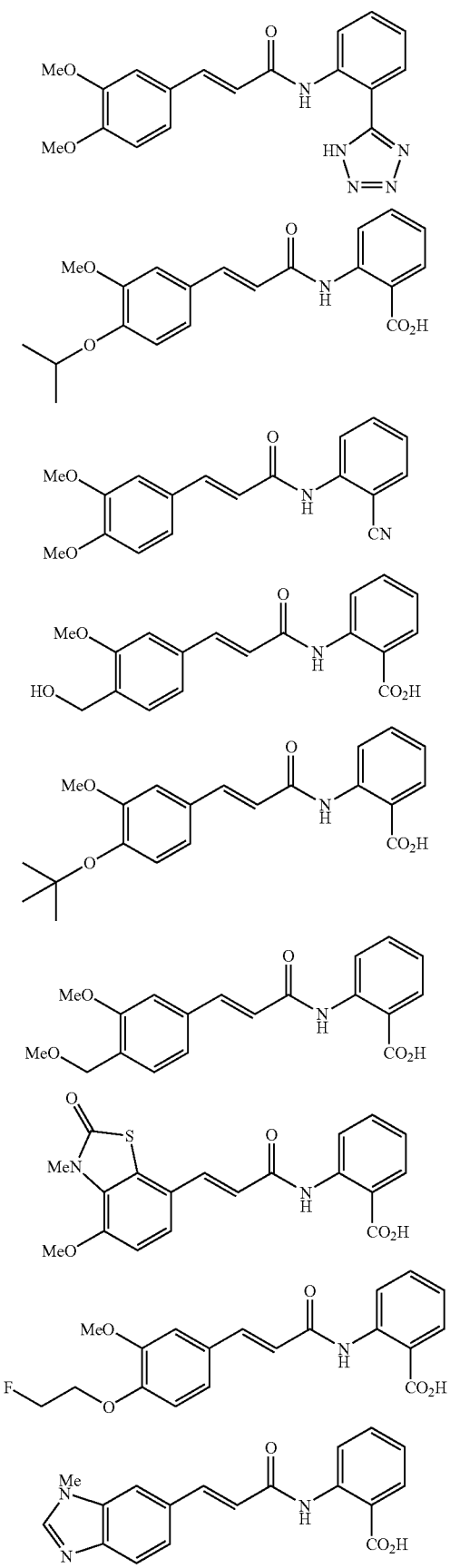
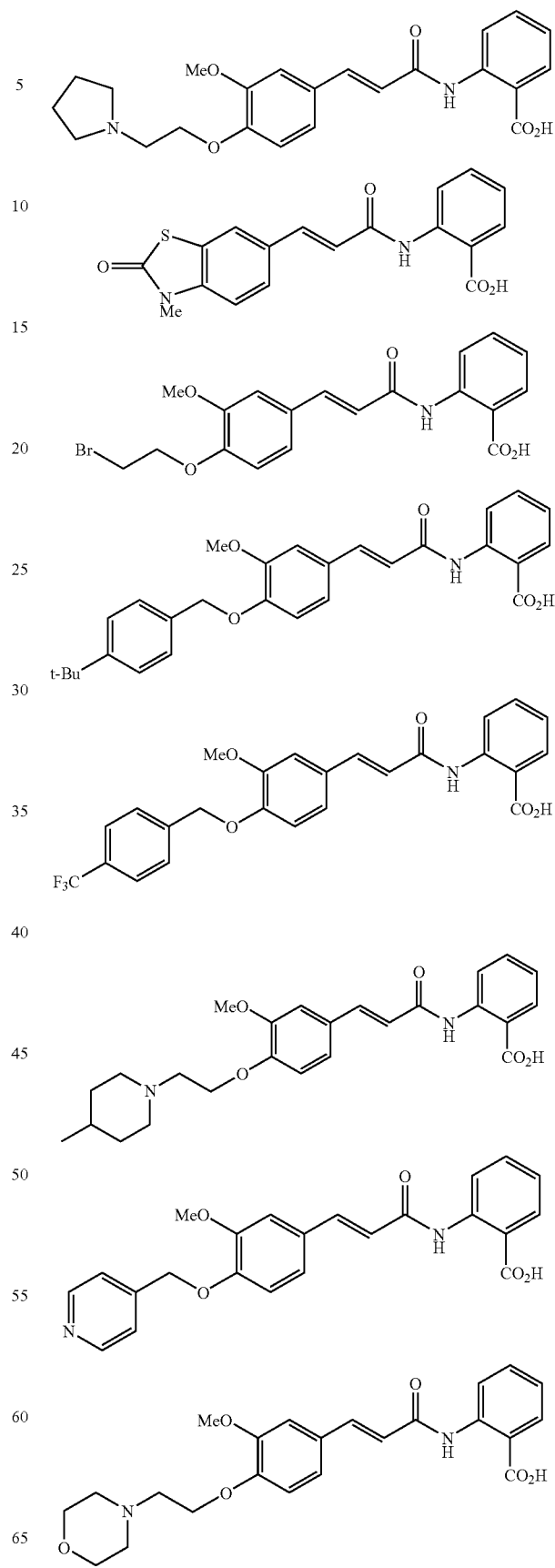

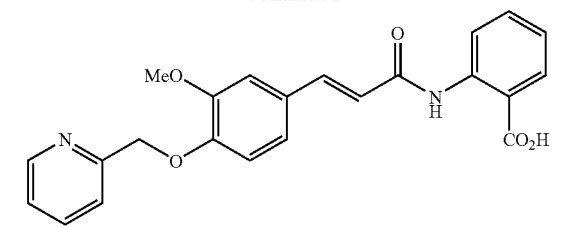 [SMILES: COc1cc(/C=C/C(=O)Nc2ccccc2C(=O)O)ccc1OCc1ccccc1]
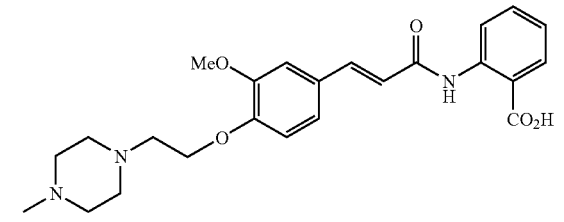
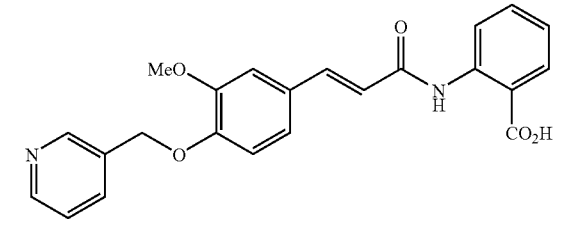 [SMILES: COc1cc(/C=C/C(=O)Nc2ccccc2C(=O)O)ccc1OCc1cccnc1]
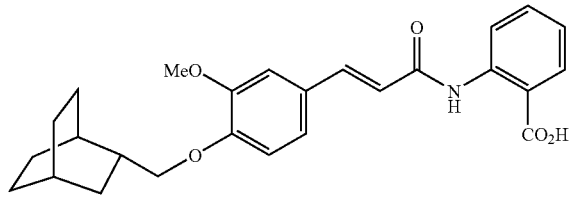
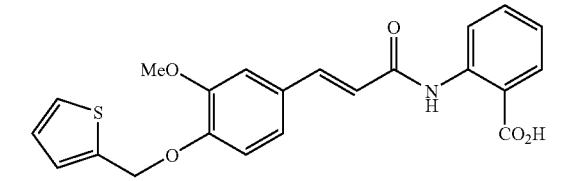
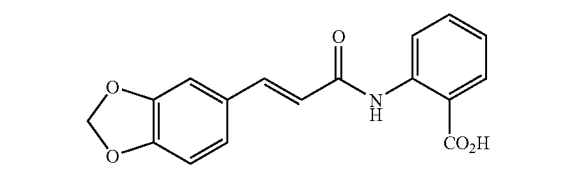
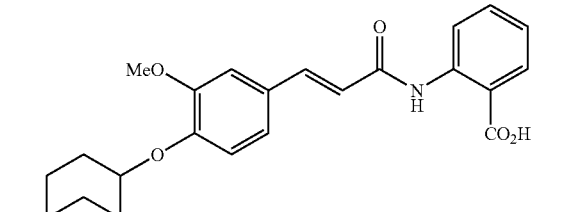
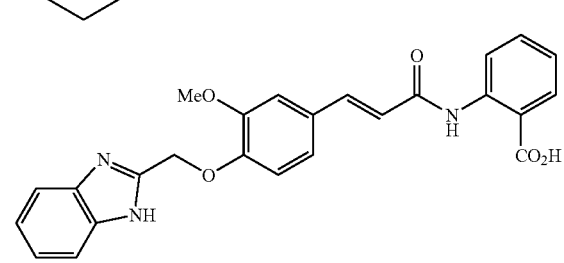
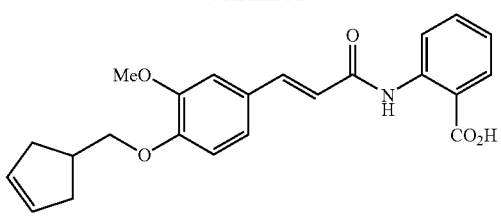
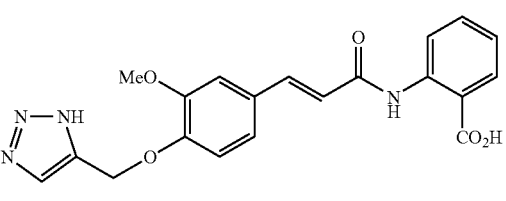
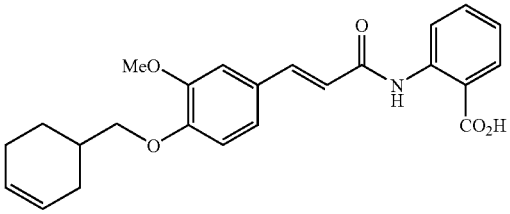
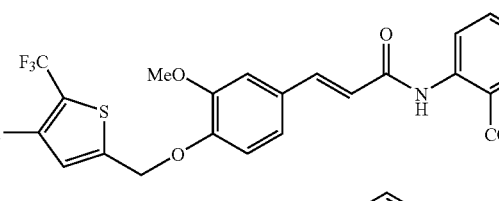
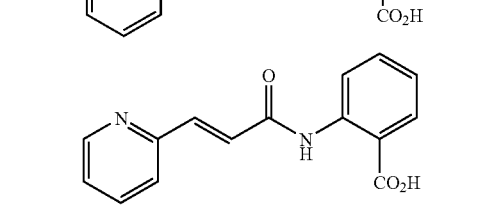
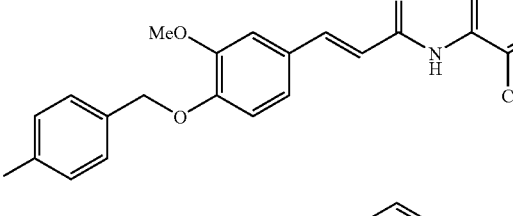
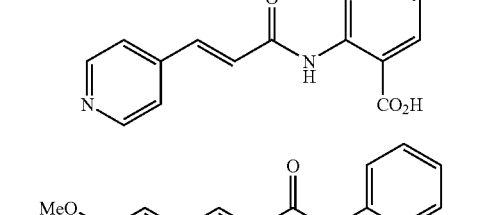
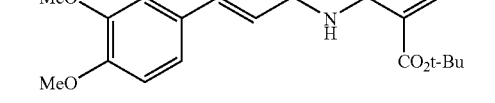

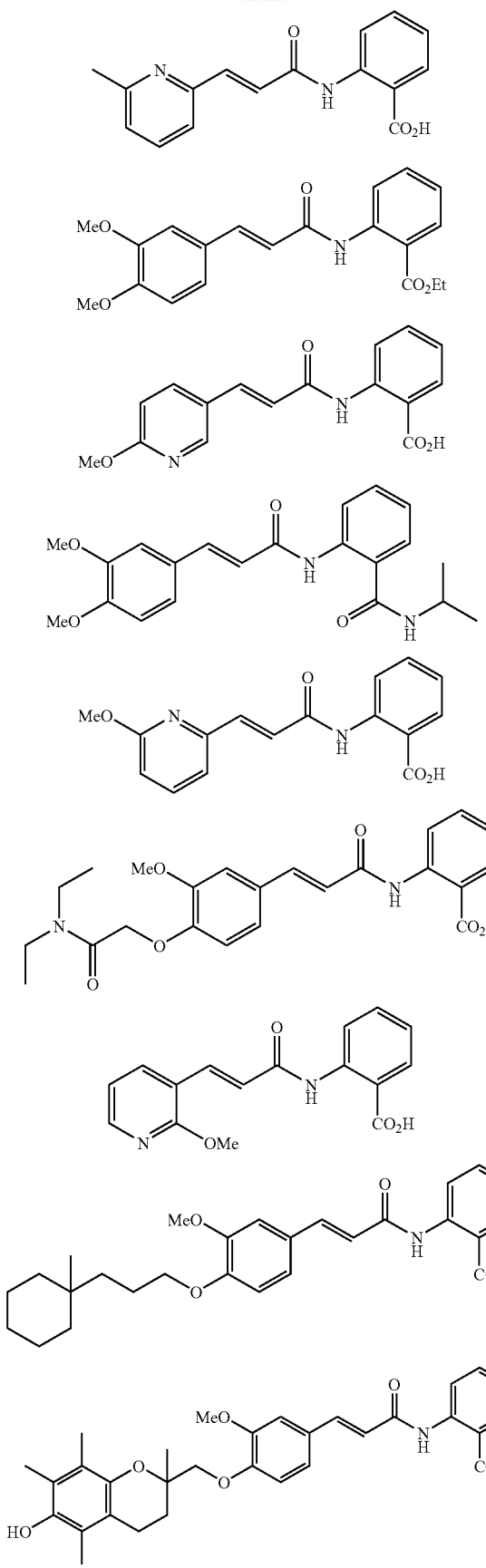
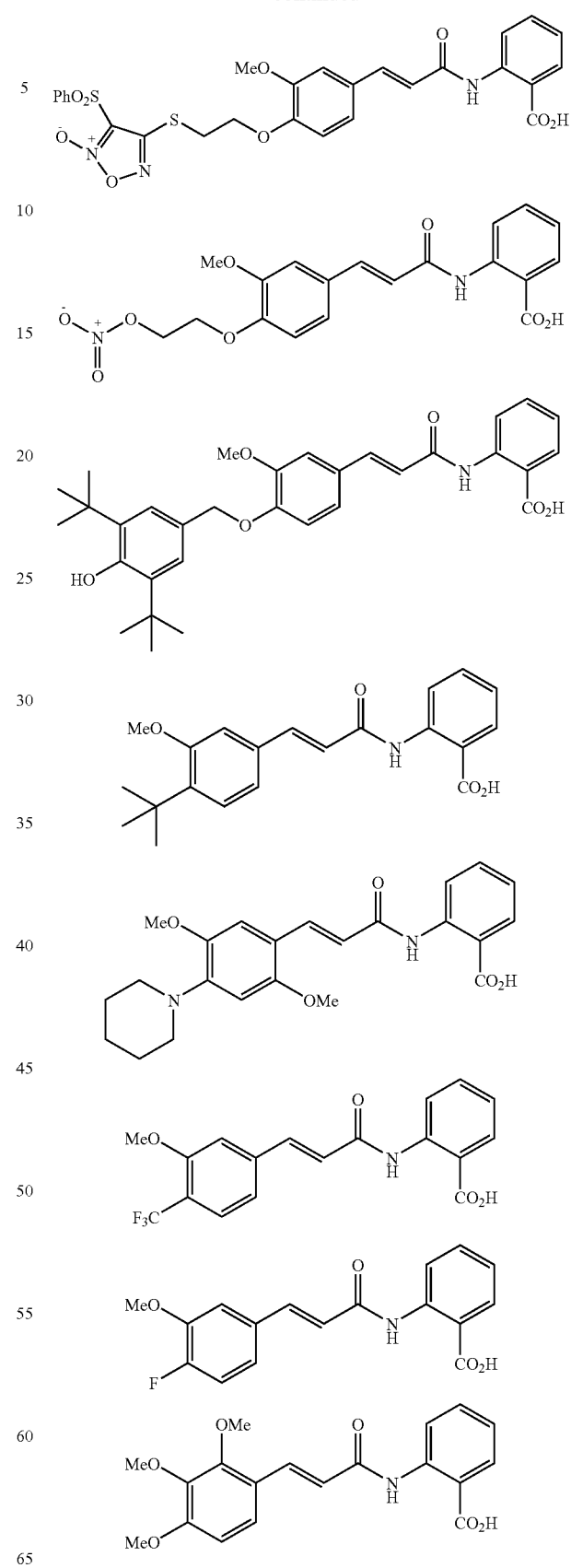

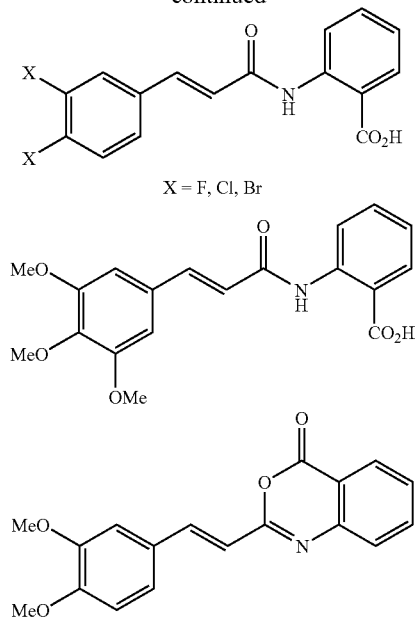

X = F, Cl, Br

Example 2

Cell Culture Studies—Transforming Growth Factor-β Stimulation

The anti-fibrotic effects of 3-methoxy-4-propargyloxybenzaldehyde (FT011) in a renal cell line were tested by measuring proline incorporation after transforming growth factor-β stimulation.

A well-characterized cloned mesangial cell line (1097) isolated from Sprague-Dawley rats [30] was used between passages 30 and 40. Cells were cultured in Dulbecco's Modified Eagle's (DME) medium (Invitrogen, Grand Island, N.Y.) with heat-inactivated fetal bovine serum (FBS), 100 u/mL penicillin and 100 ug/mL streptomycin in a humidified 5% $CO_2$ atmosphere at 37° C.

To compare the effects of tranilast and FT011 on collagen production in vitro, incorporation of tritiated proline was used [40]. Mesangial cells were plated at low density into 24-well culture plates in DME/5% FBS and allowed to adhere overnight. The subconfluent cells were starved overnight in DME/0.5% FBS and 150 mM L-ascorbic acid (Sigma-Aldrich). Tranilast or FT011 was then added to the wells, followed 4 hours later by L-[2,3,4,5-$^3$H]-proline, 0.5 µCi/well (Amersham) and TGF-β1, 5 ng/ml (R & D systems). Mesangial cells were harvested 48 hours post-stimulation, washed three times with ice cold PBS, and incubated with 10% trichloroacetic acid (TCA) for 30 minutes on ice, followed by a wash in ice cold 10% TCA. Cells were then solubilised in 750 ml 1 M NaOH. Scintillation counting was performed on 500 mL aliquots of solubilized cells neutralized with 500 mL of 1M HCl in 10 mL of Instagel Plus scintillant (Perkin-Elmer, Boston, Mass.).

Figure 2:
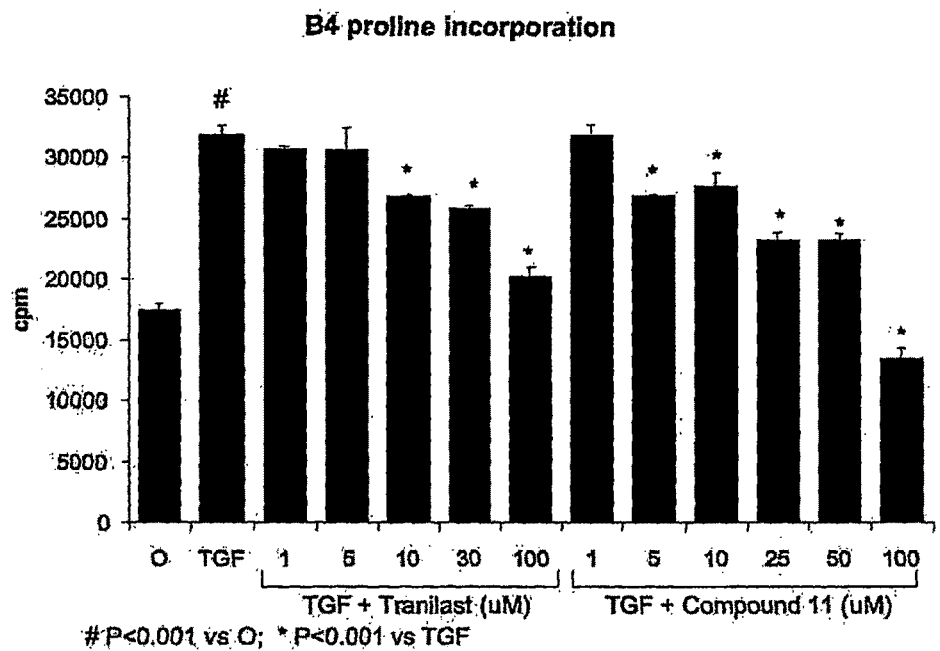

The data shown in FIGS. 1 and 2 suggest that in renal mesangial cells, both tranilast and FT011 significantly reduce proline incorporation from 30 to 100 µM. The degree of proline incorporation in vitro relates to the degree on fibrosis in vivo.

Example 3

Matrix synthesis may be stimulated by platelet derived growth factor (PDGF). Accordingly, mesangial cells incubated with PDGF will demonstrate proline incorporation, which is an indicator of matrix synthesis and thereby a model for fibrosis.

Figure 3:
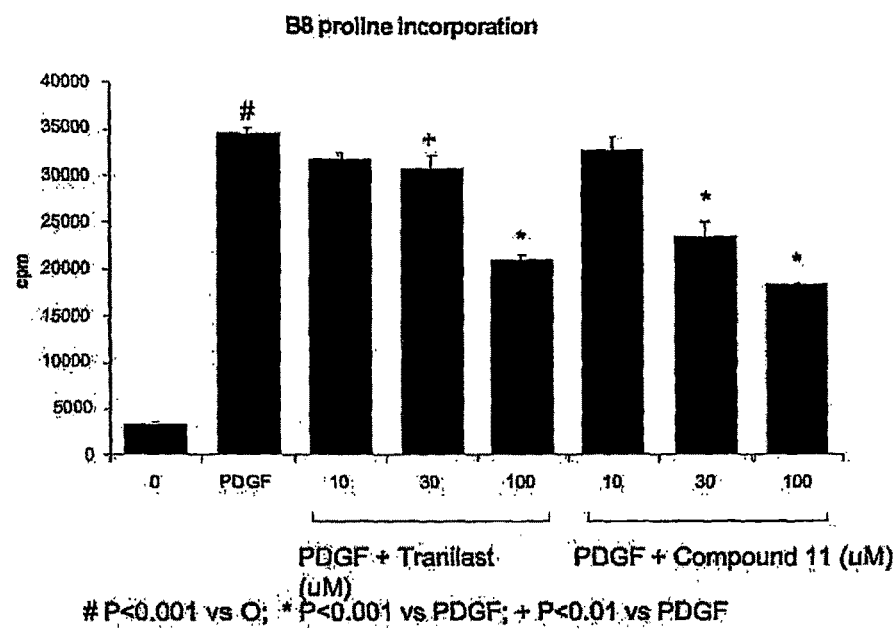
FIG. 3: Mesangial cells stimulated with Platelet derived growth factor (PDGF) to stimulate proline formation (matrix synthesis).

In order to assess the effect of FT011 on PDGF stimulated matrix synthesis, mesangial cells (prepared as described in Example 2) were incubated with FT011 or tranilast in the presence of PDGF. The results of this analysis were provided in FIG. 3. As shown in FIG. 3, FT011 inhibits PDGF-stimulated matrix synthesis (shown by reduced proline incorporation) at 30 and 100 µM concentrations. At 30 µM concentrations, FT011 is more potent at reducing proline incorporation than tranilast.

Example 4

Matrix synthesis may be stimulated by both angiotensin II or transforming growth factor beta (TGF-β). Accordingly, neonatal cardiac fibroblasts incubated with angiotensin II or TGF-β will demonstrate proline incorporation, which is an indicator of matrix synthesis and thereby a model for fibrosis.

Neonatal SD rat cardiac fibroblasts (NCFs) were isolated from one-day-old pups with enzymatic digestion. NCFs were purified by percoll gradient and seeded with DMEM in the present of 1% antibiotic/antimycotic (AB/AM) and 10% fatal bovine serum (FBS). NCFs were then subcultured when they are about 80% confluence. The second passage of NCFs was used for the assays.

NCFs were seeded at 25,000 cells/well in 12-well plates and incubated at 37° C. and 5% $CO_2$ overnight in DMEM with 1% AB/AM and 10% FBS. Cells were then washed with DMEM and then the media replaced with DMEM/F12 with 1% AB/AM, 0.5% Bovine Serum Albumin (BSA) and Vitamin C, before being incubated at 37° C. and 5% $CO_2$ for 24 hours.

Figure 4:
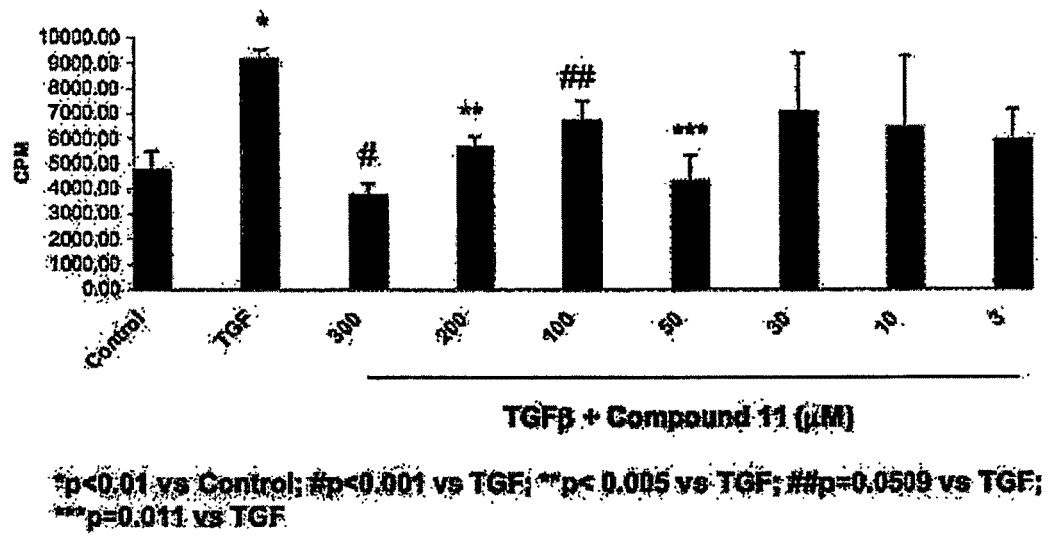
FIG. 4: Shows the inhibition of TGF-β stimulated fibrosis (indicated by proline formation) in neonatal cardiac fibroblasts.
Figure 5:
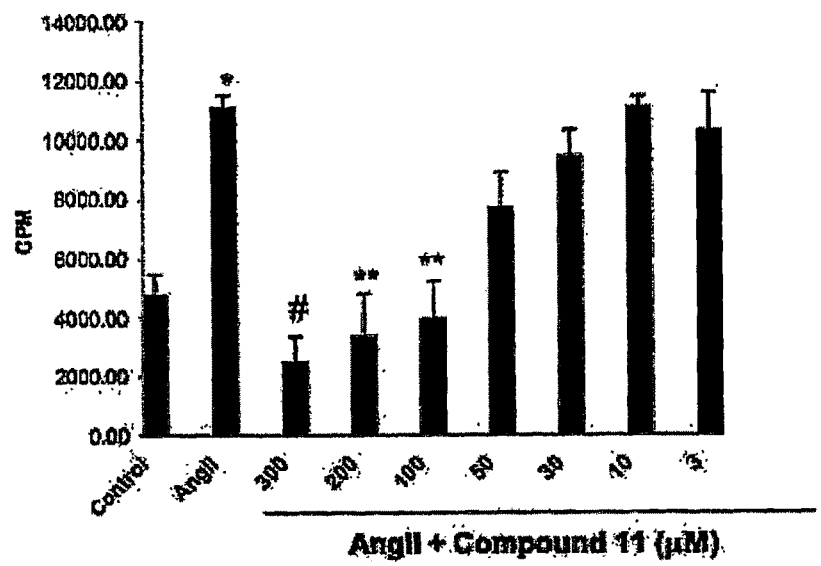
FIG. 5: Shows the inhibition of angiotensin II-stimulated fibrosis (indicated by proline formation) in neonatal cardiac fibroblasts.
Figure 6:
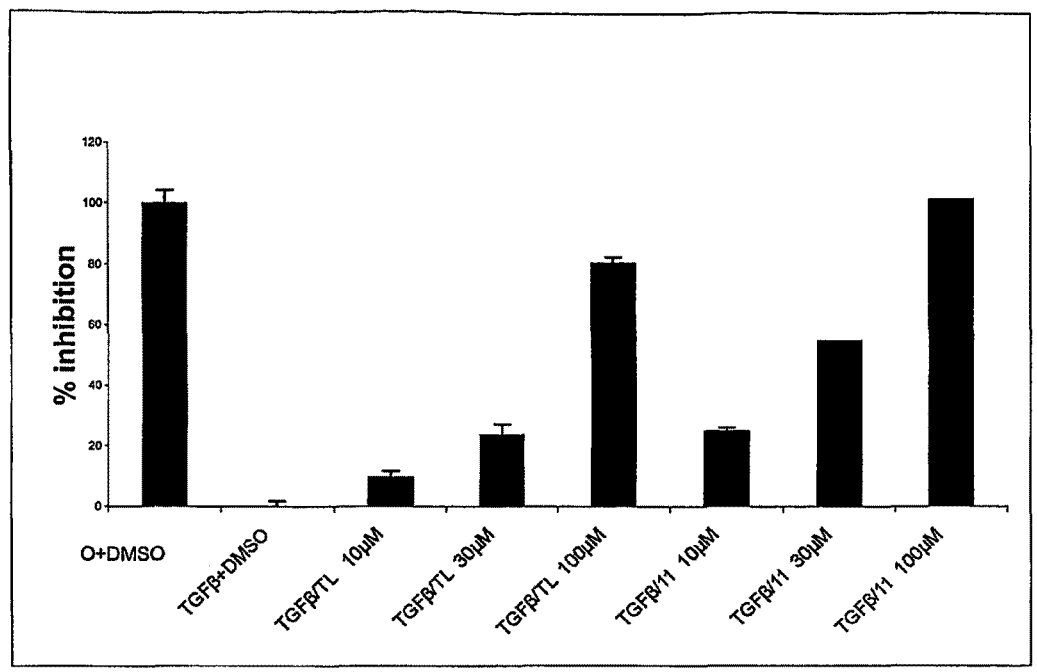
FIG. 6: Inhibition of TGF-β stimulated proline incorporation—tranilast vs FT011 (SEM).
Figure 7:
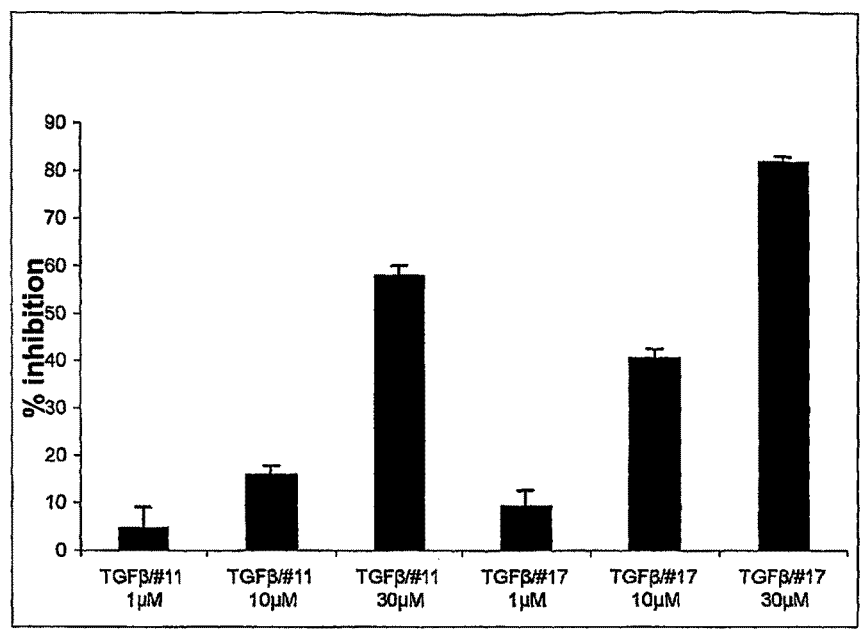
FIG. 7: Inhibition of TGF-β stimulated proline incorporation—FT017 (SEM).
Figure 8:
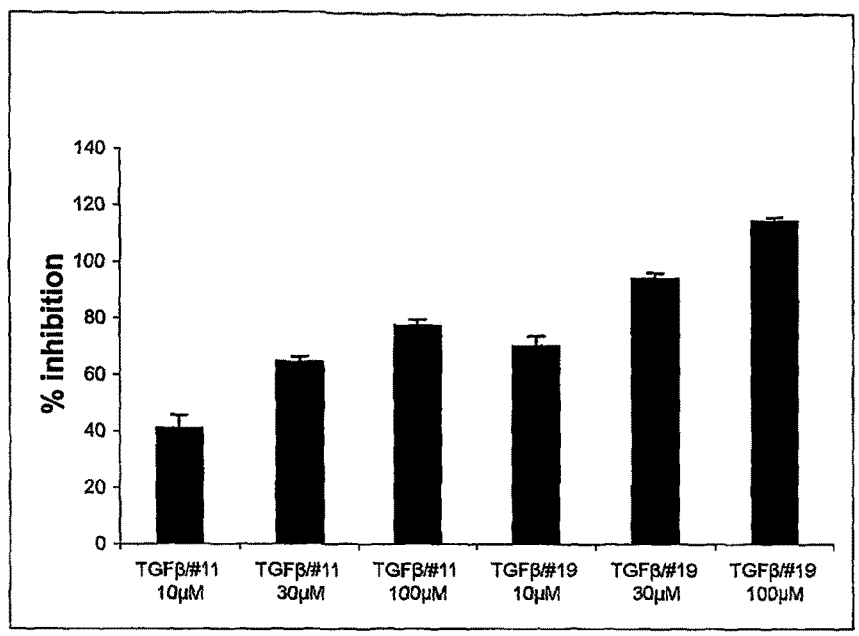
FIG. 8: Inhibition of TGF-β stimulated proline incorporation—FT019 (SEM).
Figure 9:
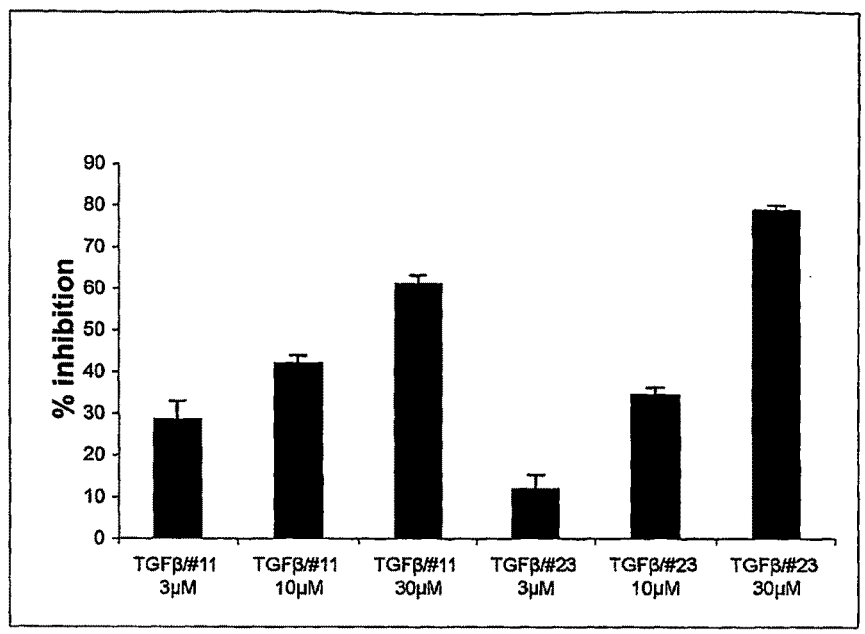
FIG. 9: Inhibition of TGF-β stimulated proline incorporation—FT023 (SEM).
Figure 10:
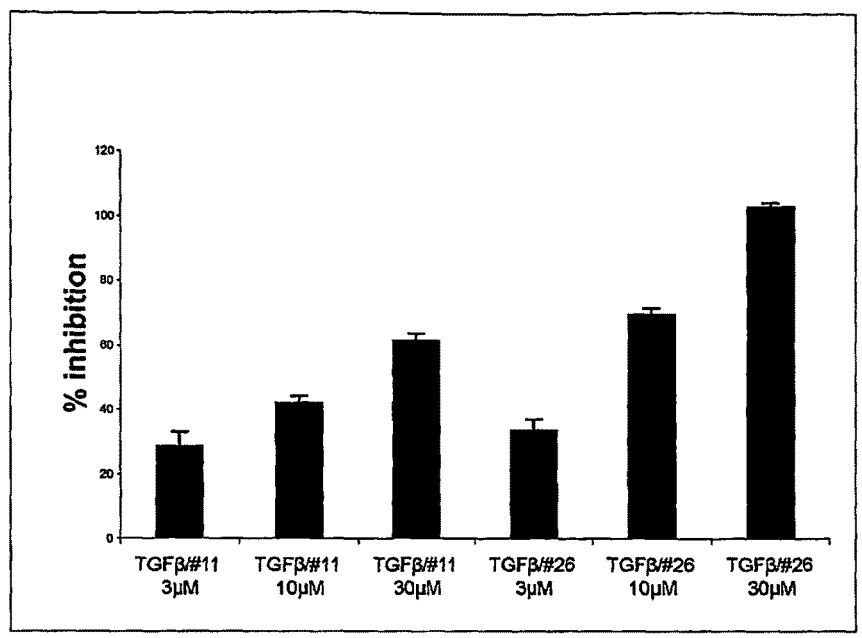
FIG. 10: Inhibition of TGF-β stimulated proline incorporation—FT026 (SEM).

The effect of FT011 on TGF-β- or angiotensin II-stimulated fibrosis in the neonatal SD rat cardiac fibroblasts was investigated. As shown in FIG. 4, FT011 inhibited TGF-β-stimulated fibrosis (indicated by proline incorporation) in rat neonatal cardiac fibroblasts. As shown in FIG. 3, FT011 inhibited angiotensin II-stimulated fibrosis (indicated by proline incorporation) in neonatal cardiac fibroblasts.

Example 5

FT Compounds in Renal Mesangial Cells, and Neonatal Cardiac Fibroblasts

Methodology
Praline Incorporation:

A well-characterized cloned rat mesangial cell line [30] (gift of D Nikolic-Patterson) is cultured in DMEM with FBS, 100 U/mL penicillin, and 100 ug/mL streptomycin in a humidified 5% $CO_2$ atmosphere at 37° C. Cells are plated into 24-well culture dishes in DMEM/10% FBS at low density and allowed to adhere overnight. Cells are used between passages 20 and 40. The subconfluent cells are starved overnight in DMEM/0.1% FBS containing 150 uM L-ascorbic acid, prior to 4 hours of pre-treatment with or without tranilast or the FT compounds, followed by the addition of 5 ng/mL rhTGF-$β_1$1 (R&D Systems) and 1 uCi/mL of L-(2,3,4,5-$^3$H)-proline. Control wells have the compounds but no TGF-$β_1$ added. Cells are incubated for a further 44 hours during which time their appearance is visually monitored. The cells are then washed three times in ice-cold PBS, twice in ice cold 10% TCA and solubilized in 750 uL 1M NaOH for 45 minutes at 37° C. or overnight at 4° C. A 500 uL aliquot is neutralized with 500 uL 1M HCl and 10 mL scintillation fluid (Instagel Plus—Perkin-Elmer) added. Counts are performed on a beta counter.

To normalize the proline incorporation counts to take into account the proliferative effects of TGF-$\beta_1$, a BioRad protein assay is performed on a 100-150 uL aliquot of the remaining solubilized cells. The sample is neutralized with an equal amount of 1M HCl prior to the assay. The BSA standards used to construct the standard curve have the same amount of 1M NaOH and 1M HCl added as is present in the samples for assay.

Proline incorporation is expressed as cpm/ug protein. In order to compare inter-assay results, the incorporation is expressed as percentage reduction of TGF stimulated proline incorporation, where TGF alone gives 0% reduction and the zero control gives 100% reduction.

MTT Assay:

Mesangial cells are plated at 15000 cells per well into 96-well culture dishes in DMEM/10% FBS and allowed to adhere overnight. The subconfluent cells are starved overnight in DMEM/0.1% FBS, prior to 4 hours of pre-treatment with or without tranilast or the FT compounds. Following the addition of 5 ng/mL rhTGF-$\beta_1$, the cells are incubated in a humidified 5% $CO_2$ atmosphere at 37° C. for 44 hours. Control wells have the compounds but no TGF-$\beta_1$ added. The culture medium is removed from each well and 100 uL MTT (0.5 mg/mL) in starve medium is added to each well. The plates are incubated for a further 4 hours at 37° C. The culture medium is then removed and replaced with 100 μL isopropanol and incubated at 37° C. for 20 to 30 minutes, until the blue formazan crystals have dissolved. The absorbance is measured at a wavelength of 570 nm with background subtraction of 690 nm.

Compounds in bold have minimal effect on cell appearance and viability

Suppressed MTT result indicates reduced cell viability

| Analogue | Formula Mol. Wt. | % reduction of TGF-$\beta$ stimulation_proline inc. | Mesangial Cell Assay TGF-$\beta$ Collagen synthesis | Effect on mesangial cell appearance | Mesangial cell MTT Assay TGF-$\beta$ |
|---|---|---|---|---|---|
| 1 | Tranilast $C_{18}H_{17}NO_5$ 327.33 | ~20-50% @ 30 μm 50-70% @ 100 μM | =T | OK, some stress @ 100 μM | |
| 11 | $C_{20}H_{17}NO_5$ 351.35 | 15% @ 3 μM 20-50% @ 10 μM 50-75% @ 30 μM 60-100% @ 100 μM | >T | OK, some stress @ 100 μM | |
| 16 | $C_{18}H_{16}BrNO_5$ 406.23 | ~20% @ 3 μM ~50% @ 10 μM | >>FT11 | OK, lifting off @ 10 μM | Suppressed @ 30 μM |
| 17 | $C_{20}H_{17}NO_5$ 353.35 | ~20-50% @ 10 μm ~55% @ 30 μM | >=FT11 | OK | OK |
| 18 | $C_{22}H_{21}NO_5$ 379.41 | ~55% @ 3 μm ~70% @ 10 μM | >>FT11 | OK, lifting off @ 30 μM | OK |
| 19 | $C_{22}H_{21}NO_5$ 379.41 | ~80% @ 10 μM 100% @ 30 μM | >FT11 | Some death with increasing concentration | OK |
| 23 | $C_{21}H_{19}NO_5$ 365.38 | ~12% @ 3 μM, 30-60% @ 10 μm 70-80% @ 30 μM ~80% @ 100 μM | >=FT11 | OK, some stress @ 100 μM | OK |
| 26 | $C_{22}H_{23}NO_5$ 381.42 | ~13% @ 1 μM 30% @ 3 μM 85% @ 10 μM, 93% @ 30 μM | >FT11 | OK, sparse @ 30 μM lifting off @ 100 μM | OK |
| 27 | $C_{23}H_{25}NO_5$ 395.45 | ~18% @ 1 μM 40% @ 3 μM 75-90% @ 10 μM | >FT11 | Sparse @ 10 μM sick @ 30 μM lifting off @ 100 μM | Suppressed @ 30 μM |
| 29 | $C_{22}H_{23}NO_5$ 381.42 | ~8% @ 1 μM 40% @ 3 μM ~90% @ 10 μM | >FT11 | Sparse @ 10 & 30 μM Stressed @ 30 & 100 μM | Suppressed @ 30 μM |
| 33 | $C_{23}H_{23}NO_5$ 393.437 | ~15% @ 1 μM 40% @ 3 μM 60% @ 10 μM 80% @ 30 μM | >FT11 | Looking bad @ 30 μM | Severely Suppressed @ 10 μM |
| 34 | $C_{23}H_{23}NO_5$ 393.437 | ~80% @ 10 μM 94% @ 30 μM | >FT11 | Looking bad @ 30 μM | Suppressed @ 30 μM |
| 35 | $C_{22}H_{21}NO_5$ 379.41 | ~25% @ 3 μm 50% @ 10 μM 60-100% @ 30 μM | =>FT11 | Looking bad @ 30μM | Suppressed @ 10 μM |
| 36 | $C_{22}H_{21}NO_5$ 379.41 | ~50% @ 10 μM 80% @ 30 μM | =>FT11 | Crystals or dead cells @ 30 μM | Severely Suppressed @ 30 μM |
| 39 | $C_{23}H_{23}NO_5$ 393.43 | ~70% @ 10 μM 100% @ 30 μM | >FT11 | Looking bad @ 30 μM | OK |
| 40 | $C_{23}H_{23}NO_5$ 393.43 | ~70% @ 10 μM 100% @ 30 μM | >FT11 | OK, dead @ 100 μM | OK |

Mesangial Cells
Derivatives for structure activity analysis (26/02/07):
(NT=not tested)
  N.B suppressed MTT result indicates reduced cell viability

| Analogue | Formula Mol. Wt. | % reduction of TGF stimulation_proline inc. | Mesangial Cell Assay TGF-β Collagen Synthesis | Effect on mesangial cell appearance | Mesangial cell MTT Assay TGF-β |
|---|---|---|---|---|---|
| 2 | $C_{16}H_{13}NO_3$ 267.28 | | <<T | OK | NT |
| 3 | $C_{17}H_{15}NO_4$ 297.31 | | <<T | OK | NT |
| 4 | $C_{17}H_{15}NO_4$ 297.31 | | <<T | OK | NT |
| 5 | $C_{16}H_{13}NO_5$ 299.28 | | May be toxic | Cells looking bad & sparse | NT |
| 6 | $C_{17}H_{15}NO_5$ 313.30 | 20% @ 10 μM 45% @ 50 μM | <=T | OK | NT |
| 7 | $C_{17}H_{15}NO_5$ 313.30 | ~50% @ 10 μM 80% @ 50 μM | > or =T | cells stressed | NT |
| 8 | $C_{22}H_{19}NO_5$ 377.39 | | Toxic | Heavily vacuolated | NT |
| 9 | $C_{20}H_{21}NO_7$ 387.38 | | <<T | | NT |
| 10 | $C_{18}H_{19}NO_5$ 329.35 | | <<T | | NT |
| 12 | $C_{18}H_{18}N_2O_4$ 326.35 | ~13% @ 10 μM 20% @ 30 μM 36% @ 100 μM | <FT11 | OK, cells sparse @ 100 μM | NT |
| 13 | $C_{17}H_{17}NO_3$ 283.32 | ~20% @ 30 μM ~55% @ 100 μM | <FT11 | OK, cells sparse @ 100 μM | NT |
| 14 | $C_{18}H_{17}NO_5$ 327.33 | ~30% @ 100 μM | <FT11 | OK | NT |
| 15 | $C_{21}H_{20}N_2O_4$ 364.39 | ~24% @ 10 μM 36% @ 30 μM 75% @ 100 μM | <FT11 | OK, cells sparse @ 30 & 100 μM | NT |
| 20 | $C_{28}H_{25}N_5O_6$ 527.53 | 30% @ 10 μM 50% @ 30 μM 90% @ 100 μM | =FT11 | OK, dead @ 100 μM | OK |
| 21 | $C_{28}H_{25}N_5O_6$ 527.53 | ~20% @ 10 μM ~65% @ 30 μM | =FT11 | OK, necrotic @ 100 μM | Suppressed @ 30 μM |
| 22 | $C_{21}H_{19}NO_5$ 365.38 | ~37% @ 3 μM 56% @ 10 μM ~70% @ 30 μM | =FT11 | OK, dead @ 100 μM | OK |
| 24 | $C_{39}H_{42}N_6O_8$ 722.79 | ~44% @ 10 μM 68% @ 30 μM | =FT11 | OK, dead @ 100 μM | NT |
| 25 | $C_{38}H_{42}N_6O_7S$ 726.84 | ~70% @ 10 μM | =FT11 | "dissolved" @ 30 μM | NT |
| 28 | $C_{24}H_{27}NO_5$ 409.47 | ~40% @ 10 μM 173% @ 30 μM | <FT11 | Stressed @ 30 μM, Dead @ 100 μM | deadly ® 10 μM |
| 30 | $C_{40}H_{45}N_7O_7$ 735.83 | ~28% @ 10 μM 50-70% @ 30 μM | Toxic | Dead @ 30 μM | NT |
| 31 | $C_{39}H_{45}N_7O_6S$ 739.88 | ~50% @ 10 μM | Toxic | Dead @ 30 μM | NT |
| 32 | $C_{29}H_{28}N_6O_5$ 540.57 | ~26% @ 10 μM 62% @ 30 μM | Toxic | Dead | NT |
| 37 | $C_{21}H_{19}NO_5$ 365.38 | ~50% @ 10 μM 70% @ 30 μM | =FT11 | Some death @ 100 μM | OK |
| 38 | $C_{21}H_{19}NO_5$ 365.38 | ~40% @ 10 μM 65% @ 30 μM | =FT11 | Some death @ 100 μM | OK |
| 41 | $C_{25}H_{27}NO_5$ 421.49 | | Toxic | Cells damaged @ all concentrations | NT |
| 42 | $C_{25}H_{27}NO_5$ 421.49 | | Toxic | Cells damaged @ all concentrations | NT |
| 43 | $C_{24}H_{21}NO_5$ 403.43 | 48% @ 10 μM 70% @ 30 μM | | Sick @ 30 & 100 μM | NT |
| 44 | $C_{28}H_{23}NO_5$ 453.49 | | Toxic | Cells damaged @ all concentrations | NT |
| 45 | $C_{22}H_{25}NO_5$ 383.44 | 80% @ 10 μM 142% @ 30 μM | >FT11 | Cells damaged @ 100 μM | NT |
| 46 | $C_{16}H_{14}NO_4$ 298.29 | | <<FT11 | OK | NT |

Example 6

Methods

Neonatal Rat Cardiomyocytes and Fibroblast Cultures

Neonatal SD rat cardiac myocytes (NCMs) and fibroblasts (NCFs) were isolated from one-day-old pups with enzymatic digestion as described in detail previously [20, 21]. NCFs were seeded and maintained in high-glucose (25 mmol/L) Dulbecco's modified Eagle's medium (DMEM) (Invitrogen Mount Waverley, Vic, Australia) in the presence of 1% antibiotic/antimycotic (AB/AM) and 10% fetal bovine serum (FBS) (JRH biosciences, Kansas, USA). NCFs were used at passage 2 [31]. Purified NCMs were seeded (1000 cells/mm$^2$) in 6-well plates and then maintained in serum-free DMEM (Invitrogen, NY, USA) supplemented with insulin and transferrin as described previously (4). Bromodeoxyuridine was included for the first 3 days. 50 mmol/L KCl was added to the medium to prevent spontaneous contraction characteristic of the plated NCMs [32].

Measurement of Neonatal Rat Cardiomyocyte Hypertrophy

NCM hypertrophy studies were performed as previously described [Please provide details of this reference][22]. Four hours after treatment with the compounds (concentrations various from 1 to 30 μM), ANG II ($10^{-7}$ mol/L) was used to stimulate hypertrophy. After 60 hours of stimulation, cells were harvested and hypertrophy defined as a significant increase in protein content (Bradford assay) in the absence of any significant change in DNA content (Burton assay) [33].

Measurement of Collagen Synthesis and Proliferation and Cell Viability in Neonatal Rat Cardiac Fibroblasts NCFs collagen synthesis assays were performed as described previously [31]. Briefly, NCFs plated at a density of 50,000 cells/well in 12-well plate and incubated overnight. NCFs were then serum starved for 24 hours in high-glucose DMEM. The cells were then preincubated for 30 min in the presence or absence of compounds (1 to 30 μM) in fresh DMEM/F12 before stimulation with $2 \times 10^{10}$ mol/L of TGF-$\beta_1$ or $10^{-7}$ mol/L of ANG II.

For collagen synthesis, 1 μCi of [$^3$H]-Proline was added to each well and incubated for further 48 hours before harvest. Cells were harvested by precipitation with 10% TCA on ice for 30 min, before solubilisation with 0.75 mL of 1 mol/L NaOH overnight at 4° C. The samples were then neutralized with 1 mol/L HCl and $^3$H level were counted with 10 ml scintillation fluid on a beta-counter to determine [$^3$H]-proline incorporation.

For proliferation studies, NCFs were treated with 1 mCi of [$^3$H]-thymidine added to each well 2 hours prior to harvesting. Cells were harvested by TCA precipitation as described for collagen synthesis above determining [$^3$H]-thymidine incorporation.

Results

Neonatal Cardiac Fibroblasts

| Analogue | Formula Mol. Wt. | NCF TGF-β Collagen Synthesis |
| --- | --- | --- |
| 1 | Tranilast $C_{18}H_{17}NO_5$ 327.33 | NT |
| 11 | $C_{20}H_{17}NO_5$ 351.35 | 32% @ 30 μM 87% @ 100 μM |
| 17 | $C_{20}H_{17}NO_5$ 353.35 | ~70% at 30 μM |
| 26 | $C_{22}H_{23}NO_5$ 381.42 | 28% at 10 μM |
| 29 | $C_{22}H_{23}NO_5$ 381.42 | 10% @ 10 μM 25% @ 30 μM |

Example 7

FT011 Treatment Post Myocardial Infarction or Diabetic Nephropathy

FT011 is Anti-Inflammatory and Anti-Fibrotic

Methods

Animals

The animal studies were conducted with the approval of the Animal Welfare and Ethics Committee of the St Vincent's Hospital and the National Health and Medical Research Foundation of Australia. All rats received normal rat chow (Certified Rodent Diet #5002, LabDiet, USA) and drinking water ad libitum. All animals were housed in a stable environment maintained at 22±1° C. with a 12-hour light/dark cycle commencing at 6 am.

Pilot Study (Toxicity Assessment)

A total of twenty male Sprague-Dawley (SD) rats weighing 200-250 g were randomised to either FT011 (Fibrotech Therapeutics Pty Ltd, Melbourne, Australia) or Tranilast (Pharm Chemical, Shanghai Lansheng Corporation, China) at the dose of 50 mg, 100 mg, 200 mg and 400 mg/kg/day by gavage twice daily (n=2-3 per group). A control group of animals were gavaged with vehicle (1% carboxy methyl cellulose). The study was conducted for 2 weeks. Animals were bled daily at one, four, and eight hours after oral gavage to measure the plasma concentration. Serum was also collected to assess renal and liver function at the end of the study (plasma creatine and urate, ALT and bilirubin). Rats were individually housed in metabolic cages at the end of the study, habituated for 2 to 3 hours, and urine collected over 24 hours. Animals continued to have free access to tap water and standard laboratory chow during this period. The biochemistry tests performed at the department of pathology, St Vincent's hospital. Major organs including lung, heart, liver, spleen and kidney were harvested and immersed fix with 10% neutral buffered formalin and then embedded paraffin for subsequent light microscope examination.

Myocardial Infarct Rats

Forty male SD rats weighing 200-250 g were randomised to two groups of 20 animals that each underwent surgery. Anaesthesia was achieved with 3% isoflurane/97% oxygen in a tidal volume of 1 ml/100 g body weight, at a rate of 72 breaths/minute. Twenty rats underwent ligation of left anterior descending coronary artery (LAD) to induce anterior myocardial infarction (MI). Briefly, surgery performed under aseptic conditions on a heated table (37° C.) to maintain body warmth during the course of the procedure. The chest swabbed with chlorhexidine in 70% ethanol to disinfect the area. An incision made into the skin to the left of the sternum and the underlying muscle layers blunt dissected. A thoracotomy performed through the fourth to fifth intercostal space and the ribs held open using retractors to enable access to the heart. The pericardial sac surrounding the heart torn open and a 6-0 prolene suture used to ligate the LAD immediately. Visible blanching and hypokinesis of the anterior wall of the left ventricle and swelling of the left atrium are indicative of successful ligation. The control groups (sham+vehicle, sham+FT011) underwent a sham operation consisting of the same procedure except that the suture passed through the myocardium beneath the LAD without ligation [34].

Echocardiography was performed on all animals 2 days post surgery and randomised to sham and MI groups. Animals were re-randomised at day 7 post surgery (10 animal each) to receive: vehicle or FT011 (100 mg/kg bid gavage). Every week, systolic blood pressure (SBP) was determined in preheated conscious rats via tail-cuff plethysmography using a non-invasive blood pressure (NIBP) controller and Powerlab (AD instruments, NSW, Australia). Cardiac function was assessed by echocardiography and cardiac catherization prior to sacrificing at day 35 post surgery for all animals [34].

Diabetic (mRen-2)27 Rats

Forty six-week old female, heterozygous (mRen-2)27 rats (St. Vincent's Hospital Animal House, Melbourne, Australia) were assigned to receive either 55 mg/kg of STZ (Sigma, St. Louis, USA) diluted in 0.1 M citrate buffer, pH 4.5 or citrate buffer alone (non-diabetic) by tail vein injection following an overnight fast. Control and diabetic groups were then each randomised into 2 groups (n=10), receiving either treatment with: the FT 011 (100 mg/kg bid gavage, Fibrotech Therapeutics Pty Ltd, Melbourne, Australia), or no treatment for 16 weeks. Treatment commenced within 24 hours of STZ or citrate buffer injection. Each week, rats were weighed and their blood glucose levels were measured (Accu-check Advantage II Blood Glucose Monitor, Roche Diagnostics, USA) and only STZ-treated animals with blood glucose >15 mmol/L were considered diabetic. Every 4 weeks, systolic blood pressure (SBP) was determined in preheated conscious rats via tail-cuff plethysmography using a non-invasive blood pressure (NIBP) controller and Powerlab (AD instruments, NSW, Australia). Hemoglobin A1c (HbA1c) was measured by HPLC at the end of the study. Diabetic rats received a daily injection of insulin (2-4 units intraperitoneally; Humulin NPH, Eli Lilly and Co., Indianapolis, Ind.) to reduce mortality and to promote weight gain [37, 39].

Heart Function

Echocardiography

Echocardiography, including Doppler examination, was performed using a Vivid 7 Dimension (GE Vingmed, Horten, Norway) echocardiograph with a 10 MHz phased array probe. Electrocardiographic data were acquired simultaneously. End-diastole was defined as the peak of the R wave, and end-systole was defined as the end of the T wave.

Animals were anaesthetized with pentobarbitone sodium 60 mg/kg i.p. injection. Animals underwent echocardiographic interrogation in the left recumbent position. M-mode echocardiography was performed using a parasternal short axis view at the level of the papillary muscles. Left ventricular posterior (LVPW) and anterior wall thickness (LVAW) were obtained during diastole (d) and systole (s), as were the left ventricular internal diameter at end-diastole (LVIDd) and end-systole (LVIDs). From the para-sternal short axis view, the end diastolic and end systolic cross sectional blood pool areas were measured. Fractional area change (FAC) was then calculated according to the formulae:

$$FAC=[(\text{end-diastolic area}-\text{end-systolic area})/\text{end-diastolic area}]*100.$$

The apical 4-chamber view was used to assess early and late transmitral peak diastolic flow velocity (E and A waves), using pulsed wave Doppler with a sample volume of 2 mm placed at the tips of the mitral valve leaflets. All Doppler spectra were recorded for 10 cardiac cycles at a sweep speed of 200 mm/s. All parameters were assessed using an average of three beats, and calculations were made in accordance with the American Society of Echocardiography guidelines [41]. All data were acquired and analyzed by a single blinded observer using EchoPAC (GE Vingmed) offline processing.

Cardiac Catheterization

Post echocardiography, animals were placed on a warming pad (37° C.), intubated using a 14 gauge catheter, and ventilated using positive pressure with a tidal volume of 10% body weight at 70 breaths per minute using room air. Animals were secured in a recumbent position and the right jugular vein was cannulated with 0.9% NaCl infused at 100 µL per hour. Pressure was calibrated after warming the catheter (Model SPR-838 Millar instruments, Houston, Tex.) in 0.9% NaCl at in 37° C. for 30 minutes. The right internal carotid was then identified and ligated cranially. A 2F miniaturized combined conductance catheter-micromanometer was inserted into the carotid artery to obtain aortic blood pressure, then advanced into the left ventricle until stable pressure volume (PV) loops were obtained. The abdomen was then opened and the inferior vena cava and portal vein identified. Elastic bands were placed around these vessels to allow rapid reduction in cardiac preload. All loops were obtained with the ventilator turned off for 5-10 seconds and the animal apnoeic.

Using the pressure conductance data, functional parameters were then calculated (Millar analysis software PVAN 3.4). These included the slope of the end diastolic pressure volume relationship (EDPVR) and the slope of the preload recruitable stroke work relationship (PRSW), defined as the relationship between stroke work and end diastolic volume, where stroke work is the pressure-volume loop area for each beat.

Renal Function

Rats were individually housed in metabolic cages at 4, 8 12 and 16 weeks, habituated for 2 to 3 hours, and urine collected over 24 hours. Animals continued to have free access to tap water and standard laboratory chow during this period. After 24 hours in metabolic cages, an aliquot of urine (5 mL) was collected from the 24-hour urine sample and stored at −70° C. for subsequent analysis of albumin by radio-immunoassay, as previously performed [36]. Prior to sacrifice, the glomerular filtration rate (GFR) was determined by injecting a single shot of 99Tc-DTPA into the tail vein and sampling the blood after 43 minutes, as previously described [37].

Tissue Preparation

Rats were anaesthetized (Nembutal 60 mg/kg body wt i.p. Boehringer-Ingelheim, Australia). Lungs, left ventricle (LV), right ventricle (RV) and atria were separated, blotted dry once and weighed, the LV was then sectioned immediately and tissue was either frozen fresh, stored frozen in OCT or fixed in neutral buffered formalin. Kidneys were excised, decapsulated, sliced transversely, half of the kidney snap frozen for tissue RNA assay and other half immersed fix with formalin and paraffin-embedded for subsequent light microscopic evaluation.

Histopathology and Immunohistochemistry

Histopathological changes in kidney and heart were assessed in a masked protocol. Sections were stained with either haematoxylin and eosin (H & E), periodic acid Schiff's stain (PAS), picrosirius red and/or Masson's modified trichrome to demonstrate collagenous matrix.

Infarct Size

The picrosirius red stained slides of heart were examined under light microscopy and digitised, then analysed using image analysis (AIS, Analytical imaging station version 6.0, Ontario, Canada). Infarct sizes assessed morphologically and calculated as the ration of circumferences of the endocardium and the epicardium to LV average circumferences of the endocardium and the epicardium, as previously described.

Glomerulosclerotic Index

In 4 μm kidney sections stained with PAS, 150 to 200 glomeruli from rats were examined in a masked protocol. The extent of sclerosis in each glomerulus was subjectively graded on a scale of 0 to 4, as previously described [39] with Grade 0, normal; Grade 1, sclerotic area up to 25% (minimal); Grade 2, sclerotic area 25-50% (moderate); Grade 3, sclerotic area 50-75% (moderate to severe) and Grade 4, sclerotic area 75-100% (severe). A glomerulosclerotic index (GSI) was then calculated using the Formula (4):

$$GSI = \sum_{i=0}^{4} Fi(i)$$

where Fi is the % of glomeruli in the rat with a given score (1).

Quantitation of Matrix Deposition

To examine extracellular matrix deposition in heart sections were stained with picrosirius red and the accumulation of matrix within the non-infarct zone (NIZ) was then quantified using a modification of the technique described by Lal et al. (Lal et al., 2004) with a blinded manner. Briefly, 5 random stained sections from the mid left ventricle were digitally captured and then loaded onto a Pentium III IBM computer. To isolate the NIZ from the infarct and the peri-infarct zone, the infarct and a 2 mm zone on either side of it were excluded. To assess the tubulointerstitial fibrosis in kidney sections were stained with modified Masson's trichrome. Briefly, 5 random non-overlapping fields from 10 rats per group were captured and digitised using a BX50 microscope attached to a Fujix HC5000 digital camera. Digital images were then loaded onto a Pentium III IBM computer as described as above. An area of red in heart and blue in kidney on picrosirius red and trichrome-stained section, respectively, were selected for its color range and the proportional area of tissue with this range of color was then quantified. Calculation of the proportional area stained red and blue (matrix) was then determined using image analysis (AIS, Analytical imaging Station Version 6.0, Ontario, Canada) [37, 39].

Immunohistochemistry

Collagen Subtypes I and III

Collagen subtypes I and III were assessed in the heart using goat and mouse anti-Collagen I (Southern Biotechnology Associates, Inc. Birmingham, Ala. 35226 USA) and III antibody (Biogenex, San Ramon Cal, 94583 USA). In brief, four micron sections were placed into histosol to remove the paraffin wax, re-hydrated in graded ethanol, and immersed into tap water before being incubated for 20 minutes with normal goat serum (NGS) diluted 1:10 with 0.1 mol/L PBS, pH 7.4. Sections were incubated respective primary antibodies overnight (18 hours) at 4° C. The following day the sections were thoroughly washed in PBS (3×5 minute changes), incubated with 3% hydrogen peroxide for 10 minutes to block endogenous peroxide, then rinsed with PBS (2×5 min), and incubated with either biotinylated swine anti-goat or goat anti mouse IgG antibody (DAKO, Carpinteria Calif.), diluted 1:200 with PBS. Sections were then rinsed with PBS (2×5 min) followed by incubation with an avidin-biotin peroxidase complex (Vector, Burlingame, Calif.), diluted 1:200 with PBS. Following rinsing with PBS (2×5 min), localization of the peroxidase conjugates was achieved by using diaminobenizidine tetrahydrochloride as a chromagen, for 1-3 minutes. Sections were rinsed in tap water for 5 minutes to stop reaction and then counterstained in Mayer's haematoxylin, differentiated in Scott's tap water, dehydrated, cleared and mounted in Depex. Sections incubated with 1:10 NGS, instead of the primary antiserum, served as the negative controls. The accumulation of immunostaining for collagen I and III were quantified using computer-assisted image analysis. Briefly, 10 random non-overlapping fields from 10 rats per group were captured and digitized as described as above. An area of brown on immunostained sections (Collagen I and III) was selected for their color ranges. To correct for variation due to shrinkage, the area of positive immunostaining (collagen/area tissue) relative to the total area (matrix+myocytes) was determined using computer-assisted image analysis (AIS, Analytical imaging Station Version 6.0, Ontario, Canada), as previously reported [40].

Macrophages

Four micron heart sections were placed into histosol to remove the paraffin wax, hydrated in graded ethanol and immersed into tap water before being incubated for 20 minutes with normal goat serum (NGS) diluted 1:10 with 0.1 M PBS at pH 7.4. Sections were then incubated for 18 hours at 4° C. with specific primary monoclonal rat macrophage marker (ED-1, 1:200 Serotec, Raleigh N.C., USA). Macrophage number was estimated by counting the number of macrophages in 10 fields under light microscope with ×200 power per animal from each group (n=10 per group) and expressed as numbers per field [38].

Statistics

Data are expressed as means±sem unless otherwise stated. Statistical significance was determined by a two-way ANOVA with a Fishers post-hoc comparison. Albuminuria was skew distributed and was analysed following log transformation and presented as geometric means x/÷ tolerance factors. Analyses were performed using Statview II+Graphics package (Abacus Concepts, Berkeley, Calif.) on an Apple Macintosh G4 computer (Apple Computer, Inc., Cupertino, Calif.). A p-value <0.05 was regarded as statistically significant.

Results

FT011 Pilot Study (Toxicity Assessment)

In the in vivo pilot study, there was no change in body weight amongst all animal groups (Table 1). Plasma levels of creatinine and urate, ALT and bilirubin were similar to control rats et all doses (Table 1). Following gavage of FT011, the level of FT011 measured in plasma increased in a dose dependent manner (FIG. 1). A significant level of FT011 was also measured in the urine of rats treated with FT011 (FIG. 2).

TABLE 1

| | Plasma biochemistry parameters of SD rats | | | | |
|---|---|---|---|---|---|
| Group | Body weight (Gram) | Plasma Creatinine (umol/L) | Plasma Urate (mmol/L) | ALT | Bilirubin (mmol/L) |
| Control | 291 ± 11 | 39 ± 2.7 | <0.09 | 42 ± 2 | 1.8 ± 0.16 |
| Tranilast 50 mg/kg/day | 315 ± 19 | 43 ± 0.5 | <0.09 | 40.5 ± 4.5 | 2 ± 0 |

TABLE 1-continued

Plasma biochemistry parameters of SD rats

| Group | Body weight (Gram) | Plasma Creatinine (umol/L) | Plasma Urate (mmol/L) | ALT | Bilirubin (mmol/L) |
|---|---|---|---|---|---|
| FT011 50 mg/kg/day | 313 ± 24 | 38 ± 2 | <0.09 | 41 ± 1 | 1 ± 0 |
| Tranilast 100 mg/kg/day | 298 ± 21 | 43 ± 3.5 | <0.09 | 41 ± 1 | 2 ± 0 |
| FT011 100 mg/kg/day | 308 ± 22 | 39 ± 0.5 | <0.09 | 44 ± 2 | 1.5 ± 0.5 |
| Tranilast 200 mg/kg/day | 293 ± 10 | 45 ± 1 | <0.09 | 41 ± 4.6 | 2.33 ± 0.33 |
| FT011 200 mg/kg/day | 301 ± 8 | 37 ± 0.6 | <0.09 | 36 ± 0.5 | 1.33 ± 0.33 |
| Tranilast 400 mg/kg/day | 314 ± 13 | 49 ± 7.8 | <0.09 | 40 ± 5 | 1.66 ± 0.33 |
| FT011 400 mg/kg/day | 264 ± 29 | 36 ± 3.9 | <0.09 | 32 ± 4.4 | 1.66 ± 0.33 |

Post-Myocardial Infarct in Rats Treated with FT011

Animal Characteristics

In rats post myocardial infarct, RV and lung:body weight ratio was increased. The increase in lung:body weight ratio, a marker of pulmonary edema secondary to left heart failure was significantly reduced with FT011 treatment (Table 2).

TABLE 2

Animal parameters of SD rats

| Group | BW (g) | LV/BW | RV/BW | Lung/BW |
|---|---|---|---|---|
| Sham | 378 ± 11 | 0.19 ± 0.004 | 0.04 ± 0.001 | 0.33 ± 0.015 |
| Sham + Vehicle | 377 ± 6 | 0.2 ± 0.003 | 0.045 ± 0.001 | 0.27 ± 0.045 |
| MI + Vehicle | 424 ± 6* | 0.21 ± 0.003 | 0.056 ± 0.001* | 0.39 ± 0.016* |
| MI + FT011 | 382 ± 6 | 0.22 ± 0.004 | 0.048 ± 0.002 | 0.32 ± 0.011# |

*P < 0.05 versus shams and
p < 0.05 versus MI + Vehicle.

Cardiac Structure

Figure 23:
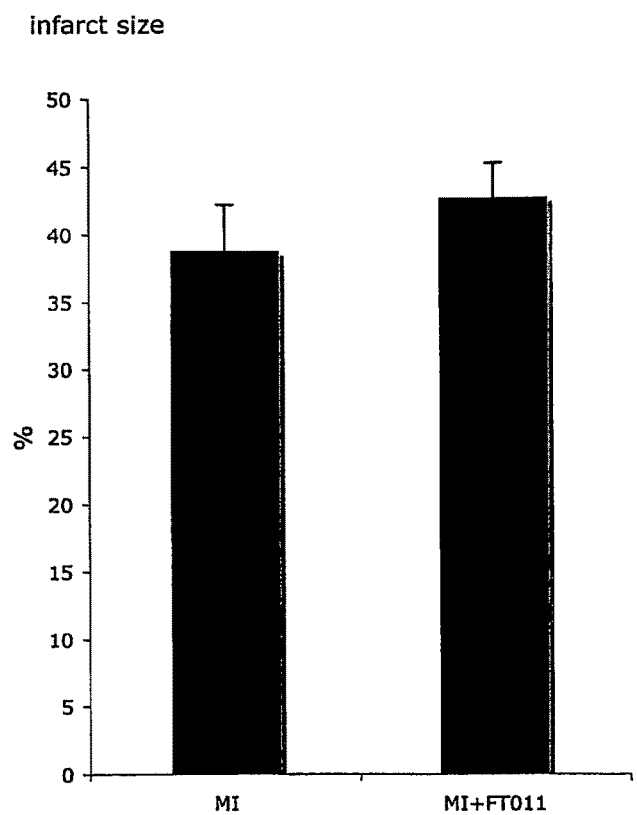
FIG. 23: Comparison of myocardial infarct (MI) size in treated and untreated MI groups.
Figure 24:
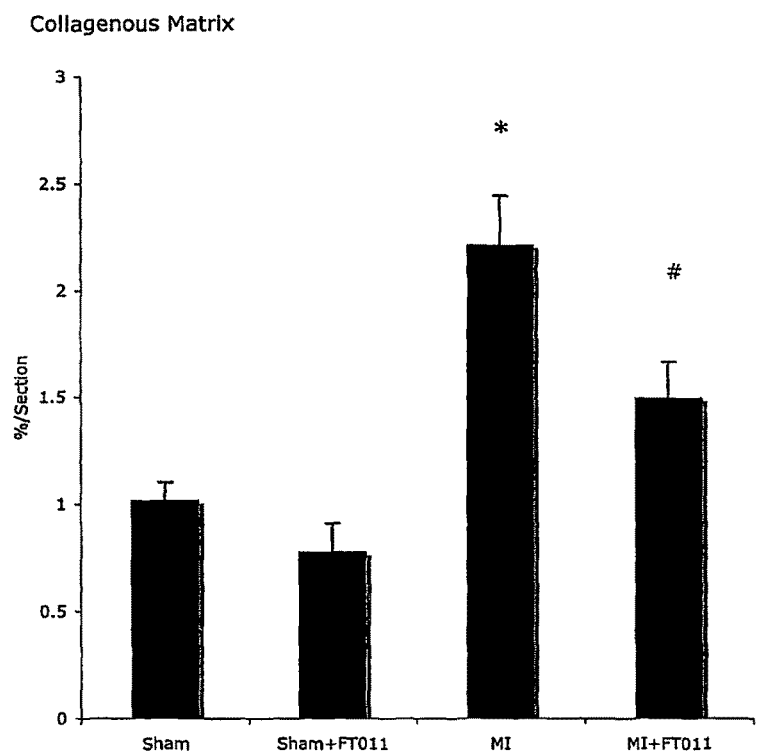
FIG. 24: Quantitation of collagenous matrix in the NIZ (non-infarct zone), expressed as the proportional area stained blue on Masson's trichrome stained sections of rat heart. *P<0.01 versus shams and #P<0.05 versus untreated MI rats.
Figure 25:
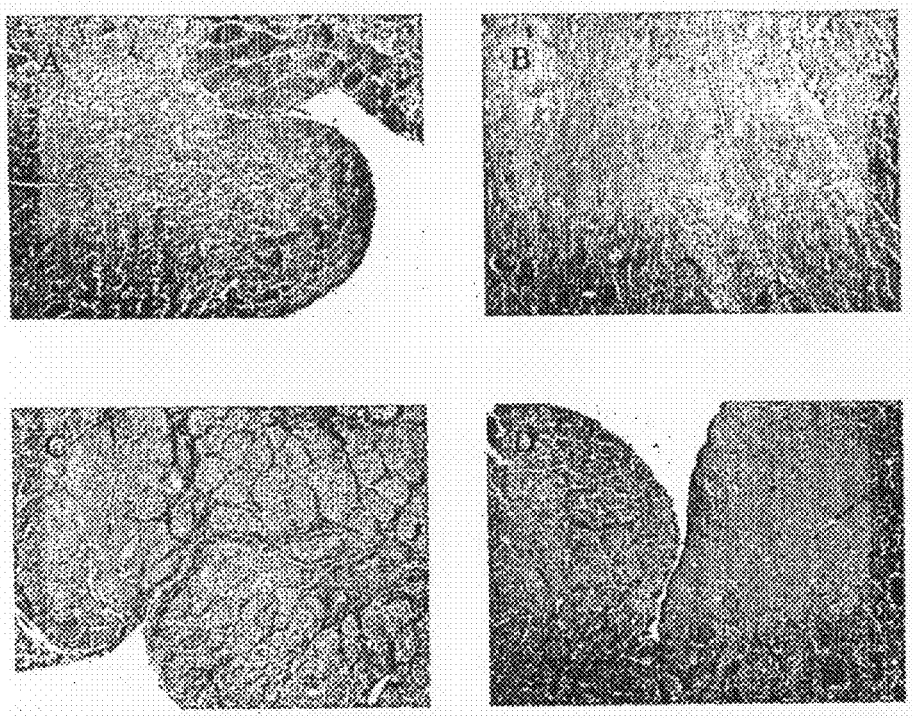
FIG. 25: Representative Masson's trichrome-stained sections from sham and MI rats treated with FT011. In sham (A) and sham rats treated with FT011 (B), very little collagen (blue staining) is present within the interstitium, while extensive myocardial interstitial fibrosis was noted in NIZ of rats post MI (C). Treatment of MI rats with FT011 (D) was associated with a marked reduction in the extent of interstitial fibrosis in NIZ. Magnification ×350.
Figure 26:
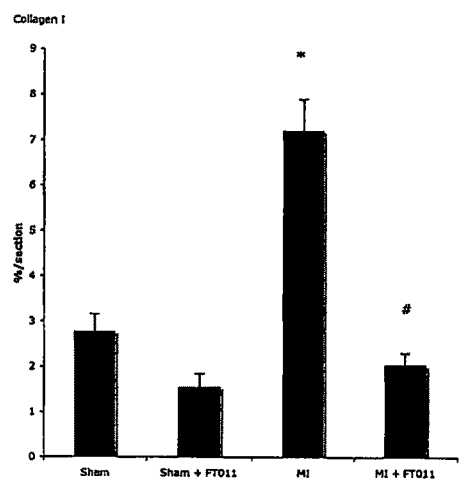
FIG. 26: Quantitation of collagen I (A) and III (B) immunostaining in rat heart from sham, sham treated with FT011, MI and MI rats treated with FT011. Values are expressed as mean±SEM. *P<0.05 versus shams. #P<0.05 versus MI. Magnification ×350.
Figure 26:
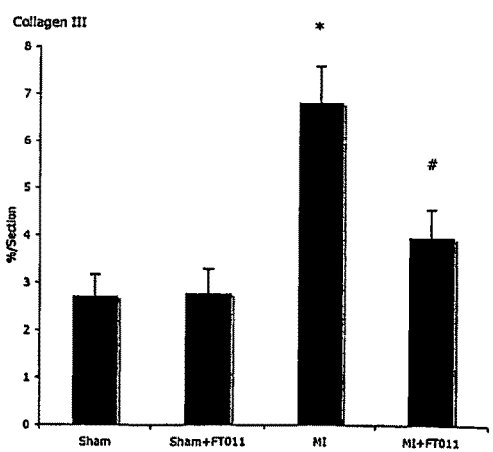
Figure 27:
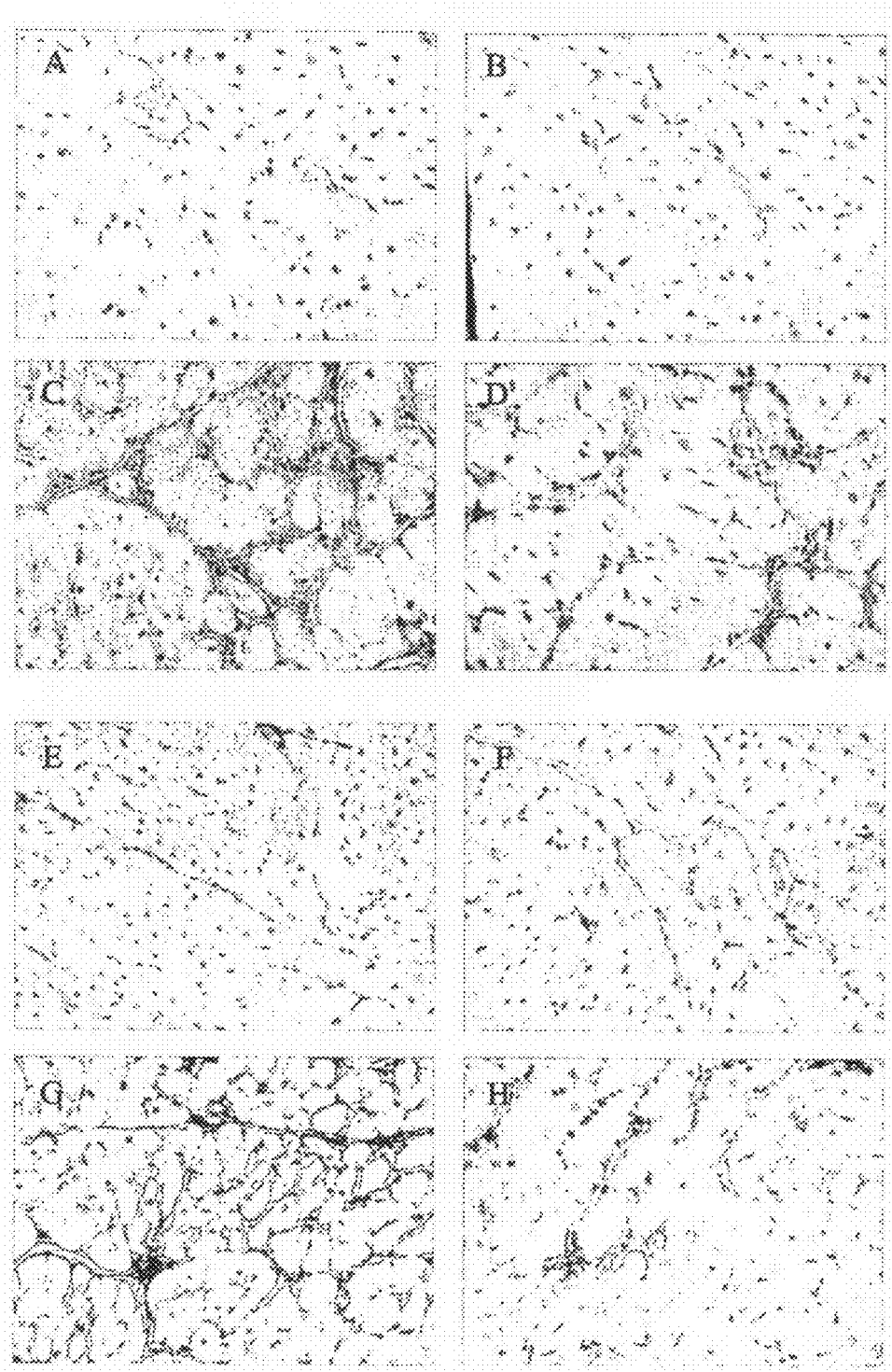
FIG. 27: Representative sections of immunohistochemistry for type I (A-D) and type III (E-H) collagen in sham (A, E), sham treated with FT011 (B, F), MI (C, G) and MI rats treated with FT011 (D, H). In sham rats there was minimal evidence of immunostaining for type I or III collagen, while MI rats were associated with a marked increase in collagen immunostaining. Treatment with FT011 was associated with a reduction in immunostaining for types I and III collagen.
Figure 28:
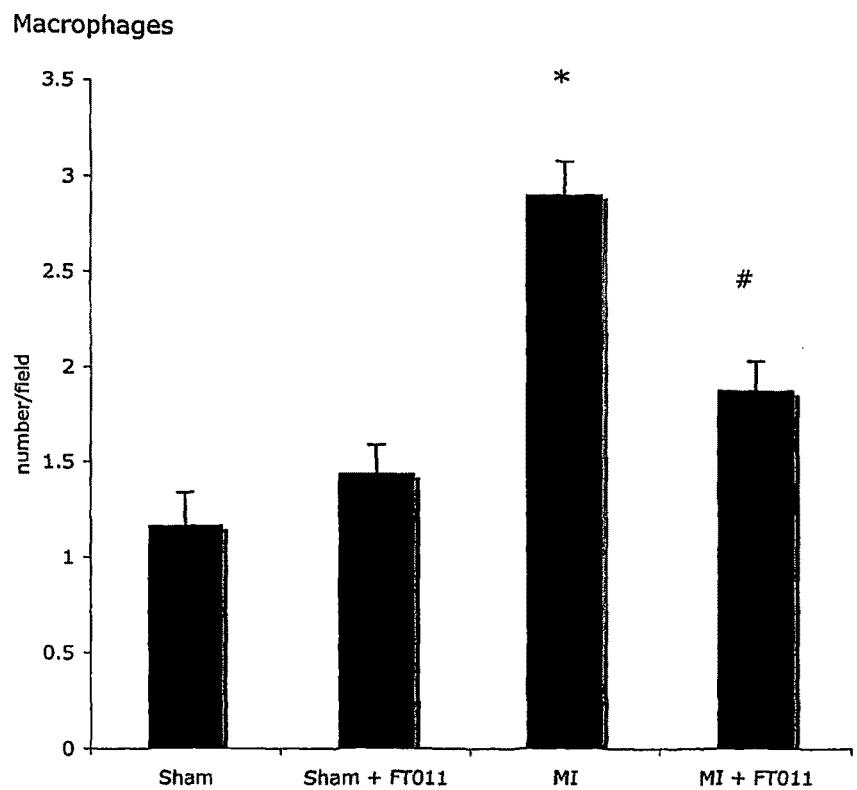
FIG. 28: Quantitation of ED-1 positive macrophages in rat heart from Sham, sham+FT011, MI and MI+FT011 (NIZ) groups. Values are represented as mean±sem.
*p<0.05 when compared to shams. #p<0.05 when compared to MI.
Figure 29:
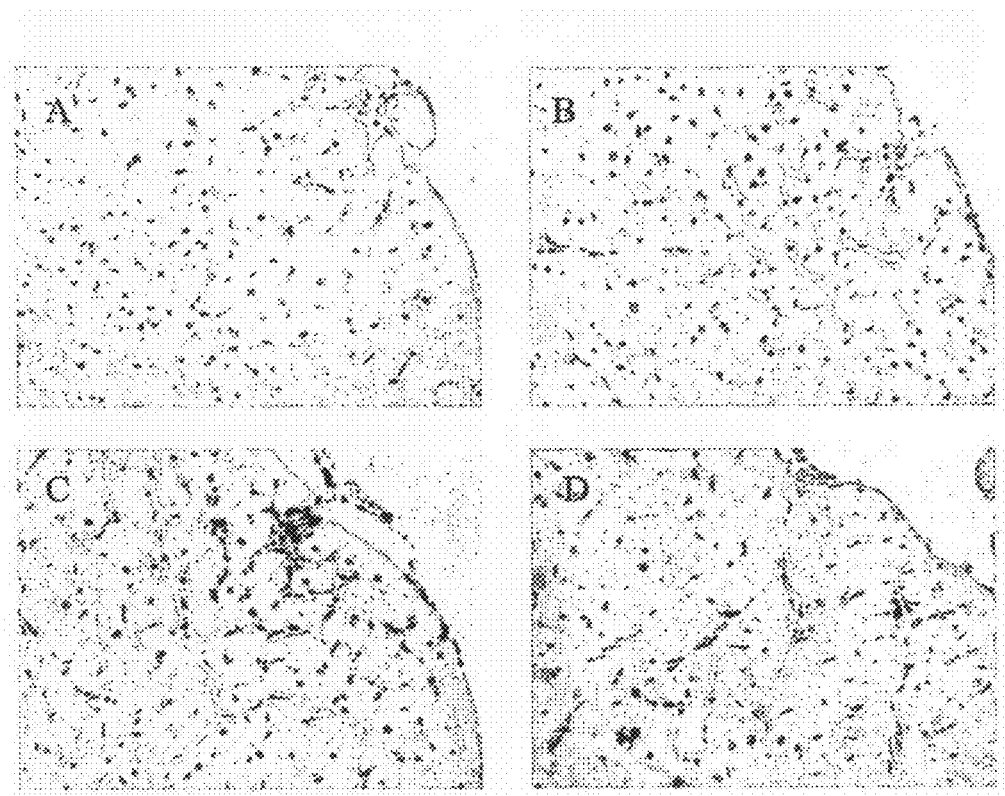
FIG. 29: ED-1 positive macrophages from sham, sham treated with FT011, MI and MI rats treated with FT011. In sham and sham+FT011 (A-B) only an occasional macrophage were observed while MI (C) was associated with increased macrophages (brown) at NIZ. Treatment of MI rats with FT011 was associated with a reduction in macrophage number. Magnification ×350.

Myocardial infarct size was similar in the treated and untreated MI groups (FIG. 23; P=0.36). In comparison with sham rats, MI rats displayed increased interstitial fibrosis as evidenced by Masson's trichrome staining (FIGS. 24 and 25) and a greater abundance of interstitial cardiac fibrillar collagenous subtype I and III within the non-infarct zone (NIZ, FIGS. 26 and 27). MI animals also showed evidence of an increase in the infiltration of macrophages in NIZ (FIGS. 28 and 29). All of these changes were attenuated by FT011 treatment, indicative of a diminution in adverse remodelling post-MI.

Echocardiography

Following MI, over the 5 weeks duration of the study, echocardiography demonstrated the hallmarks of adverse LV remodelling including: ventricular dilatation, as evidenced by an increase in LVIDd and LVIDs; impaired systolic and diastolic function as evidenced by a reduction in percentage of fractional area change (FAC), and an increased E:A ratio and deceleration time, respectively (Table 3). All of these changes were significantly attenuated by FT011 treatment (Table 3).

In Vivo Pressure Volume Loop Analysis

Pressure volume loop analysis was used to assess both load-sensitive and load-insensitive measures of systolic and diastolic function.

The preload recruitable stroke work index, used to assess systolic function, was significantly reduced in the MI animals when compared to sham (p<0.05). Treatment with FT011 preserved systolic function (P<0.05) in the MI animals. (Table 3)

Figure 30:
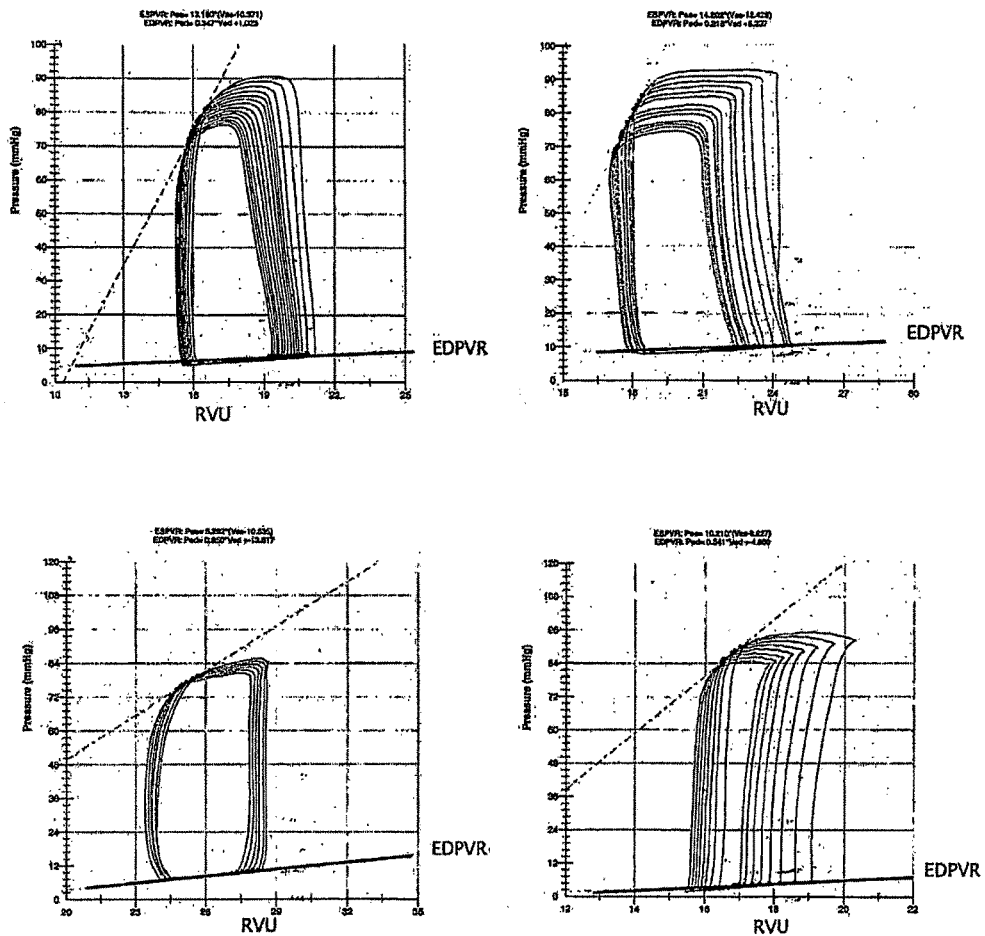
FIG. 30: Representative PV loop analysis of systolic and diastolic function from sham (A), sham treated with FT011 (B), MI (C) and MI treated with FT011 (D).
Figure 31:
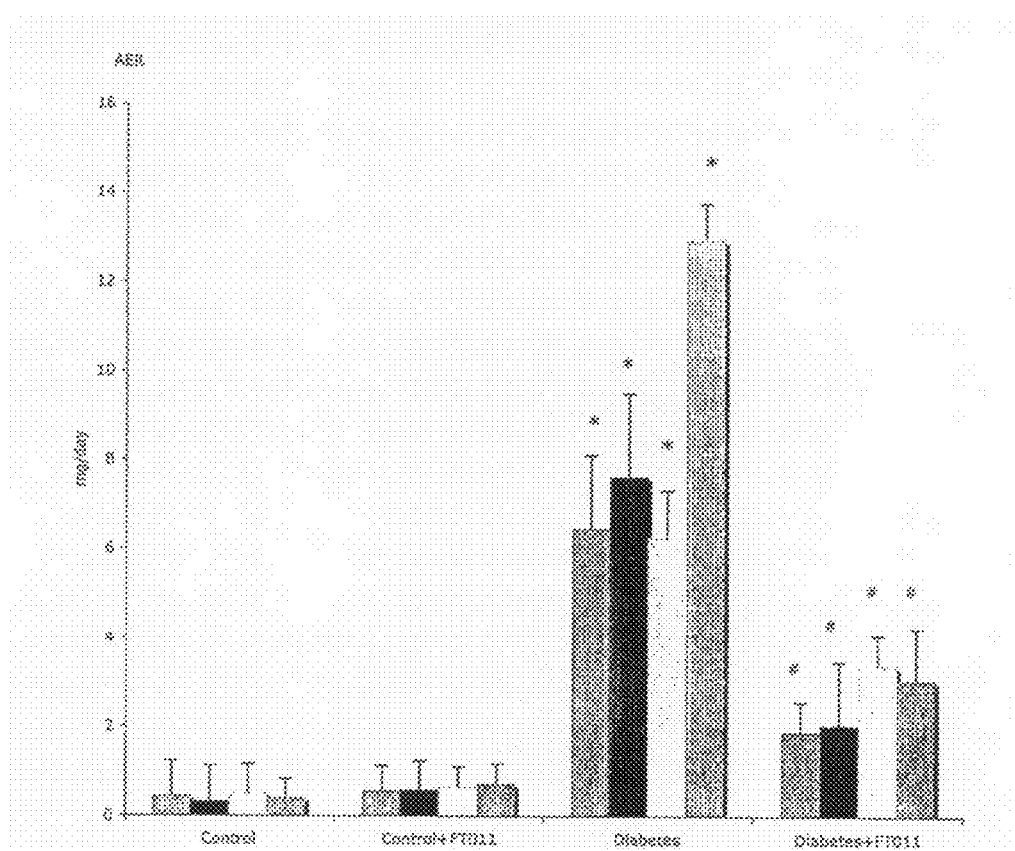
FIG. 31: Albumin excretion rate in control and diabetic Ren-2 rats with and without treatment with FT011.
*p<0.01 when compared to control
p<0.05 when compared to diabetes
Legend: Blue 4 weeks post streptozotocin (STZ), red 8 weeks post STZ, yellow 12 weeks post STZ, green 16 weeks post STZ.
Figure 32:
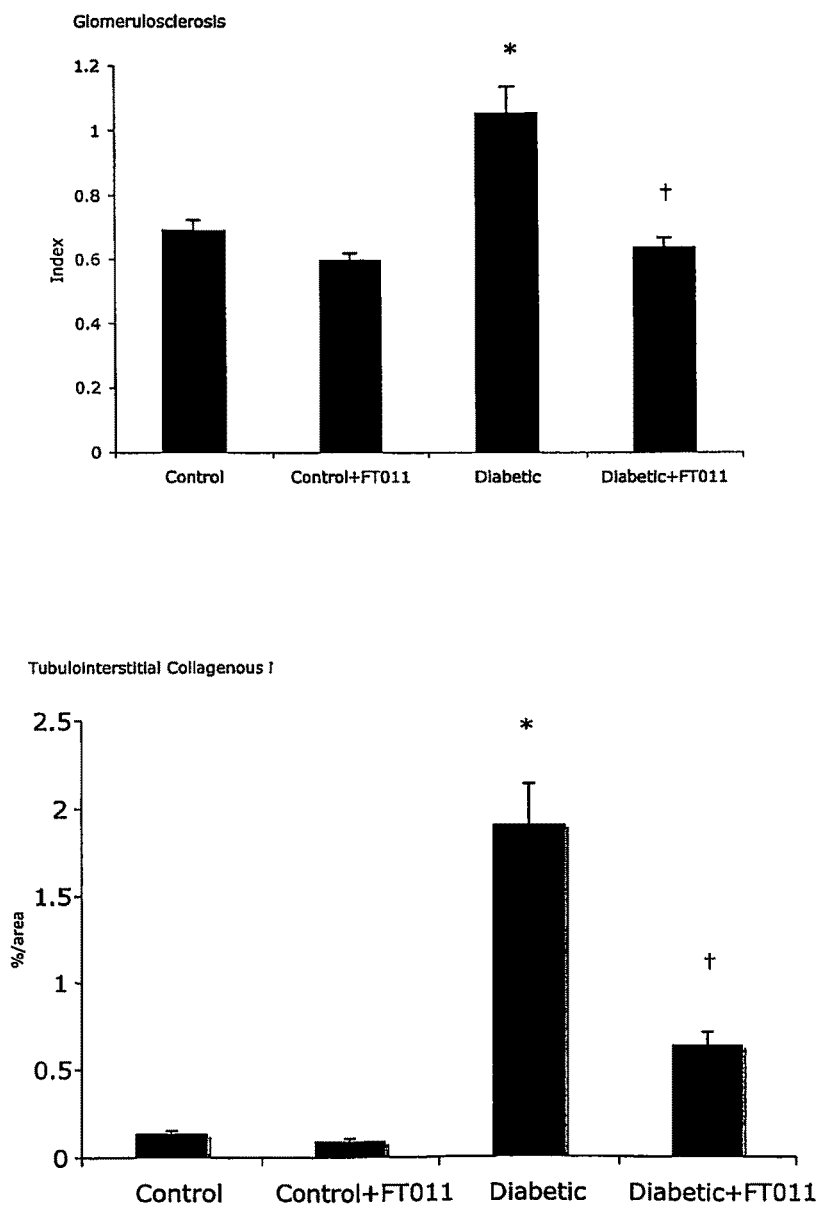
FIG. 32: Glomerulosclerotic Index (upper panel) and tubulointerstitial fibrosis (lower panel) in control and diabetic rats treated with and without FT011. Data are expressed as mean±SEM. * p<0.01 compared with controls, † p<0.01 versus untreated diabetic rat kidneys.
Figure 33:
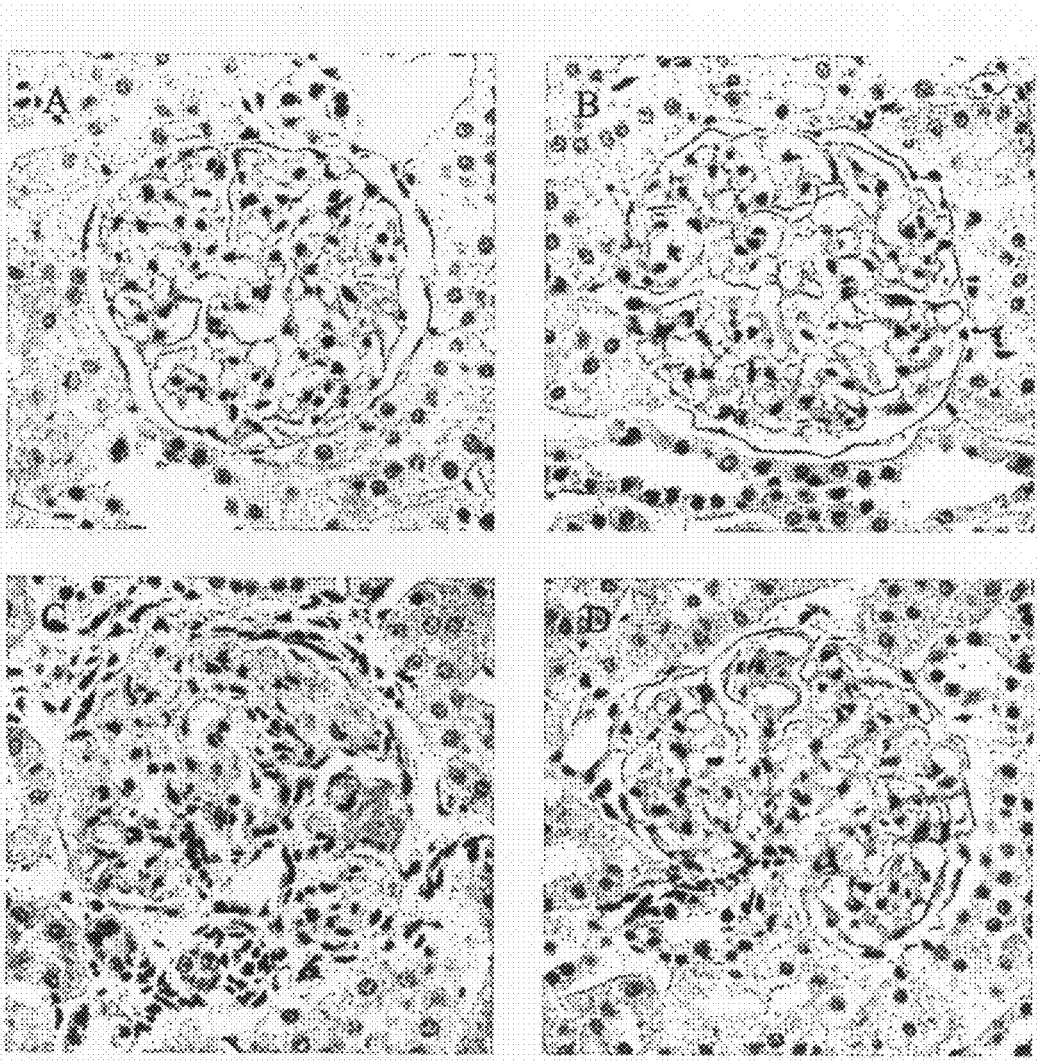
FIG. 33: Representative photomicrograph of periodic acid Schiff (PAS)-stained sections from control, diabetic and diabetic rats treated with FT011. In control (A) and control treated with FT011 (B) rats, there is no glomerulosclerosis, while diabetic (C) is associated with a dramatic increase in glomerulosclerosis. Treatment of diabetic rats with FT011 (D) was associated with a reduction in extent of glomerulosclerosis. Magnification ×350.
Figure 34:
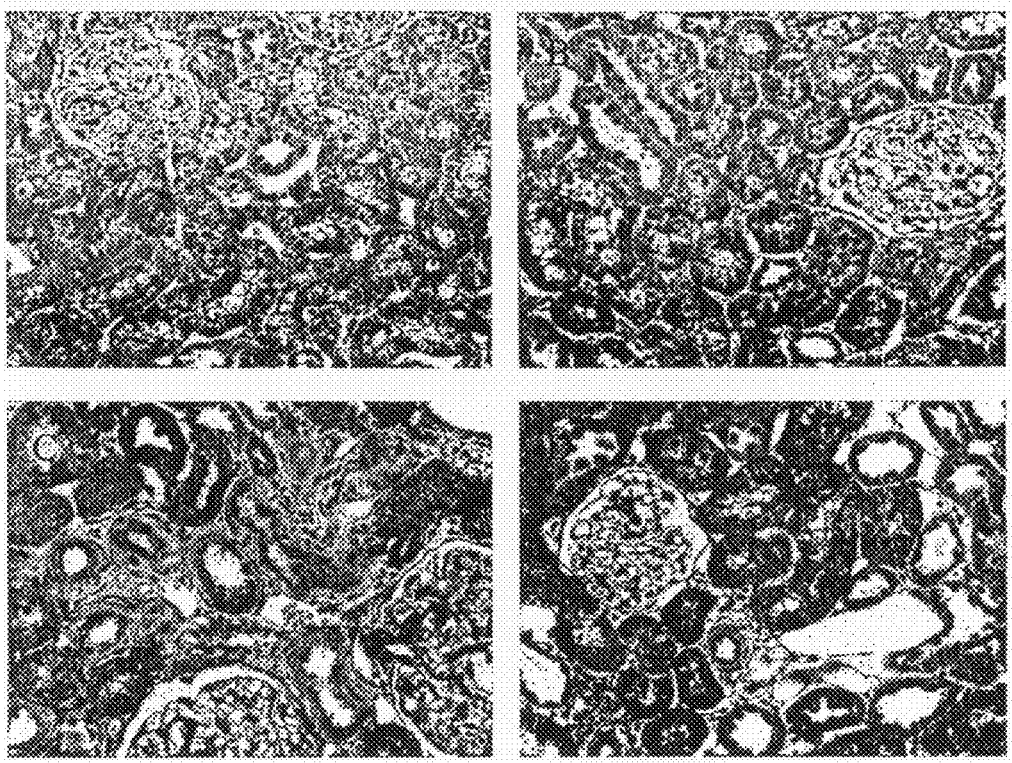
FIG. 34: Representative trichrome-stained sections showing tubulointerstitial fibrosis in control, diabetic and diabetic rats treated with FT011. In control and control treated with FT011 (A, B) there is minimal cortical tubular fibrosis, while diabetic (C) was associated with marked increase in interstitial fibrosis (blue). Treatment of diabetic rats with FT011 was associated with a reduction in tubular fibrosis (D). Magnification ×350.

Chamber compliance, measured by the slope of the end diastolic pressure volume relationship was increased in the MI animals when compared to sham, indicating impaired diastolic function. Treatment with FT011 restored compliance in the MI animals to levels comparable with sham (FIG. 30).

TABLE 3

Echocardiographic and pressure volume loop parameters of SD rats

| Group | FAC % | LVED (ml) | LVES (ml) | LVIDd (cm) | LVIDs (cm) |
|---|---|---|---|---|---|
| Sham + Vehicle | 66.40 ± 1.52 | 0.43 ± 0.04 | 0.08 ± 0.01 | 0.83 ± 0.02 | 0.46 ± 0.03 |
| MI + Vehicle | 27.56 ± 1.2** | 0.90 ± 0.08# | 0.48 ± 0.04** | 0.99 ± 0.03# | 0.81 ± 0.03** |

TABLE 3-continued

Echocardiographic and pressure volume loop parameters of SD rats

| | | | | | |
|---|---|---|---|---|---|
| MI + FT011 | 42.69 ± 2.3** | 0.53 ± 0.04# | 0.15 ± 0.02** | 0.92 ± 0.03 | 0.70 ± 0.03* |

| Group | E:A ratio | Deceleration time (ms) | PRSW slop (mmHg/ul) | EDPVR slop (mmHg/sec) |
|---|---|---|---|---|
| Sham + Vehicle | 2.45 ± 0.17 | 34.75 ± 1.49 | 72.77 ± 6.70 | 0.66 ± 0.19 |
| MI + Vehicle | 3.46 ± 0.52 | 50.09 ± 1.78# | 53.49 ± 4.66* | 0.86 ± 0.15 |
| MI + FT011 | 2.00 ± 0.26* | 38.64 ± 1.2** | 65.15 ± 3.04* | 0.51 ± 0.05† |

*P < 0.05,
p < 0.01,
**p < 0.0001 and
†P = 0.06 (MI + Vehicle compared to Sham + Vehicle and MI + FT011 compared to MI + Vehicle).
PRSW = preload recruitable stroke work;
EDPVR = end diastolic pressure volume relationship.

Diabetic (mRen-2)27 Rats Treated with FT011
Animal Characteristics

Figure 11:
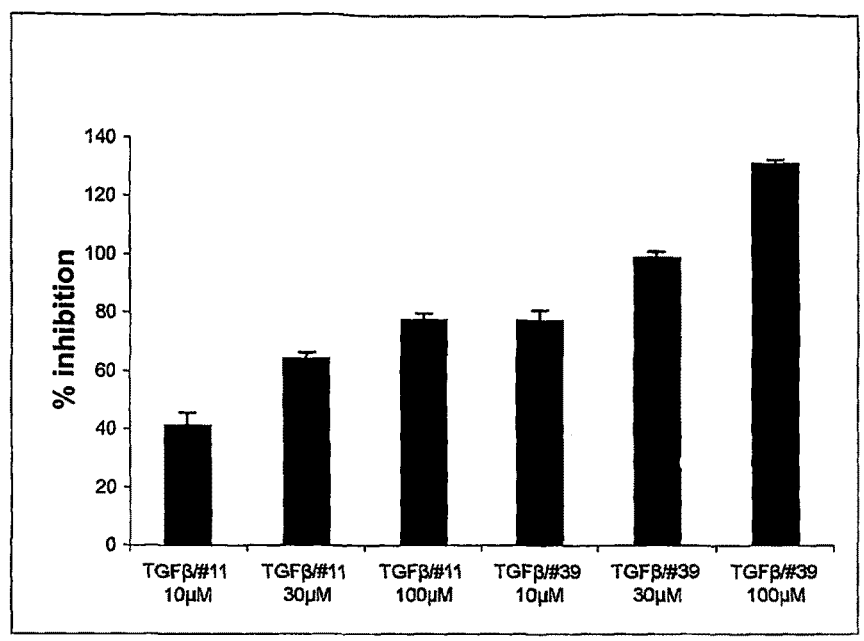
FIG. 11: Inhibition of TGF-β stimulated proline incorporation—FT039 (SEM).
Figure 12:
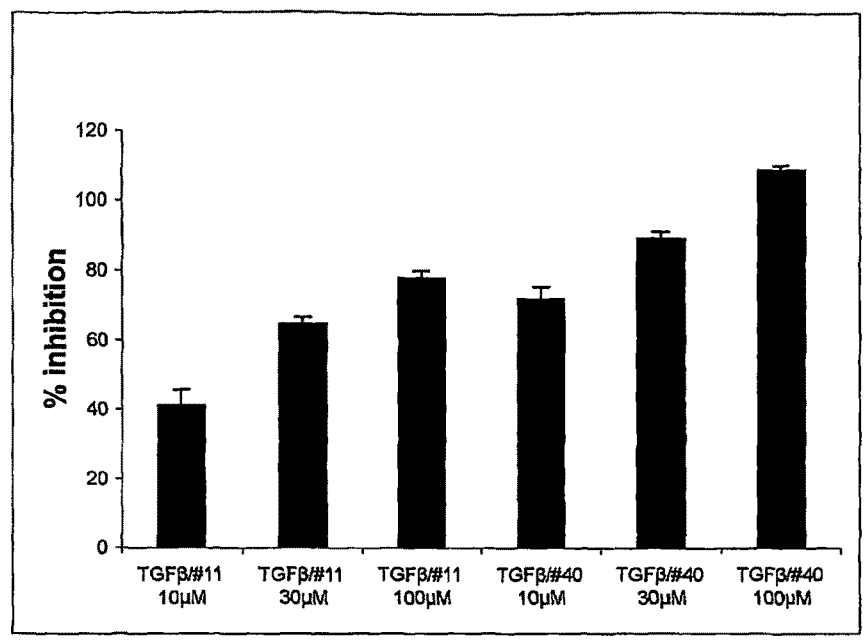
FIG. 12: Inhibition of TGF-β stimulated proline incorporation—FT040 (SEM).
Figure 13:
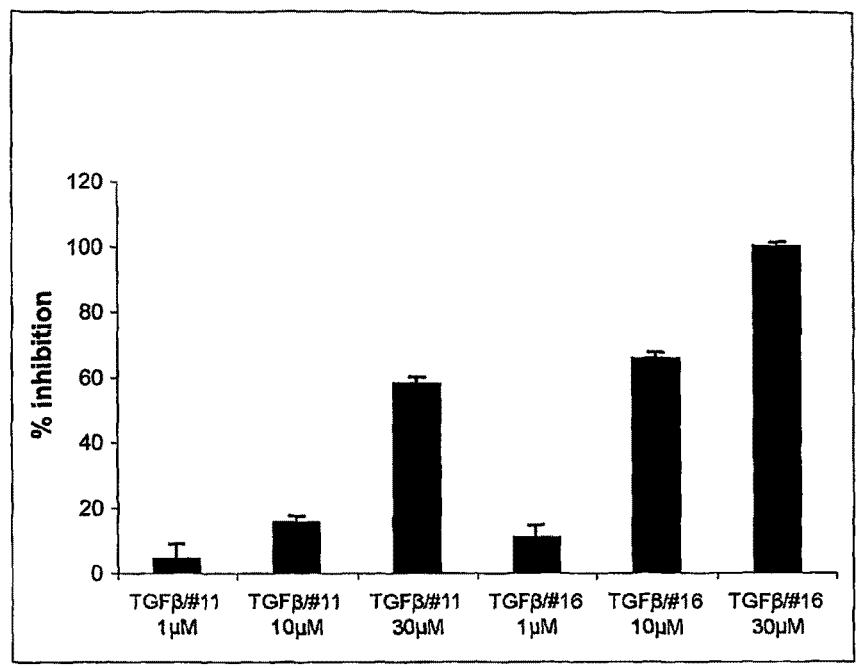
FIG. 13: Inhibition of TGF-β stimulated proline incorporation—FT016 (SEM).
Figure 14:
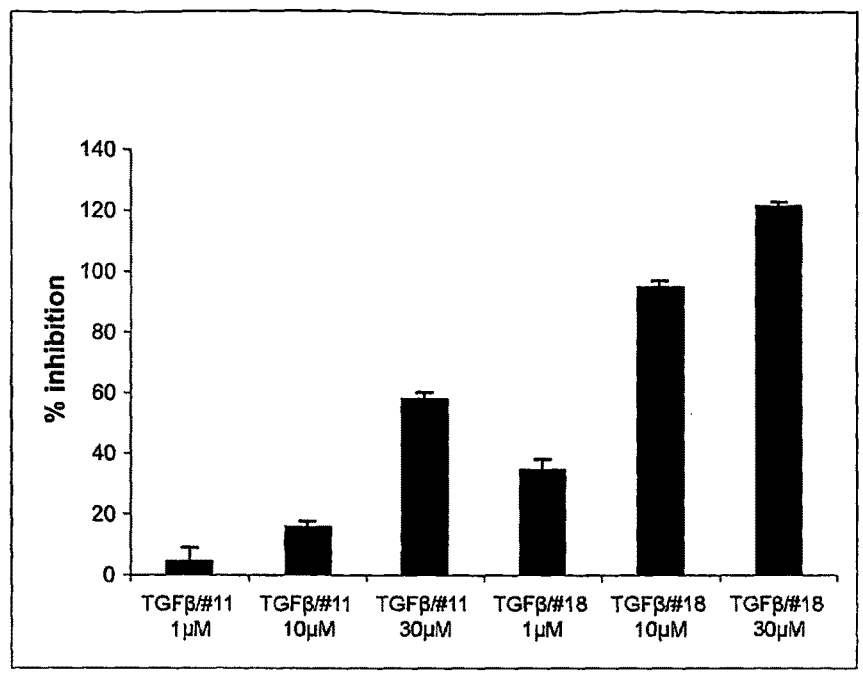
FIG. 14: Inhibition of TGF-β stimulated praline incorporation—FT018 (SEM).
Figure 15:
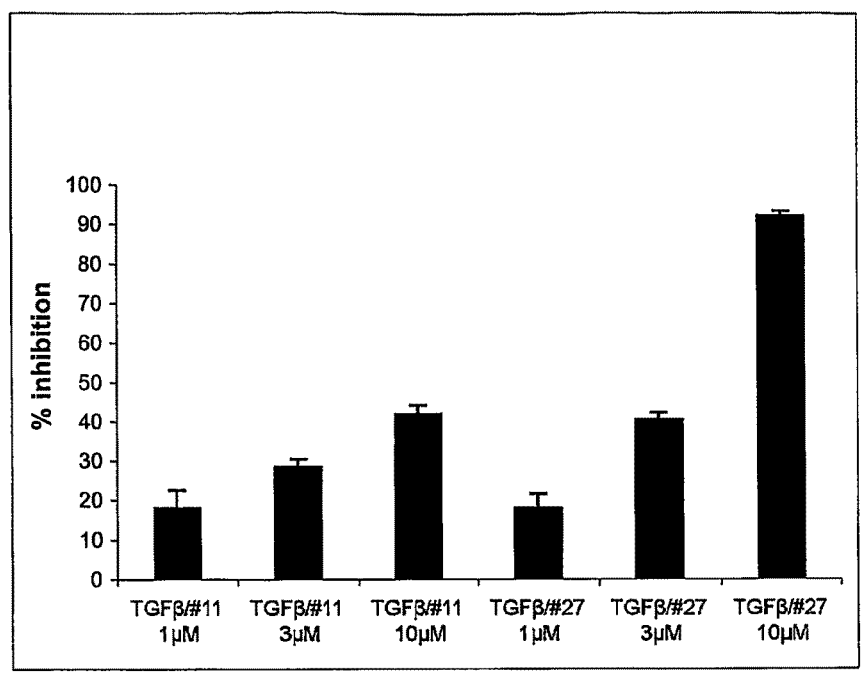
FIG. 15: Inhibition of TGF-β stimulated proline incorporation—FT027 (SEM).
Figure 16:
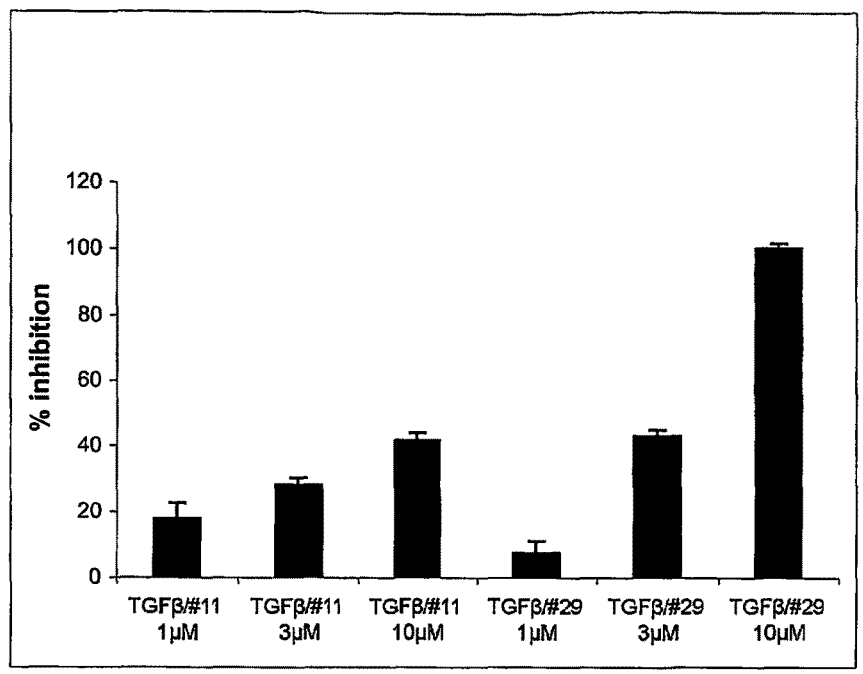
FIG. 16: Inhibition of TGF-β stimulated proline incorporation—FT029 (SEM).
Figure 17:
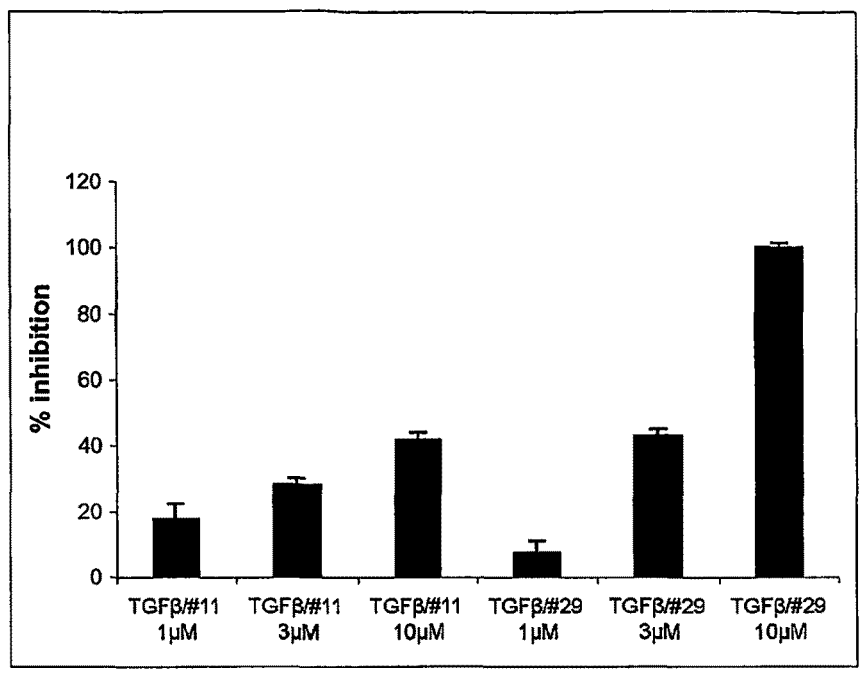
FIG. 17: Inhibition of TGF-β stimulated proline incorporation—FT033 (SEM).
Figure 18:
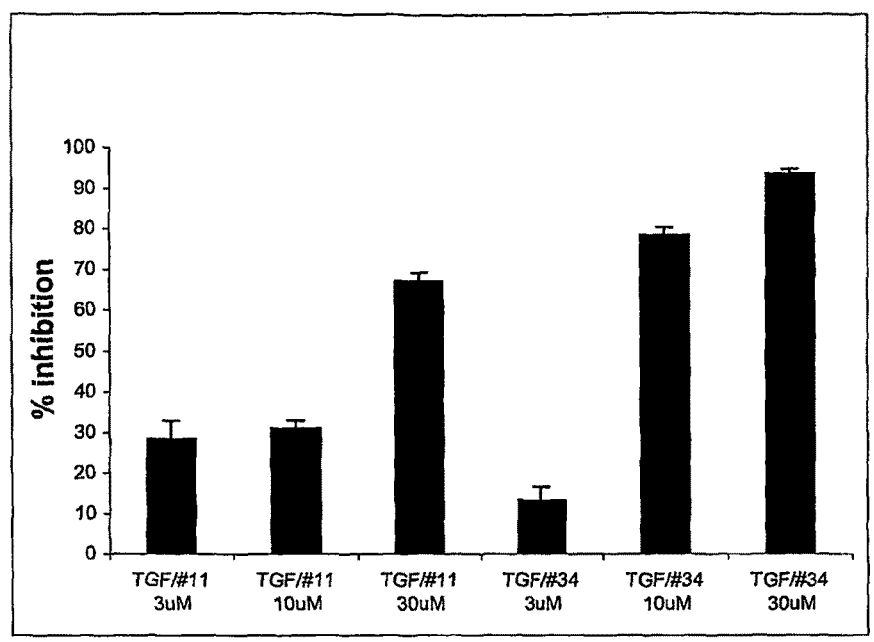
FIG. 18: Inhibition of TGF-β stimulated proline incorporation—FT034.
Figure 19:
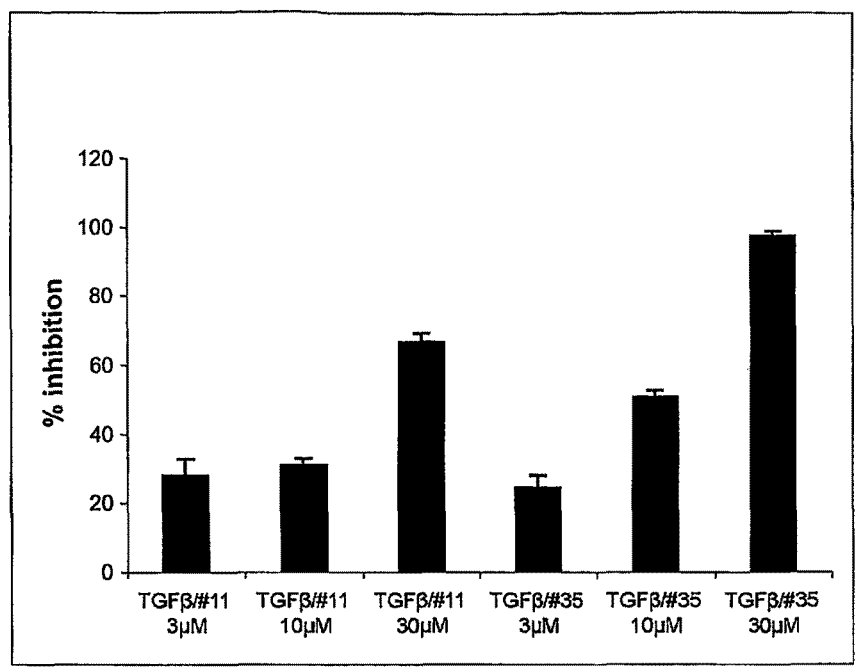
FIG. 19: Inhibition of TGF-β stimulated proline incorporation—FT035 (SEM).
Figure 20:
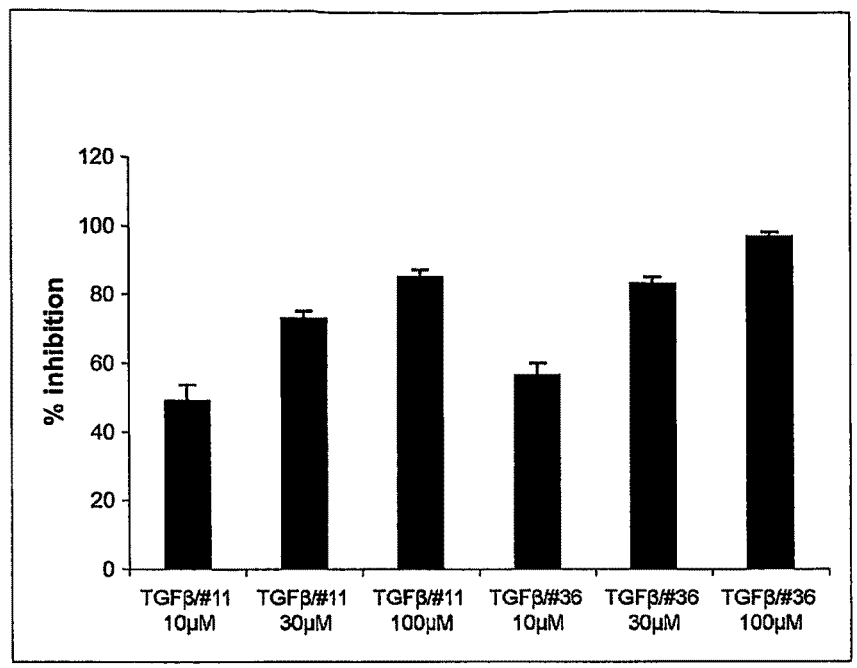
FIG. 20: Inhibition of TGF-β stimulated proline incorporation—FT036 (SEM).
Figure 21:
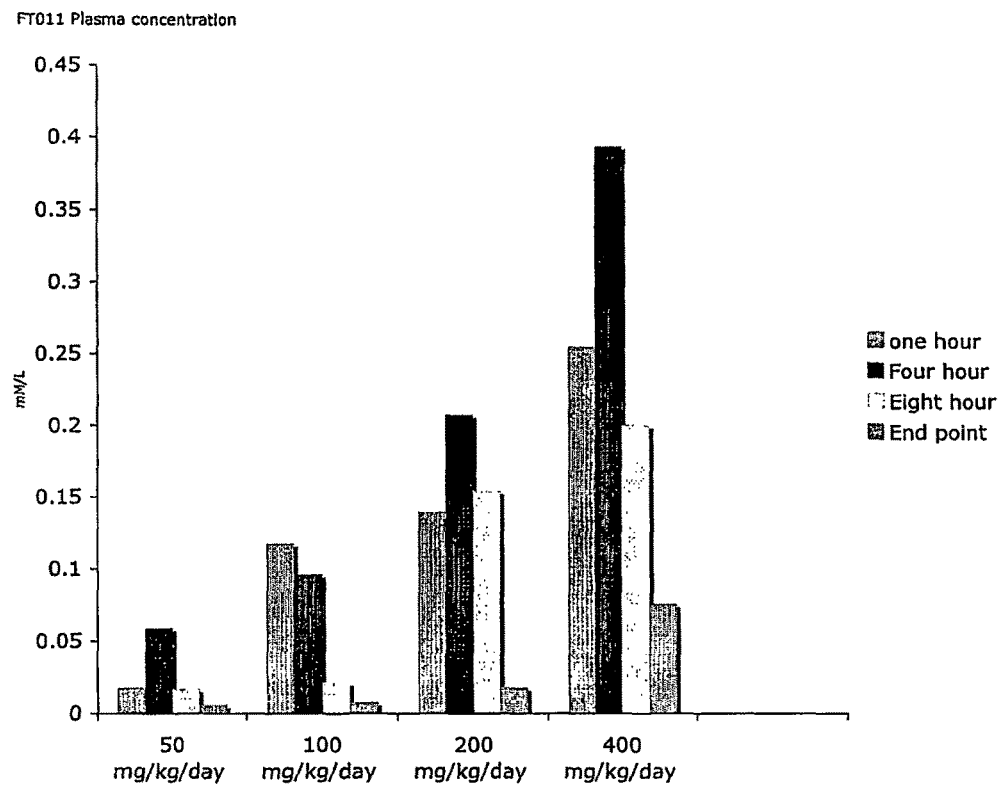
FIG. 21: Plasma levels of FT011 in Sprague Dawley rats.
Figure 22:
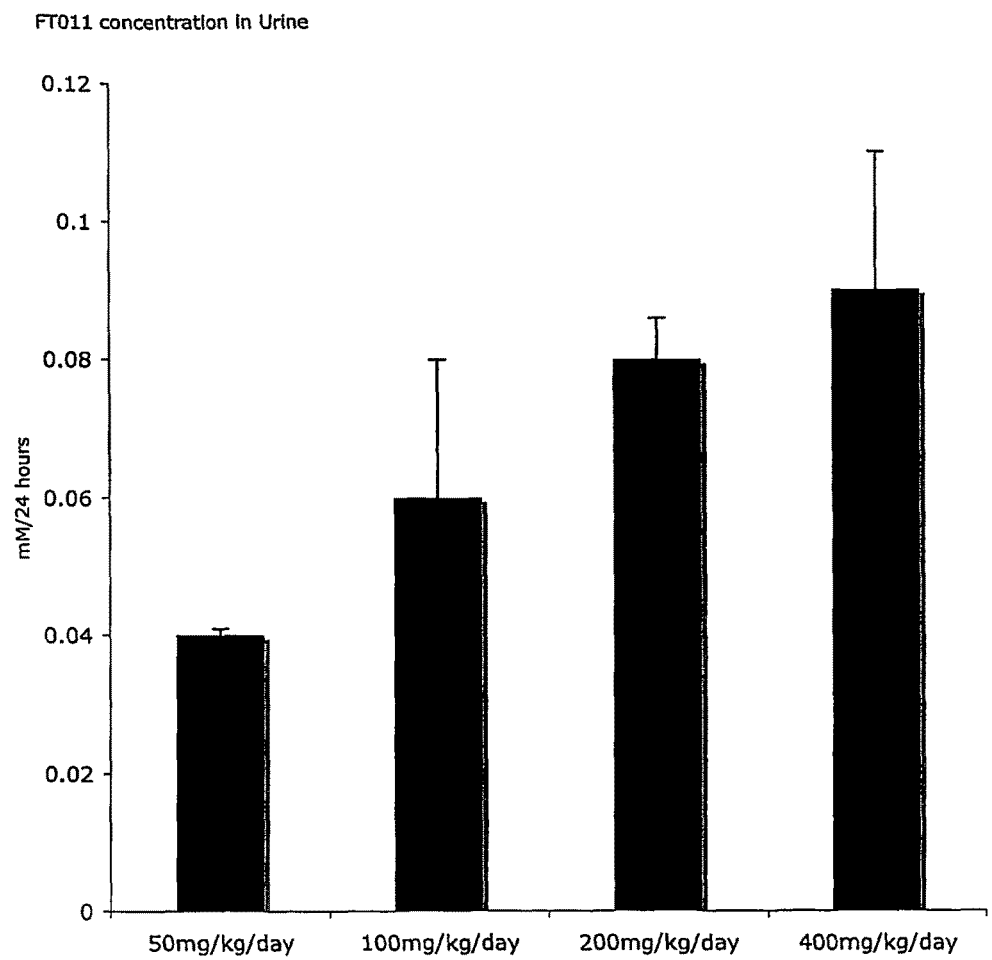
FIG. 22: Urinary levels of FT011.

Diabetic rats had reduced body weight and were all equally hyperglycaemic Table 4). Diabetic rats had increased albuminuria and FT011 significantly attenuated the rise in albuminuria (FIG. 11)

TABLE 4

Animal characteristic of Ren-2 rats

| Group | Body Weight (Gram) | Plasma Glucose (mmol/L) | GFR (ml/min) |
|---|---|---|---|
| Control | 294 ± 11 | 5 ± 0.2 | 3.77 ± 0.23 |
| Control + FT011 | 309 ± 7 | 7 ± 0.2 | 3.63 ± 0.08 |
| Diabetic | 281 ± 22 | 33 ± 0.2* | 5.33 ± 0.47* |
| Diabetic + FT011 | 278 ± 12 | 30 ± 1.5* | 5.90 ± 0.20* |

*p < 0.01 when compared to control

CONCLUSION

The above results would suggest that treatment with FT011 may provide a potential in disease or conditions characterised by inflammation and/or benign or malignant neoplastic diseases.

It will be understood that the invention disclosed and defined in this specification extends to all alternative combinations of two or more of the individual features mentioned or evident from the text or drawings. All of these different combinations constitute various alternative aspects of the invention.

REFERENCES

1 Krum, H., et al., Lancet 2003; 362:147-58.
2 He, J., et al., Arch Intern Med 2001; 161:996-1002.
3 Gustafsson I., et al., Diabetes Care 2001; 24:3-4.
4 Poirier, P., et al., Diabetes Care 2001; 24:5-10.
5 Zabalgoitia, M., et al., Am J Cardiol 2001; 87:320-3.
6 Bell, D. S., Diabetes Care 1995; 18:708-14.
7 Way, K. J., et al., Diabetes 2002; 51:2709-18.
8 Shigeki, S., et al., Scand J Plast Reconstr Surg Hand Surg 1997; 31:151-8.
9 Taniguchi, S., et al., Clin Exp Dermatol 1994; 19:391-3.
10 Miyazawa, K., et al., Atherosclereosis 1995; 118:213-21.
11 Yamada, H., et al., J Biochem (Tokyo) 1994; 116:892-7.
12 Border, W. A., et al., New Engl J Med 1994; 331:1286-392.
13 Pinto, Y. M., et al., Hypertension 2000; 36:747-54.
14 Mifsud, S., et al., Nephron 2003; 95:83-91.
15 Martin, J., et al., Cardiovascular Research 2005; 65:694-701.
16 Jugdutt, B. I., et al., Circulation 2003; 108:1395-403.
17 Border, W. A., et al., Contrib Nephrol 1994; 107:140-5.
18 Ikeda, H., et al., Biochem Biophys Res Commun 1996; 227:322-7.
19 Dannott, T. M. et al. The Pharmacogenomics Journal (2004) 4, 49-53
20 Still, W. C. et al., J. Org. Chem., 1978, 43, 2923-2924.
21 Jierujii, T. et al., "Manufacture of N-(3',4'-dimethoxycinnamoyl)-aniline derivatives", Biogal Gyogyszergyar, JP 1016755, 1989.
22 Spoors, P. G., "Process and product", Smithkline Beecham Corp., WO 02055454, 2002.
23 Bassoli, A., et al., "Use of amide derivatives as taste-modifying agents, flavouring compositions and products containing them", Univ degli studi Milano, WO 2006117602, 2006.
24 Harita, K. et al., "Aromatic carboxylic amide derivatives", Kissei Pharmaceutical, U.S. Pat. No. 3,940,422, 1976.
25 Iizuka, K. et al., "Process for the production of nuclear substituted cinnamoylanthranilic acid derivatives", Kissei Pharmaceutical, U.S. Pat. No. 4,587,356, 1986.
26 Noda, K. et al., "Novel anthranilic acid derivatives", Husamitsu Pharmaceutical Co., JP 54132544, 1979.
27 Ono, S.; Ebihara, Y., "Novel aminobenzoic acid amide derivatives and production thereof", Maruko Pharmaceutical Co., JP 63295543, 1988.
28 Ahluwalia, G. S. et al., J. Chem. Soc., 1931, 2059.
29 Twin, H.; Batey. R. A., Org. Lett., 2004, 6, 4913.
30. Kakizaki, Y., et al., "Differential control of mesangial cell proliferation by interferon-gamma". Clin Exp Immunol 85: 157-163, 1991.
31. See, F. et al., p38 mitogen-activated protein kinase inhibition improves cardiac function and attenuates left ventricular remodeling following myocardial infarction in the rat. J Am Coll Cardiol 44: 1679-1689, 2004.
32. Thomas, W. G. et al., Adenoviral-directed expression of the type 1A angiotensin receptor promotes cardiomyocyte hypertrophy via transactivation of the epidermal growth factor receptor. Circ Res 90: 135-142, 2002.
33. Woodcock, E. A. et al., Inositol polyphosphate 1-phosphatase is a novel antihypertrophic factor. J Biol Chem 277: 22734-22742, 2002.

34. Boyle, A. J. et al., Inhibition of protein kinase C reduces left ventricular fibrosis and dysfunction following myocardial infarction. *J Mol Cell Cardiol* 39: 213-221, 2005.
35. Connelly, K. A., et al., Load-sensitive measures may overestimate global systolic function in the presence of left ventricular hypertrophy: a comparison with load-insensitive measures. *Am J Physiol Heart Circ Physiol* 290: H1699-1705, 2006.
36. Kelly, D. J. et al., Effects of endothelin or angiotensin II receptor blockade on diabetes in the transgenic (mRen-2) 27 rat. *Kidney Int* 57: 1882-1894, 2000.
37. Kelly, D. J. et al., A new model of diabetic nephropathy with progressive renal impairment in the transgenic (mRen-2)27 rat (TGR). *Kidney Int* 54: 343-352, 1998.
38. Kelly, D. J. et al., Progression of tubulointerstitial injury by osteopontin-induced macrophage recruitment in advanced diabetic nephropathy of transgenic (mRen-2)27 rats. *Nephrol Dial Transplant* 17: 985-991, 2002.
39. Kelly, D. J. et al., Protein kinase C beta inhibition attenuates the progression of experimental diabetic nephropathy in the presence of continued hypertension. *Diabetes* 52: 512-518, 2003.
40. Martin, J. et al., Tranilast attenuates cardiac matrix deposition in experimental diabetes: role of transforming growth factor-beta. *Cardiovasc Res* 65: 694-701, 2005.
41. Schiller, N. B. et al., Recommendations for quantitation of the left ventricle by two-dimensional echocardiography. American Society of Echocardiography Committee on Standards, Subcommittee on Quantitation of Two-Dimensional Echocardiograms. *J Am Soc Echocardiogr* 2: 358-367, 1989.
42. Kelly, D. J. et al., *J. Am. Soc. Nephroi.*, 2004, 15, 2619-2629.
43. Hocher et al., *J. Hypertens.*, 2002, 20(4), 611-613.
44. Isaji et al., *Cardiovascular Drug Review*, 1998, 16(3), 288-299.

The invention claimed is:
1. A compound of the Formula 2

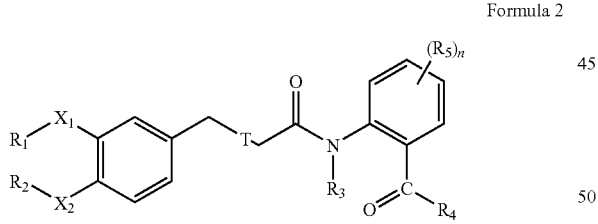

Formula 2 wherein:
$R_1$ and $R_2$, which may be the same or different, are selected from the group consisting of a $C_1$ to $C_{10}$ alkyl, $C_3$ to $C_{10}$ cycloalkyl, $C_3$ to $C_{10}$ cycloalkylmethyl, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ and $NR_6R_7$;

$R_5$ is selected from the group consisting of H, $NHR_6$, $NR_6R_7$, $OR_8$, halogen, $C_3$ to $C_{10}$ alkene, and $C_3$ to $C_{10}$ alkyne, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or pharmaceutically acceptable salts thereof;

with the proviso that when $X_1$ and $X_2$ are both O or a bond, and one of $R_1$ or $R_2$ is a $C_1$ to $C_4$ alkyl, the other of $R_1$ or $R_2$ is a $C_3$ to $C_{10}$ cycloalkyl, $C_3$ to $C_{10}$ cycloalkylmethyl, $C_3$ to $C_{10}$ alkyne, or a chain containing a heterocyclic or fused ring.

2. A compound as claimed in claim 1 of the Formula 3

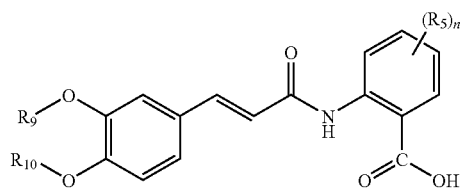

Formula 3 wherein:
$R_9$ or $R_{10}$, which may be the same or different, are selected from the group consisting of $C_1$ to $C_{10}$ alkyl, $C_3$ to $C_8$ terminal or non-terminal alkyne or a cyclopentyl, cyclohexyl, cyclohexylmethyl or cyclopentylmethyl group;

or pharmaceutically acceptable salts thereof;

with the proviso that when one of $R_9$ or $R_{10}$ is a $C_1$ to $C_4$ alkyl, the other of $R_9$ or $R_{10}$ is a $C_3$ to $C_{10}$ cycloalkyl, $C_3$ to $C_{10}$ cycloalkylmethyl, $C_3$ to $C_{10}$ alkyne or a chain containing a heterocyclic or fused ring, er-any of which are optionally substituted.

3. A compound of the Formula 4 or Formula 5,

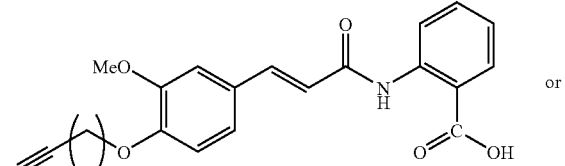

Formula 4 or

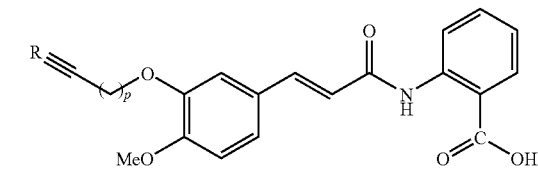

Formula 5 wherein:

p is an integer between 1 and 10; and

R is selected from the group consisting of H and C$_1$ to C$_{10}$ alkyl;

or pharmaceutically acceptable salts thereof.

4. A compound of the Formula 6 or Formula 7,

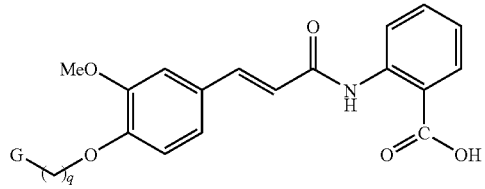

Formula 6 or

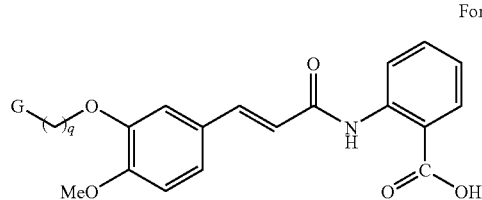

Formula 7

G is a cyclopentyl ring, a cyclohexyl ring or a 1,4-disubstituted 1,2,3-triazole ring; and q is an integer between 0 and 6;

or pharmaceutically acceptable salts thereof.

5. A compound as claimed in claim 1, selected from the group consisting of:

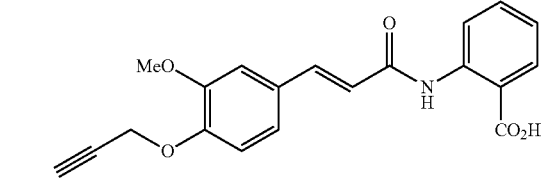

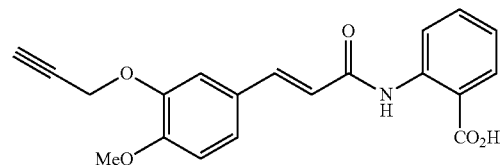

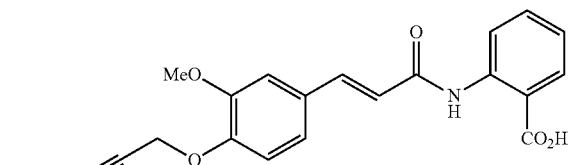

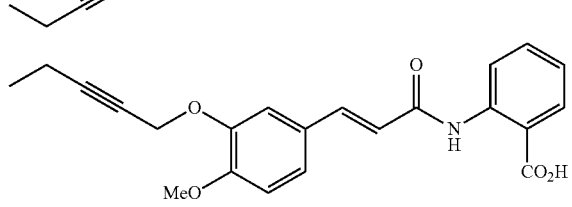

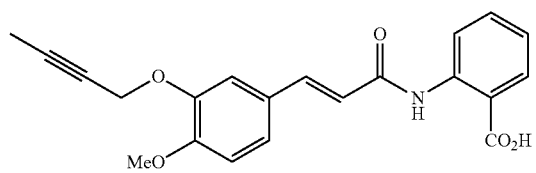

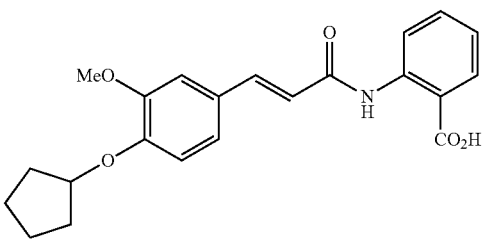

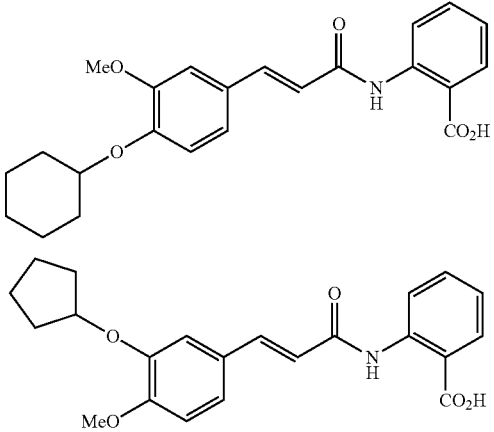

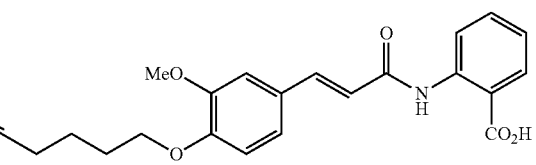

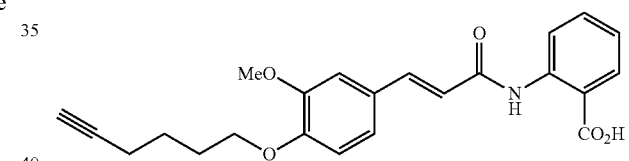

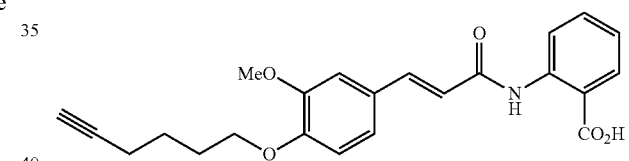

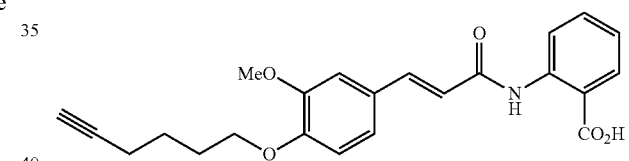

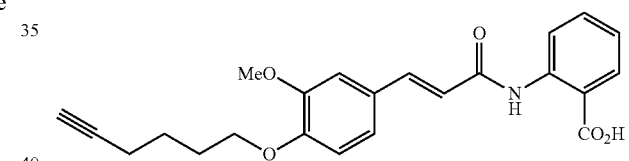

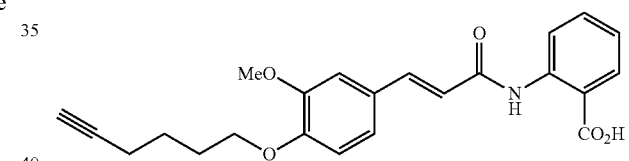

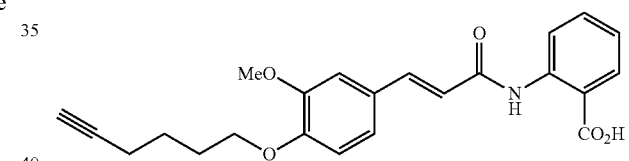

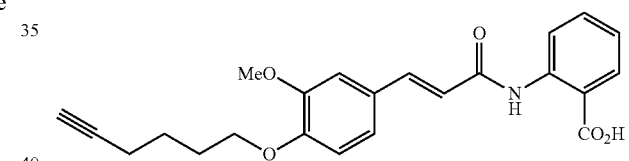

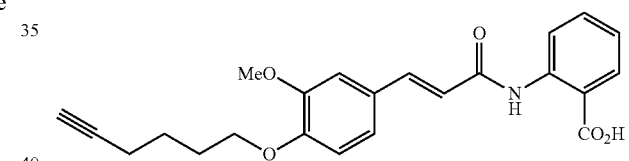

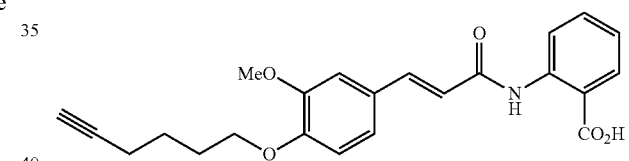

-continued

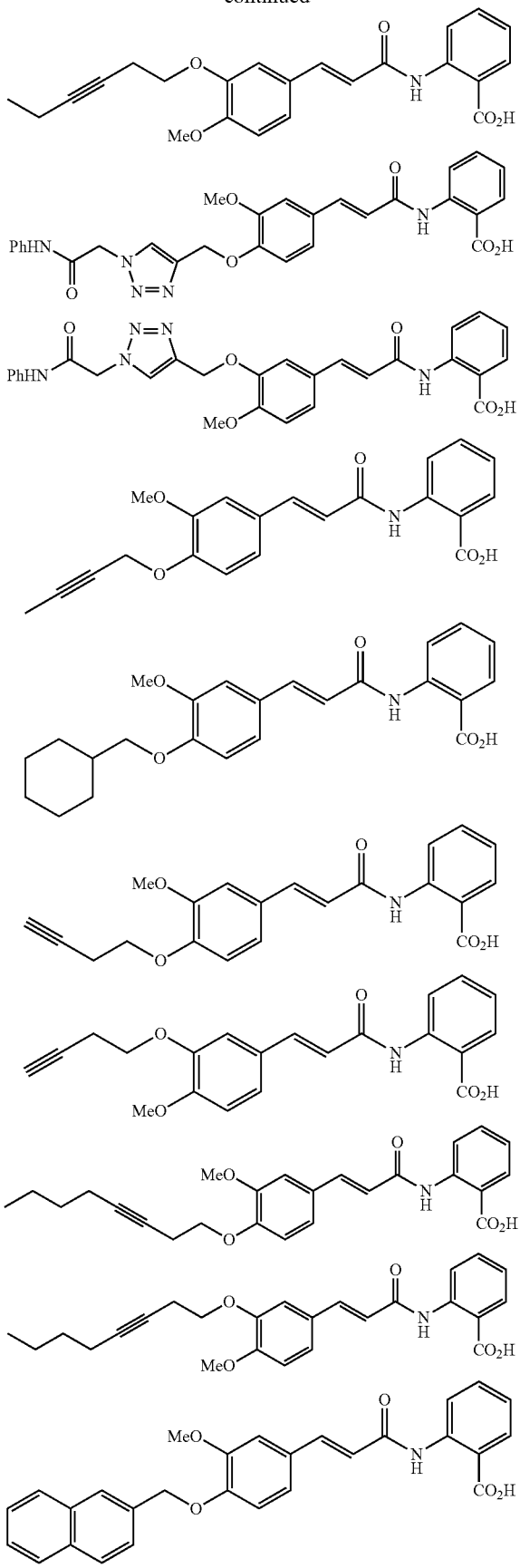

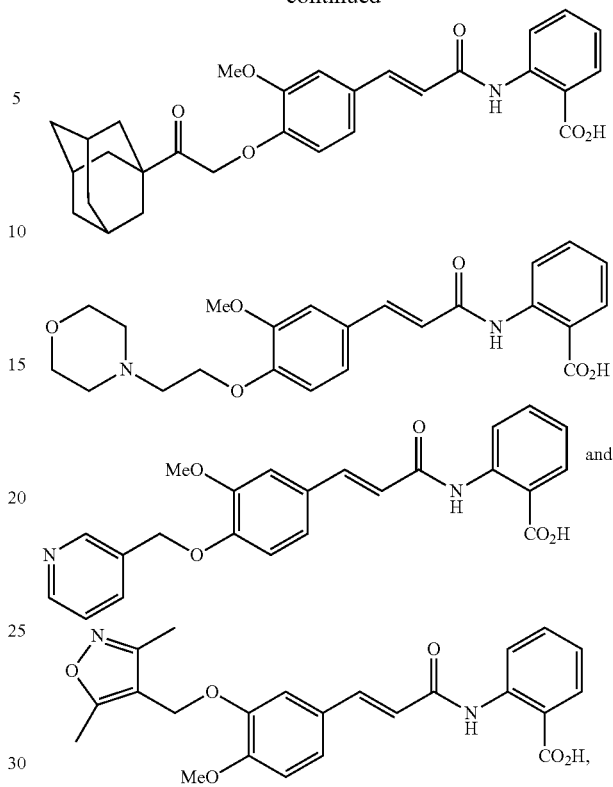

or pharmaceutically acceptable salts thereof.

6. A pharmaceutical composition, comprising a compound of the Formula 2,

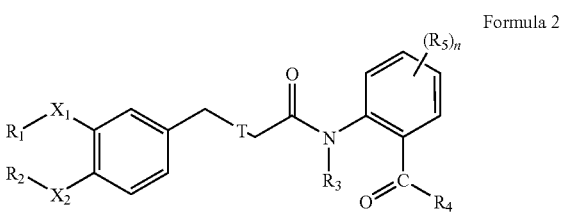

wherein:
$R_1$ and $R_2$, which may be the same or different, are selected from the group consisting of a $C_1$ to $C_{10}$ alkyl, $C_3$ to $C_{10}$ cycloalkyl, $C_3$ to $C_{10}$ cycloalkylmethyl, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ or $NR_6R_7$;

$R_5$ is selected from the group consisting of H, $NHR_6$, $NR_6R_7$, $OR_8$, halogen, $C_3$ to $C_{10}$ alkene, and $C_3$ to $C_{10}$ alkyne, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or pharmaceutically acceptable salts thereof;

with the proviso that when $X_1$ and $X_2$ are both O or a bond and one of $R_1$ or $R_2$ is a $C_1$ to $C_4$ alkyl, the other of $R_1$ or $R_2$ is a $C_3$ to $C_{10}$ cycloalkyl, $C_3$ to $C_{10}$ cycloalkylmethyl, $C_3$ to $C_{10}$ alkyne, or a chain containing a heterocyclic or fused ring;

together with a pharmaceutically acceptable carrier, diluent or excipient therefor.

7. A method of treating a disease or condition associated with fibrosis, comprising administering to an animal, including a human, in need of such treatment, a pharmaceutical composition according to claim 6, wherein the disease or condition is diabetic heart disease or diabetic kidney disease.

8. A method of treating a disease or condition characterised by inflammation comprising administering to an animal, including a human, in need of such treatment a pharmaceutical composition according to claim 6.

9. A compound as claimed in claim 1, selected from the group consisting of

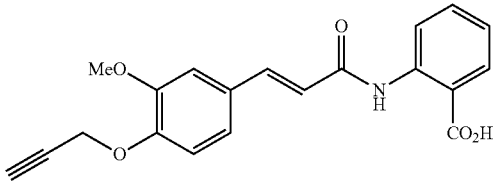 [SMILES: C#CCOc1ccc(/C=C/C(=O)Nc2ccccc2C(=O)O)cc1OC]

-continued

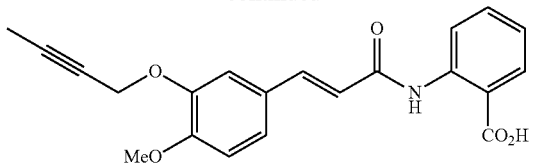

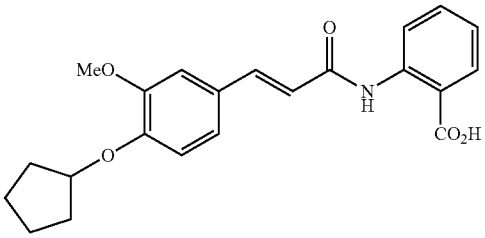

and

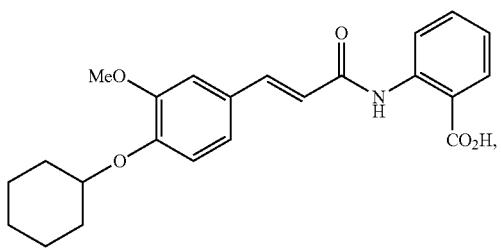

or a pharmaceutically acceptable salt thereof.

10. A compound as claimed in claim 1 of the formula,

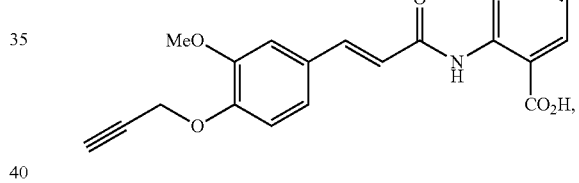

or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,765,812 B2 |
| APPLICATION NO. | : 12/309010 |
| DATED | : July 1, 2014 |
| INVENTOR(S) | : Williams et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twenty-fifth Day of August, 2015

Michelle K. Lee
*Director of the United States Patent and Trademark Office*